(12) United States Patent
Vervecken et al.

(10) Patent No.: US 11,040,114 B2
(45) Date of Patent: Jun. 22, 2021

(54) HUMAN ALPHA-N-ACETYLGALACTOSAMINIDASE POLYPEPTIDE

(71) Applicant: Oxyrane UK Limited, Manchester (GB)

(72) Inventors: Wouter Vervecken, Landskouter-Oosterzele (BE); Steven Geysens, Wannegem-Lede (BE)

(73) Assignee: Oxyrane UK Limited

( * ) Notice: Subject to any disclaimer, the term of this patent is extended or adjusted under 35 U.S.C. 154(b) by 0 days.

(21) Appl. No.: 16/063,408

(22) PCT Filed: Dec. 22, 2016

(86) PCT No.: PCT/EP2016/082304
§ 371 (c)(1),
(2) Date: Jun. 18, 2018

(87) PCT Pub. No.: WO2017/109034
PCT Pub. Date: Jun. 29, 2017

(65) Prior Publication Data
US 2018/0360991 A1    Dec. 20, 2018

(30) Foreign Application Priority Data
Dec. 24, 2015 (EP) .................................. 15202729

(51) Int. Cl.
| C12N 1/20 | (2006.01) |
| A61K 48/00 | (2006.01) |
| C12N 9/24 | (2006.01) |
| C12N 15/81 | (2006.01) |
| A61P 43/00 | (2006.01) |
| C12N 15/80 | (2006.01) |
| A61K 38/00 | (2006.01) |

(52) U.S. Cl.
CPC ............ A61K 48/005 (2013.01); A61P 43/00 (2018.01); C12N 9/2402 (2013.01); C12N 15/80 (2013.01); C12N 15/815 (2013.01); C12Y 302/01049 (2013.01); *A61K 38/00* (2013.01); *C07K 2319/02* (2013.01)

(58) Field of Classification Search
CPC ................................................ C12Y 302/1049
USPC ......................................................... 435/201
See application file for complete search history.

(56) References Cited

U.S. PATENT DOCUMENTS

| 4,879,231 A | 11/1989 | Stroman et al. |
| 4,929,555 A | 5/1990 | Cregg et al. |
| 6,265,185 B1 | 7/2001 | Muller et al. |
| 6,806,084 B1 | 10/2004 | Debs et al. |
| 2004/0248833 A1 | 12/2004 | Emanuele et al. |
| 2006/0014264 A1 | 1/2006 | Sauer et al. |
| 2010/0166728 A1 | 7/2010 | Sakuraba et al. |
| 2018/0360991 A1* | 12/2018 | Vervecken ............. A61P 43/00 |

FOREIGN PATENT DOCUMENTS

| EP | 2 166 093 A1 | 3/2010 |
| JP | 2013-539974 | 4/2012 |
| JP | 2013-505735 | 2/2013 |
| WO | WO 1993/24641 | 2/1992 |
| WO | WO 1994/13788 | 6/1994 |
| WO | WO 2006/129080 | 12/2006 |
| WO | WO 2007/058381 | 5/2007 |
| WO | WO 2008/120107 | 10/2008 |
| WO | WO 2011/039634 | 4/2011 |
| WO | WO 2012/042386 | 4/2012 |
| WO | WO 2013/136189 | 9/2013 |
| WO | WO 2016/105889 A1 | 6/2016 |

OTHER PUBLICATIONS

Alpha-N-acetylgalactosaminidase isoform X1 [Propithecus coquereli]—2 page printout of NCBI website (Year: 2015).*
Altschul et al. "Basic Local Alignment Search Tool," J Mol Biol., 1990, 215:403-10.
Anderson, "Human Gene Therapy," Science, 1992, 256: 808-813.
Bodensteiner et al, "Successful reinstitution of agalsidase beta therapy in Fabry disease patients with previous IgE-antibody or skin-test reactivity to the recombinant enzyme," Genet Med, May 2008, 10(5):353-8.
Brady et al., "Enzymatic defect in Fabry's disease," N. Engl. J. Med., 1967, 276(21):1163-7.
Brigham et al, "Rapid communication: in vivo transfection of murine lungs with a functioning prokaryotic gene using a liposome vehicle," Oct. 1989, Am J Med Sci, 298:278-281.
Burton & Harding, "Hydrophobic charge induction chromatography: salt independent protein adsorption and facile elution with aqueous buffers," Jul. 24, 1998, J. Chromatography, A 814:71-81.
Callewaert et al., "Ultrasensitive profiling and sequencing of N-linked oligosaccharides using standard DNA-sequencing equipment," 2001, Glycobiology, 11(4):275-281.
Canonico et al, "Expression of a CMV promoter driven human alpha-1 antitrypsin gene in culture lung endothelial-cells and in the lungs of rabbits," 1991, Clinical Research, vol. 39, pp. A219.
Christensen et al., "Distribution of α-Galactosidase A in normal human kidney and renal accumulation and distribution of recombinant α-Galactosidase A in Fabry mice," J Am Soc Nephrol., 2007, 18(3):698-706.
Christensen et al., "Receptor-mediated endocytosis in renal proximal tubule," Pflugers Arch., 2009, 458(6):1039-48.
Clarke et al., "Narrative review: Fabry disease," Ann Intern Med., 2007, 146(6):425-33.

(Continued)

*Primary Examiner* — Tekchand Saidha
(74) *Attorney, Agent, or Firm* — Fish & Richardson P.C.

(57) ABSTRACT

The present invention provides new forms of human α-N-acetylgalactosaminidase (NAGAL) polypeptide or a functionally active variant or fragment thereof, nucleic acids encoding the same, and related products and uses, including use in methods of treating Fabry disease, Schindler disease or Kanzaki disease.

37 Claims, 30 Drawing Sheets
Specification includes a Sequence Listing.

(56) References Cited

OTHER PUBLICATIONS

Cregg and Russel, Methods in Molecular Biology: Pichia Protocols, vol. 103, Chapter 3, Humana Press, Totowa, N.J., pp. 27-39 (1998).
Eng et al, Safety and efficacy of recombinant human α-galactosidase A replacement therapy in Fabry's disease, N Engl J Med., Jul. 5, 2001, 345(1):9-16.
Fraley et al, "New generation liposomes: the engineering of an efficient vehicle for intracellular delivery of nucleic acids," 1981, Trends Biochem ScL 6: 77.
Freire et al., "Efficient monitoring of enzymatic conjugation reaction by surface-enhanced laser desorption/ionization time of flight mass spectrometry for process optimization," 2006, Bioconjug. Chem., 17(2):559-564.
Friedmann, "Progress toward human gene therapy," Jun. 16, 1989, Science, 244: 1275-1280.
Garman et al., "The 1.9 A structure of α-N-acetylgalactosaminidase: molecular basis of glycosidase deficiency disease," Mar. 2002, Structure, 10(3):425-34.
Gasmi et al., "A molecular approach to optimize hIFN a2b expression and secretion in Yarrowia lipolytica," Appl. Microbiol. Biotechnol., 2011, 89(1):109-19.
Gasmi et al., "Production and characterization of human granulocyte-macrophage colony-stimulating factor (hGM-CSF) expressed in the oleaginous yeast *Yarrowia lipolytica*," Appl. Microbiol. Biotechnol., Oct. 2012, 96(1):89-101.
Gebski et al., "Morpholino antisense oligonucleotide induced dystrophin exon 23 skipping in mdx mouse muscle," May 28, 2003, Human Molecular Genetics 12(15):1801-1811.
GenBank Accession No. 5IK5_A, "Chain A, Laminin A21g45 C-form, G6/7 Bound" Jul. 12, 2006, 4 page.
GenBank Accession No. Ab139526.1, "*Homo sapiens* DNA, STS on chromosome 3, D3S0537i," May 5, 2008, 2 pages.
GenBank Accession No. AF310423.1, "Neisseria meningitides strain M7257 16S ribosomal RNA gene, partial sequence," Sep. 17, 2003, 2 pages.
GenBank Accession No. BAA08634.1, "Alpha-mannosidase [Aspergillus phoenicis]," Jul. 12, 2006, 1 page.
GenBank Accession No. GANE01008126.1, "TSA: Stevia rebaudiana SteviaLeaf_m5573 transcribed RNA sequence" Aug. 29, 2013, 1 page.
GenBank Accession No. LN824141.1, "Defluviitoga tunisiensis genome assembly DTL3, chromosome : I," Feb. 27, 2015, 576 pages.
GenBank Accession No. NM_000262.2, "*Homo sapiens* alpha-N-acetylgalactosaminidase (NAGA), transcript variant 1, mRNA," May 10, 2014, 6 pages.
GenBank Accession No. NP_000253.1, "alpha-N-acetylgalactosaminidase precursor [*Homo sapiens*]," May 10, 2014, 3 pages.
GenBank Accession No. XM_503217.1, "Yarrowia lipolytica CLM122 YALI0D24101p partial mRNA" Oct. 29, 2008, 2 page.
Gossen & Bujard., "Studying gene function in eukaryotes by conditional gene inactivation," Feb. 2002, Ann. Rev. Genetics, 36:153-173.
Goyenvalle et al, "Rescue of dystrophic muscle through U7 snRNA-mediated exon skipping," Dec. 3, 2004, Science, 306: 1796-1799.
Guarente et al., "A GAL10-CYC1 hybrid yeast promoter identifies the GAL4 regulatory region as an upstream site," Dec. 1982, Proc. Natl. Acad. Sci. USA, 79(23):7410-7414.
Hazinski et al. "Localization and induced expression of fusion genes in the rat lung," Mar. 1, 1991, Am J Resp Cell Molec Biol 4: 206-209.
Hinnen et al., "Transformation of yeast," Apr. 1978, Proc. Nat. Acad. Sci. USA, 75:1929-1933.
Ito et al., "Transformation of intact yeast cells treated with alkali cations," Jan. 1983, J. Bacteriol., 163-168.
Kumar and Nussinov, "Relationship between ion pair geometric and electrostatic strengths in proteins," Biophys. J, Sep. 2002, 83(3): 1595-612.

Laroy et al., "Glycome mapping on DNA sequencing equipment," Jun. 27, 2006, Nat Protoc, 1(1):397-405G.
Lee et al., "A biochemical and pharmacological comparison of enzyme replacement therapies for the glycolipid storage disorder Fabry disease," Glycobiology, 2003, 13(4):305-13.
MacDermot et al., "Anderson-Fabry disease: clinical manifestations and impact of disease in a cohort of 60 obligate carrier females,", J Med Genet, 2001, 38(11):769-75.
Mann et al., "Antisense-induced exon skipping and synthesis of dystrophin in the mdx mouse," ProcNatl Acad Science, Jan. 2, 2001, 98(1): 42-47.
Mannino et al. "Liposome mediated gene transfer," 1988 Biotechniques 6: 682.
Moreau & Morre., "Trafficking of lipids from the endoplasmic reticulum to the golgi apparatus in a cell-free system from rat liver," J. Biol. Chem., Mar. 5, 1991, 266(7):4322-4328.
Moreau et al., "Cell-free transfer of membrane lipids," J. Biol. Chem, Mar. 5, 1991, 266(7):4329-4333.
Nabel et al. "Site-specific gene expression in vivo by direct gene transfer into the arterial wall" 1990, Science 249: 1285-1288.
Newman and Ferro-Novick, "Characterization of new mutants in the early part of the yeast secretory pathway isolated by a [$^3$H]mannose suicide selection," Oct. 1, 1987, J. Cell Biol., 105(4):1587.
Ohashi et al, "Influence of antibody formation on reduction of globotriaosylceramide (GL-3) in urine from Fabry patients during agalsidase beta therapy," Mol Genet Metab, Nov. 3, 2007, 92(3):271-3.
Ohashi et al, "Reduced α-Gal A enzyme activity in Fabry fibroblast cells and Fabry mice tissues induced by serum from antibody positive patients with Fabry disease," Mol Genet Metab, Jul. 2008, 94(3):313-8.
Paulik et al, "Cell-Free Transfer of the Vesicular Stomatitis Virus G Protein from an Endoplasmic Reticulum Compartment of Baby Hamster Kidney Cells to a Rat Liver Golgi Apparatus," Arch. Biochem. Biophys. 1999, 367(2):265-273.
Pignède et al., "Characterization of an extracellular lipase encoded by LIP2 in yarrowia lipolytica," Jun. 2000, J. Bacteriol., 182(10):2802-10.
Prabakaran et al., "Receptor-mediated endocytosis of α-galactosidase A in human podocytes in Fabry disease," PLoS One, Sep. 2011, 6(9).
PyMol.org [online], "The PyMOL Molecular Graphics System," available online before Sep. 15, 2002, via Internet Archive: Wayback Machine URL <https://web.archive.org/web/20020915003113/http://pymol.sourceforge.net/>, [retrieved on Mar. 29, 2019], retrieved from: URL <www.pymol.org>, 9 pages.
Rexach et al., "Distinct biochemical requirements for the budding, targeting, and fusion of er-derived transport vesicle," J. Cell Biol., Jul. 15, 1991, 114(2):219-229.
Rombach et al, Long-term effect of antibodies against infused alpha-galactosidase A in Fabry disease on plasma and urinary (lyso)Gb3 reduction and treatment outcome, PLoS One, Oct. 2012, 7(10).
Rosenberg, "Immunotherapy and gene therapy of cancer," Sep. 15, 1991, Cancer Research, 51(18), suppl.: 5074S-5079S.
Rosenfeld et al, "Adenovirus-mediated transfer of a recombinant alpha 1-antitrypsin gene to the lung epithelium in vivo," Apr. 19, 1991, Science 252: 431-434.
Rosenfeld et al, "In vivo transfer of the human cystic fibrosis transmembrane conductance regulator gene to the airway epithelium," Jan. 10, 1992, Cell 68: 143-155.
Sakuraba et al, "Corrective effect on Fabry mice of yeast recombinant human α-galactosidase with N-linked sugar chains suitable for lysosomal delivery,"α-galactosidase, J Hum Genet, Mar. 11, 2006, 51(4):341-52.
Sambrook et al., Molecular Cloning: A Laboratory Manual, 2d ed., 1989, Cold Spring Harbor Laboratory Pres.
Spada et al., "High incidence of later-onset Fabry disease revealed by newborn screening," Am J Hum Genet., 2006, 79(1):31-25 40.
Sreekrishna et al., "Invertase gene (SUC2) of *Saccharomyces cerevisiae* as a dominant marker for transformation of pichia pastoris," 1987, Gene, 59:115-125.

(56) References Cited

OTHER PUBLICATIONS

Tajima et al, "Use of a modified α-N-acetyl galactosaminidase in the development of enzyme replacement therapy for Fabry disease," Am J Hum Genet, Nov. 13, 2009, 85(5):569-80.

Tomasic et al, "Interconversion of the specificities of human lysosomal enzymes associated with Fabry and Schindler disease," J. Biol. Chem, Feb. 26, 2010, 285(28):21560-6.

Vedder et al, "Treatment of Fabry disease with different dosing regimens of agalsidase: effects on antibody formation and GL-3," Mol Genet Metab, Jul. 2008, 94(3):319-25.

Wang & Huang, "pH-sensitive immunoliposomes mediate target-cell-specific delivery and controlled expression of a foreign gene in mouse," Nov. 1987, Proc Natl Acad Sci USA,84:7851-7855.

Wilcox et al, "Anti-α-galactosidase A antibody response to agalsidase beta treatment: data from the Fabry registry," Mol Genet Metab, 2012, 105(3):443-449.

Wolff et al, "Direct gene transfer into mouse muscle in vivo," Mar. 23, 1990, Science 247: 1465-1468.

Wu & Wu, "Receptor-mediated gene delivery and expression in Vivo*," 1988, J Biol Chem, 263:14621-14624.

Xia H et al, "siRNA-mediated gene silencing in vitro and in vivo", Sep. 16, 2002, Nat. Biotech, 20: 1006-1010.

Zarate et al. "Fabry's Disease," Lancet., 2008, 18;372(9647):1427-35.

Zhu & Zhang, "SCPD: a promoter database of the yeast *Saccharomyces cerevisiae*," 1999, Bioinformatics 15(7-8):608-611.

Zhu et al., "Expression, Purification, and Characterization of Recombinant a-N-Acetylgalactosaminidase Produced in the Yeast *Pichia pastoris*," Protein Expr Purif., 1996, 8(4):456-62.

Clark et al., "The 1.9 A Structure of Human alpha-N-Acetylgalactosaminidase: The Molecular Basis of Schindler and Kanzaki Diseases", J. Mol. Biol., 393(2):435-447 (2009).

Database Geneseq [online] Nov. 8, 2012, "Plant agronomic trait enhancing protein", SEQ ID 23834, retrieved from EBI accession No. GSP:AZZ93686 Database accession No. AZZ93686 (2 pages).

International Search Report dated Apr. 7, 2017 for Intl. App. No. PCT/EP2016/082304 (5 pages).

NCBI Reference, "Predicted: alpha-N-acetylgalactosaminidase isoform X1 (Propithecus coquereli)", Jun. 1, 2015, Retrieved from the Internet: URL:www.ncbi.nlm.nih.gov/protein/XP-012493 587 [retrieved on Mar. 23, 2017] (2 pages).

Written Opinion of the International Searching Authority dated Apr. 7, 2017 for Int. App No. PCT/EP2016/082304 (7 pages).

GenBank Accession No. G3QXZ9, "NAGA alpha-N-acetylgalactosaminidase [ *Gorilla gorilla* (western gorilla) ]," Oct. 14, 2015, 3 pages.

GenBank Accession No. XM_012638133.1, "Predicted: Propithecus coquereli N-acetylgalactosaminidase, alpha- (NAGA), transcript variant X1, mRNA," Jun. 1, 2015, 3 pages.

JP Office Action in Japanese Appln. No. 2018-532655, dated Nov. 11, 2020, 10 pages.

Henikoff et al., "Amino acid substitution matrices from protein blocks," Proceedings of the National Academy of Sciences of the United States of America, Nov. 1992, 89:10915-10919.

Tatusova et al., "BLAST 2 Sequences, a new tool for comparing protein and nucleotide sequences," Fems Microbiology Letters, 1999, 174:247-250.

\* cited by examiner

SEQ ID NO: 1:

LDNGLLQTPPMGWLAWERFRCNINCDEDPKNCISEQLFMEMADRMAQDGWRDMGYTYL
NIDDCWIGGRDASGRLMPDPKRFPHGIPFLADYVHSLGLKLGIYADMGNFTCMGYPGTTL
DKVVQDAQTFAEWKVDMLKLDGCFSTPEERAQGYPKMAAALNATGRPIAFSCSWPAYE
GGLPPRVNYSLLADICNLWRNYDDIQDSWWSVLSIL<u>N</u>WFVEHQDILQPVAGPGHWNDPD
MLLIGNFGLSLEQSRAQMALWTVLAAPLLMSTDLRTISAQNMDILQNPLMIKINQDPLGIQ
GRRIHKEKSLIEVYMRPLSNKASALVFFS<u>C</u>RTDMPYRYHSSLGQLNFTGSVIYEAQDVYSG
DIISGLRDETNFTVIINPSGVVMWYLYPIKNLEMSQQ

Fig.1

SEQ ID NO: 2:

LDNGLLQTPPMGWLAWERFRCNINCDEDPKNCISEQLFMEMADRMAQDGWRDMGYTYL
NIDDCWIGGRDASGRLMPDPKRFPHGIPFLADYVHSLGLKLGIYADMGNFTCMGYPGTTL
DKVVQDAQTFAEWKVDMLKLDGCFSTPEERAQGYPKMAAALNATGRPIAFSCSWPAYE
GGLPPRVNYSLLADICNLWRNYDDIQDSWWSVLSIL<u>D</u>WFVEHQDILQPVAGPGHWNDPD
MLLIGNFGLSLEQSRAQMALWTVLAAPLLMSTDLRTISAQNMDILQNPLMIKINQDPLGIQ
GRRIHKEKSLIEVYMRPLSNKASALVFFS<u>R</u>RTDMPYRYHSSLGQLNFTGSVIYEAQDVYSG
DIISGLRDETNFTVIINPSGVVMWYLYPIKNLEMSQQ

Fig.2

SEQ ID NO: 3

LDNGLLQTPPMGWLAWERFRCNINCDEDPKNCISEQLFMEMADRMAQDGWRDMGYTYL
NIDDCWIGGRDASGRLMPDPKRFPHGIPFLADYVHSLGLKLGIYADMGNFTCMGYPGTTL
DKVVQDAQTFAEWKVDMLKLDGCFSTPEERAQGYPKMAAALNATGRPIAFSCSWPAYE
GGLPPRVNYSLLADICNLWRNYDDIQDSWWSVLSIL<u>N</u>WFVEHQDILQPVAGPGHWNDPD
MLLIGNFGLSLEQSRAQMALWTVLAAPLLMSTDLRTISAQNMDILQNPLMIKINQDPLGIQ
GRRIHKEKSLIEVYMRPLSNKASALVFFS<u>R</u>RTDMPYRYHSSLGQLNFTGSVIYEAQDVYSG
DIISGLRDETNFTVIINPSGVVMWYLYPIKNLEMSQQ

Fig.3

SEQ ID NO: 4

LDNGLLQTPPMGWLAWERFRCNINCDEDPKNCISEQLFMEMADRMAQDGWRDMGYTYL
NIDDCWIGGRDASGRLMPDPKRFPHGIPFLADYVHSLGLKLGIYADMGNFTCMGYPGTTL
DKVVQDAQTFAEWKVDMLKLDGCFSTPEERAQGYPKMAAALNATGRPIAFSCSWPAYE
GGLPPRVNYSLLADICNLWRNYDDIQDSWWSVLSIL<u>D</u>WFVEHQDILQPVAGPGHWNDPD
MLLIGNFGLSLEQSRAQMALWTVLAAPLLMSTDLRTISAQNMDILQNPLMIKINQDPLGIQ
GRRIHKEKSLIEVYMRPLSNKASALVFFS<u>S</u>RTDMPYRYHSSLGQLNFTGSVIYEAQDVYSG
DIISGLRDETNFTVIINPSGVVMWYLYPIKNLEMSQQ

Fig.4

SEQ ID NO: 5

LDNGLLQTPPMGWLAWERFRCNINCDEDPKNCISEQLFMEMADRMAQDGWRDMGYTYL
NIDDCWIGGRDASGRLMPDPKRFPHGIPFLADYVHSLGLKLGIYADMGNFTCMGYPGTTL
DKVVQDAQTFAEWKVDMLKLDGCFSTPEERAQGYPKMAAALNATGRPIAFSCSWPAYE
GGLPPRVNYSLLADICNLWRNYDDIQDSWWSVLSIL<u>N</u>WFVEHQDILQPVAGPGHWNDPD
MLLIGNFGLSLEQSRAQMALWTVLAAPLLMSTDLRTISAQNMDILQNPLMIKINQDPLGIQ
GRRIHKEKSLIEVYMRPLSNKASALVFFS<u>S</u>RTDMPYRYHSSLGQLNFTGSVIYEAQDVYSG
DIISGLRDETNFTVIINPSGVVMWYLYPIKNLEMSQQ

Fig.5

SEQ ID NO: 6

LDNGLLQTPPMGWLAWERFRCNINCDEDPKNCISEQLFMEMADRMAQDGWRDMGYTYL
NIDDCWIGGRDASGRLMPDPKRFPHGIPFLADYVHSLGLKLGIYADMGNFTCMGYPGTTL
DKVVQDAQTFAEWKVDMLKLDGCFSTPEERAQGYPKMAAALNATGRPIAFSC<u>E</u>WP<u>L</u>YE
GGLPPRVNYSLLADICNLWRNYDDIQDSWWSVLSIL<u>D</u>WFVEHQDILQPVAGPGHWNDPD
MLLIGNFGLSLEQSRAQMALWTVLAAPLLMSTDLRTISAQNMDILQNPLMIKINQDPLGIQ
GRRIHKEKSLIEVYMRPLSNKASALVFFS<u>R</u>RTDMPYRYHSSLGQLNFTGSVIYEAQDVYSG
DIISGLRDETNFTVIINPSGVVMWYLYPIKNLEMSQQ

Fig.6

SEQ ID NO: 7

LDNGLLQTPPMGWLAWERFRCNINCDEDPKNCISEQLFMEMADRMAQDGWRDMGYTYL
NIDDCWIGGRDASGRLMPDPKRFPHGIPFLADYVHSLGLKLGIYADMGNFTCMGYPGTTL
DKVVQDAQTFAEWKVDMLKLDGCFSTPEERAQGYPKMAAALNATGRPIAFSC*E*WP*L*YE
GGLPPRVNYSLLADICNLWRNYDDIQDSWWSVLSIL*N*WFVEHQDILQPVAGPGHWNDPD
MLLIGNFGLSLEQSRAQMALWTVLAAPLLMSTDLRTISAQNMDILQNPLMIKINQDPLGIQ
GRRIHKEKSLIEVYMRPLSNKASALVFFS*R*RTDMPYRYHSSLGQLNFTGSVIYEAQDVYSG
DIISGLRDETNFTVIINPSGVVMWYLYPIKNLEMSQQ

*Fig.7*

SEQ ID NO: 8

LDNGLLQTPPMGWLAWERFRCNINCDEDPKNCISEQLFMEMADRMAQDGWRDMGYTYL
NIDDCWIGGRDASGRLMPDPKRFPHGIPFLADYVHSLGLKLGIYADMGNFTCMGYPGTTL
DKVVQDAQTFAEWKVDMLKLDGCFSTPEERAQGYPKMAAALNATGRPIAFSC*E*WP*L*YE
GGLPPRVNYSLLADICNLWRNYDDIQDSWWSVLSIL*D*WFVEHQDILQPVAGPGHWNDPD
MLLIGNFGLSLEQSRAQMALWTVLAAPLLMSTDLRTISAQNMDILQNPLMIKINQDPLGIQ
GRRIHKEKSLIEVYMRPLSNKASALVFFS*S*RTDMPYRYHSSLGQLNFTGSVIYEAQDVYSG
DIISGLRDETNFTVIINPSGVVMWYLYPIKNLEMSQQ

*Fig.8*

SEQ ID NO: 9

LDNGLLQTPPMGWLAWERFRCNINCDEDPKNCISEQLFMEMADRMAQDGWRDMGYTYL
NIDDCWIGGRDASGRLMPDPKRFPHGIPFLADYVHSLGLKLGIYADMGNFTCMGYPGTTL
DKVVQDAQTFAEWKVDMLKLDGCFSTPEERAQGYPKMAAALNATGRPIAFSC*E*WP*L*YE
GGLPPRVNYSLLADICNLWRNYDDIQDSWWSVLSIL*N*WFVEHQDILQPVAGPGHWNDPD
MLLIGNFGLSLEQSRAQMALWTVLAAPLLMSTDLRTISAQNMDILQNPLMIKINQDPLGIQ
GRRIHKEKSLIEVYMRPLSNKASALVFFS*S*RTDMPYRYHSSLGQLNFTGSVIYEAQDVYSG
DIISGLRDETNFTVIINPSGVVMWYLYPIKNLEMSQQ

*Fig.9*

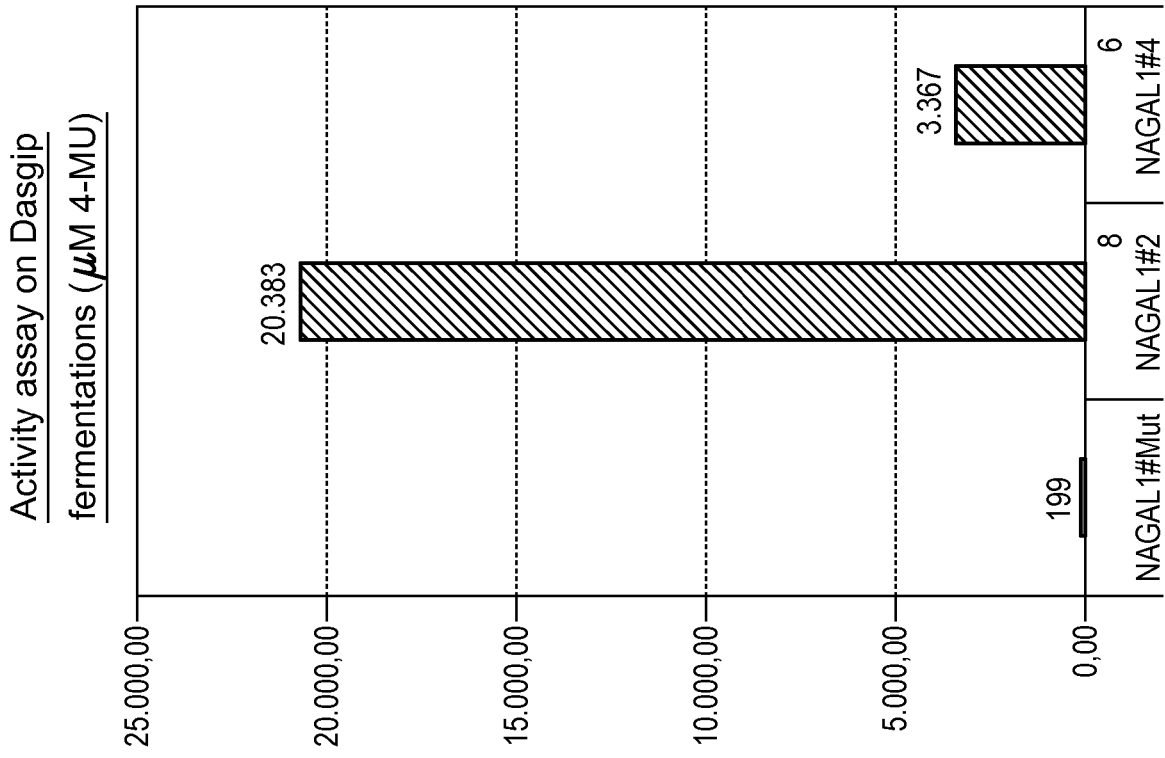
Fig. 31 (Continue)

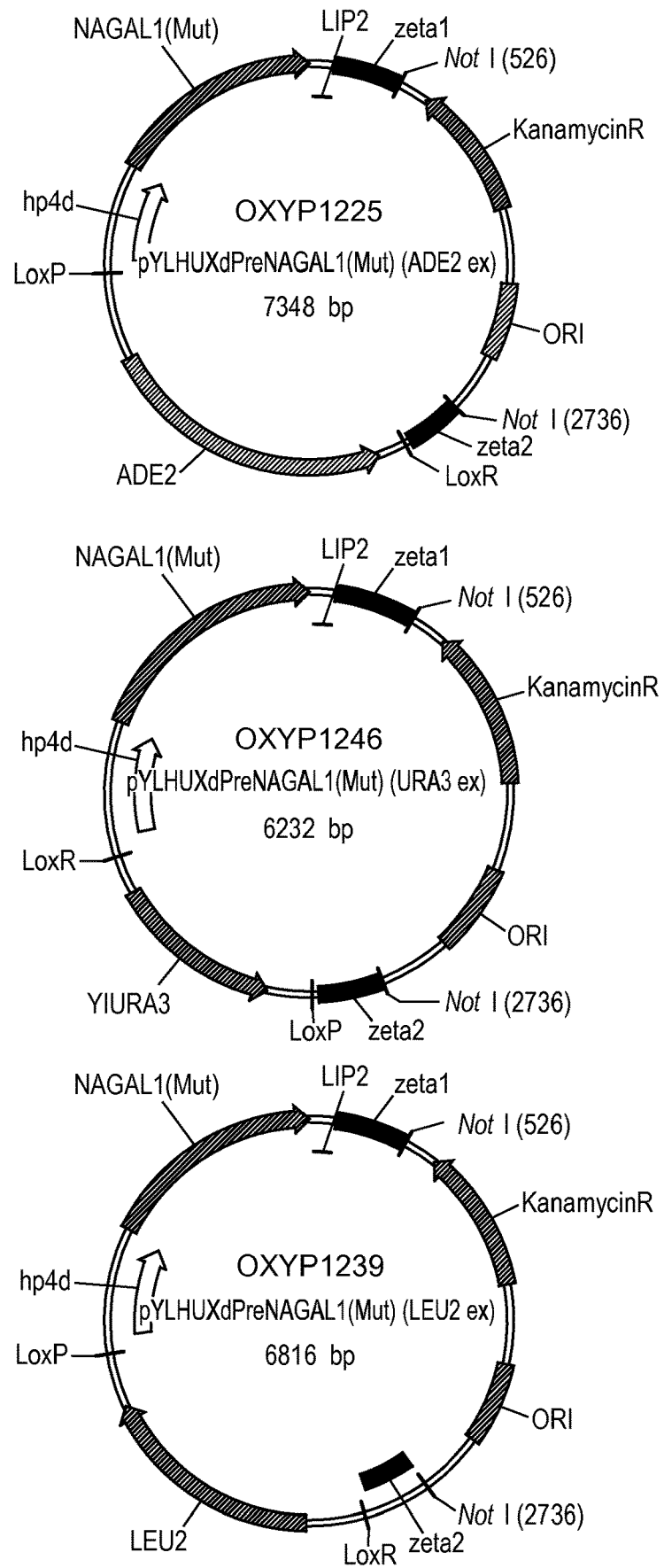
Fig. 32 (Continue)

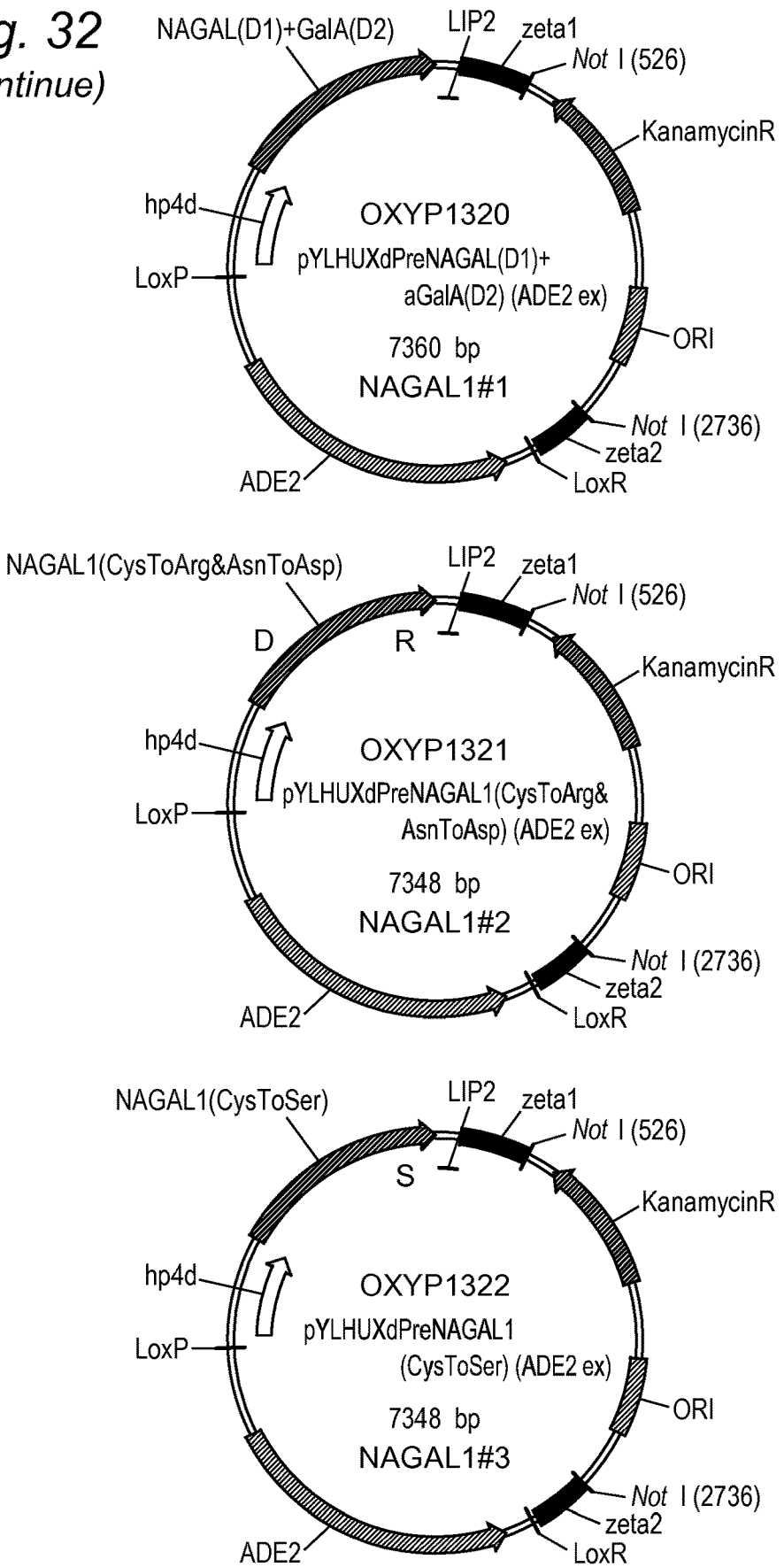
Fig. 32 (Continue)

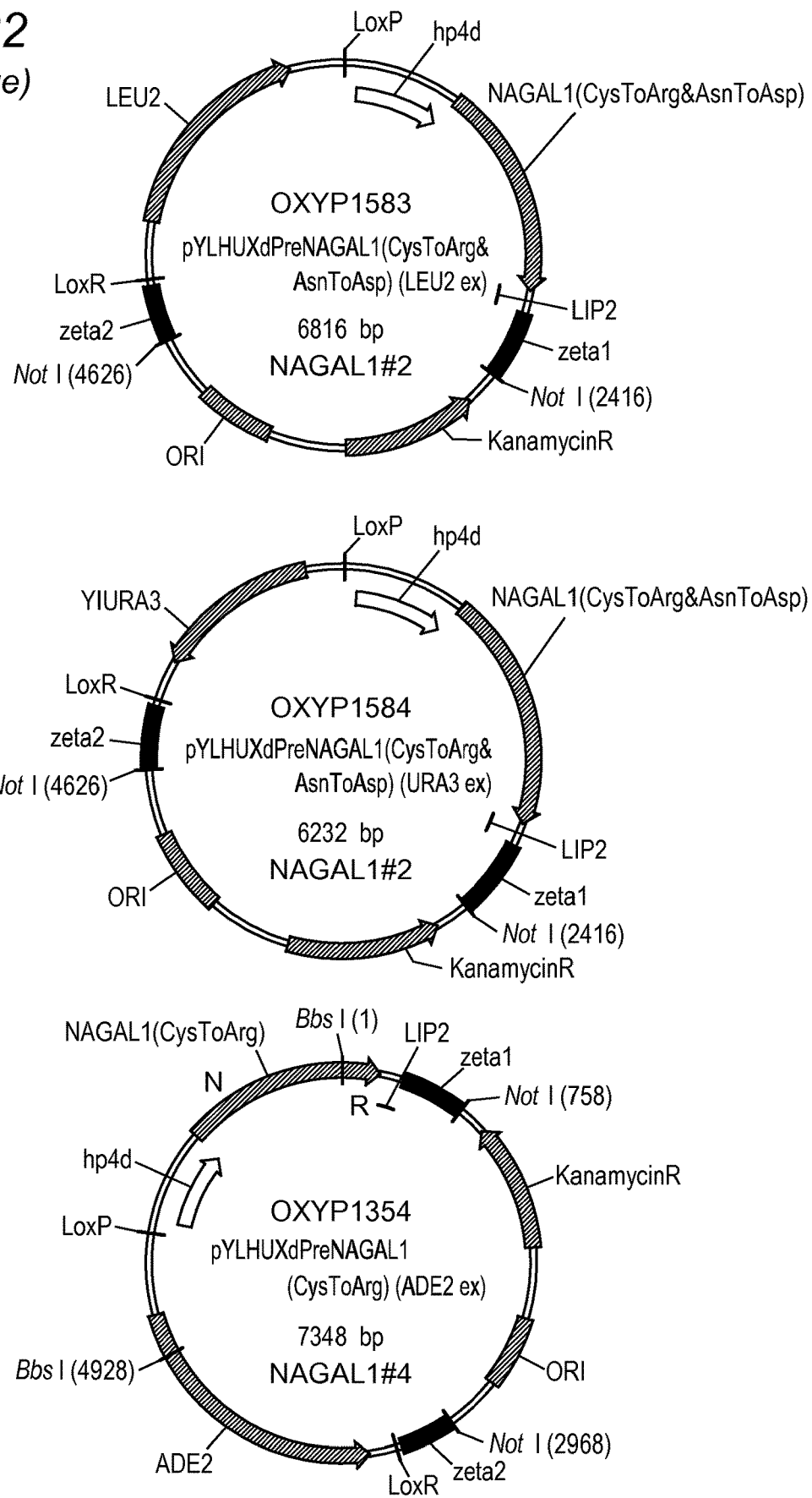
Fig. 32 (Continue)

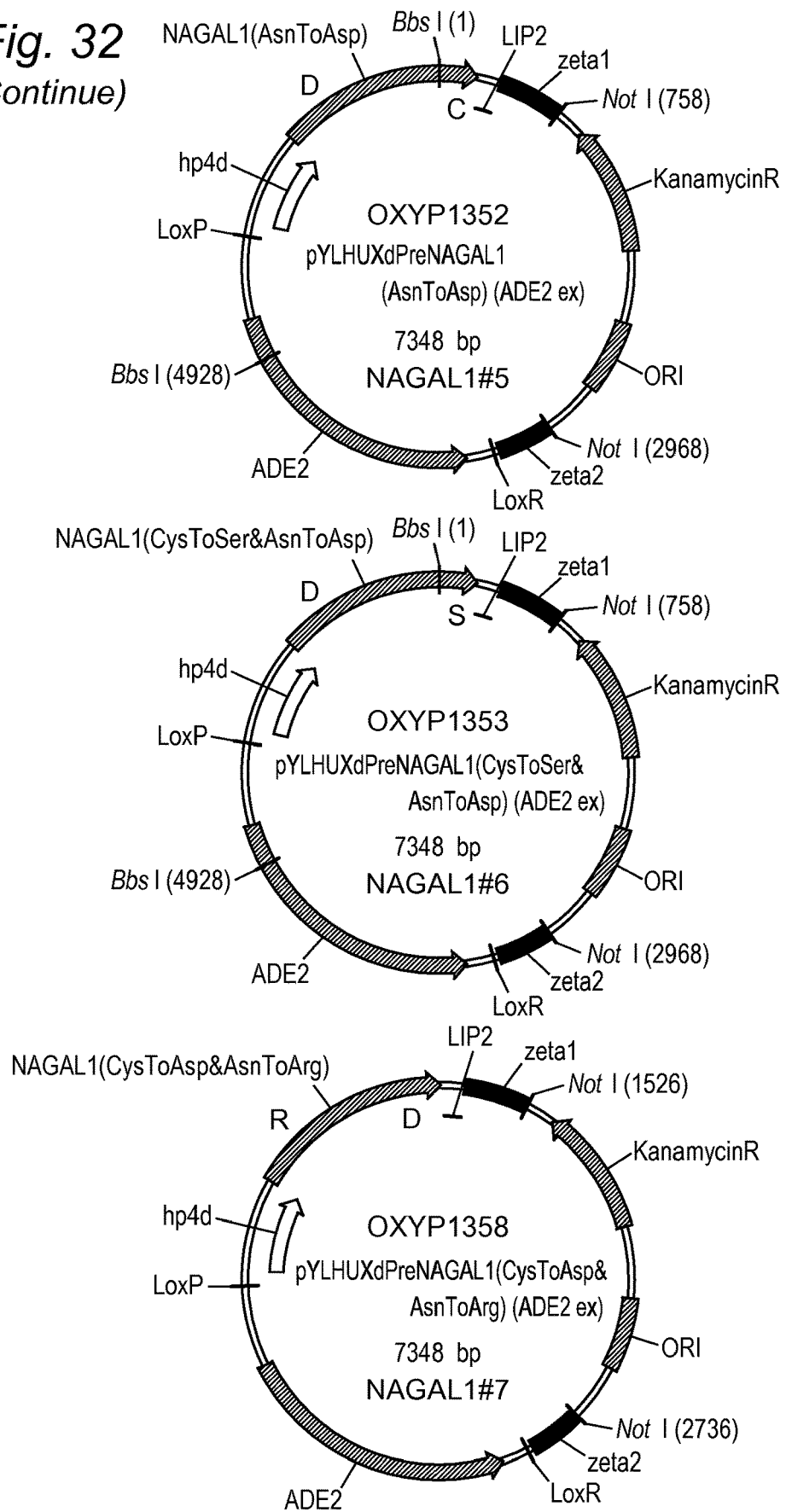
Fig. 32 (Continue)

| OXYP | Description/Name | Resistance | Marker Yl | Promoter | Cloned gene | Leader | Integration in Yl |
|---|---|---|---|---|---|---|---|
| P1219 | pYLHUXdL2preGalase (ADE2 ex) | KanR | Ade2Ex | Hp4d | Human lysosmal a-Galactosidase | preYlLip2p | random |
| P1225 | pYLHUXdL2preNAGAL1(Mut) (ADE2 ex) | KanR | Ade2Ex | Hp4d | Human lysosmal modified a-N-Acetylgalactosaminidase (= NAGAL1) | preYlLip2p | random |
| P1239 | pYLHUXdL2preNAGAL1(Mut) (LEU2 ex) | KanR | Leu2Ex | Hp4d | Human lysosmal modified a-N-Acetylgalactosaminidase (= NAGAL1) | preYlLip2p | random |
| P1246 | pYLHUXdL2preNAGAL1(Mut) (URA3 ex) | KanR | Ura3Ex | Hp4d | Human lysosmal modified a-N-Acetylgalactosaminidase (= NAGAL1) | preYlLip2p | random |
| P1320 | pYLHUXdL2preNAGAL(D1)+a GalA(D2) (ADE2ex) | KanR | Ade2Ex | Hp4d | fusion between domain I of huNAGAL1 and domain II of human aGalA (= NAGAL1#1) | preYlLip2p | random |
| P1321 | pYLHUXdL2PreNAGAL1#2(=Ct oR&NtoD) (ADE2ex) | KanR | Ade2Ex | Hp4d | NAGAL1 with following Aa changes: Cys326 to Arg and Asn213 to Asp (= NAGAL1#2) | preYlLip2p | random |
| P1322 | pYLHUXdL2PreNAGAL1#3(=Ct oS) (ADE2ex) | KanR | Ade2Ex | Hp4d | NAGAL1 with following Aa changes: Cys326 to Ser (= NAGAL1#3) | preYlLip2p | random |
| P1352 | pYLHUXdL2PreNAGAL1#5(=Nt oD) (ADE2ex) | KanR | Ade2Ex | Hp4d | NAGAL1 with following Aa changes: Asn213 to Asp (= NAGAL1#5) | preYlLip2p | random |
| P1353 | pYLHUXdL2PreNAGAL1#6(=Ct oS&NtoD) (ADE2ex) | KanR | Ade2Ex | Hp4d | NAGAL1 with following Aa changes: Cys326 to Ser and Asn213 to Asp (= NAGAL1#6) | preYlLip2p | random |
| P1354 | pYLHUXdL2PreNAGAL1#4(=Ct oR) (ADE2ex) | KanR | Ade2Ex | Hp4d | NAGAL1 with following Aa changes: Cys326 to Arg (= NAGAL1#4) | preYlLip2p | random |
| P1358 | pYLHUXdL2PreNAGAL1#7(=Ct oD&NtoR) (ADE2ex) | KanR | Ade2Ex | Hp4d | NAGAL1 with following Aa changes: Cys326 to Asp and Asn213 to Arg (= NAGAL1#7) | preYlLip2p | random |
| P1583 | pYLHUXdL2PreNAGAL1#2(=Ct oR&NtoD) (LEU2ex) | KanR | Leu2Ex | Hp4d | NAGAL1 with following Aa changes: Cys326 to Arg and Asn213 to Asp (= NAGAL1#2) | preYlLip2p | random |
| P1584 | pYLHUXdL2PreNAGAL1#2(=Ct oR&NtoD) (URA3ex) | KanR | Ura3Ex | Hp4d | NAGAL1 with following Aa changes: Cys326 to Arg and Asn213 to Asp (= NAGAL1#2) | preYlLip2p | random |

Fig. 33

| OXYY | Alt. name | Strain description | Ura | Leu | Ade | Gut |
|---|---|---|---|---|---|---|
| Y2163 | | genotype features: Δoch1 Hp4dMNN4 Pox2MNN4 | Ura- | Leu- | Ade- | Gut+ |
| Y1315 | | Y2163 (Δoch1 Hp4dMNN4 Pox2MNN4) transformed with NotI-digested pYLTmAX(-Tef)(LEU2ex) and pYLTmAX(-Tef)(URA3ex) | Ura+ | Leu+ | Ade- | Gut+ |
| Y1318 | G318 | Y2163 transformed with NotI-digested pYLHUXdpreL2Galase (ADE2ex) (P1219) | Ura- | Leu- | Ade+ | Gut+ |
| Y1349 | G349 | Y1318 transformed with NotI-digested pYLHUXdpreL2Galase (LEU2ex) (P1238) and pYLHUXdpreL2Galase (URA3ex) (P1245) | Ura+ | Leu+ | Ade+ | Gut+ |
| Y1324 | G324 | Y2163 transformed with NotI-digested pYLHUXdpreL2NAGAL1(Mut) (ADE2ex) (P1225) | Ura- | Leu- | Ade+ | Gut+ |
| Y1344 | G344 | Y1324 transformed with NotI-digested pYLHUXdpreL2NAGAL1(Mut) (LEU2ex) (P1239) and pYLHUXdpreL2NAGAL1(Mut) (URA3ex) (P1246) | Ura+ | Leu+ | Ade+ | Gut+ |
| Y1368 | G368 | Y1324 transformed with NotI-digested pYLHUXdpreL2NAGAL1(Mut) (LEU2ex) (P1239) and pYLHUXdpreL2NAGAL1(Mut) (URA3ex) (P1246) | Ura+ | Leu+ | Ade+ | Gut+ |
| Y1369 | G369 | Y1324 transformed with NotI-digested pYLHUXdpreL2NAGAL1(Mut) (LEU2ex) (P1239) and pYLHUXdpreL2NAGAL1(Mut) (URA3ex) (P1246) | Ura+ | Leu+ | Ade+ | Gut+ |
| Y1352 | G352 | Y1324 transformed with NotI-digested pYLTmAX(-Tef)(LEU2ex) and pYLTmAX(-Tef)(URA3ex) | Ura+ | Leu+ | Ade+ | Gut+ |
| Y1855 | | Y1315 transformed with NotI-digested pYLHUXdPreNAGAL1#2(=CysToArg&AsnToAsp) (ADE2ex) (P1321), clone 5 | Ura+ | Leu+ | Ade+ | Gut+ |
| Y1856 | | Y1315 transformed with NotI-digested pYLHUXdPreNAGAL1#2(=CysToArg&AsnToAsp) (ADE2ex) (P1321), clone 6 | Ura+ | Leu+ | Ade+ | Gut+ |
| Y1857 | | Y1315 transformed with NotI-digested pYLHUXdPreNAGAL1#2(=CysToArg&AsnToAsp) (ADE2ex) (P1321), clone 7 | Ura+ | Leu+ | Ade+ | Gut+ |
| Y1858 | | Y1315 transformed with NotI-digested pYLHUXdPreNAGAL1#2(=CysToArg&AsnToAsp) (ADE2ex) (P1321), clone 8 | Ura+ | Leu+ | Ade+ | Gut+ |
| Y1859 | | Y1315 transformed with NotI-digested pYLHUXdPreNAGAL1#3(=CysToSer) (ADE2ex) (P1322), clone5 | Ura+ | Leu+ | Ade+ | Gut+ |

Fig.34A

| | | | | | |
|---|---|---|---|---|---|
| Y1860 | Y1315 transformed with NotI-digested pYLHUXdPreNAGAL1#3(=CysToSer) (ADE2ex) (P1322), clone 6 | Ura+ | Leu+ | Ade+ | Gut+ |
| Y1861 | Y1315 transformed with NotI-digested pYLHUXdPreNAGAL1(Mut) (ADE2ex) (P1322), clone 6 | Ura+ | Leu+ | Ade+ | Gut+ |
| Y1862 | Y1315 transformed with NotI-digested pYLHUXdPreNAGAL1(Mut) (ADE2ex) (P1322), clone 8 | Ura+ | Leu+ | Ade+ | Gut+ |
| Y1863 | Y2163 transformed with NotI-digested pYLHUXdPreNAGAL1#2(= CysToArg&AsnToAsp) (ADE2ex) (P1321), clone1 | Ura- | Leu- | Ade+ | Gut+ |
| Y1864 | Y2163 transformed with NotI-digested pYLHUXdPreNAGAL1#2(= CysToArg&AsnToAsp) (ADE2ex) (P1321), clone7 | Ura- | Leu- | Ade+ | Gut+ |
| Y1868 | Y1863 transformed with NotI-digested pYLHUXdPreNAGAL1#2(=CysToArg&AsnToAsp) (LEU2ex) (P1583) and pYLHUXdPreNAGAL1#2(=CysToArg&AsnToAsp) (URA3ex) (P1584), clone 3 | Ura+ | Leu+ | Ade+ | Gut+ |
| Y1869 | Y1864 transformed with NotI-digested pYLHUXdPreNAGAL1#2(=CysToArg&AsnToAsp) (LEU2ex) (P1583) and pYLHUXdPreNAGAL1#2(=CysToArg&AsnToAsp) (URA3ex) (P1584), clone 28 | Ura+ | Leu+ | Ade+ | Gut+ |
| Y4621 | Y1315 transformed with NotI-digested pYLHUX dPreNAGAL1#4(= CysToArg) (ADE2Ex) (P1354) clone 2.1 | Ura+ | Leu+ | Ade+ | Gut+ |
| Y4622 | Y1315 transformed with NotI-digested pYLHUX dPreNAGAL1#4(= CysToArg) (ADE2Ex) (P1354) clone 2.2 | Ura+ | Leu+ | Ade+ | Gut+ |
| Y4623 | Y1315 transformed with NotI-digested pYLHUX dPreNAGAL1#4(= CysToArg) (ADE2Ex) (P1354) clone 2.5 | Ura+ | Leu+ | Ade+ | Gut+ |
| Y4624 | Y1315 transformed with NotI-digested pYLHUX dPreNAGAL1#4(= CysToArg) (ADE2Ex) (P1354) clone 2.6 | Ura+ | Leu+ | Ade+ | Gut+ |
| Y4625 | Y1315 transformed with NotI-digested pYLHUX dPreNAGAL1#5(= AsnToAsp) (ADE2Ex) (P1352) clone 2.1 | Ura+ | Leu+ | Ade+ | Gut+ |
| Y4626 | Y1315 transformed with NotI-digested pYLHUX dPreNAGAL1#5(= AsnToAsp) (ADE2Ex) (P1352) clone 2.2 | Ura+ | Leu+ | Ade+ | Gut+ |
| Y4627 | Y1315 transformed with NotI-digested pYLHUX dPreNAGAL1#6(=CysToSer&AsnToAsp) (ADE2Ex) (P1353) clone 2.3 | Ura+ | Leu+ | Ade+ | Gut+ |
| Y4628 | Y1315 transformed with NotI-digested pYLHUX dPreNAGAL1#6(=CysToSer&AsnToAsp) (ADE2Ex) (P1353) clone 2.4 | Ura+ | Leu+ | Ade+ | Gut+ |

Fig.34B

| Y4629 | Y1315 transformed with NotI-digested pYLHUX dPreNAGAL1#7(=CysToAsp&AsnToArg) (ADE2Ex) (P1358) clone 5 | Ura+ | Leu+ | Ade+ | Gut+ |
|---|---|---|---|---|---|
| Y4630 | Y1315 transformed with NotI-digested pYLHUX dPreNAGAL1#7(=CysToAsp&AsnToArg) (ADE2Ex) (P1358) clone 8 | Ura+ | Leu+ | Ade+ | Gut+ |

Fig.34C

HUMAN ALPHA-N-ACETYLGALACTOSAMINIDASE POLYPEPTIDE

CROSS REFERENCE TO RELATED APPLICATIONS

This application is a U.S. National Phase Application, and claims priority of International Application No. PCT/EP2016/082304, filed on Dec. 22, 2016, which claims the benefit of European Application No. 15202729.8, filed on Dec. 24, 2015, the entire contents of which are hereby incorporated by reference in their entireties.

FIELD

The invention is broadly in the field of enzyme replacement therapy (ERT), more precisely in the field of polypeptide products for use in the treatment of Lysosomal Storage Diseases (LSDs). In particular, the invention concerns human α-N-acetylgalactosaminidase (NAGAL) polypeptide products, and related products, uses and methods.

BACKGROUND

Lysosomal Storage Diseases (LSDs) are a diverse group of hereditary metabolic disorders characterized by the accumulation of storage products in the lysosomes due to impaired activity of catabolic enzymes involved in their degradation. The build-up of storage products leads to cell dysfunction and progressive clinical manifestations. Deficiencies in lysosomal enzyme activities, particularly in lysosomal hydrolase activities, can be corrected by enzyme replacement therapy (ERT), provided that the administered enzyme can be effectively targeted to the lysosomes of the diseased cells. At present, ERT is the preferred path of intervention to treat LSDs, in particular systemic LSDs.

Classical Fabry disease is a rare X-linked metabolic disorder caused by a deficiency in the lysosomal enzyme α-galactosidase A (α-Gal A), which cleaves terminal α-D-galactose residues from glycolipids (Brady et al., 1967, N. Engl. J. Med., 276(21):1163-7). Enzyme deficiency results in a systemic and lifetime lysosomal accumulation of glycosphingolipids, primarily globotriaosylceramide (Gb3), in the vascular endothelium and other tissues. This leads to a multi-organ pathology that mostly affects the kidneys, the heart and the cerebrovascular system (Clarke et al., 2007, Ann Intern Med., 146(6):425-33; Zarate and Hopkin, 2008, Lancet, 372(9647):1427-35). Male individuals are more prone to develop Fabry disease due to its X-linked nature, with an estimated incidence of 1 out of 40,000 male births (Spada et al., 2006, Am J Hum Genet., 79(1):31-40). Heterozygous females carrying one mutant α-Gal A allele are also affected, but the α-Gal A activity level and the onset and progression rate of the disease is more variable (MacDermot et al., 2001, J Med Genet, 38(11):769-75).

Currently, two distinct recombinant α-Gal A proteins are used for the ERT treatment of Fabry patients: agalsidase alpha (Replagal®: Shire Human Genetic Therapies, Dublin, Ireland) and agalsidase beta (Fabrazyme®: Genzyme Corporation—a Sanofi company, Cambridge, USA). Agalsidase alpha is produced in a human cell line and administered intravenously at 0.2 mg/kg every other week, while agalsidase beta is produced recombinantly in Chinese hamster ovary (CHO) cells and administered at 1 mg/kg body weight every other week.

These mammalian expression systems are expensive to run due to the high costs of raw materials and low turnover of fermentation plants. In addition, there are considerable challenges concerning scalability and due to the nature of these production processes, there is an increased chance of viral contamination.

Also, the complex nature of the mammalian glycosylation system results in a considerable N-glycan heterogeneity, which poses significant problems to prove batch-to-batch reproducibility and further increases costs associated with downstream processing. Since the nature of the glycans is a crucial factor determining the efficacy of the product, the absence of the ability to control the glycosylation is a major concern. More specifically, the secreted glycoproteins produced by these mammalian cell expression systems exhibit a heterogeneous mixture of complex type and high-mannose type glycosylation (more than 30 different N-glycan structures are found on both forms of recombinant α-galactosidase A), which limits the amount of N-glycans with terminal mannose-6-phosphate (M6P) residues (Lee et al., 2003, Glycobiology, 13(4):305-13) and hence the efficiency of uptake of these enzymes into the lysosome. Indeed, in recent years it was shown that the uptake of α-Gal A by kidney interstitial cells, proximal tubular cells and podocytes happens amongst others through the M6P-receptor (Christensen et al., 2007, J Am Soc Nephrol., 18(3):698-706; Christensen et al., 2009, Pflugers Arch., 458(6):1039-48; Prabakaran et al., 2011, PLoS One, 6(9)).

Moreover, the circulation half-life of the current mammalian-expressed recombinant α-galactosidase products is low. This is in part due to their poor protein stability (Sakuraba et al., 2006, J Hum Genet., 51(4):341-52; Tajima et al., 2009, Am J Hum Genet., 85(5):569-80). At both physiological pH (pH 7) and lysosomal pH (pH 4.5), the enzyme activity dropped to approximately 30% or 20%, respectively, after 2 hrs incubation at 37° C., and an almost complete loss of activity was observed after 15 hrs at pH 4.5. Incubation in human serum at 37° C. already resulted in 75% loss of activity after only 30 minutes, with little to no activity observed after as little as 2 hours.

Additionally, many of the male patients that are hemizygous for the disease produce no α-Gal A at all and therefore the enzyme is not recognized as self by these patients' immune system. This results in an additional problem when treating such patients with the current Fabry disease ERT, i.e., the repeated lifetime high dose administration of the therapeutic enzyme frequently causes allergic reactions (Eng et al., 2001, N Engl J Med., 345(1):9-16; Wilcox et al., 2012, Mol Genet Metab., 105(3):443-9), including potentially life-threatening anaphylactic reactions (Bodensteiner et al., 2008, Genet Med., 10(5):353-8). Also, the elicited antibody response to the therapeutic protein results in a decreased effect of the ERT during further treatment of Fabry patients (Ohashi et al., 2007, Mol Genet Metab., 92(3):271-3; Ohashi et al., 2008, Mol Genet Metab., 94(3):313-8; Vedder et al., 2008, Mol Genet Metab., 94(3):319-25; Rombach et al., 2012, PLoS One, 7(10)).

In view thereof, there remains a need in the art to provide additional and improved products for use in methods of treating Lysosomal Storage Diseases such as Fabry disease.

SUMMARY

The present inventors sought to address the aforementioned problem(s) by producing human α-N-acetylgalactosaminidase (NAGAL) enzyme with increased α-galactosidase (α-Gal A) activity, rather than human α-Gal A itself, in fungal cells. The human NAGAL gene is closely related to the gene encoding human α-Gal A. Their encoded proteins share 46% sequence identity and have a similar fold, but different substrate specificities (Tomasic et al., 2010, J. Biol. Chem., 285(28):21560-6). It has been previously shown by others that by introducing two amino acid substitutions (Ser188Glu and Ala191Leu, numbering starting from the starting methionine of human NAGAL) into the active site of human NAGAL, an enzyme with increased α-galactosidase activity was obtained (Tajima et al., 2009, Am J Hum Genet., 85(5): 569-80; Tomasic et al., 2010, supra). This altered NAGAL displayed higher plasma stability than α-Gal A and showed no immuno-reactivity to the serum of Fabry patients containing antibodies against α-Gal A.

As illustrated in the experimental section, the present inventors set out to express human NAGAL in fungal cells, but realised that the expression levels of human NAGAL in fungal cells, in particular in *Yarrowia lipolytica*, were unsatisfactory compared with the expression levels obtained for human α-Gal A. However, as further corroborated by the experiments described herein, which illustrate certain representative embodiments of the invention, the inventors realised that a remarkable increase in NAGAL expression was obtained for modified forms of human NAGAL polypeptide disclosed herein.

Accordingly, in a first aspect, the invention provides a human α-N-acetylgalactosaminidase (NAGAL) polypeptide or a functionally active variant or fragment thereof, wherein:

a first amino acid, corresponding to asparagine 213 of human NAGAL polypeptide as set forth in SEQ ID NO: 1, is substituted with one or more amino acids; or a second amino acid, corresponding to cysteine 326 of human NAGAL polypeptide as set forth in SEQ ID NO: 1, is substituted with one or more amino acids; or a first amino acid, corresponding to asparagine 213 of human NAGAL polypeptide as set forth in SEQ ID NO: 1, is substituted with one or more amino acids, and a second amino acid, corresponding to cysteine 326 of human NAGAL polypeptide as set forth in SEQ ID NO: 1, is substituted with one or more amino acids.

In a second aspect, the invention provides a human NAGAL polypeptide or a functionally active variant or fragment thereof, wherein:

a first amino acid, corresponding to asparagine 213 of human NAGAL polypeptide as set forth in SEQ ID NO: 1, is substituted with one or more amino acids, such that at least one of said one or more amino acids is capable of directly or indirectly interacting with a second amino acid corresponding to cysteine 326 of human NAGAL polypeptide as set forth in SEQ ID NO: 1; or a second amino acid, corresponding to cysteine 326 of human NAGAL polypeptide as set forth in SEQ ID NO: 1, is substituted with one or more amino acids, such that at least one of said one or more amino acids is capable of directly or indirectly interacting with a first amino acid corresponding to asparagine 213 of human NAGAL polypeptide as set forth in SEQ ID NO: 1; or a first amino acid, corresponding to asparagine 213 of human NAGAL polypeptide as set forth in SEQ ID NO: 1, is substituted with one or more amino acids, and a second amino acid, corresponding to cysteine 326 of human NAGAL polypeptide as set forth in SEQ ID NO: 1, is substituted with one or more amino acids, such that at least one of said one or more amino acids substituting the first amino acid is capable of directly or indirectly interacting with at least one of said one or more amino acids substituting the second amino acid.

In a third aspect, the invention provides a human NAGAL polypeptide or a functionally active variant or fragment thereof comprising a first domain and a second domain, wherein the human NAGAL polypeptide or functionally active variant or fragment thereof is modified such that the first domain is capable of forming at least one (additional) ion pair with the second domain. Said ion pair may be the sole ion pair formed between the first domain and the second domain of the human NAGAL polypeptide, or may be additional to one or more other ion pairs formed between the first and second domains. By means of an example and without limitation, analysis of the three-dimensional structure of human NAGAL by the inventors predicted that an ion pair may be formed in wild-type human NAGAL between aspartic acid 220 and arginine 298 of human NAGAL polypeptide as set forth in SEQ ID NO: 1.

Advantageously, the human NAGAL polypeptide or functionally active variant or fragment thereof as taught in any one of the first to third aspects displays satisfactory expression levels when recombinantly expressed in host cells, such as in fungal cells, in particular in *Yarrowia lipolytica*. Without limitation, the inventors postulate that the human NAGAL polypeptide or functionally active variant or fragment thereof as taught herein may also display substantially increased stability compared with a non-modified human NAGAL polypeptide.

A further aspect relates to the human NAGAL polypeptide or functionally active variant or fragment thereof, as taught herein, for use in therapy.

A further aspect relates to the human NAGAL polypeptide or functionally active variant or fragment thereof, as taught herein, for use in a method of treating Schindler disease or Kanzaki disease.

A further aspect relates to the human NAGAL polypeptide or functionally active variant or fragment thereof, as taught herein, for use in a method of treating Fabry disease. Advantageously, when used to treat Fabry diseases the human NAGAL polypeptide or functionally active variant or fragment thereof, as taught herein, may be further modified such as to acquire α-galactosidase activity.

A further aspect of the invention provides a method of treating Schindler disease or Kanzaki disease in a human subject in need of such treatment comprising administering to said subject a therapeutically effective amount of the human NAGAL polypeptide or functionally active variant or fragment thereof, as taught herein.

A further aspect of the invention provides a method of treating Fabry disease in a human subject in need of such treatment comprising administering to said subject a therapeutically effective amount of the human NAGAL polypeptide or functionally active variant or fragment thereof, as taught herein. Advantageously, when used to treat Fabry diseases the human NAGAL polypeptide or functionally active variant or fragment thereof, as taught herein, may be further modified such as to acquire α-galactosidase activity.

A further aspect relates to a pharmaceutical composition comprising the human NAGAL polypeptide or functionally active variant or fragment thereof, as taught herein.

Yet further aspects relate to:

A nucleic acid molecule comprising a nucleic acid sequence encoding the human NAGAL polypeptide or functionally active variant or fragment thereof as taught herein.

An expression cassette or an expression vector comprising the nucleic acid molecule as defined herein and a promoter operably linked to the nucleic acid molecule.

The nucleic acid molecule as defined herein or the expression cassette or expression vector as defined herein for use in therapy.

The nucleic acid molecule as defined herein or the expression cassette or expression vector as defined herein for use in a method of treating Fabry disease, or for use in a method of treating Schindler disease or Kanzaki disease.

A method of treating Fabry disease, or a method of treating Schindler disease or Kanzaki disease, in a human subject in need of such treatment comprising administering to said subject a therapeutically effective amount of the nucleic acid molecule as defined herein or the expression cassette or expression vector as defined herein.

A pharmaceutical composition comprising the nucleic acid molecule as defined herein or the expression cassette or expression vector as defined herein.

A host cell comprising the nucleic acid molecule as defined herein or the expression cassette or expression vector as defined herein.

A substantially pure culture of host cells as defined herein.

Use of the nucleic acid molecule as defined herein or the expression cassette or expression vector as defined herein for achieving expression of the human NAGAL polypeptide or functionally active variant or fragment thereof, as taught herein, in a host cell.

A method for producing the human NAGAL polypeptide or functionally active variant or fragment thereof, as taught herein, comprising:
 a) culturing the host cell as defined herein, such that the host cell expresses the human NAGAL polypeptide or functionally active variant or fragment thereof,
 b) collecting, and optionally isolating, the human NAGAL polypeptide or functionally active variant or fragment thereof from the host cell, or from the host cell cultivation medium.

The above and further aspects and preferred embodiments of the invention are described in the following sections and in the appended claims. The subject matter of appended claims is hereby specifically incorporated in this specification.

BRIEF DESCRIPTION OF DRAWINGS

FIG. 1 shows the amino acid sequence of a human NAGAL polypeptide (SEQ ID NO: 1). Underlined: asparagine (N) 213 of the human NAGAL polypeptide as set forth in SEQ ID NO: 1; bold underlined: cysteine (C) 326 of the human NAGAL polypeptide as set forth in SEQ ID NO: 1.

FIG. 2 shows the amino acid sequence of a human NAGAL polypeptide according to an embodiment of the present invention (SEQ ID NO: 2). Underlined: aspartic acid (D) substituting the first amino acid corresponding to asparagine 213 of the human NAGAL polypeptide as set forth in SEQ ID NO: 1; bold underlined: arginine (R) substituting the second amino acid corresponding to cysteine 326 of the human NAGAL polypeptide as set forth in SEQ ID NO: 1.

FIG. 3 shows the amino acid sequence of a human NAGAL polypeptide according to an embodiment of the present invention (SEQ ID NO: 3). Underlined: the first amino acid (asparagine, N) corresponding to asparagine 213 of the human NAGAL polypeptide as set forth in SEQ ID NO: 1; bold underlined: arginine (R) substituting the second amino acid corresponding to cysteine 326 of the human NAGAL polypeptide as set forth in SEQ ID NO: 1.

FIG. 4 shows the amino acid sequence of a human NAGAL polypeptide according to an embodiment of the present invention (SEQ ID NO: 4). Underlined: aspartic acid (D) substituting the first amino acid corresponding to asparagine 213 of the human NAGAL polypeptide as set forth in SEQ ID NO: 1; bold underlined: serine (S) substituting the second amino acid corresponding to cysteine 326 of the human NAGAL polypeptide as set forth in SEQ ID NO: 1.

FIG. 5 shows the amino acid sequence of a human NAGAL polypeptide according to an embodiment of the present invention (SEQ ID NO: 5). Underlined: the first amino acid (asparagine, N) corresponding to asparagine 213 of the human NAGAL polypeptide as set forth in SEQ ID NO: 1; bold underlined: serine (S) substituting the second amino acid corresponding to cysteine 326 of the human NAGAL polypeptide as set forth in SEQ ID NO: 1.

FIG. 6 shows the amino acid sequence of a human NAGAL polypeptide further modified such as to acquire α-galactosidase activity according to an embodiment of the present invention (SEQ ID NO: 6). Underlined: aspartic acid (D) substituting the first amino acid corresponding to asparagine 213 of the human NAGAL polypeptide as set forth in SEQ ID NO: 1; bold underlined: arginine (R) substituting the second amino acid corresponding to cysteine 326 of the human NAGAL polypeptide as set forth in SEQ ID NO: 1; bold italic underlined: glutamic acid (E) substituting the amino acid corresponding to serine 171 of the human NAGAL polypeptide as set forth in SEQ ID NO: 1; bold italic double underlined: leucine (L) substituting the amino acid corresponding to alanine 174 of the human NAGAL polypeptide as set forth in SEQ ID NO: 1.

FIG. 7 shows the amino acid sequence of a human NAGAL polypeptide further modified such as to acquire α-galactosidase activity according to an embodiment of the present invention (SEQ ID NO: 7). Underlined: the first amino acid (asparagine, N) corresponding to asparagine 213 of the human NAGAL polypeptide as set forth in SEQ ID NO: 1; bold underlined: arginine (R) substituting the second amino acid corresponding to cysteine 326 of the human NAGAL polypeptide as set forth in SEQ ID NO: 1; bold italic underlined: glutamic acid (E) substituting the amino acid corresponding to serine 171 of the human NAGAL polypeptide as set forth in SEQ ID NO: 1; bold italic double underlined: leucine (L) substituting the amino acid corresponding to alanine 174 of the human NAGAL polypeptide as set forth in SEQ ID NO: 1.

FIG. 8 shows the amino acid sequence of a human NAGAL polypeptide further modified such as to acquire α-galactosidase activity according to an embodiment of the present invention (SEQ ID NO: 8). Underlined: aspartic acid (D) substituting the first amino acid corresponding to asparagine 213 of the human NAGAL polypeptide as set forth in SEQ ID NO: 1; bold underlined: serine (S) substituting the second amino acid corresponding to cysteine 326 of the human NAGAL polypeptide as set forth in SEQ ID NO: 1; bold italic underlined: glutamic acid (E) substituting the amino acid corresponding to serine 171 of the human NAGAL polypeptide as set forth in SEQ ID NO: 1; bold italic double underlined: leucine (L) substituting the amino acid corresponding to alanine 174 of the human NAGAL polypeptide as set forth in SEQ ID NO: 1.

FIG. 9 shows the amino acid sequence of a human NAGAL polypeptide further modified such as to acquire α-galactosidase activity according to an embodiment of the present invention (SEQ ID NO: 9). Underlined: the first amino acid (asparagine, N) corresponding to asparagine 213 of the human NAGAL polypeptide as set forth in SEQ ID NO: 1; bold underlined: serine (S) substituting the second amino acid corresponding to cysteine 326 of the human NAGAL polypeptide as set forth in SEQ ID NO: 1; bold italic underlined: glutamic acid (E) substituting the amino acid corresponding to serine 171 of the human NAGAL polypeptide as set forth in SEQ ID NO: 1; bold italic double underlined: leucine (L) substituting the amino acid corresponding to alanine 174 of the human NAGAL polypeptide as set forth in SEQ ID NO: 1.

FIGS. 32 and 33 provide overview of plasmids generated and used in the example section of the present specification.

FIG. 34A-C provides overview of strains generated and used in the example section of the present specification.

DESCRIPTION OF EMBODIMENTS

Figure 10:
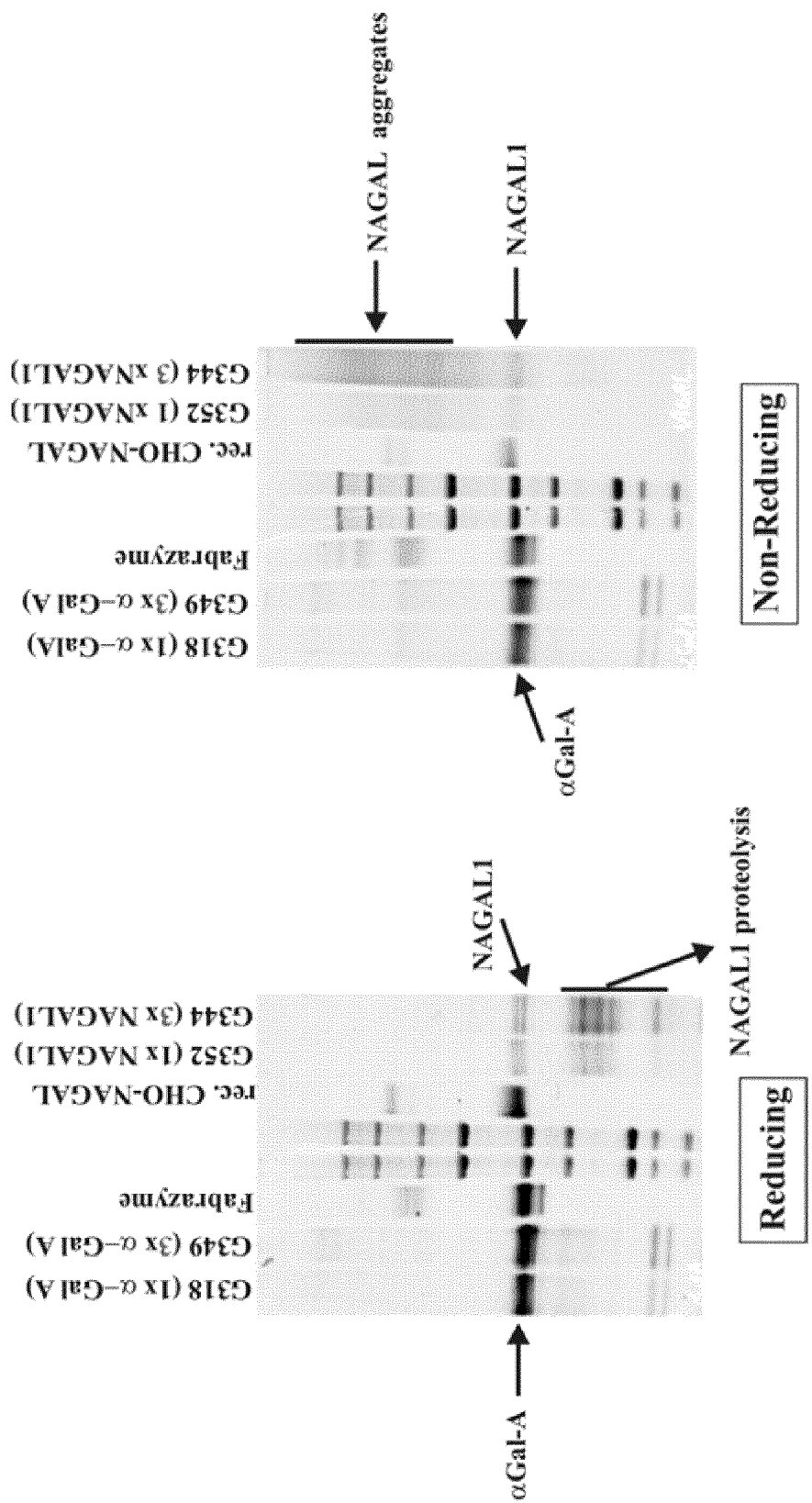
FIG. 10 represents a Western blot analysis on reduced (left) or non-reduced (right) medium samples derived from 24-well cultivations of a *Yarrowia lipolytica* expression strain containing either a single or three copies of the α-GalA or NAGAL1 expression cassette. Note that, unless the context dictates otherwise, in the present experiments, a single copy strain refers to a strain resulting from the random integration of a single expression cassette, whereas a 3-copy strain results from the random integration of 3 expression cassettes, using 3 different selection markers. Any expression cassette may be integrated once or more than once into the genome upon transformation, e.g., via tandem insertion. Hence, the number of expression cassettes integrated into the genome of a strain denoted in the examples as a single copy strain may be one or may be more than one (e.g., 2, 3, or 4), and the number of expression cassettes integrated into the genome of a strain denoted in the examples as a 3-copy strain may be three or may be more than three (e.g., 3, 4, 5, 6, 7, 8, 9, 10, 11, or 12). The number of copies in any particular strain can be readily determined by genomic analysis of the strain, if desired. 40 ng of Fabrazyme® (agalsidase beta, recombinant human α-galactosidase A) (Genzyme Corporation, a Sanofi company, Cambridge, USA) or commercial recombinant human NAGAL (catalogue #6717-GH-020, R&D Systems, Inc., Minneapolis, USA) was loaded as reference. Detection was done using an anti-Fabrazyme® antibody (polyclonal rabbit antibody produced by conventional immunisations of rabbits using Fabrazyme®) (lanes left from the marker) and an anti-NAGAL antibody (Abcam; Ab139526) (lanes at right hand side of the marker). Here and in other examples, secondary antibody for detection of the near infrared fluorescent signal was (using the Odyssey Infrared Imaging System (Li-Cor)) was goat anti-Rabbit IRDye 680LT (Westburg; 926-68024); and Western blot detection of the near infrared fluorescent signal was done using the Odyssey Infrared Imaging System (Li-Cor).

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The present inventors realised that a spectacular increase in recombinant expression level of human NAGAL polypeptide was obtained for modified forms of human NAGAL polypeptide disclosed herein.

Accordingly, a first aspect of the present invention provides:

a human α-N-acetylgalactosaminidase (NAGAL) polypeptide or a functionally active variant or fragment thereof, wherein a first amino acid, corresponding to asparagine 213 of human NAGAL polypeptide as set forth in SEQ ID NO: 1, is substituted with one or more amino acids; or a human NAGAL polypeptide or a functionally active variant or fragment thereof, wherein a second amino acid, corresponding to cysteine 326 of human NAGAL polypeptide as set forth in SEQ ID NO: 1, is substituted with one or more amino acids; or a human NAGAL polypeptide or a functionally active variant or fragment thereof, wherein a first amino acid, corresponding to asparagine 213 of human NAGAL polypeptide as set forth in SEQ ID NO: 1, is substituted with one or more amino acids, and a second amino acid, corresponding to cysteine 326 of human NAGAL polypeptide as set forth in SEQ ID NO: 1, is substituted with one or more amino acids.

A second aspect of the present invention provides:

a human NAGAL polypeptide or a functionally active variant or fragment thereof, wherein a first amino acid, corresponding to asparagine 213 of human NAGAL polypeptide as set forth in SEQ ID NO: 1, is substituted with one or more amino acids, such that at least one of said one or more amino acids is capable of directly or indirectly interacting with a second amino acid corresponding to cysteine 326 of human NAGAL polypeptide as set forth in SEQ ID NO: 1; or a human NAGAL polypeptide or a functionally active variant or fragment thereof, wherein a second amino acid, corresponding to cysteine 326 of human NAGAL polypeptide as set forth in SEQ ID NO: 1, is substituted with one or more amino acids, such that at least one of said one or more amino acids is capable of directly or indirectly interacting with a first amino acid corresponding to asparagine 213 of human NAGAL polypeptide as set forth in SEQ ID NO: 1; or a human NAGAL polypeptide or a functionally active variant or fragment thereof, wherein a first amino acid, corresponding to asparagine 213 of human NAGAL polypeptide as set forth in SEQ ID NO: 1, is substituted with one or more amino acids, and a second amino acid, corresponding to cysteine 326 of human NAGAL polypeptide as set forth in SEQ ID NO: 1, is substituted with one or more amino acids, such that at least one of said one or more amino acids substituting the first amino acid is capable of directly or indirectly interacting with at least one of said one or more amino acids substituting the second amino acid.

A third aspect of the present invention provides a human NAGAL polypeptide or a functionally active variant or fragment thereof comprising a first domain and a second domain, wherein the human NAGAL polypeptide or functionally active variant or fragment thereof is modified such that the first domain is capable of forming at least one (additional) ion pair with the second domain.

The terms "peptide", "polypeptide", or "protein" can be used interchangeably and relate to any natural, synthetic, or recombinant molecule comprising amino acids joined together by peptide bonds between adjacent amino acid residues. A "peptide bond", "peptide link" or "amide bond" is a covalent bond formed between two amino acids when the carboxyl group of one amino acid reacts with the amino group of the other amino acid, thereby releasing a molecule of water. The polypeptide can be from any source, e.g., a naturally occurring polypeptide, a chemically synthesized polypeptide, a polypeptide produced by recombinant molecular genetic techniques, or a polypeptide from a cell or translation system. Preferably, the polypeptide is a polypeptide produced by recombinant molecular genetic techniques. The polypeptide may be a linear chain or may be folded into a globular form. The terms "amino acid" and "amino acid residue" may be used interchangeably herein.

The term "recombinant" is generally used to indicate that the material (e.g., a nucleic acid, a genetic construct or a protein) has been altered by technical means (i.e., non-naturally) through human intervention. The term "recombinant nucleic acid" can commonly refer nucleic acids comprised of segments joined together using recombinant DNA technology. As used herein, the term may preferably denote material (e.g., a nucleic acid, a genetic construct or a protein) that has been altered by technical means of mutagenesis. As used herein the term "recombinant protein or polypeptide" refers to a protein or polypeptide that can result from the expression of recombinant nucleic acid such as recombinant DNA.

By "nucleic acid" is meant oligomers and polymers of any length composed essentially of nucleotides, e.g., deoxyribonucleotides and/or ribonucleotides. Nucleic acids can comprise purine and/or pyrimidine bases and/or other natural (e.g., xanthine, inosine, hypoxanthine), chemically or biochemically modified (e.g., methylated), non-natural, or derivatised nucleotide bases. The backbone of nucleic acids can comprise sugars and phosphate groups, as can typically be found in RNA or DNA, and/or one or more modified or substituted sugars and/or one or more modified or substituted phosphate groups. Modifications of phosphate groups or sugars may be introduced to improve stability, resistance to enzymatic degradation, or some other useful property. A "nucleic acid" can be for example double-stranded, partly double stranded, or single-stranded. Where single-stranded, the nucleic acid can be the sense strand or the antisense strand. In addition, nucleic acid can be circular or linear. The term "nucleic acid" as used herein preferably encompasses DNA and RNA, specifically including RNA, genomic RNA, cDNA, DNA, provirus, pre-mRNA and mRNA.

Human α-N-acetylgalactosaminidase (EC 3.2.1.49) is a glycoside hydrolase that removes terminal alpha-N-acetylgalactosamine (α-GalNAc) monosaccharides from glycolipids and glycoproteins. Human α-N-acetylgalactosaminidase catalyzes the cleavage of non-reducing α-(1→3)-N-acetylgalactosamine residues from human blood group A and AB mucin glycoproteins, Forssman hapten and blood group A lacto series glycolipids. Human α-N-acetylgalactosaminidase has been described in the literature, such as in Clark and Garman (2009, J. Mol. Biol., 393(2): 435-447).

The terms "alpha-N-acetylgalactosaminidase", "α-N-acetylgalactosaminidase", "α-galactosidase B", "α-acetylgalactosaminidase", "N-acetyl-α-D-galactosaminidase", "N-acetyl-α-galactosaminidase", "alpha-GalNAcase", "α-NAGA", "α-NAGAL", and "NAGAL" can be used interchangeably herein.

Exemplary human NAGAL protein sequence may be as annotated under U.S. government's National Center for Biotechnology Information (NCBI) Genbank (http://www.ncbi.nlm.nih.gov/) accession number NP_000253.1 (sequence version 1), or Swissprot/Uniprot (http://www.uniprot.org/) accession number P17050-2 (sequence version 2). Exemplary human NAGAL mRNA (cDNA) sequence may be as annotated under NCBI Genbank accession number NM_000262.2 (sequence version 2).

The human NAGAL amino acid sequence annotated under NP_000253.1 is reproduced below:

(SEQ ID NO: 21)
MLLKTVLLLGHVAQVLMLDNGLLQTPPMGWLAWERFRCNINCDEDPKNCI

SEQLFMEMADRMAQDGWRDMGYTYLNIDDCWIGGRDASGRLMPDPKRFPH

GIPFLADYVHSLGLKLGIYADMGNFTCMGYPGTTLDKVVQDAQTFAEWKV

DMLKLDGCFSTPEERAQGYPKMAAALNATGRPIAFSCSWPAYEGGLPPRV

NYSLLADICNLWRNYDDIQDSWWSVLSILNWFVEHQDILQPVAGPGHWND

PDMLLIGNFGLSLEQSRAQMALWTVLAAPLLMSTDLRTISAQNMDILQNP

LMIKINQDPLGIQGRRIHKEKSLIEVYMRPLSNKASALVFFSCRTDMPYR

YHSSLGQLNFTGSVIYEAQDVYSGDIISGLRDETNFTVIINPSGVVMWYL

YPIKNLEMSQQ.

The above representative human NAGAL polypeptide sequence is that of a NAGAL precursor, including an N-terminal signal peptide. During processing of human NAGAL, the signal peptide, corresponding to amino acids 1 to 17 in SEQ ID NO: 21, is processed away to form the mature human NAGAL protein, corresponding to amino acids 18 to 411 of SEQ ID NO: 21, which is thus 394-amino acids long.

Hence, the amino acid sequence of an exemplary mature human NAGAL is reproduced below:

(SEQ ID NO: 1)
LDNGLLQTPPMGWLAWERFRCNINCDEDPKNCISEQLFMEMADRMAQDGW

RDMGYTYLNIDDCWIGGRDASGRLMPDPKRFPHGIPFLADYVHSLGLKLG

IYADMGNFTCMGYPGTTLDKVVQDAQTFAEWKVDMLKLDGCFSTPEERAQ

GYPKMAAALNATGRPIAFSCSWPAYEGGLPPRVNYSLLADICNLWRNYDD

IQDSWWSVLSILNWFVEHQDILQPVAGPGHWNDPDMLLIGNFGLSLEQSR

AQMALWTVLAAPLLMSTDLRTISAQNMDILQNPLMIKINQDPLGIQGRRI

HKEKSLIEVYMRPLSNKASALVFFSCRTDMPYRYHSSLGQLNFTGSVIYE

AQDVYSGDIISGLRDETNFTVIINPSGVVMWYLYPIKNLEMSQQ.

Reference to human NAGAL polypeptide as used herein encompasses both human NAGAL precursor polypeptides and mature human NAGAL polypeptides, as apparent from the context.

Furthermore, human NAGAL polypeptides in which the native signal peptide is replaced by a signal peptide active in a suitable host cell (e.g., signal peptide active in fungal cells), are also encompassed, as apparent from the context.

The qualifier "human" as used herein in connection with the NAGAL polypeptide relates to the primary amino acid sequence of the NAGAL polypeptide, rather than to its origin or source. For example, the human NAGAL polypeptide may be obtained by technical means, e.g., by recombinant expression, cell-free translation, or non-biological peptide synthesis.

Mature human NAGAL polypeptide forms a homodimer with each monomer containing 394 residues (not including the 17 residue signal sequence). Human NAGAL polypeptide comprises two domains. The first domain (i.e., domain I or domain 1) forms a $(\beta/\alpha)_8$ barrel, and the second domain (i.e., domain II or domain 2) contains eight antiparallel $\beta$ strands in two $\beta$ sheets (Clark and Garman, 2009, J. Mol. Biol., 393(2):435-447).

The first domain of human NAGAL is located N-terminally relative to the second domain, and the second domain is located C-terminally relative to the first domain, i.e., domain I of human NAGAL is N-terminal and domain II is C-terminal. The notional boundary between the first and second domains of human NAGAL can be conveniently placed at an amino acid position corresponding to a position between amino acids 292 and 296 (e.g., a position between amino acids 292-295, 292-294, 292-293, 293-296, 293-295, 293-294, 294-296, 294-295, or 295-296) of human NAGAL polypeptide as set forth in SEQ ID NO: 1. Hence, by means of an example and not limitation, domain I of human NAGAL polypeptide as set forth in SEQ ID NO: 1 may be comprised by amino acids 1-296, or 1-295, or 1-294, or 1-293, or 1-292, and preferably 1-291 of SEQ ID NO: 1. Domain II of human NAGAL polypeptide as set forth in SEQ ID NO: 1 may be comprised by amino acids 292-394, or 293-394, or 294-394, or 295-394, or 296-394, and preferably 297-394 of SEQ ID NO: 1.

Hence, the amino acid sequence of an exemplary first domain (domain I) of human NAGAL polypeptide can be as reproduced below:

(SEQ ID NO: 22)
LDNGLLQTPPMGWLAWERFRCNINCDEDPKNCISEQLFMEMADRMAQDGW

RDMGYTYLNIDDCWIGGRDASGRLMPDPKRFPHGIPFLADYVHSLGLKLG

IYADMGNFTCMGYPGTTLDKVVQDAQTFAEWKVDMLKLDGCFSTPEERAQ

GYPKMAAALNATGRPIAFSCSWPAYEGGLPPRVNYSLLADICNLWRNYDD

IQDSWWSVLSILNWFVEHQDILQPVAGPGHWNDPDMLLIGNFGLSLEQSR

AQMALWTVLAAPLLMSTDLRTISAQNMDILQNPLMIKINQD.

The amino acid sequence of an exemplary second domain (domain II) of human NAGAL polypeptide can be as reproduced below:

(SEQ ID NO: 23)
GRRIHKEKSLIEVYMRPLSNKASALVFFSCRTDMPYRYHSSLGQLNFTGS

VIYEAQDVYSGDIISGLRDETNFTVIINPSGVVMWYLYPIKNLEMSQQ.

The active site of human NAGAL is found in the $(\beta/\alpha)_8$ barrel domain (i.e., the first domain), at the C-terminal end of the $\beta$ strands. In particular, the active site of human NAGAL is formed by loops C-terminal to six consecutive $\beta$ strands, strands $\beta1$-$\beta6$. Consistent with its exoglycosidase function, the active site forms a small pocket on the surface of the molecule. The residues forming the active site include W33, D78, D79, Y119, C127, K154, D156, C158, S188, A191, Y192, 8213, and D217 (with amino acid numbering starting from the starting methionine, see for example SEQ ID NO: 21).

The mature human NAGAL polypeptide contains five N-linked glycosylation sites (i.e., N124, N177, N201, N359, and N385), four disulfide bonds (C38-C80, C42-C49, C127-C158, C187-C209), and a free cysteine (C343) (with amino acid numbering starting from the starting methionine, see for example SEQ ID NO: 21).

The human NAGAL polypeptide or functionally active variant or fragment thereof as disclosed herein may be conveniently denoted as "modified", or as "mutated" or "mutant", or as comprising one or more mutations, i.e., comprising one or more amino acid sequence changes compared to the amino acid sequence of human NAGAL that has not been so-mutated, such as, particularly, compared to the amino acid sequence of wild-type human NAGAL.

As used herein, the term "wild-type" as applied to a nucleic acid or polypeptide refers to a nucleic acid or a polypeptide that occurs in, or is produced by, a biological organism as that biological organism exists in nature. The term "wild-type" may to some extent be synonymous with "native", the latter encompassing nucleic acids or polypeptides having a native sequence, i.e., ones of which the primary sequence is the same as that of the nucleic acids or polypeptides found in or derived from nature. A skilled person understands that native sequences may differ between or within different individuals of the same species due to normal genetic diversity (variation) within a given species. Also, native sequences may differ between or within different individuals of the same species due to post-transcriptional or post-translational modifications. Any such variants or isoforms of nucleic acids or polypeptides are encompassed herein as being "native". Accordingly, all sequences of nucleic acids or polypeptides found in or derived from nature are considered "native". The term "native" encompasses the nucleic acids or polypeptides when forming a part of a living organism, organ, tissue or cell, when forming a part of a biological sample, as well as when at least partly isolated from such sources. The term also encompasses the nucleic acids or polypeptides when produced by recombinant or synthetic means. However, even though most native human NAGAL nucleic acids or polypeptides may be considered "wild-type", those carrying naturally-occurring mutations associated with or causing a disease phenotype, such as Schindler disease or Kanzaki disease (such mutations may diminish or eliminate the expression and/or activity of NAGAL), are generally excluded from the scope of the term "wild-type". Hence, in certain embodiments, human NAGAL polypeptide or functionally active variant or fragment thereof to be modified as intended herein is not one associated with or causing a disease phenotype, such as Schindler disease or Kanzaki disease. However, insofar a naturally-occurring mutation interfering with human NAGAL expression and/or activity does not interfere with potential α-Gal A activity of the NAGAL polypeptide or functionally active variant or fragment thereof, when further modified to acquire said α-Gal A activity, such NAGAL polypeptide or functionally active variant or fragment thereof may be useful herein.

In certain embodiments, human NAGAL polypeptide or the functionally active variant or fragment thereof may be modified during chemical polypeptide synthesis (e.g., by chemically building in the desired amino acids), or during production of the polypeptide by recombinant molecular genetic techniques, or by cell-free translation.

The present disclosure also relates to "functionally active variants or fragments" of the human NAGAL polypeptide disclosed herein. The expression comprises functionally active variants of the human NAGAL polypeptide, functionally active fragments of the human NAGAL polypeptide, as well as functionally active variants of fragments of the human NAGAL polypeptide.

The term "fragment" of a protein, polypeptide, or peptide generally refers to N-terminally and/or C-terminally deleted or truncated forms of said protein, polypeptide or peptide. The term encompasses fragments arising by any mechanism, such as, without limitation, by alternative translation, exo- and/or endo-proteolysis and/or degradation of said peptide, polypeptide or protein, such as, for example, in vivo or in vitro, such as, for example, by physical, chemical and/or enzymatic proteolysis. Without limitation, a fragment of a protein, polypeptide, or peptide may represent at least about 5% (by amino acid number), or at least about 10%, e.g., 20% or more, 30% or more, or 40% or more, such as preferably 50% or more, e.g., 60% or more, 70% or more, 80% or more, 90% or more, or 95% or more of the amino acid sequence of said protein, polypeptide, or peptide, e.g., a corresponding human NAGAL polypeptide, e.g., a corresponding mature human NAGAL polypeptide, e.g., human NAGAL polypeptide as set forth in SEQ ID NO: 1, 2, 3, 4, 5, 6, 7, 8 or 9.

For example, a fragment of a protein, polypeptide, or peptide may include a sequence of 5 or more consecutive amino acids, 10 or more consecutive amino acids, 20 or more consecutive amino acids, 30 or more consecutive amino acids, e.g., 40 or more consecutive amino acids, such as for example 50 or more consecutive amino acids, 60 or more, 70 or more, 80 or more, 90 or more, 100 or more, 200 or more, 300 or more, 310 or more, 320 or more, 330 or more, 340 or more, 350 or more, 360 or more, 370 or more, 380 or more, or 390 or more consecutive amino acids of the corresponding full-length protein or polypeptide, e.g., a corresponding human NAGAL polypeptide, e.g., a corresponding mature human NAGAL polypeptide, e.g., human NAGAL polypeptide as set forth in SEQ ID NO: 1, 2, 3, 4, 5, 6, 7, 8 or 9.

In an embodiment, a fragment of a protein, polypeptide, or peptide may be N-terminally and/or C-terminally truncated by between 1 and about 20 amino acids, such as by between 1 and about 15 amino acids, or by between 1 and about 10 amino acids, or by between 1 and about 5 amino acids, compared with the corresponding full-length protein or polypeptide, e.g., a corresponding human NAGAL polypeptide, e.g., a corresponding mature human NAGAL polypeptide, e.g., human NAGAL polypeptide as set forth in SEQ ID NO: 1, 2, 3, 4, 5, 6, 7, 8 or 9.

The term "variant" of a protein, polypeptide or peptide generally refers to proteins, polypeptides or peptides the amino acid sequence of which is substantially identical (i.e., largely but not wholly identical) to the sequence of the protein, polypeptide, or peptide, e.g., at least about 80% identical or at least about 85% identical, e.g., preferably at least about 90% identical, e.g., at least 91% identical, 92% identical, more preferably at least about 93% identical, e.g., at least 94% identical, even more preferably at least about 95% identical, e.g., at least 96% identical, yet more preferably at least about 97% identical, e.g., at least 98% identical, and most preferably at least 99% identical to the sequence of the protein, polypeptide, or peptide, e.g., to the sequence of a corresponding human NAGAL polypeptide, e.g., a corresponding mature human NAGAL polypeptide, e.g., human NAGAL polypeptide as set forth in SEQ ID NO: 1, 2, 3, 4, 5, 6, 7, 8 or 9. Preferably, a variant may display such degrees of identity to a recited protein, polypeptide or peptide when the whole sequence of the recited protein, polypeptide or peptide is queried in the sequence alignment (i.e., overall sequence identity). Sequence identity may be determined using suitable algorithms for performing sequence alignments and determination of sequence identity as know per se. Exemplary but non-limiting algorithms include those based on the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250), for example using the published default settings or other suitable settings (such as, e.g., for the BLASTN algorithm: cost to open a gap=5, cost to extend a gap=2, penalty for a mismatch=−2, reward for a match=1, gap x_dropoff=50, expectation value=10.0, word size=28; or for the BLASTP algorithm: matrix=Blosum62 (Henikoff et al., 1992, Proc. Natl. Acad. Sci., 89:10915-10919), cost to open a gap=11, cost to extend a gap=1, expectation value=10.0, word size=3).

An example procedure to determine the percent identity between a particular amino acid sequence and the amino acid sequence of a query polypeptide (e.g., human NAGAL polypeptide, e.g., mature human NAGAL polypeptide, e.g., human NAGAL polypeptide as set forth in SEQ ID NO: 1, 2, 3, 4, 5, 6, 7, 8 or 9) will entail aligning the two amino acid sequences using the Blast 2 sequences (Bl2seq) algorithm, available as a web application or as a standalone executable programme (BLAST version 2.2.31+) at the NCBI web site (www.ncbi.nlm.nih.gov), using suitable algorithm parameters. An example of suitable algorithm parameters include: matrix=Blosum62, cost to open a gap=11, cost to extend a gap=1, expectation value=10.0, word size=3). If the two compared sequences share homology, then the output will present those regions of homology as aligned sequences. If the two compared sequences do not share homology, then the output will not present aligned sequences. Once aligned, the number of matches will be determined by counting the number of positions where an identical amino acid residue is presented in both sequences. The percent identity is determined by dividing the number of matches by the length of the query polypeptide, followed by multiplying the resulting value by 100. The percent identity value may, but need not, be rounded to the nearest tenth. For example, 78.11, 78.12, 78.13, and 78.14 may be rounded down to 78.1, while 78.15, 78.16, 78.17, 78.18, and 78.19 may be rounded up to 78.2. It is further noted that the detailed view for each segment of alignment as outputted by Bl2seq already conveniently includes the percentage of identities.

A variant of a protein, polypeptide, or peptide may be a homologue (e.g., orthologue or paralogue) of said protein, polypeptide, or peptide. As used herein, the term "homology" generally denotes structural similarity between two macromolecules, particularly between two proteins or polypeptides, from same or different taxons, wherein said similarity is due to shared ancestry.

A variant of a protein, polypeptide, or peptide may comprise one or more amino acid additions, deletions, or substitutions relative to (i.e., compared with) the corresponding protein or polypeptide, e.g., a corresponding human NAGAL polypeptide, e.g., a corresponding mature human NAGAL polypeptide, e.g., human NAGAL polypeptide as set forth in SEQ ID NO: 1, 2, 3, 4, 5, 6, 7, 8 or 9.

For example, a variant (substitution variant) of a protein, polypeptide, or peptide may comprise up to 50 (e.g., not more than one, two, three, four, five, six, seven, eight, nine, ten, 12, 15, 20, 25, 30, 35, 40, or 50) conservative amino acid substitutions relative to (i.e., compared with) the corresponding protein or polypeptide, e.g., a corresponding human NAGAL polypeptide, e.g., a corresponding mature human NAGAL polypeptide, e.g., human NAGAL polypeptide as set forth in SEQ ID NO: 1, 2, 3, 4, 5, 6, 7, 8 or 9.

A conservative amino acid substitution is a substitution of one amino acid for another with similar characteristics. Conservative amino acid substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (i.e., basic) amino acids include arginine, lysine and histidine. The negatively charged (i.e., acidic) amino acids include aspartic acid and glutamic acid. Any substitution of one member of the above-mentioned polar, basic, or acidic groups by another member of the same group can be deemed a conservative substitution. By contrast, a non-conservative substitution is a substitution of one amino acid for another with dissimilar characteristics.

Alternatively or in addition, for example, a variant (deletion variant) of a protein, polypeptide, or peptide may lack up to 20 amino acid segments (e.g., one, two, three, four, five, six, seven, eight, nine, ten, 11, 12, 13, 14, 15, 16, 17, 18, 19, or 20 segments) relative to (i.e., compared with) the corresponding protein or polypeptide, e.g., a corresponding human NAGAL polypeptide, e.g., a corresponding mature human NAGAL polypeptide, e.g., human NAGAL polypeptide as set forth in SEQ ID NO: 1, 2, 3, 4, 5, 6, 7, 8 or 9. The deletion segment(s) may each independently consist of one amino acid, two contiguous amino acids or three contiguous amino acids. The deletion segments may be non-contiguous, or two or more or all of the deletion segments may be contiguous.

As disclosed herein, human NAGAL polypeptide may also be fused with one or more internal and/or terminal (i.e., N- and/or C-terminal) irrelevant or heterologous amino acid sequences (i.e., fusion protein). A heterologous sequence can be, for example a sequence used for purification of the recombinant protein (e.g., FLAG, polyhistidine (e.g., hexahistidine), hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). In some embodiments, the fusion protein may contain a signal sequence from another protein. In certain host cells (e.g., yeast host cells), expression and/or secretion of the target protein can be increased through use of a heterologous signal sequence. In certain embodiments, the fusion protein can contain a carrier (e.g., KLH) useful, e.g., in eliciting an immune response (e.g., for antibody generation; see below) or endoplasmic reticulum or Golgi apparatus retention signals. Heterologous sequences can be of varying length and in some cases can be a longer sequences than the full-length protein or polypeptide to which the heterologous sequences are attached.

Where the present specification refers to or encompasses variants and/or fragments of proteins, polypeptides or peptides, this denotes variants or fragments which are functionally active or functional, i.e., which at least partly retain the biological activity or intended functionality of the respective or corresponding proteins, polypeptides, or peptides. By means of an example and not limitation, a functionally active variant or fragment of human NAGAL polypeptide as disclosed herein shall at least partly retain the biological activity of human NAGAL polypeptide. For example, it may retain one or more aspects of the biological activity of human NAGAL polypeptide, such as its glycoside hydrolase activity. Preferably, a functionally active variant or fragment may retain at least about 20%, e.g., at least about 25%, or at least 30%, or at least about 40%, or at least about 50%, e.g., at least 60%, more preferably at least about 70%, e.g., at least 80%, yet more preferably at least about 85%, still more preferably at least about 90%, and most preferably at least about 95% or even about 100% or higher of the intended biological activity or functionality compared with the corresponding protein, polypeptide, or peptide. Reference to the "activity" of a protein, polypeptide, or peptide such as human NAGAL polypeptide may generally encompass any one or more aspects of the biological activity of the protein, polypeptide, or peptide, such as without limitation any one or more aspects of its biochemical activity, enzymatic activity, signalling activity, interaction activity, ligand activity, and/or structural activity, e.g., within a cell, tissue, organ or an organism. By means of an example and not limitation, reference to the activity of human NAGAL polypeptide or functionally active variant or fragment thereof may particularly denote its activity as a glycoside hydrolase, i.e., its ability to remove terminal α-GalNAc monosaccharides. Where the activity of a given protein, polypeptide, or peptide such as human NAGAL polypeptide can be readily measured in an established assay, e.g., an enzymatic assay (such as, for example, by a fluorimetric assay), a functionally active variant or fragment of the protein, polypeptide, or peptide may display activity in such assays, which is at least about 20%, e.g., at least about 25%, or at least 30%, or at least about 40%, or at least about 50%, e.g., at least 60%, more preferably at least about 70%, e.g., at least 80%, yet more preferably at least about 85%, still more preferably at least about 90%, and most preferably at least about 95% or even about 100% or higher of the activity of the respective or corresponding protein, polypeptide, or peptide.

For example, the α-N-acetylgalactosaminidase activity of human NAGAL or functionally active variant or fragment thereof can be measured in an enzymatic assay, such as by a fluorometric assay with MU-α-D-N-acetylgalactosamine (e.g., MU-2-acetamide-2-deoxy-a-D-galactopyranoside; Toronto Research Chemicals, North York, ON, Canada) as a substrate. The NAGAL activity can be measured, for instance with a Wallac 1420 ARVO MX multilabel counter (Perkin Elmer, Waltham, Mass.), at 460 nm after excitation at 355 nm.

As detailed elsewhere in this specification, in certain embodiments, human NAGAL polypeptide modified as taught herein or functionally active variant or fragment thereof may be further modified to acquire α-galactosidase activity. The term "acquire" (obtain, attain, gain) is used broadly, encompassing a situation where the further modification causes the polypeptide to exhibit α-galactosidase activity where no such activity was detectable before the further modification, as well as a situation where the further modification causes the polypeptide to exhibit additional (increased, enhanced) α-galactosidase activity compared with any α-galactosidase activity detectable before the further modification. As also described elsewhere in this specification, the further modification may entail S to E substitution at an amino acid position corresponding to the position of amino acid 171 of human NAGAL polypeptide as set forth in SEQ ID NO: 1, and A to L substitution at an amino acid position corresponding to the position of amino acid 174 of human NAGAL polypeptide as set forth in SEQ ID NO: 1.

In such embodiments, a functionally active variant or fragment of such further modified human NAGAL polypeptide shall at least partly retain the α-galactosidase activity of the further modified human NAGAL polypeptide. Preferably, in these embodiments, a functionally active variant or fragment may retain at least about 20%, e.g., at least about 25%, or at least 30%, or at least about 40%, or at least about 50%, e.g., at least 60%, more preferably at least about 70%, e.g., at least 80%, yet more preferably at least about 85%, still more preferably at least about 90%, and most preferably at least about 95% or even about 100% or higher of the α-galactosidase activity of the further modified human NAGAL polypeptide.

For example, the α-galactosidase activity of the further modified human NAGAL polypeptide or a functionally active variant or fragment thereof can be measured in an enzymatic assay, such as, for example by a fluorometric assay as described by Tajima et al. 2009, Am. J. Hum. Genet., 85(5): 569-80 and Tomasic et al., 2010, J. Biol. Chem., 285(28):21560-6. In brief, the fluorometric assay is performed at pH 4.5 and a temperature of 37° C., using 4-methylumberriferyl-α-D-galactopyranoside (4MU-α-Gal) as a substrate. When active α-galactosidase is present (e.g., in the cultivation medium), the 4MU-α-Gal is hydrolysed, thereby releasing 4-methylumbelliferyl. The latter can be measured at 450 nm after excitation at 365 nm.

In certain examples, a functionally active variant or fragment of human NAGAL may have at least 25% (e.g., at least 30%, at least 40%, at least 50%, at least 60%, at least 70%, at least 75%, at least 80%, at least 85%, at least 90%, at least 95%, at least 98%, at least 99%, at least 100%, or even greater than 100%) of the NAGAL enzymatic activity of the human NAGAL polypeptide as set forth in SEQ ID NO: 1, 2, 3, 4 or 5. The functional variant or fragment can generally, but not always, be comprised of a continuous region of the protein, wherein the region has functional activity. The amino acid sequence of the active site of human NAGAL polypeptide has been described in the literature (Clark and Garman, 2009, J. Mol. Biol., 393(2): 435-447). The residues forming the active site are located in the first domain and include W33, D78, D79, Y119, C127, K154, D156, C158, S188, A191, Y192, R213, and D217 (with amino acid numbering given as starting from the starting methionine). Candidate functional variants or fragments of human NAGAL polypeptides can therefore be produced by one skilled in the art using well established methods, such as homology modelling and computational engineering, and tested for the desired enzymatic activity.

In certain examples, a functionally active variant or fragment of the further modified human NAGAL as taught herein may have at least 25% (e.g., at least 30%, at least 40%, at least 50%, at least 60%, at least 70%, at least 75%, at least 80%, at least 85%, at least 90%, at least 95%, at least 98%, at least 99%, at least 100%, or even greater than 100%) of the α-galactosidase enzymatic activity of the further modified human NAGAL polypeptide as set forth in SEQ ID NO: 6, 7, 8 or 9. As described elsewhere in this specification, the further modification may entail S to E substitution at an amino acid position corresponding to the position of amino acid 171 of human NAGAL polypeptide as set forth in SEQ ID NO: 1, and A to L substitution at an amino acid position corresponding to the position of amino acid 174 of human NAGAL polypeptide as set forth in SEQ ID NO: 1. The functional variant or fragment can generally, but not always, be comprised of a continuous region of the protein, wherein the region has functional activity. Candidate functional variants or fragments of the further modified human NAGAL polypeptides can be produced by one skilled in the art using well established methods, such as homology modelling and computational engineering, and tested for the desired enzymatic activity.

Further, unless otherwise apparent from the context, reference herein to any nucleic acid, peptide, polypeptide or protein and variants or fragments thereof may generally also encompass altered forms of said nucleic acid, peptide, polypeptide or protein and variants or fragments such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

Conveniently, certain amino acid(s) of the human NAGAL polypeptide or functionally active variant or fragment thereof as disclosed herein may be referred to herein as "corresponding to" certain amino acid(s) of a reference human NAGAL polypeptide, usually the human NAGAL polypeptide as set forth in SEQ ID NO: 1.

The skilled person will have an immediate understanding of the correspondence between amino acid(s) of two forms of human NAGAL polypeptide. By means of example, such corresponding amino acids may be located at the same position in an alignment of the primary amino acid sequences of the two forms of human NAGAL polypeptide. The sequence alignment may be generated as explained elsewhere in the specification, in connection with the determination of the extent of sequence identity. Such corresponding amino acids may also co-locate in the secondary and/or tertiary structures of the two forms of human NAGAL polypeptide.

For convenience, the amino acid of the human NAGAL polypeptide or functionally active variant or fragment thereof as disclosed herein, in particular as disclosed in accordance with the first and second aspects of the invention, corresponding to asparagine 213 of human NAGAL polypeptide as set forth in SEQ ID NO: 1, may be referred to herein as "a first amino acid" or "the first amino acid"; whereas the amino acid of the human NAGAL polypeptide or functionally active variant or fragment thereof as disclosed herein, in particular as disclosed in accordance with the first and second aspects of the invention, corresponding to cysteine 326 of human NAGAL polypeptide as set forth in SEQ ID NO: 1, may be referred to herein as "a second amino acid" or "the second amino acid".

For avoidance of doubt, the ordinals "first" and "second" in this context serve to denote the particular amino acids in the human NAGAL polypeptide or functionally active variant or fragment thereof, corresponding to asparagine 213 and cysteine 326 of human NAGAL polypeptide as set forth in SEQ ID NO: 1, respectively, and more particularly, to distinguish between said amino acids. Consequently, the terms "first" and "second" amino acids are not intended to refer to the amino acids which come, respectively, $1^{st}$ and $2^{nd}$ in the primary amino acid sequence of the human NAGAL polypeptide or functionally active variant or fragment thereof.

The position of the "first" and "second" amino acids may be conveniently defined by referring to the corresponding position of an amino acid of human NAGAL polypeptide as set forth in SEQ ID NO: 1. The position of amino acid 1 (i.e., leucine) of the human NAGAL polypeptide as set forth in SEQ ID NO: 1 denotes position 1.

The terms "amino acid substitution" or "amino acid exchange" may be used interchangeably herein and encompass the replacement of an amino acid in an amino acid sequence by another amino acid, or the replacement of an amino acid in an amino acid sequence by a segment of two or more amino acids.

The term amino acid as used herein generally refers to a molecule that contains both amine and carboxyl functional groups. In biochemistry, this term particularly refers to alpha-amino acids with the general formula $H_2NCHRCOOH$, where R is an organic substituent. In the alpha-amino acids, the amino and carboxylate groups are attached to the same carbon, i.e., the α-carbon. The term includes the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, norvaline, norleucine and ornithine. The term includes both D- and L-amino acids. L-amino acids are preferred.

Hence, a first amino acid of the human NAGAL polypeptide or functionally active variant or fragment thereof, said first amino acid corresponding to asparagine 213 of human NAGAL polypeptide as set forth in SEQ ID NO: 1, may be substituted with one or more amino acids, e.g., with between 1 and 20 amino acids, preferably with between 1 and 15 amino acids, more preferably with between 1 and 10 amino acids, e.g., with 1, 2, 3, 4, 5, 6, 7, 8, 9 or 10 amino acids, even more preferably with between 1 and 5 amino acids, such as with between 1 and 4 amino acids, between 1 and 3 amino acids, or between 1 and 2 amino acids.

Hence, a second amino acid of the human NAGAL polypeptide or functionally active variant or fragment thereof, said second amino acid corresponding to cysteine 326 of human NAGAL polypeptide as set forth in SEQ ID NO: 1, may be substituted with one or more amino acids, e.g., with between 1 and 20 amino acids, preferably with between 1 and 15 amino acids, more preferably with between 1 and 10 amino acids, e.g., with 1, 2, 3, 4, 5, 6, 7, 8, 9 or 10 amino acids, even more preferably with between 1 and 5 amino acids, such as with between 1 and 4 amino acids, between 1 and 3 amino acids, or between 1 and 2 amino acids.

Hence, a first amino acid of the human NAGAL polypeptide or functionally active variant or fragment thereof, said first amino acid corresponding to asparagine 213 of human NAGAL polypeptide as set forth in SEQ ID NO: 1, may be substituted with one or more amino acids, e.g., with between 1 and 20 amino acids, preferably with between 1 and 15 amino acids, more preferably with between 1 and 10 amino acids, e.g., with 1, 2, 3, 4, 5, 6, 7, 8, 9 or 10 amino acids, even more preferably with between 1 and 5 amino acids, such as with between 1 and 4 amino acids, between 1 and 3 amino acids, or between 1 and 2 amino acids; and a second amino acid of the human NAGAL polypeptide or functionally active variant or fragment thereof, said second amino acid corresponding to cysteine 326 of human NAGAL polypeptide as set forth in SEQ ID NO: 1, may be substituted with one or more amino acids, e.g., with between 1 and 20 amino acids, preferably with between 1 and 15 amino acids, more preferably with between 1 and 10 amino acids, e.g., with 1, 2, 3, 4, 5, 6, 7, 8, 9 or 10 amino acids, even more preferably with between 1 and 5 amino acids, such as with between 1 and 4 amino acids, between 1 and 3 amino acids, or between 1 and 2 amino acids.

Certain embodiments provide a human NAGAL polypeptide or a functionally active variant or fragment thereof, wherein the first amino acid, corresponding to asparagine 213 of human NAGAL polypeptide as set forth in SEQ ID NO: 1, is substituted with one, two or three amino acids, preferably with one or two amino acids.

Certain other embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with one, two or three amino acids, preferably with one or two amino acids.

Certain further embodiments provide a human NAGAL polypeptide or a functionally active variant or fragment thereof, wherein the first amino acid, corresponding to asparagine 213 of human NAGAL polypeptide as set forth in SEQ ID NO: 1, is substituted with one, two or three amino acids, preferably with one or two amino acids; and the second amino acid, corresponding to cysteine 326 of human NAGAL polypeptide as set forth in SEQ ID NO: 1, is substituted with one, two or three amino acids, preferably with one or two amino acids.

Accordingly, certain embodiments provide a human NAGAL polypeptide or a functionally active variant or fragment thereof, wherein the first amino acid, corresponding to asparagine 213 of human NAGAL polypeptide as set forth in SEQ ID NO: 1, is substituted with one amino acid.

Certain other embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with one amino acid.

Certain further embodiments provide a human NAGAL polypeptide or a functionally active variant or fragment thereof, wherein the first amino acid, corresponding to asparagine 213 of human NAGAL polypeptide as set forth in SEQ ID NO: 1, is substituted with one amino acid; and the second amino acid, corresponding to cysteine 326 of human NAGAL polypeptide as set forth in SEQ ID NO: 1, is substituted with one amino acid.

Certain embodiments provide a human NAGAL polypeptide or a functionally active variant or fragment thereof, wherein the first amino acid, corresponding to asparagine 213 of human NAGAL polypeptide as set forth in SEQ ID NO: 1, is an asparagine, and wherein the asparagine is substituted with one or more amino acids other than asparagine.

Preferred embodiments provide a human NAGAL polypeptide or a functionally active variant or fragment thereof, wherein the first amino acid, corresponding to asparagine 213 of human NAGAL polypeptide as set forth in SEQ ID NO: 1, is an asparagine, and wherein the asparagine is substituted with one, two or three amino acids other than asparagine, preferably with one or two amino acids other than asparagine.

More preferred embodiments provide a human NAGAL polypeptide or a functionally active variant or fragment thereof, wherein the first amino acid, corresponding to asparagine 213 of human NAGAL polypeptide as set forth in SEQ ID NO: 1, is an asparagine, and wherein the asparagine is substituted with one amino acid other than asparagine.

Hence, certain particularly preferred embodiments provide a human NAGAL polypeptide or a functionally active variant or fragment thereof, comprising an amino acid (more particularly one amino acid) other than asparagine at the amino acid position corresponding to asparagine 213 of human NAGAL polypeptide as set forth in SEQ ID NO: 1.

Certain embodiments provide a human NAGAL polypeptide or a functionally active variant or fragment thereof, wherein the second amino acid, corresponding to cysteine 326 of human NAGAL polypeptide as set forth in SEQ ID NO: 1, is a cysteine, and wherein the cysteine is substituted with one or more amino acids other than cysteine.

Preferred embodiments provide a human NAGAL polypeptide or a functionally active variant or fragment thereof, wherein the second amino acid, corresponding to cysteine 326 of human NAGAL polypeptide as set forth in SEQ ID NO: 1, is a cysteine, and wherein the cysteine is substituted with one, two or three amino acids other than cysteine, preferably with one or two amino acids other than cysteine.

More preferred embodiments provide a human NAGAL polypeptide or a functionally active variant or fragment thereof, wherein the second amino acid, corresponding to cysteine 326 of human NAGAL polypeptide as set forth in SEQ ID NO: 1, is a cysteine, and wherein the cysteine is substituted with one amino acid other than cysteine.

Hence, certain particularly preferred embodiments provide a human NAGAL polypeptide or a functionally active variant or fragment thereof, comprising an amino acid (more particularly one amino acid) other than cysteine at the amino acid position corresponding to cysteine 326 of human NAGAL polypeptide as set forth in SEQ ID NO: 1.

Certain embodiments provide a human NAGAL polypeptide or a functionally active variant or fragment thereof, wherein the first amino acid, corresponding to asparagine 213 of human NAGAL polypeptide as set forth in SEQ ID NO: 1, is an asparagine, and wherein the asparagine is substituted with one or more amino acids other than asparagine; and wherein the second amino acid, corresponding to cysteine 326 of human NAGAL polypeptide as set forth in SEQ ID NO: 1, is a cysteine, and wherein the cysteine is substituted with one or more amino acids other than cysteine.

Preferred embodiments provide a human NAGAL polypeptide or a functionally active variant or fragment thereof, wherein the first amino acid, corresponding to asparagine 213 of human NAGAL polypeptide as set forth in SEQ ID NO: 1, is an asparagine, and wherein the asparagine is substituted with one, two or three amino acids other than asparagine, preferably with one or two amino acids other than asparagine; and wherein the second amino acid, corresponding to cysteine 326 of human NAGAL polypeptide as set forth in SEQ ID NO: 1, is a cysteine, and wherein the cysteine is substituted with one, two or three amino acids other than cysteine, preferably with one or two amino acids other than cysteine.

More preferred embodiments provide a human NAGAL polypeptide or a functionally active variant or fragment thereof, wherein the first amino acid, corresponding to asparagine 213 of human NAGAL polypeptide as set forth in SEQ ID NO: 1, is an asparagine, and wherein the asparagine is substituted with one amino acid other than asparagine; and wherein the second amino acid, corresponding to cysteine 326 of human NAGAL polypeptide as set forth in SEQ ID NO: 1, is a cysteine, and wherein the cysteine is substituted with one amino acid other than cysteine.

Hence, certain particularly preferred embodiments provide a human NAGAL polypeptide or a functionally active variant or fragment thereof, comprising an amino acid (more particularly one amino acid) other than asparagine at the amino acid position corresponding to asparagine 213 of human NAGAL polypeptide as set forth in SEQ ID NO: 1, and an amino acid (more particularly one amino acid) other than cysteine at the amino acid position corresponding to cysteine 326 of human NAGAL polypeptide as set forth in SEQ ID NO: 1.

Certain embodiments provide a human NAGAL polypeptide or a functionally active variant or fragment thereof, wherein the amino acid or amino acids substituting the first amino acid, corresponding to asparagine 213 of human NAGAL polypeptide as set forth in SEQ ID NO: 1, is or are each independently selected from the group consisting of alanine, arginine, aspartic acid, cysteine, glutamic acid, glutamine, glycine, histidine, isoleucine, leucine, lysine, methionine, phenylalanine, proline, serine, threonine, tryptophane, tyrosine, and valine. As mentioned, L-amino acids are preferably envisaged.

Hence, certain embodiments provide a human NAGAL polypeptide or a functionally active variant or fragment thereof, comprising one or more amino acids, preferably one, two or three amino acids, more preferably one or two amino acids, even more preferably one amino acid, at the amino acid position corresponding to asparagine 213 of human NAGAL polypeptide as set forth in SEQ ID NO: 1, wherein the amino acid or amino acids is or are each independently selected from the group consisting of alanine, arginine, aspartic acid, cysteine, glutamic acid, glutamine, glycine, histidine, isoleucine, leucine, lysine, methionine, phenylalanine, proline, serine, threonine, tryptophane, tyrosine, and valine. As mentioned, L-amino acids are preferably envisaged.

Certain embodiments provide a human NAGAL polypeptide or a functionally active variant or fragment thereof, wherein the amino acid or amino acids substituting the second amino acid, corresponding to cysteine 326 of human NAGAL polypeptide as set forth in SEQ ID NO: 1, is or are each independently selected from the group consisting of alanine, arginine, asparagine, aspartic acid, glutamic acid, glutamine, glycine, histidine, isoleucine, leucine, lysine, methionine, phenylalanine, proline, serine, threonine, tryptophane, tyrosine, and valine. As mentioned, L-amino acids are preferably envisaged.

Hence, certain embodiments provide a human NAGAL polypeptide or a functionally active variant or fragment thereof, comprising one or more amino acids, preferably one, two or three amino acids, more preferably one or two amino acids, even more preferably one amino acid, at the amino acid position corresponding to cysteine 326 of human NAGAL polypeptide as set forth in SEQ ID NO: 1, wherein the amino acid or amino acids is or are each independently selected from the group consisting of alanine, arginine, asparagine, aspartic acid, glutamic acid, glutamine, glycine, histidine, isoleucine, leucine, lysine, methionine, phenylalanine, proline, serine, threonine, tryptophane, tyrosine, and valine. As mentioned, L-amino acids are preferably envisaged.

Certain embodiments provide a human NAGAL polypeptide or a functionally active variant or fragment thereof, wherein the amino acid or amino acids substituting the first amino acid, corresponding to asparagine 213 of human NAGAL polypeptide as set forth in SEQ ID NO: 1, is or are each independently selected from the group consisting of alanine, arginine, aspartic acid, cysteine, glutamic acid, glutamine, glycine, histidine, isoleucine, leucine, lysine, methionine, phenylalanine, proline, serine, threonine, tryptophane, tyrosine, and valine; and wherein the amino acid or amino acids substituting the second amino acid, corresponding to cysteine 326 of human NAGAL polypeptide as set forth in SEQ ID NO: 1, is or are each independently selected from the group consisting of alanine, arginine, asparagine, aspartic acid, glutamic acid, glutamine, glycine, histidine, isoleucine, leucine, lysine, methionine, phenylalanine, proline, serine, threonine, tryptophane, tyrosine, and valine. As mentioned, L-amino acids are preferably envisaged.

Hence, certain embodiments provide a human NAGAL polypeptide or a functionally active variant or fragment thereof, comprising one or more amino acids, preferably one, two or three amino acids, more preferably one or two amino acids, even more preferably one amino acid, at the amino acid position corresponding to asparagine 213 of human NAGAL polypeptide as set forth in SEQ ID NO: 1, wherein the amino acid or amino acids is or are each independently selected from the group consisting of alanine, arginine, aspartic acid, cysteine, glutamic acid, glutamine, glycine, histidine, isoleucine, leucine, lysine, methionine, phenylalanine, proline, serine, threonine, tryptophane, tyrosine, and valine; and comprising one or more amino acids, preferably one, two or three amino acids, more preferably one or two amino acids, even more preferably one amino acid, at the amino acid position corresponding to cysteine 326 of human NAGAL polypeptide as set forth in SEQ ID NO: 1, wherein the amino acid or amino acids is or are each independently selected from the group consisting of alanine, arginine, asparagine, aspartic acid, glutamic acid, glutamine, glycine, histidine, isoleucine, leucine, lysine, methionine, phenylalanine, proline, serine, threonine, tryptophane, tyrosine, and valine. As mentioned, L-amino acids are preferably envisaged.

Certain preferred embodiments provide a human NAGAL polypeptide or a functionally active variant or fragment thereof, wherein the first amino acid, corresponding to asparagine 213 of human NAGAL polypeptide as set forth in SEQ ID NO: 1, is substituted with one or more amino acids at least one of which contains a negatively charged side-chain group.

Certain more preferred embodiments provide a human NAGAL polypeptide or a functionally active variant or fragment thereof, wherein the first amino acid, corresponding to asparagine 213 of human NAGAL polypeptide as set forth in SEQ ID NO: 1, is substituted with one, two or three amino acids, preferably one or two amino acids, at least one of which contains a negatively charged side-chain group.

Certain even more preferred embodiments provide a human NAGAL polypeptide or a functionally active variant or fragment thereof, wherein the first amino acid, corresponding to asparagine 213 of human NAGAL polypeptide as set forth in SEQ ID NO: 1, is substituted with one amino acid which contains a negatively charged side-chain group.

Hence, certain embodiments provide a human NAGAL polypeptide or a functionally active variant or fragment thereof, comprising one or more amino acids at least one of which contains a negatively charged side-chain group, preferably one, two or three amino acids at least one of which contains a negatively charged side-chain group, more preferably one or two amino acids at least one of which contains a negatively charged side-chain group, even more preferably one amino acid which contains a negatively charged side-chain group, at the amino acid position corresponding to asparagine 213 of human NAGAL polypeptide as set forth in SEQ ID NO: 1.

Preferably, the at least one amino acid which contains a negatively charged side-chain group is aspartic acid or glutamic acid, preferably aspartic acid.

Hence, certain preferred embodiments provide a human NAGAL polypeptide or a functionally active variant or fragment thereof, wherein the first amino acid, corresponding to asparagine 213 of human NAGAL polypeptide as set forth in SEQ ID NO: 1, is substituted with one or more amino acids at least one of which is aspartic acid or glutamic acid (preferably aspartic acid).

Certain more preferred embodiments provide a human NAGAL polypeptide or a functionally active variant or fragment thereof, wherein the first amino acid, corresponding to asparagine 213 of human NAGAL polypeptide as set forth in SEQ ID NO: 1, is substituted with one, two or three amino acids, preferably one or two amino acids, at least one of which is aspartic acid or glutamic acid (preferably aspartic acid).

Certain more preferred embodiments provide a human NAGAL polypeptide or a functionally active variant or fragment thereof, wherein the first amino acid, corresponding to asparagine 213 of human NAGAL polypeptide as set forth in SEQ ID NO: 1, is substituted with aspartic acid or glutamic acid (preferably aspartic acid).

Hence, certain embodiments provide a human NAGAL polypeptide or a functionally active variant or fragment thereof, comprising one or more amino acids at least one of which is aspartic acid or glutamic acid (preferably aspartic acid), preferably one, two or three amino acids at least one of which is aspartic acid or glutamic acid (preferably aspartic acid), more preferably one or two amino acids at least one of which is aspartic acid or glutamic acid (preferably aspartic acid), even more preferably one amino acid which is aspartic acid or glutamic acid (preferably aspartic acid,) at the amino acid position corresponding to asparagine 213 of human NAGAL polypeptide as set forth in SEQ ID NO: 1.

Certain preferred embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with one or more amino acids at least one of which contains a positively charged side-chain group or a polar uncharged side-chain group.

Certain more preferred embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with one, two or three amino acids, preferably one or two amino acids, at least one of which contains a positively charged side-chain group or a polar uncharged side-chain group.

Certain even more preferred embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with one amino acid which contains a positively charged side-chain group or a polar uncharged side-chain group.

Hence, certain embodiments provide a human NAGAL polypeptide or a functionally active variant or fragment thereof, comprising one or more amino acids at least one of which contains a positively charged side-chain group or a polar uncharged side-chain group, preferably one, two or three amino acids at least one of which contains a positively charged side-chain group or a polar uncharged side-chain group, more preferably one or two amino acids at least one of which contains a positively charged side-chain group or a polar uncharged side-chain group, even more preferably one amino acid which contains a positively charged side-chain group or a polar uncharged side-chain group, at the amino acid position corresponding to cysteine 326 of human NAGAL polypeptide as set forth in SEQ ID NO: 1.

Preferably, the at least one amino acid which contains a positively charged side-chain group is arginine, histidine or lysine, preferably arginine, or the at least one amino acid which contains a polar uncharged side-chain group is serine, threonine, asparagine or glutamine, preferably serine.

Hence, certain preferred embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with one or more amino acids at least one of which is arginine, histidine or lysine (preferably arginine).

Certain more preferred embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with one, two or three amino acids, preferably one or two amino acids, at least one of which is arginine, histidine or lysine (preferably arginine).

Certain even more preferred embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with arginine, histidine or lysine (preferably arginine).

Hence, certain embodiments provide a human NAGAL polypeptide or a functionally active variant or fragment thereof, comprising one or more amino acids at least one of which is arginine, histidine or lysine (preferably arginine), preferably one, two or three amino acids at least one of which is arginine, histidine or lysine (preferably arginine), more preferably one or two amino acids at least one of which is arginine, histidine or lysine (preferably arginine), even more preferably one amino acid which is arginine, histidine or lysine (preferably arginine), at the amino acid position corresponding to cysteine 326 of human NAGAL polypeptide as set forth in SEQ ID NO: 1.

Hence, certain preferred embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with one or more amino acids at least one of which is serine, threonine, asparagine or glutamine (preferably serine).

Certain more preferred embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with one, two or three amino acids, preferably one or two amino acids, at least one of which is serine, threonine, asparagine or glutamine (preferably serine).

Certain even more preferred embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with serine, threonine, asparagine or glutamine (preferably serine).

Hence, certain embodiments provide a human NAGAL polypeptide or a functionally active variant or fragment thereof, comprising one or more amino acids at least one of which is serine, threonine, asparagine or glutamine (preferably serine), preferably one, two or three amino acids at least one of which is serine, threonine, asparagine or glutamine (preferably serine), more preferably one or two amino acids at least one of which is serine, threonine, asparagine or glutamine (preferably serine), even more preferably one amino acid which is serine, threonine, asparagine or glutamine (preferably serine), at the amino acid position corresponding to cysteine 326 of human NAGAL polypeptide as set forth in SEQ ID NO: 1.

Certain preferred embodiments provide a human NAGAL polypeptide or a functionally active variant or fragment thereof, wherein:

the first amino acid, corresponding to asparagine 213 of human NAGAL polypeptide as set forth in SEQ ID NO: 1, is substituted with one or more amino acids at least one of which contains a negatively charged side-chain group, preferably at least one of which is aspartic acid or glutamic acid (preferably aspartic acid); and the second amino acid, corresponding to cysteine 326 of human NAGAL polypeptide as set forth in SEQ ID NO: 1, is substituted with one or more amino acids at least one of which contains a positively charged side-chain group, preferably at least one of which is arginine, histidine or lysine (preferably arginine); or one or more amino acids at least one of which contains a polar uncharged side-chain group, preferably at least one of which is serine, threonine, asparagine or glutamine (preferably serine).

Certain more preferred embodiments provide a human NAGAL polypeptide or a functionally active variant or fragment thereof, wherein:

the first amino acid, corresponding to asparagine 213 of human NAGAL polypeptide as set forth in SEQ ID NO: 1, is substituted with one, two or three amino acids, preferably one or two amino acids, at least one of which contains a negatively charged side-chain group, preferably at least one of which is aspartic acid or glutamic acid (preferably aspartic acid); and the second amino acid, corresponding to cysteine 326 of human NAGAL polypeptide as set forth in SEQ ID NO: 1, is substituted with one, two or three amino acids, preferably one or two amino acids, at least one of which contains a positively charged side-chain group, preferably at least one of which is arginine, histidine or lysine (preferably arginine); or one, two or three amino acids, preferably one or two amino acids, at least one of which contains a polar uncharged side-chain group, preferably at least one of which is serine, threonine, asparagine or glutamine (preferably serine).

Certain even more preferred embodiments provide a human NAGAL polypeptide or a functionally active variant or fragment thereof, wherein:

the first amino acid, corresponding to asparagine 213 of human NAGAL polypeptide as set forth in SEQ ID NO: 1, is substituted with one amino acid which contains a negatively charged side-chain group, preferably with aspartic acid or glutamic acid (preferably with aspartic acid); and the second amino acid, corresponding to cysteine 326 of human NAGAL polypeptide as set forth in SEQ ID NO: 1, is substituted with one amino acid which contains a positively charged side-chain group, preferably with arginine, histidine or lysine (preferably with arginine); or one amino acid which contains a polar uncharged side-chain group, preferably with serine, threonine, asparagine or glutamine (preferably with serine).

Hence, certain embodiments provide a human NAGAL polypeptide or a functionally active variant or fragment thereof, comprising:

one or more amino acids at least one of which contains a negatively charged side-chain group, preferably one, two or three amino acids at least one of which contains a negatively charged side-chain group, more preferably one or two amino acids at least one of which contains a negatively charged side-chain group, even more preferably one amino acid which contains a negatively charged side-chain group, at the amino acid position corresponding to asparagine 213 of human NAGAL polypeptide as set forth in SEQ ID NO: 1; and one or more amino acids at least one of which contains a positively charged side-chain group or a polar uncharged side-chain group, preferably one, two or three amino acids at least one of which contains a positively charged side-chain group or a polar uncharged side-chain group, more preferably one or two amino acids at least one of which contains a positively charged side-chain group or a polar uncharged side-chain group, even more preferably one amino acid which contains a positively charged side-chain group or a polar uncharged side-chain group, at the amino acid position corresponding to cysteine 326 of human NAGAL polypeptide as set forth in SEQ ID NO: 1.

Hence, certain embodiments provide a human NAGAL polypeptide or a functionally active variant or fragment thereof, comprising:

one or more amino acids at least one of which is aspartic acid or glutamic acid (preferably aspartic acid), preferably one, two or three amino acids at least one of which is aspartic acid or glutamic acid (preferably aspartic acid), more preferably one or two amino acids at least one of which is aspartic acid or glutamic acid (preferably aspartic acid), even more preferably one amino acid which is aspartic acid or glutamic acid (preferably aspartic acid,) at the amino acid position corresponding to asparagine 213 of human NAGAL polypeptide as set forth in SEQ ID NO: 1; and one or more amino acids at least one of which is arginine, histidine or lysine (preferably arginine), preferably one, two or three amino acids at least one of which is arginine, histidine or lysine (preferably arginine), more preferably one or two amino acids at least one of which is arginine, histidine or lysine (preferably arginine), even more preferably one amino acid which is arginine, histidine or lysine (preferably arginine), at the amino acid position corresponding to cysteine 326 of human NAGAL polypeptide as set forth in SEQ ID NO: 1.

Hence, certain embodiments provide a human NAGAL polypeptide or a functionally active variant or fragment thereof, comprising:

one or more amino acids at least one of which is aspartic acid or glutamic acid (preferably aspartic acid), preferably one, two or three amino acids at least one of which is aspartic acid or glutamic acid (preferably aspartic acid), more preferably one or two amino acids at least one of which is aspartic acid or glutamic acid (preferably aspartic acid), even more preferably one amino acid which is aspartic acid or glutamic acid (preferably aspartic acid,) at the amino acid position corresponding to asparagine 213 of human NAGAL polypeptide as set forth in SEQ ID NO: 1; and one or more amino acids at least one of which is serine, threonine, asparagine or glutamine (preferably serine), preferably one, two or three amino acids at least one of which is serine, threonine, asparagine or glutamine (preferably serine), more preferably one or two amino acids at least one of which is serine, threonine, asparagine or glutamine (preferably serine), even more preferably one amino acid which is serine, threonine, asparagine or glutamine (preferably serine), at the amino acid position corresponding to cysteine 326 of human NAGAL polypeptide as set forth in SEQ ID NO: 1.

Certain preferred embodiments thus provide a human NAGAL polypeptide or a functionally active variant or fragment thereof, wherein the first amino acid, corresponding to asparagine 213 of human NAGAL polypeptide as set forth in SEQ ID NO: 1, is substituted with aspartic acid and the second amino acid, corresponding to cysteine 326 of human NAGAL polypeptide as set forth in SEQ ID NO: 1, is substituted with arginine.

Accordingly, also provided is a human NAGAL polypeptide or a functionally active variant or fragment thereof comprising aspartic acid at the amino acid position corresponding to asparagine 213 of human NAGAL polypeptide as set forth in SEQ ID NO: 1, and arginine at the amino acid position corresponding to cysteine 326 of human NAGAL polypeptide as set forth in SEQ ID NO: 1.

Certain further preferred embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with arginine.

Accordingly, also provided is a human NAGAL polypeptide or a functionally active variant or fragment thereof comprising arginine at the amino acid position corresponding to cysteine 326 of human NAGAL polypeptide as set forth in SEQ ID NO: 1.

Certain further preferred embodiments provide a human NAGAL polypeptide or a functionally active variant or fragment thereof, wherein the first amino acid, corresponding to asparagine 213 of human NAGAL polypeptide as set forth in SEQ ID NO: 1, is substituted with aspartic acid and the second amino acid, corresponding to cysteine 326 of human NAGAL polypeptide as set forth in SEQ ID NO: 1, is substituted with serine.

Accordingly, also provided is a human NAGAL polypeptide or a functionally active variant or fragment thereof comprising aspartic acid at the amino acid position corresponding to asparagine 213 of human NAGAL polypeptide as set forth in SEQ ID NO: 1, and serine at the amino acid position corresponding to cysteine 326 of human NAGAL polypeptide as set forth in SEQ ID NO: 1.

Certain further preferred embodiments provide a human NAGAL polypeptide or a functionally active variant or fragment thereof, wherein the second amino acid, corresponding to cysteine 326 of human NAGAL polypeptide as set forth in SEQ ID NO: 1, is substituted with serine.

Accordingly, also provided is a human NAGAL polypeptide or a functionally active variant or fragment thereof comprising serine at the amino acid position corresponding to cysteine 326 of human NAGAL polypeptide as set forth in SEQ ID NO: 1.

Preferred embodiments provide a human NAGAL polypeptide or functionally active variant or fragment thereof, wherein the amino acid sequence of the human NAGAL polypeptide is as set forth in SEQ ID NO: 2 (FIG. 2).

Preferred embodiments provide a human NAGAL polypeptide or functionally active variant or fragment thereof, wherein the functionally active variant displays at least 90% sequence identity to SEQ ID NO: 2, such as wherein the functionally active variant displays, in ascending order of preference, 90%, at least 91% (e.g., 91%), at least 92% (e.g., 92%), at least 93% (e.g., 93%), at least 94% (e.g., 94%), at least 95% (e.g., 95%), at least 96% (e.g., 96%), at least 97% (e.g., 97%), at least 98% (e.g., 98%), or at least 99% (e.g., 99%, 99.5%, 99.6%, 99.7%, 99.8%, or 99.9%) sequence identity to SEQ ID NO: 2.

Preferred embodiments provide a human NAGAL polypeptide or functionally active variant or fragment thereof, wherein the amino acid sequence of the human NAGAL polypeptide is as set forth in SEQ ID NO: 3 (FIG. 3).

Preferred embodiments provide a human NAGAL polypeptide or functionally active variant or fragment thereof, wherein the functionally active variant displays at least 90% sequence identity to SEQ ID NO: 3, such as wherein the functionally active variant displays, in ascending order of preference, 90%, at least 91% (e.g., 91%), at least 92% (e.g., 92%), at least 93% (e.g., 93%), at least 94% (e.g., 94%), at least 95% (e.g., 95%), at least 96% (e.g., 96%), at least 97% (e.g., 97%), at least 98% (e.g., 98%), or at least 99% (e.g., 99%, 99.5%, 99.6%, 99.7%, 99.8%, or 99.9%) sequence identity to SEQ ID NO: 3.

Preferred embodiments provide a human NAGAL polypeptide or functionally active variant or fragment thereof, wherein the amino acid sequence of the human NAGAL polypeptide is as set forth in SEQ ID NO: 4 (FIG. 4).

Preferred embodiments provide a human NAGAL polypeptide or functionally active variant or fragment thereof, wherein the functionally active variant displays at least 90% sequence identity to SEQ ID NO: 4, such as wherein the functionally active variant displays, in ascending order of preference, 90%, at least 91% (e.g., 91%), at least 92% (e.g., 92%), at least 93% (e.g., 93%), at least 94% (e.g., 94%), at least 95% (e.g., 95%), at least 96% (e.g., 96%), at least 97% (e.g., 97%), at least 98% (e.g., 98%), or at least 99% (e.g., 99%, 99.5%, 99.6%, 99.7%, 99.8%, or 99.9%) sequence identity to SEQ ID NO: 4.

Preferred embodiments provide a human NAGAL polypeptide or functionally active variant or fragment thereof, wherein the amino acid sequence of the human NAGAL polypeptide is as set forth in SEQ ID NO: 5 (FIG. 5).

Preferred embodiments provide a human NAGAL polypeptide or functionally active variant or fragment thereof, wherein the functionally active variant displays at least 90% sequence identity to SEQ ID NO: 5, such as wherein the functionally active variant displays, in ascending order of preference, 90%, at least 91% (e.g., 91%), at least 92% (e.g., 92%), at least 93% (e.g., 93%), at least 94% (e.g., 94%), at least 95% (e.g., 95%), at least 96% (e.g., 96%), at least 97% (e.g., 97%), at least 98% (e.g., 98%), or at least 99% (e.g., 99%, 99.5%, 99.6%, 99.7%, 99.8%, or 99.9%) sequence identity to SEQ ID NO: 5.

The human NAGAL polypeptide or a functionally active variant or fragment thereof as taught herein may advantageously comprise a direct or indirect interaction between the amino acids located at the amino acid positions corresponding to asparagine 213 and cysteine 326 of human NAGAL polypeptide as set forth in SEQ ID NO: 1.

Accordingly, as mentioned, a second aspect provides a human NAGAL polypeptide or a functionally active variant or fragment thereof, wherein:

a first amino acid, corresponding to asparagine 213 of human NAGAL polypeptide as set forth in SEQ ID NO: 1, is substituted as taught herein with one or more amino acids, such that at least one of said one or more amino acids is capable of directly or indirectly interacting with a second amino acid corresponding to cysteine 326 of human NAGAL polypeptide as set forth in SEQ ID NO: 1; or a second amino acid, corresponding to cysteine 326 of human NAGAL polypeptide as set forth in SEQ ID NO: 1, is substituted as taught herein with one or more amino acids, such that at least one of said one or more amino acids is capable of directly or indirectly interacting with a first amino acid corresponding to asparagine 213 of human NAGAL polypeptide as set forth in SEQ ID NO: 1; or a first amino acid, corresponding to asparagine 213 of human NAGAL polypeptide as set forth in SEQ ID NO: 1, is substituted as taught herein with one or more amino acids, and a second amino acid, corresponding to cysteine 326 of human NAGAL polypeptide as set forth in SEQ ID NO: 1, is substituted with one or more amino acids, such that at least one of said one or more amino acids substituting the first amino acid is capable of directly or indirectly interacting with at least one of said one or more amino acids substituting the second amino acid.

In certain embodiments, the first amino acid, corresponding to asparagine 213 of human NAGAL polypeptide as set forth in SEQ ID NO: 1, may be substituted with one, two or three amino acids.

In certain further embodiments, the second amino, corresponding to cysteine 326 of human NAGAL polypeptide as set forth in SEQ ID NO: 1, may be substituted with one, two or three amino acids.

In certain other embodiments, the first amino acid, corresponding to asparagine 213 of human NAGAL polypeptide as set forth in SEQ ID NO: 1, may be substituted with one, two or three amino acids, and the second amino, corresponding to cysteine 326 of human NAGAL polypeptide as set forth in SEQ ID NO: 1, may be substituted with one, two or three amino acids.

In certain embodiments, the first amino acid, corresponding to asparagine 213 of human NAGAL polypeptide as set forth in SEQ ID NO: 1, may be substituted with one amino acid.

In certain further embodiments, the second amino, corresponding to cysteine 326 of human NAGAL polypeptide as set forth in SEQ ID NO: 1, may be substituted with one amino acid.

In certain other embodiments, the first amino acid, corresponding to asparagine 213 of human NAGAL polypeptide as set forth in SEQ ID NO: 1, may be substituted with one amino acid, and the second amino, corresponding to cysteine 326 of human NAGAL polypeptide as set forth in SEQ ID NO: 1, may be substituted with one amino acid.

In certain embodiments, the first amino acid, corresponding to asparagine 213 of human NAGAL polypeptide as set forth in SEQ ID NO: 1, may be an asparagine substituted with one or more amino acids other than asparagine, preferably with one, two or three amino acids other than asparagine, more preferably with one amino acid other than asparagine.

In certain embodiments, the second amino acid, corresponding to cysteine 326 of human NAGAL polypeptide as set forth in SEQ ID NO: 1, may be cysteine substituted with one or more amino acids other than cysteine, preferably with one, two or three amino acids other than cysteine, more preferably with one amino acid other than cysteine.

In certain embodiments, the first amino acid, corresponding to asparagine 213 of human NAGAL polypeptide as set forth in SEQ ID NO: 1, may be an asparagine substituted with one or more amino acids other than asparagine, preferably with one, two or three amino acids other than asparagine, more preferably with one amino acid other than asparagine; and the second amino acid, corresponding to cysteine 326 of human NAGAL polypeptide as set forth in SEQ ID NO: 1, may be cysteine substituted with one or more amino acids other than cysteine, preferably with one, two or three amino acids other than cysteine, more preferably with one amino acid other than cysteine.

The terms "interaction", "interacting", "capable of interacting" or similar broadly refer to non-covalent interaction(s) existing between or within molecules.

More particularly herein, the terms may refer to non-covalent interaction(s) between amino acids, more particularly between side-chains of amino acids, more typically between side-chains of two amino acids, of the human NAGAL polypeptide or a functionally active variant or fragment thereof as taught herein.

To participate in a non-covalent interaction, amino acids, e.g., two amino acids, more particularly the side-chains of the amino acids, may be spatially proximate in the three-dimensional structure of the human NAGAL polypeptide or a functionally active variant or fragment thereof. By means of example, the distance between the side-chains of the amino acids, more particularly the distance between the atoms or functional groups which underlie a direct interaction between the side-chains, may in case of an ionic interaction be at most about 5.0 Å, preferably at most about 4.5 Å, more preferably at most about 4.0 Å (e.g., 4.0 Å, 3.9 Å, 3.8 Å, 3.7 Å, 3.6 Å, 3.5 Å, 3.4 Å, 3.3 Å, 3.2 Å, 3.1 Å, 3.0 Å, or lower). By means of example, the distance between the side-chains of the amino acids, more particularly the distance between the atoms or functional groups which underlie a direct interaction between the side-chains, may in case of a hydrogen bonding interaction be at most about 4.0 Å (donor-acceptor distance), e.g., between 2.2 Å and 2.5 Å, or between 2.5 Å and 3.2 Å, or between 3.2 Å and 4.0 Å (donor-acceptor distance). By means of example, the distance between the side-chains of the amino acids, more particularly the distance between the atoms or functional groups which underlie a direct interaction between the side-chains, may in case of a Van der Waals interaction be substantially equal to or less than the sum of the Van der Waals radii of the respective interacting atoms or functional groups.

Reference to a direct interaction between amino acids denotes that the amino acids, particularly the side-chains of the amino acids, more particularly certain atoms or functional groups of the side-chains, interact with one another, more particularly by forming ionic interaction, or a hydrogen bonding interaction, or a Van der Waals interaction between one another.

Reference to an indirect interaction between amino acids indicates that the amino acids, particularly the side-chains of the amino acids, more particularly certain atoms or functional groups of the side-chains, may interact with one or more molecules interposed between them. By means of an example, each of two amino acid side-chains may form a hydrogen bond with the same molecule of solvent, such as water, thereby participating in an indirect interaction.

Hence, in certain embodiments, the interaction may be an ionic interaction or a hydrogen bonding interaction or a Van der Waals interaction, said terms being well understood in the art. By means of illustration and not limitation, an ionic interaction refers to a non-covalent interaction or bond involving electrostatic attraction between oppositely charged ions; a hydrogen bonding interaction refers to a non-covalent interaction or bond involving the electrostatic attraction between polar groups, that occurs when a hydrogen atom bound to a highly electronegative atom, such as N, O or F is attracted to another highly electronegative atom (e.g., N, O or F) in its proximity; Van der Waals interactions include London Dispersion Forces and dipole-dipole forces.

In certain embodiments, the ionic interaction comprises the formation of at least one ion pair.

The term "ion pair" generally refers to a duplex of charged particles (ordinarily charged atoms or molecules) consisting of a positive ion and a negative ion temporarily bonded together by the electrostatic force of attraction between them.

Preferably herein, the term "ion pair" refers to an electrostatic interaction between a nitrogen atom (N atom) of a basic amino acid residue and a carboxylate oxygen atom (O atom) of an acidic amino acid residue. The basic amino acid residue may be arginine, histidine or lysine. The acidic amino acid residue may be aspartic acid (or aspartate) or glutamic acid (or glutamate).

For the basic amino acid residues, the ND1 atom and/or NE2 atom of histidine, the NH1 atom and/or NH2 atom of arginine, and/or the NZ atom of lysine may be involved in the formation of an ion pair. For the acidic amino acid residues, the OD1 atom and/or OD2 atom of aspartate, and/or the OE1 atom and/or OE2 atom of glutamate may be involved in the formation of an ion pair.

In certain embodiments, the ion pair may be a complete ion pair or an incomplete ion pair.

The term "complete ion pair" refers to an ion pair wherein 1) both atoms of each amino acid residue (i.e., the acidic amino acid residue and the basic amino acid residue), or 2) both atoms from the acidic amino acid residue (e.g., the two carboxylate oxygen atoms of aspartic acid) and one atom (e.g., the nitrogen atom of lysine) or both atoms (e.g., the two nitrogen atoms of arginine) from the basic amino acid residue, or 3) both atoms from the basic amino acid residue (e.g., the two nitrogen atoms of arginine) and one atom (e.g., one carboxylate oxygen atom of aspartic acid) or both atoms (e.g., the two carboxylate oxygen atoms of aspartic acid) from the acidic amino acid residue are involved in or participate in the ion pair.

The term "incomplete ion pair" refers to an ion pair wherein only one atom of each amino acid residue (i.e., the acidic amino acid residue and the basic amino acid residue) is involved in or participates in the ion pair. An ion pair may be classified as a salt bridge, nitrogen-oxygen (N—O) bridge, carbon-carbon (C—C) bridge, or longer-range ion pair on the basis of geometrical criteria (Kumar and Nussinov, 2002, Biophys. J., 83(3): 1595-612).

The presence of an ion pair may be determined using methods as known in the art such as nuclear magnetic resonance (NMR) spectroscopy or x-ray crystallography. Analysis of the protein structure using crystal structure visualization and molecular design programs allows insight into contacts between individual atoms. The detection of contacts like ion pairs is mainly driven by their interatomic distance and geometric configuration.

The term "salt bridge" refers to an ion pair wherein the centroids of the side chain atoms of the charged amino acid residues are within a distance of 2.5 Å and 4.0 Å, and at least one pair of side chain carboxylate oxygen atoms of aspartic acid or glutamic acid and the side chain nitrogen atoms of arginine, histidine, or lysine is within a distance of 4.0 Å.

The term "C—C bridge" refers to an ion pair wherein the centroids of the side chain atoms of the charged amino acid residues are within a distance of 2.5 Å and 4.0 Å, but the distance between the side chain carboxylate oxygen atoms of aspartic acid or glutamic acid and the side chain nitrogen atoms of arginine, histidine, or lysine is greater than 4.0 Å.

The term "N—O bridge" refers to an ion pair wherein at least one pair of side chain carboxylate oxygen atoms of aspartic acid or glutamic acid and the side chain nitrogen atoms of arginine, histidine, or lysine is within a distance of 4.0 Å, but the distance between the centroids of the side chain atoms of the charged amino acid residues is greater than 4.0 Å.

The term "longer-range ion pair" refers to an ion pair wherein the distance between the centroids of the side chain atoms of the charged amino acid residues as well as between the side chain nitrogen and oxygen atoms is more than 4.0 Å.

In certain embodiments, the ion pair may be a salt bridge, an N—O bridge, a C—C bridge, or a longer-range ion pair. Preferably, the ion pair is a salt bridge or an N—O bridge. More preferably, the ion pair is a salt bridge.

In certain embodiments, the distance between the centroids of the side chain atoms of the charged (i.e., basic and acidic) amino acid residues may be at most 5.0 Å, preferably at most 4.0 Å, more preferably from 2.5 Å to 4.0 Å, as measured by NMR spectroscopy.

In certain embodiments, the distance between at least one pair of side chain carboxylate oxygen atoms of aspartic acid or glutamic acid and the side chain nitrogen atoms of arginine, histidine, or lysine may be at most 4.0 Å, preferably from 2.5 Å to 4.0 Å, as measured by NMR spectroscopy.

In certain embodiments, the ion pair may be an intramolecular or intermolecular ion pair. As described elsewhere in this specification with reference to Clark and Garman 2009, mature human NAGAL polypeptide forms a homodimer. Hence, an intramolecular ion pair refers to an ion pair formed between the first domain and the second domain of the same NAGAL polypeptide, i.e., between the first domain and the second domain of one and the same NAGAL monomer. An intermolecular ion pair refers to an ion pair formed between the first domain of one of the NAGAL polypeptides in a NAGAL homodimer and the second domain of the other NAGAL polypeptide in the NAGAL homodimer, i.e., between the first domain and the second domain of two distinct NAGAL monomers. Preferably, the ion pair may be an intramolecular ion pair.

In certain preferred embodiments, the at least one ion pair may be formed between a negatively charged side-chain group of an amino acid comprised by the one or more (preferably one, two or three, more preferably one or two, even more preferably one) amino acids substituting the first amino acid, corresponding to asparagine 213 of human NAGAL polypeptide as set forth in SEQ ID NO: 1, and a positively charged side-chain group of an amino acid comprised by the one or more (preferably one, two or three, more preferably one or two, even more preferably one) amino acids substituting the second amino acid, corresponding to cysteine 326 of human NAGAL polypeptide as set forth in SEQ ID NO: 1.

In certain preferred embodiments, the at least one ion pair may be formed between a negatively charged side-chain group of aspartic acid or glutamic acid comprised by the one or more (preferably one, two or three, more preferably one or two, even more preferably one) amino acids substituting the first amino acid, corresponding to asparagine 213 of human NAGAL polypeptide as set forth in SEQ ID NO: 1, and a positively charged side-chain group of arginine, histidine or lysine comprised by the one or more (preferably one, two or three, more preferably one or two, even more preferably one) amino acids substituting the second amino acid, corresponding to cysteine 326 of human NAGAL polypeptide as set forth in SEQ ID NO: 1.

In certain preferred embodiments, the at least one ion pair may be formed between a negatively charged side-chain group of aspartic acid comprised by the one or more (preferably one, two or three, more preferably one or two, even more preferably one) amino acids substituting the first amino acid, corresponding to asparagine 213 of human NAGAL polypeptide as set forth in SEQ ID NO: 1, and a positively charged side-chain group of arginine comprised by the one or more (preferably one, two or three, more preferably one or two, even more preferably one) amino acids substituting the second amino acid, corresponding to cysteine 326 of human NAGAL polypeptide as set forth in SEQ ID NO: 1.

In certain embodiments, the hydrogen bonding interaction may be a direct interaction, or may comprise one or more solvent molecules, preferably one or more water molecules.

As mentioned previously, a third aspect provides a human NAGAL polypeptide or a functionally active variant or fragment thereof comprising a first domain and a second domain, wherein the human NAGAL polypeptide or functionally active variant or fragment thereof is modified such that the first domain is capable of forming at least one (additional) ion pair with the second domain.

The term "modified such that the first domain is capable of forming at least one ion pair with the second domain" as intended herein broadly encompasses any modification or modifications (alteration(s), change(s), adaptation(s)) of the human NAGAL polypeptide or functionally active variant or fragment thereof, which allow(s) for the capability of at least one ion pair being formed between the first and second domains of the human NAGAL polypeptide or functionally active variant or fragment thereof. By means of example and not limitation, such modification(s) can entail altering the primary amino acid sequence of the human NAGAL polypeptide or functionally active variant or fragment thereof, and/or altering, e.g., by chemical reaction, one or more amino acid side chains of the human NAGAL polypeptide or functionally active variant or fragment thereof.

Particularly preferably, "modified such that the first domain is capable of forming at least one ion pair with the second domain" as intended herein refers to the human NAGAL polypeptide or functionally active variant or fragment thereof, the primary amino acid sequence of which has been modified, such as to allow for at least one ion pair being formed between its first and second domains.

By means of an example, modification(s) may be in the first domain only, or in the second domain only, or in both the first and second domains.

For example, the term "modified" as used herein may refer to the substitution of at least one amino acid (residue) in the amino acid sequence of the human NAGAL polypeptide or functionally active variant or fragment thereof by another amino acid (residue); the addition of at least one amino acid (residue) to the amino acid sequence of the human NAGAL polypeptide or functionally active variant or fragment thereof; or the deletion of at least one amino acid (residue) from the amino acid sequence of the human NAGAL polypeptide or functionally active variant or fragment thereof; or any combination thereof.

In certain embodiments, the modification as intended herein may comprise, consist essentially of, or consist of, at least one amino acid substitution in the amino acid sequence of human NAGAL polypeptide or functionally active variant or fragment thereof.

In certain embodiments, the modification as intended herein may comprise, consist essentially of, or consist of, one or more amino acid substitutions, preferably one or two amino acid substitutions, more preferably two amino acid substitutions, in the amino acid sequence of human NAGAL polypeptide or functionally active variant or fragment thereof.

In certain embodiments, the modification as intended herein may comprise, consist essentially of, or consist of, one or more amino acid substitutions, preferably one or two amino acid substitutions, more preferably one amino acid substitution, in the amino acid sequence of the first domain of human NAGAL polypeptide or functionally active variant or fragment thereof.

In certain embodiments, the modification as intended herein may comprise, consist essentially of, or consist of, one or more amino acid substitutions, preferably one or two amino acid substitutions, more preferably one amino acid substitution, in the amino acid sequence of the second domain of human NAGAL polypeptide or functionally active variant or fragment thereof.

In certain embodiments, the modification as intended herein may comprise, consist essentially of, or consist of, one or more amino acid substitutions, preferably one or two amino acid substitutions, more preferably one amino acid substitution, in the amino acid sequence of the first domain of human NAGAL polypeptide or functionally active variant or fragment of the human NAGAL polypeptide; and one or more amino acid substitutions, preferably one or two amino acid substitutions, more preferably one amino acid substitution, in the amino acid sequence of the second domain of the human NAGAL polypeptide or the functionally active variant or fragment of the human NAGAL polypeptide.

Mutations leading to the modification of the amino acid sequence of human NAGAL polypeptide or functionally active variant or fragment thereof such that the first domain is capable of forming at least one ion pair with the second domain as intended herein typically reside in nucleic acid sequence(s) comprised in the open reading frame (ORF) coding for said polypeptide. An "open reading frame" or "ORF" as used herein refers to a succession of coding nucleotide triplets (codons) starting with a translation initiation codon and closing with a translation termination codon known per se, and not containing any internal in-frame translation termination codon, and potentially capable of encoding a protein or polypeptide.

Any types of mutations achieving the intended effects, such as modifying the amino acid sequence of human NAGAL polypeptide, are contemplated herein. For example, suitable mutations may include nucleic acid deletions, insertions, and/or substitutions. The term "nucleic acid deletion" refers to a mutation wherein one or more nucleotides, typically consecutive nucleotides, of a nucleic acid are removed, i.e., deleted, from the nucleic acid. The term "nucleic acid insertion" refers to a mutation wherein one or more nucleotides, typically consecutive nucleotides, are added, i.e., inserted, into a nucleic acid. The term "nucleic acid substitution" refers to a mutation wherein one or more nucleotides of a nucleic acid are each independently replaced, i.e., substituted, by another nucleotide.

The recitation "the first domain is capable of forming at least one ion pair with the second domain" can be used interchangeably with the recitations "the second domain is capable of forming at least one ion pair with the first domain" and "the first and second domain are capable of forming at least one ion pair", and refers to the capability of an amino acid of the first domain and an amino acid of the second domain to engage in an ion pair, more particularly to the capability of an amino acid side chain of the first domain and an amino acid side chain of the second domain to engage in an ion pair.

In certain embodiments, the first domain comprises a $(\beta/\alpha)_8$ barrel and the second domain comprises 8 antiparallel $\beta$ strands in 2 $\beta$ sheets.

Certain embodiments relate to a human NAGAL polypeptide or a functionally active variant or fragment thereof comprising a $(\beta/\alpha)_8$ barrel and eight antiparallel $\beta$ strands, wherein the human NAGAL polypeptide or functionally active variant or fragment thereof is modified such that the $(\beta/\alpha)_8$ barrel is capable of forming at least one ion pair with the eight antiparallel $\beta$ strands.

In certain embodiments, the ion pair may be formed by a first amino acid and a second amino acid. In certain embodiments, the ion pair may be formed by a first amino acid and a second amino acid, wherein the first domain comprises the first amino acid and the second domain comprises the second amino acid. In certain embodiments, the ion pair may be formed by a first amino acid and a second amino acid, wherein the first amino acid is part of the first domain and the second amino acid is part of the second domain.

For convenience, the amino acids of the human NAGAL polypeptide or functionally active variant or fragment thereof as disclosed herein, in particular as disclosed in accordance with the third aspect of the invention, which participate in the formation of the ion pair, may be referred to herein as "a first amino acid" or "the first amino acid", and as "a second amino acid" or "the second amino acid".

For avoidance of doubt, the ordinals "first" and "second" in this context serve to denote the particular amino acids in the human NAGAL polypeptide or functionally active variant or fragment thereof participating in the formation of the ion pair, and more particularly, to distinguish between said amino acids. Consequently, the terms "first" and "second" amino acids are not intended to refer to the amino acids which come, respectively, $1^{st}$ and $2^{nd}$ in the rimary amino acid sequence of the human NAGAL polypeptide or functionally active variant or fragment thereof.

When the ion pair is formed by a first amino acid and a second amino acid, the position of the first amino acid and/or the second amino acid may be conveniently defined by referring to the corresponding position of an amino acid of human NAGAL polypeptide as set forth in SEQ ID NO: 1. The position of amino acid 1 (i.e., leucine) of the human NAGAL polypeptide as set forth in SEQ ID NO: 1 denotes position 1.

In certain embodiments, the first amino acid of the ion pair may be located at an amino acid position of the modified human NAGAL polypeptide or functionally active variant or fragment thereof corresponding to a position between amino acids 208 and 218 of human NAGAL polypeptide as set forth in SEQ ID NO: 1.

In certain embodiments, the second amino acid of the ion pair may be located at an amino acid position of the modified human NAGAL polypeptide or functionally active variant or fragment thereof corresponding to a position between amino acids 321 and 331 of human NAGAL polypeptide as set forth in SEQ ID NO: 1.

By means of an example, the modification of human NAGAL polypeptide or functionally active variant or fragment thereof may entail introducing the first amino acid of the ion pair, while the second amino acid of the ion pair is already present in unmodified human NAGAL; or introducing the second amino acid of the ion pair, while the first amino acid of the ion pair is already present in unmodified human NAGAL; or introducing both the first and the second amino acids of the ion pair.

By means of an example, introducing the first amino acid may entail substituting one or more (e.g., 2, 3, 4 or 5 or up to 10) contiguous amino acids of human NAGAL by an amino acid sequence comprising or consisting of said first amino acid, or introducing the first amino acid may entail adding to human NAGAL an amino acid sequence comprising or consisting of said first amino acid. The amino acid sequence comprising the first amino acid may be, for example, 2, 3, 4 or 5 or up to 10-amino acids long. Independently, By means of an example, introducing the second amino acid may entail substituting one or more (e.g., 2, 3, 4 or 5 or up to 10) contiguous amino acids of human NAGAL by an amino acid sequence comprising or consisting of said second amino acid, or introducing the second amino acid may entail adding to human NAGAL an amino acid sequence comprising or consisting of said second amino acid. The amino acid sequence comprising the second amino acid may be, for example, 2, 3, 4 or 5 or up to 10-amino acids long.

In certain embodiments, the ion pair may be formed by a first amino acid and a second amino acid, and wherein:

the first amino acid may be located at an amino acid position of the modified human NAGAL polypeptide or functionally active variant or fragment thereof corresponding to a position between amino acids 208 and 218 of human NAGAL polypeptide as set forth in SEQ ID NO: 1; and/or (preferably "and")

the second amino acid may be located at an amino acid position of the modified human NAGAL polypeptide or functionally active variant or fragment thereof corresponding to a position between amino acids 321 and 331 of human NAGAL polypeptide as set forth in SEQ ID NO: 1.

In the recitation "a position between amino acids xx and xx+n of human NAGAL polypeptide as set forth in SEQ ID NO: 1" as used herein, the term "between" is meant to include also the positions of the recited amino acids xx and xx+n (xx and n being positive integers).

Hence, the recitation "a position between amino acids xx and xx+n of human NAGAL polypeptide as set forth in SEQ ID NO: 1" as used herein refers to the position of amino acid xx, amino acid xx+1, amino acid xx+2, amino acid xx+3, amino acid xx+4, . . . , or amino acid xx+n of human NAGAL polypeptide as set forth in SEQ ID NO: 1.

For example, the recitation "a position between amino acids 208 and 218 of human NAGAL polypeptide as set forth in SEQ ID NO: 1" as used herein refers to the position of amino acid 208, amino acid 209, amino acid 210, amino acid 211, amino acid 212, amino acid 213, amino acid 214, amino acid 215, amino acid 216, amino acid 217, or amino acid 218 of human NAGAL polypeptide as set forth in SEQ ID NO: 1.

For example, the recitation "a position between amino acids 321 and 331 of human NAGAL polypeptide as set forth in SEQ ID NO: 1" as used herein refers to the position of amino acid 321, amino acid 322, amino acid 323, amino acid 324, amino acid 325, amino acid 326, amino acid 327, amino acid 328, amino acid 329, amino acid 330, or amino acid 331 of human NAGAL polypeptide as set forth in SEQ ID NO: 1.

In certain embodiments, the first amino acid may be located at an amino acid position of the modified human NAGAL polypeptide or functionally active variant or fragment thereof corresponding to a position between amino acids 209 and 217, preferably to a position between amino acids 210 and 216, more preferably to a position between amino acids 211 and 215, even more preferably to a position between amino acids 212 and 214, most preferably to the position of amino acid 213 of human NAGAL polypeptide as set forth in SEQ ID NO: 1; and/or (preferably "and")

the second amino acid may be located at an amino acid position of the modified human NAGAL polypeptide or functionally active variant or fragment thereof corresponding to a position between amino acids 322 and 330, preferably to a position between amino acids 323 and 329, more preferably to a position between amino acids 324 and 328, even more preferably to a position between amino acids 325 and 327, most preferably to the position of amino acid 326 of human NAGAL polypeptide as set forth in SEQ ID NO: 1.

In certain embodiments, the first amino acid may be located at an amino acid position of the modified human NAGAL polypeptide or functionally active variant or fragment thereof corresponding to a position between amino acids 209 and 217 of human NAGAL polypeptide as set forth in SEQ ID NO: 1; and/or the second amino acid may be located at an amino acid position of the modified human NAGAL polypeptide or functionally active variant or fragment thereof corresponding to a position between amino acids 322 and 330 of human NAGAL polypeptide as set forth in SEQ ID NO: 1. In certain embodiments, the first amino acid may be located at an amino acid position of the modified human NAGAL polypeptide or functionally active variant or fragment thereof corresponding to a position between amino acids 210 and 216 of human NAGAL polypeptide as set forth in SEQ ID NO: 1; and/or the second amino acid may be located at an amino acid position of the modified human NAGAL polypeptide or functionally active variant or fragment thereof corresponding to a position between amino acids 323 and 329 of human NAGAL polypeptide as set forth in SEQ ID NO: 1. In certain embodiments the first amino acid may be located at an amino acid position of the modified human NAGAL polypeptide or functionally active variant or fragment thereof corresponding to a position between amino acids 211 and 215 of human NAGAL polypeptide as set forth in SEQ ID NO: 1; and/or the second amino acid may be located at an amino acid position of the modified human NAGAL polypeptide or functionally active variant or fragment thereof corresponding to a position between amino acids 324 and 328 of human NAGAL polypeptide as set forth in SEQ ID NO: 1. In certain embodiments, the first amino acid may be located at an amino acid position of the modified human NAGAL polypeptide or functionally active variant or fragment thereof corresponding to a position between amino acids 212 and 214 of human NAGAL polypeptide as set forth in SEQ ID NO: 1; and/or the second amino acid may be located at an amino acid position of the modified human NAGAL polypeptide or functionally active variant or fragment thereof corresponding to a position between amino acids 325 and 327 of human NAGAL polypeptide as set forth in SEQ ID NO: 1.

In certain embodiments,
the first amino acid may be located at an amino acid position of the modified human NAGAL polypeptide or functionally active variant or fragment thereof corresponding to a position as described in Table 1; and/or (preferably "and")
the second amino acid may be located at an amino acid position of the modified human NAGAL polypeptide or functionally active variant or fragment thereof corresponding to a position as described in Table 1.

In certain embodiments, the first amino acid may be located at an amino acid position of the modified human NAGAL polypeptide or functionally active variant or fragment thereof corresponding to a position of an amino acid "AAx" of human NAGAL polypeptide as set forth in SEQ ID NO: 1, as described in Table 1; and/or (preferably "and") the second amino acid may be located at an amino acid position of the modified human NAGAL polypeptide or functionally active variant or fragment thereof corresponding to a position of an amino acid "AAy" of human NAGAL polypeptide as set forth in SEQ ID NO: 1, as described in Table 1.

In certain embodiments, the first amino acid may be located at an amino acid position of the modified human NAGAL polypeptide or functionally active variant or fragment thereof corresponding to the position of an amino acid AA208, AA209, AA210, AA211, AA212, AA213, AA214, AA215, AA216, AA2017, or AA218 of human NAGAL polypeptide as set forth in SEQ ID NO: 1, as described in Table 1; and/or (preferably "and") the second amino acid may be located at an amino acid position of the modified human NAGAL polypeptide or functionally active variant or fragment thereof corresponding to the position of an amino acid AA321, AA322, AA323, AA324, AA325, AA326, AA327, AA328, AA329, AA330, or AA331 of human NAGAL polypeptide as set forth in SEQ ID NO: 1, as described in Table 1.

The recitation "the first amino acid may be located at an amino acid position of the modified human NAGAL polypeptide or functionally active variant or fragment thereof corresponding to the position of an amino acid 'AAx' of human NAGAL polypeptide as set forth in SEQ ID NO: 1, as described in Table 1; and the second amino acid may be located at an amino acid position of the modified human NAGAL polypeptide or functionally active variant or fragment thereof corresponding to the position of an amino acid 'AAy' of human NAGAL polypeptide as set forth in SEQ ID NO: 1, as described in Table 1" refers to any one or more combinations, such as all combinations, of amino acid positions of the first amino acid and the second amino acid as described in Table 1, and in particular the combinations specified in each field of Table 1 by the expression "AAx+AAy".

TABLE 1

Combinations of the amino acid positions of the first amino acid and the second amino acid corresponding to the position of an amino acid AAx and AAy, respectively, of human NAGAL polypeptide as set forth in SEQ ID NO: 1

| | AAx | | | | | | | | | | |
|---|---|---|---|---|---|---|---|---|---|---|---|
| AAy | AA208 | AA209 | AA210 | AA211 | AA212 | AA213 | AA214 | AA215 | AA216 | AA217 | AA218 |
| AA321 | AA208 + AA321 | AA209 + AA321 | AA210 + AA321 | AA211 + AA321 | AA212 + AA321 | AA213 + AA321 | AA214 + AA321 | AA215 + AA321 | AA216 + AA321 | AA217 + AA321 | AA218 + AA321 |
| AA322 | AA208 + AA322 | AA209 + AA322 | AA210 + AA322 | AA211 + AA322 | AA212 + AA322 | AA213 + AA322 | AA214 + AA322 | AA215 + AA322 | AA216 + AA322 | AA217 + AA322 | AA218 + AA322 |
| AA323 | AA208 + AA323 | AA209 + AA323 | AA210 + AA323 | AA211 + AA323 | AA212 + AA323 | AA213 + AA323 | AA214 + AA323 | AA215 + AA323 | AA216 + AA323 | AA217 + AA323 | AA218 + AA323 |
| AA324 | AA208 + AA324 | AA209 + AA324 | AA210 + AA324 | AA211 + AA324 | AA212 + AA324 | AA213 + AA324 | AA214 + AA324 | AA215 + AA324 | AA216 + AA324 | AA217 + AA324 | AA218 + AA324 |
| AA325 | AA208 + AA325 | AA209 + AA325 | AA210 + AA325 | AA211 + AA325 | AA212 + AA325 | AA213 + AA325 | AA214 + AA325 | AA215 + AA325 | AA216 + AA325 | AA217 + AA325 | AA218 + AA325 |
| AA326 | AA208 + AA326 | AA209 + AA326 | AA210 + AA326 | AA211 + AA326 | AA212 + AA326 | AA213 + AA326 | AA214 + AA326 | AA215 + AA326 | AA216 + AA326 | AA217 + AA326 | AA218 + AA326 |
| AA327 | AA208 + AA327 | AA209 + AA327 | AA210 + AA327 | AA211 + AA327 | AA212 + AA327 | AA213 + AA327 | AA214 + AA327 | AA215 + AA327 | AA216 + AA327 | AA217 + AA327 | AA218 + AA327 |

TABLE 1-continued

Combinations of the amino acid positions of the first amino acid and the second amino acid corresponding to the position of an amino acid AAx and AAy, respectively, of human NAGAL polypeptide as set forth in SEQ ID NO: 1

| AAy | AAx |  |  |  |  |  |  |  |  |  |  |
|---|---|---|---|---|---|---|---|---|---|---|---|
|  | AA208 | AA209 | AA210 | AA211 | AA212 | AA213 | AA214 | AA215 | AA216 | AA217 | AA218 |
| AA328 | AA208 + AA328 | AA209 + AA328 | AA210 + AA328 | AA211 + AA328 | AA212 + AA328 | AA213 + AA328 | AA214 + AA328 | AA215 + AA328 | AA216 + AA328 | AA217 + AA328 | AA218 + AA328 |
| AA329 | AA208 + AA329 | AA209 + AA329 | AA210 + AA329 | AA211 + AA329 | AA212 + AA329 | AA213 + AA329 | AA214 + AA329 | AA215 + AA329 | AA216 + AA329 | AA217 + AA329 | AA218 + AA329 |
| AA330 | AA208 + AA330 | AA209 + AA330 | AA210 + AA330 | AA211 + AA330 | AA212 + AA330 | AA213 + AA330 | AA214 + AA330 | AA215 + AA330 | AA216 + AA330 | AA217 + AA330 | AA218 + AA330 |
| AA331 | AA208 + AA331 | AA209 + AA331 | AA210 + AA331 | AA211 + AA331 | AA212 + AA331 | AA213 + AA331 | AA214 + AA331 | AA215 + AA331 | AA216 + AA331 | AA217 + AA331 | AA218 + AA331 |

In certain embodiments, the first amino acid may be located at an amino acid position of the modified human NAGAL polypeptide or functionally active variant or fragment thereof corresponding to the position of amino acid 213 of human NAGAL polypeptide as set forth in SEQ ID NO: 1 (preferably the first amino acid may be located at an amino acid position of the modified human NAGAL polypeptide or functionally active variant or fragment thereof corresponding to and substituting the asparagine 213 of human NAGAL polypeptide as set forth in SEQ ID NO: 1); and/or the second amino acid may be located at an amino acid position of the modified human NAGAL polypeptide or functionally active variant or fragment thereof corresponding to the position of amino acid 326 of human NAGAL polypeptide as set forth in SEQ ID NO: 1 (preferably the second amino acid may be located at an amino acid position of the modified human NAGAL polypeptide or functionally active variant or fragment thereof corresponding to and substituting the cysteine 326 of human NAGAL polypeptide as set forth in SEQ ID NO: 1).

In certain embodiments, the first amino acid may be located at an amino acid position of the modified human NAGAL polypeptide or functionally active variant or fragment thereof corresponding to the position of amino acid 213 of human NAGAL polypeptide as set forth in SEQ ID NO: 1 (preferably the first amino acid may be located at an amino acid position of the modified human NAGAL polypeptide or functionally active variant or fragment thereof corresponding to and substituting the asparagine 213 of human NAGAL polypeptide as set forth in SEQ ID NO: 1); and the second amino acid may be located at an amino acid position of the modified human NAGAL polypeptide or functionally active variant or fragment thereof corresponding to the position of amino acid 326 of human NAGAL polypeptide as set forth in SEQ ID NO: 1 (preferably the second amino acid may be located at an amino acid position of the modified human NAGAL polypeptide or functionally active variant or fragment thereof corresponding to and substituting the cysteine 326 of human NAGAL polypeptide as set forth in SEQ ID NO: 1).

In certain embodiments, the first amino acid may contain a negatively charged side-chain group, preferably the first amino acid is aspartic acid or glutamic acid, more preferably the first amino acid is aspartic acid, and the second amino acid may contain a positively charged side-chain group, preferably the second amino acid is arginine, histidine, or lysine, more preferably the second amino acid is arginine; or the first amino acid may contain a positively charged side-chain group, preferably the first amino acid is arginine, histidine, or lysine, and the second amino acid may contain a negatively charged side-chain group, preferably the second amino acid is aspartic acid or glutamic acid.

In certain embodiments, the first amino acid may be an acidic amino acid residue, and the second amino acid may be a basic amino acid residue; or the first amino acid may be a basic amino acid residue, and the second amino acid may be an acidic amino acid residue.

In certain embodiments, the first amino acid may be aspartic acid or glutamic acid, and the second amino acid may be arginine, histidine, or lysine; or the first amino acid may be arginine, histidine, or lysine, and the second amino acid may be aspartic acid or glutamic acid.

In certain embodiments, the first amino acid may be aspartic acid and the second amino acid may be arginine; or the first amino acid may be arginine and the second amino acid may be aspartic acid.

In certain embodiments, the first amino acid may be located at an amino acid position of the modified human NAGAL polypeptide or functionally active variant or fragment thereof corresponding to a position between amino acids 208 and 218 of human NAGAL polypeptide as set forth in SEQ ID NO: 1; and/or (preferably "and") the second amino acid may be located at an amino acid position of the modified human NAGAL polypeptide or functionally active variant or fragment thereof corresponding to a position between amino acids 321 and 331 of human NAGAL polypeptide as set forth in SEQ ID NO: 1; and the first amino acid may contain a negatively charged side-chain group and the second amino acid may contain a positively charged side-chain group; or the first amino acid may contain a positively charged side-chain group and the second amino acid may contain a negatively charged side-chain group; preferably the first amino acid contains a negatively charged side-chain group and the second amino acid may contain a positively charged side-chain group.

In certain embodiments, the first amino acid may be located at an amino acid position of the modified human NAGAL polypeptide or functionally active variant or fragment thereof corresponding to a position of an amino acid "AAx" of human NAGAL polypeptide as set forth in SEQ ID NO: 1, as described in Table 1; and/or (preferably "and") the second amino acid may be located at an amino acid position of the modified human NAGAL polypeptide or functionally active variant or fragment thereof corresponding to a position of an amino acid "AAy" of human NAGAL polypeptide as set forth in SEQ ID NO: 1, as described in Table 1; and the first amino acid may contain a negatively charged side-chain group and the second amino acid may contain a positively charged side-chain group; or the first amino acid may contain a positively charged side-chain group and the second amino acid may contain a negatively charged side-chain group; preferably the first amino acid contains a negatively charged side-chain group and the second amino acid may contains a positively charged side-chain group.

In certain embodiments, the first amino acid may be located at an amino acid position of the modified human NAGAL polypeptide or functionally active variant or fragment thereof corresponding to the position of amino acid 213 of human NAGAL polypeptide as set forth in SEQ ID NO: 1 (preferably the first amino acid may be located at an amino acid position of the modified human NAGAL polypeptide or functionally active variant or fragment thereof corresponding to and substituting the asparagine 213 of human NAGAL polypeptide as set forth in SEQ ID NO: 1); and the second amino acid may be located at an amino acid position of the modified human NAGAL polypeptide or functionally active variant or fragment thereof corresponding to the position of amino acid 326 of human NAGAL polypeptide as set forth in SEQ ID NO: 1 (preferably the second amino acid may be located at an amino acid position of the modified human NAGAL polypeptide or functionally active variant or fragment thereof corresponding to and substituting the cysteine 326 of human NAGAL polypeptide as set forth in SEQ ID NO: 1); and the first amino acid may contain a negatively charged side-chain group and the second amino acid may contain a positively charged side-chain group; or the first amino acid may contain a positively charged side-chain group and the second amino acid may contain a negatively charged side-chain group; preferably the first amino acid contains a negatively charged side-chain group and the second amino acid may contains a positively charged side-chain group.

In certain embodiments, the first amino acid may be located at an amino acid position of the modified human NAGAL polypeptide or functionally active variant or fragment thereof corresponding to a position between amino acids 208 and 218 of human NAGAL polypeptide as set forth in SEQ ID NO: 1; and/or (preferably "and") the second amino acid may be located at an amino acid position of the modified human NAGAL polypeptide or functionally active variant or fragment thereof corresponding to a position between amino acids 321 and 331 of human NAGAL polypeptide as set forth in SEQ ID NO: 1; and the first amino acid is aspartic acid or glutamic acid and the second amino acid is arginine, histidine, or lysine; or the first amino acid is arginine, histidine, or lysine and the second amino acid is aspartic acid or glutamic acid; preferably the first amino acid is aspartic acid or glutamic acid and the second amino acid is arginine, histidine, or lysine.

In certain embodiments, the first amino acid may be located at an amino acid position of the modified human NAGAL polypeptide or functionally active variant or fragment thereof corresponding to a position of an amino acid "AAx" of human NAGAL polypeptide as set forth in SEQ ID NO: 1, as described in Table 1; and/or (preferably "and") the second amino acid may be located at an amino acid position of the modified human NAGAL polypeptide or functionally active variant or fragment thereof corresponding to a position of an amino acid "AAy" of human NAGAL polypeptide as set forth in SEQ ID NO: 1, as described in Table 1; and the first amino acid is aspartic acid or glutamic acid and the second amino acid is arginine, histidine, or lysine; or the first amino acid is arginine, histidine, or lysine and the second amino acid is aspartic acid or glutamic acid; preferably the first amino acid is aspartic acid or glutamic acid and the second amino acid is arginine, histidine, or lysine.

In certain embodiments, the first amino acid may be located at an amino acid position of the modified human NAGAL polypeptide or functionally active variant or fragment thereof corresponding to the position of amino acid 213 of human NAGAL polypeptide as set forth in SEQ ID NO: 1 (preferably the first amino acid may be located at an amino acid position of the modified human NAGAL polypeptide or functionally active variant or fragment thereof corresponding to and substituting the asparagine 213 of human NAGAL polypeptide as set forth in SEQ ID NO: 1); and the second amino acid may be located at an amino acid position of the modified human NAGAL polypeptide or functionally active variant or fragment thereof corresponding to the position of amino acid 326 of human NAGAL polypeptide as set forth in SEQ ID NO: 1 (preferably the second amino acid may be located at an amino acid position of the modified human NAGAL polypeptide or functionally active variant or fragment thereof corresponding to and substituting the cysteine 326 of human NAGAL polypeptide as set forth in SEQ ID NO: 1); and the first amino acid is aspartic acid or glutamic acid and the second amino acid is arginine, histidine, or lysine; or the first amino acid is arginine, histidine, or lysine and the second amino acid is aspartic acid or glutamic acid; preferably the first amino acid is aspartic acid or glutamic acid and the second amino acid is arginine, histidine, or lysine.

In certain embodiments, the first amino acid may be located at an amino acid position of the modified human NAGAL polypeptide or functionally active variant or fragment thereof corresponding to a position between amino acids 208 and 218 of human NAGAL polypeptide as set forth in SEQ ID NO: 1; and/or (preferably "and") the second amino acid may be located at an amino acid position of the modified human NAGAL polypeptide or functionally active variant or fragment thereof corresponding to a position between amino acids 321 and 331 of human NAGAL polypeptide as set forth in SEQ ID NO: 1; and the first amino acid is aspartic acid and the second amino acid is arginine; or the first amino acid is arginine and the second amino acid is aspartic acid; preferably the first amino acid is aspartic acid and the second amino acid is arginine.

In certain embodiments, the first amino acid may be located at an amino acid position of the modified human NAGAL polypeptide or functionally active variant or fragment thereof corresponding to a position of an amino acid "AAx" of human NAGAL polypeptide as set forth in SEQ ID NO: 1, as described in Table 1; and/or (preferably "and") the second amino acid may be located at an amino acid position of the modified human NAGAL polypeptide or functionally active variant or fragment thereof corresponding to a position of an amino acid "AAy" of human NAGAL polypeptide as set forth in SEQ ID NO: 1, as described in Table 1; and the first amino acid is aspartic acid and the second amino acid is arginine; or the first amino acid is arginine and the second amino acid is aspartic acid; preferably the first amino acid is aspartic acid and the second amino acid is arginine.

In certain embodiments, the first amino acid may be located at an amino acid position of the modified human NAGAL polypeptide or functionally active variant or fragment thereof corresponding to the position of amino acid 213 of human NAGAL polypeptide as set forth in SEQ ID NO: 1 (preferably the first amino acid may be located at an amino acid position of the modified human NAGAL polypeptide or functionally active variant or fragment thereof corresponding to and substituting the asparagine 213 of human NAGAL polypeptide as set forth in SEQ ID NO: 1); and the second amino acid may be located at an amino acid position of the modified human NAGAL polypeptide or functionally active variant or fragment thereof corresponding to the position of amino acid 326 of human NAGAL polypeptide as set forth in SEQ ID NO: 1 (preferably the second amino acid may be located at an amino acid position of the modified human NAGAL polypeptide or functionally active variant or fragment thereof corresponding to and substituting the cysteine 326 of human NAGAL polypeptide as set forth in SEQ ID NO: 1); and the first amino acid is aspartic acid and the second amino acid is arginine; or the first amino acid is arginine and the second amino acid is aspartic acid; preferably the first amino acid is aspartic acid and the second amino acid is arginine.

In certain embodiments, the first amino acid may be aspartic acid located at an amino acid position of the modified human NAGAL polypeptide or functionally active variant or fragment thereof corresponding to the position of amino acid 213 of human NAGAL polypeptide as set forth in SEQ ID NO: 1; and the second amino acid may be arginine located at an amino acid position of the modified human NAGAL polypeptide or functionally active variant or fragment thereof corresponding to the position of amino acid 326 of human NAGAL polypeptide as set forth in SEQ ID NO: 1.

In certain embodiments, the first amino acid may be aspartic acid located at an amino acid position of the modified human NAGAL polypeptide or functionally active variant or fragment thereof corresponding to and substituting the asparagine 213 of human NAGAL polypeptide as set forth in SEQ ID NO: 1; and the second amino acid may be arginine located at an amino acid position of the modified human NAGAL polypeptide or functionally active variant or fragment thereof corresponding to and substituting the cysteine 326 of human NAGAL polypeptide as set forth in SEQ ID NO: 1.

Certain embodiments provide a human NAGAL polypeptide or a functionally active variant or fragment thereof comprising a first amino acid and a second amino acid, wherein the first amino acid is aspartic acid located at an amino acid position of the human NAGAL polypeptide or functionally active variant or fragment thereof corresponding to the position of amino acid 213 of human NAGAL polypeptide as set forth in SEQ ID NO: 1; and the second amino acid is arginine located at an amino acid position of the human NAGAL polypeptide or functionally active variant or fragment thereof corresponding to the position of amino acid 326 of human NAGAL polypeptide as set forth in SEQ ID NO: 1. In certain embodiments, the first amino acid is part of the first domain and the second amino acid is part of the second domain.

In certain embodiments, the stability of the human NAGAL polypeptide or functionally active variant or fragment thereof as taught herein may be increased by at least 1% compared with the stability of a corresponding unmodified human NAGAL polypeptide or functionally active variant or fragment thereof. For example, the stability of the modified human NAGAL polypeptide or functionally active variant or fragment thereof may be increased by at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, at least 80%, or at least 90% compared with the stability of a corresponding unmodified human NAGAL polypeptide or functionally active variant or fragment thereof.

The terms "a corresponding human NAGAL polypeptide or functionally active variant or fragment thereof" or "a corresponding unmodified human NAGAL polypeptide or functionally active variant or fragment thereof" as used herein refer to a human NAGAL polypeptide or functionally active variant or fragment thereof which has not been modified as taught herein. A corresponding (unmodified) human NAGAL polypeptide or functionally active variant or fragment thereof can be altered in other ways, however, for instance such as to acquire α-galactosidase activity. For example, a corresponding (unmodified) human NAGAL polypeptide or functionally active variant or fragment thereof can comprise S to E substitution at an amino acid position corresponding to the position of amino acid 171 of human NAGAL polypeptide as set forth in SEQ ID NO: 1, and A to L substitution at an amino acid position corresponding to the position of amino acid 174 of human NAGAL polypeptide as set forth in SEQ ID NO: 1.

The stability of the human NAGAL protein or polypeptide may be determined by a method comprising incubating the protein or polypeptide for a certain time period (e.g., for 16 hours) at a certain temperature (e.g., at 37° C.), under certain conditions (e.g., in buffers having different composition and pH (e.g., 10 mM sodium citrate buffer (pH 4.0), 10 mM sodium acetate buffer (pH 4.5 and 5.0), 10 mM citric acid/sodium phosphate buffer (pH 5.5, 6.0 and 6.5), or 10 mM phosphate buffer (pH 7.0, 7.5 and 8.0)), in a buffer with different pH values (e.g., pH of 4.5 and pH of 7.0), or in plasma), and measuring the NAGAL activity (e.g., by a fluorometric assay with MU-α-D-N-acetylgalactosamine as a substrate, as described elsewhere in this specification) in function of the time. As a control, a corresponding unmodified human NAGAL polypeptide or functionally active variant or fragment can be used. The enzyme activity at time zero (e.g., 2 mmol/h/ml of NAGAL activity as measured by a fluorometric assay with MU-α-D-N-acetylgalactosamine as a substrate, as described herein) can be set to be 100% under each condition. The stability of each enzyme can be calculated and expressed as the ratio (e.g., percent) of the enzyme activity at a particular incubation time point to the value at time zero. Similarly, stability can be determined by measuring the preservation of α-galactosidase activity, where the modified or unmodified human NAGAL or functionally active variant or fragment thereof has been further modified to acquire α-galactosidase activity.

Alternatively or in addition, the stability of a protein or polypeptide such as modified human NAGAL polypeptide or functionally active variant or fragment thereof may be predicted by a thermal shift assay, also called differential scanning fluorimetry (DSF).

Alternatively or in addition, the stability of a protein or polypeptide such as modified human NAGAL polypeptide or functionally active variant or fragment thereof may be predicted by measuring the melting temperature (Tm) of the protein or polypeptide.

The "melting temperature (Tm)" of a protein or polypeptide such as modified human NAGAL polypeptide or functionally active variant or fragment thereof refers to the temperature at which 50% of the protein or polypeptide is inactivated during reversible heat denaturation.

The melting temperature of a protein or polypeptide can be determined using circular dichroism (CD) spectroscopy. The term "circular dichroism spectroscopy" generally refers to a tool to study the secondary structure of proteins or protein folding. Circular dichroism spectroscopy measures the absorption of circularly polarized light. In proteins, secondary structures such as alpha helices and beta sheets are chiral, and thus absorb such light. The absorption of this light acts as a marker of the degree of folding of the protein. CD is a valuable tool for showing changes in conformation. The technique can be used to study how the secondary structure of a protein changes by measuring the change in the absorption as a function of temperature. In this way, CD can reveal important thermodynamic information about the protein (such as the enthalpy and Gibbs free energy of denaturation) that cannot otherwise be easily obtained.

In certain embodiments, the melting temperature of the modified human NAGAL polypeptide or functionally active variant or fragment thereof may be increased by at least 2.0° C. compared with the stability of a corresponding unmodified human NAGAL polypeptide or functionally active variant or fragment thereof. For example, the melting temperature of the modified human NAGAL polypeptide or functionally active variant or fragment thereof may be increased by at least 2.0° C., at least 3.0° C., at least 4.0° C., at least 5.0° C., at least 10.0° C., at least 15.0° C., at least 20.0° C., at least 25.0° C., or at least 30.0° C. compared with the melting temperature of a corresponding unmodified human NAGAL polypeptide or functionally active variant or fragment thereof.

In certain embodiments, the stability of the human NAGAL polypeptide or functionally active variant or fragment thereof may be increased such as to promote or result in protein folding as detectable by suitable methods such as circular dichroism. In certain embodiments, the stability of the human NAGAL polypeptide or functionally active variant or fragment thereof may be increased such as to result in recombinant protein expression as detectable by suitable methods such as standard SDS-PAGE and Western blot detection or Coomassie staining.

Hence, a fourth aspect provides a human NAGAL polypeptide or a functionally active variant or fragment thereof modified such as to display increased stability (e.g., as explained above) compared with the stability of a corresponding unmodified human NAGAL polypeptide or functionally active variant or fragment thereof.

In certain embodiments, the amino acid sequence of the modified human NAGAL polypeptide is as set forth in SEQ ID NO: 2 (as illustrated in FIG. 2). The position of amino acid 213 (i.e., aspartic acid) of modified human NAGAL polypeptide as set forth in SEQ ID NO: 2 is indicated in FIG. 2 (underlined). The position of amino acid 326 (i.e., arginine) of modified human NAGAL polypeptide as set forth in SEQ ID NO: 2 is indicated in FIG. 2 (bold underlined).

In certain embodiments the functionally active variant displays at least 90% sequence identity to SEQ ID NO: 2.

In certain embodiments, the functionally active variant may display at least 91% sequence identity to SEQ ID NO: 2, such as at least 92%, at least 93%, at least 94%, at least 95%, at least 96%, at least 97%, at least 98%, at least 99%, or at least 99.5% sequence identity to SEQ ID NO: 2.

In certain embodiments, the modified human NAGAL polypeptide or functionally active variant or fragment thereof may be obtainable by modifying the amino acid sequence of human NAGAL polypeptide as set forth in SEQ ID NO: 1 or a functionally active variant thereof having at least 90% sequence identity to SEQ ID NO: 1, such that the first domain is capable of forming at least one ion pair with the second domain. In certain embodiments, the modified human NAGAL polypeptide or functionally active variant or fragment thereof may be obtainable by modifying a functionally active variant having at least 91%, at least 92%, at least 93%, at least 94%, at least 95%, at least 96%, at least 97%, at least 98%; at least 99%, or at least 99.5% sequence identity to SEQ ID NO: 1, such that the first domain is capable of forming at least one ion pair with the second domain.

The following sections of the specification further describe and develop the subject-matter concerning, relating to or making use of the human NAGAL polypeptide or functionally active variant or fragment thereof as taught herein. It shall be understood that the phrase "the human NAGAL polypeptide or functionally active variant or fragment thereof as taught herein" or similar encompasses any human NAGAL polypeptide or functionally active variant or fragment thereof as disclosed herein, more particularly including the human NAGAL polypeptide or functionally active variant or fragment thereof in accordance with any one or more or all of the first, second, third and fourth aspects, as set forth above, and embodiments thereof.

In certain embodiments the human NAGAL polypeptide or functionally active variant or fragment thereof as taught herein may be further modified such as to acquire α-galactosidase activity.

For example, the human NAGAL polypeptide or functionally active variant or fragment thereof may further comprise S to E substitution at an amino acid position corresponding to the position of amino acid 171 of human NAGAL polypeptide as set forth in SEQ ID NO: 1, and A to L substitution at an amino acid position corresponding to the position of amino acid 174 of human NAGAL polypeptide as set forth in SEQ ID NO: 1.

Preferred embodiments provide a human NAGAL polypeptide or functionally active variant or fragment thereof, wherein the amino acid sequence of the human NAGAL polypeptide is as set forth in SEQ ID NO: 6 (FIG. 6).

Preferred embodiments provide a human NAGAL polypeptide or functionally active variant or fragment thereof, wherein the functionally active variant displays at least 90% sequence identity to SEQ ID NO: 6, such as wherein the functionally active variant displays, in ascending order of preference, 90%, at least 91% (e.g., 91%), at least 92% (e.g., 92%), at least 93% (e.g., 93%), at least 94% (e.g., 94%), at least 95% (e.g., 95%), at least 96% (e.g., 96%), at least 97% (e.g., 97%), at least 98% (e.g., 98%), or at least 99% (e.g., 99%, 99.5%, 99.6%, 99.7%, 99.8%, or 99.9%) sequence identity to SEQ ID NO: 6.

Preferred embodiments provide a human NAGAL polypeptide or functionally active variant or fragment thereof, wherein the amino acid sequence of the human NAGAL polypeptide is as set forth in SEQ ID NO: 7 (FIG. 7).

Preferred embodiments provide a human NAGAL polypeptide or functionally active variant or fragment thereof, wherein the functionally active variant displays at least 90% sequence identity to SEQ ID NO: 7, such as wherein the functionally active variant displays, in ascending order of preference, 90%, at least 91% (e.g., 91%), at least 92% (e.g., 92%), at least 93% (e.g., 93%), at least 94% (e.g., 94%), at least 95% (e.g., 95%), at least 96% (e.g., 96%), at least 97% (e.g., 97%), at least 98% (e.g., 98%), or at least 99% (e.g., 99%, 99.5%, 99.6%, 99.7%, 99.8%, or 99.9%) sequence identity to SEQ ID NO: 7.

Preferred embodiments provide a human NAGAL polypeptide or functionally active variant or fragment thereof, wherein the amino acid sequence of the human NAGAL polypeptide is as set forth in SEQ ID NO: 8 (FIG. 8).

Preferred embodiments provide a human NAGAL polypeptide or functionally active variant or fragment thereof, wherein the functionally active variant displays at least 90% sequence identity to SEQ ID NO: 8, such as wherein the functionally active variant displays, in ascending order of preference, 90%, at least 91% (e.g., 91%), at least 92% (e.g., 92%), at least 93% (e.g., 93%), at least 94% (e.g., 94%), at least 95% (e.g., 95%), at least 96% (e.g., 96%), at least 97% (e.g., 97%), at least 98% (e.g., 98%), or at least 99% (e.g., 99%, 99.5%, 99.6%, 99.7%, 99.8%, or 99.9%) sequence identity to SEQ ID NO: 8.

Preferred embodiments provide a human NAGAL polypeptide or functionally active variant or fragment thereof, wherein the amino acid sequence of the human NAGAL polypeptide is as set forth in SEQ ID NO: 9 (FIG. 9).

Preferred embodiments provide a human NAGAL polypeptide or functionally active variant or fragment thereof, wherein the functionally active variant displays at least 90% sequence identity to SEQ ID NO: 9, such as wherein the functionally active variant displays, in ascending order of preference, 90%, at least 91% (e.g., 91%), at least 92% (e.g., 92%), at least 93% (e.g., 93%), at least 94% (e.g., 94%), at least 95% (e.g., 95%), at least 96% (e.g., 96%), at least 97% (e.g., 97%), at least 98% (e.g., 98%), or at least 99% (e.g., 99%, 99.5%, 99.6%, 99.7%, 99.8%, or 99.9%) sequence identity to SEQ ID NO: 9.

In certain embodiments the human NAGAL polypeptide or functionally active variant or fragment thereof as taught herein may further comprise one or more heterologous (non-NAGAL) amino acid sequences, such as one or more heterologous amino acid sequences connected, optionally by means of one or more linker peptides, to either the C- or N-terminus or to both termini of the human NAGAL polypeptide or functionally active variant or fragment thereof.

In certain embodiments,
the heterologous amino acid sequence may be a receptor targeting amino acid sequence, such as a receptor targeting amino acid sequence selected from the group consisting of: a sequence for targeting a mannose-6-phosphate receptor; or the heterologous amino acid sequence may be or may comprise a secretion signal sequence, such as a *Yarrowia* Lip2 prepro, a *Yarrowia* Lip2 pre, a *Saccharomyces cerevisiae* α-mating factor, a *Yarrowia* XPR2 prepro, or a *Yarrowia* XPR2 pre sequence; or the heterologous amino acid sequence may comprise a secretion signal sequence, such as a *Yarrowia* Lip2 prepro, a *Yarrowia* Lip2 pre, a *Saccharomyces cerevisiae* α-mating factor, a *Yarrowia* XPR2 prepro, or a *Yarrowia* XPR2 pre sequence, and may further comprise two X-Ala repeats C-terminally to the secretion signal sequence; or the heterologous amino acid sequence may allow for purification of the modified human NAGAL polypeptide or functionally active variant or fragment thereof; or the heterologous amino acid sequence may be configured for use as a diagnostic or detectable marker.

In some embodiments, the heterologous amino acid sequence is used to enhance the efficiency of transport of the modified human NAGAL polypeptide or functionally active variant or fragment thereof into a mammalian cell. For example, the modified human NAGAL polypeptide or functionally active variant or fragment thereof can be fused to a ligand for an extracellular receptor, a targeting domain that binds an extracellular domain of a receptor on the surface of a target cell, a urokinase-type plasminogen activator receptor, or domains of human insulin-like growth factor II that bind to the mannose-6-phosphate receptor (e.g., amino acids 1-67 or 1-87; at least amino acids 48-55; at least amino acids 8-28 and 41-61; or at least amino acids 8-87 of human insulin-like growth factor; a sequence variant thereof of human insulin-like growth factor II (e.g., R68A) or truncated form of human insulin-like growth factor (e.g., C-terminally truncated from position 62)). The heterologous amino acid sequence can be fused at the N-terminus or C-terminus of the polypeptide, or at both N-terminus and C-terminus. In one embodiment, a peptide tag is fused to the N- or C-terminus of the polypeptide by a spacer (e.g., 5-30 amino acids or 10-25 amino acids).

In certain embodiments the human NAGAL polypeptide or functionally active variant or fragment thereof as taught herein may comprise one or more N-linked glycans (N-glycans). By means of example, human NAGAL polypeptide has been reported by Clark and Garman 2009 (supra) to contain five N-linked glycosylation sites (N124, N177, N201, N359, and N385; amino acid numbering starting from the starting methionine). Hence, in certain embodiments the human NAGAL polypeptide or functionally active variant or fragment thereof may carry one, two, three, four or five N-glycans, such as at any one or more Asn residues corresponding to the aforementioned sites. Where the human NAGAL polypeptide or functionally active variant or fragment thereof forms a homodimer, at least one of the monomers may comprise one or more N-linked glycans, e.g., may carry one, two, three, four or five N-glycans.

In certain embodiments, the human NAGAL polypeptide or functionally active variant or fragment thereof may comprise one or more N-glycans, wherein one or more of said N-glycans may be phosphorylated. In certain embodiments, the human NAGAL polypeptide or functionally active variant or fragment thereof may comprise one or more N-glycans, wherein 40% or more by number of said N-glycans may be phosphorylated. For instance, 50% or more, 60% or more, 70% or more, 80% or more, 90% or more, or 95% or more by number of said N-glycans may be phosphorylated. N-glycans typically carry one or two phosphate groups. The reference to a phosphorylated N-glycan encompasses both mono- and di-phosphorylated N-glycans. Hence, 40% or more by number (e.g., 50% or more, 60% or more, 70% or more, 80% or more, 90% or more, or 95% or more by number) of the N-glycans may carry at least one phosphate group. Where the human NAGAL polypeptide or functionally active variant or fragment thereof forms a homodimer, at least one of the monomers may comprise one or more N-linked glycans, of which one or more may be phosphorylated.

In certain embodiments, the one or more of said phosphorylated N-glycans may be uncapped. In certain embodiments, 40% or more by number of said phosphorylated N-glycans may be uncapped. For instance, 50% or more, 60% or more, 70% or more, 80% or more, 90% or more, or 95% or more by number of said phosphorylated N-glycans may be uncapped.

In this connection, "uncapped" particularly means that the phosphate group in the phospho-6-mannose moiety is not covalently linked to another moiety, e.g., to a mannos-1-yl moiety. By means of example, certain organisms, such as fungal cells, may synthesise phosphorylated N-glycans in which the phosphate moiety is "capped" with a mannose residue, forming a mannose-1-phospho-6-mannose group. In such circumstances, "uncapping" may refer to removing the mannos-1-yl residue, thereby exposing the phosphate moiety. Where an N-glycan contains more than one phosphate groups, the N-glycan may be denoted as "uncapped" if at least one of said phosphate groups is uncapped. Preferably, both said phosphate groups may be uncapped. N-glycans containing uncapped phosphate group(s) bind substantially better to mannose-6-phosphate receptors on mammalian cells than N-glycans containing capped phosphate group(s), thereby increasing the efficiency with which the modified human NAGAL polypeptide or functionally active variant or fragment thereof is transported to the interior of mammalian cells and eventually to the lysosome.

In certain embodiments, the one or more of said phosphorylated N-glycans may be demannosylated. In certain embodiments, 40% or more by number of said phosphorylated N-glycans may be demannosylated. For instance, 50% or more, 60% or more, 70% or more, 80% or more, 90% or more, or 95% or more by number of said phosphorylated N-glycans may be demannosylated. In this connection, "demannosylated" may refer to at least the hydrolysis of terminal alpha-1,2 mannose moieties of phosphate-containing N-glycans, including the terminal alpha-1,2-mannose when the underlying mannose is phosphorylated. Hence, this results in the mannose containing the phosphate at the 6 position becoming the terminal mannose. In certain embodiments, "demmanosylated" may refer to hydrolysis of terminal alpha-1,2 mannose, alpha-1,3 mannose and/or (preferably "and") alpha-1,6 mannose linkages or moieties of phosphate-containing N-glycans. More particularly, in a phosphorylated (mono- or di-phosphorylated) N-glycan, demannosylation may include hydrolysis of the non-phosphorylated arm of the N-glycan and hydrolysis of the terminal alpha-1,2-mannose when the underlying mannose is phosphorylated. In such case, final hydrolysis products of demannosylation may be selected from the group comprising, consisting essentially of or consisting of ManPMan$_3$GlcNAc$_2$ and (ManP)$_2$Man$_5$GlcNAc$_2$ (Man denotes mannose residues and GlcNAc denotes N-acetylglucosamine residues). Demannosylated N-glycans containing uncapped phosphate group(s) bind substantially better to mannose-6-phosphate receptors on mammalian cells than non-demannosylated N-glycans containing uncapped phosphate group(s), thereby increasing the efficiency with which the modified human NAGAL polypeptide or functionally active variant or fragment thereof is transported to the interior of mammalian cells and eventually to the lysosome.

In certain embodiments, the one or more of said phosphorylated N-glycans may be uncapped and demannosylated. In certain embodiments, 40% or more by number of said phosphorylated N-glycans may be uncapped and demannosylated. For instance, 50% or more, 60% or more, 70% or more, 80% or more, 90% or more, or 95% or more by number of said phosphorylated N-glycans may be uncapped and demannosylated. The final hydrolysis products of demannosylation and uncapping may be selected from the group comprising, consisting essentially of or consisting of PMan$_3$GlcNAc$_2$ and P$_2$Man$_5$GlcNAc$_2$ (Man denotes mannose residues and GlcNAc denotes N-acetylglucosamine residues).

Hence, in certain embodiments, the human NAGAL polypeptide or functionally active variant or fragment thereof may comprise one or more N-glycans, e.g., one, two, three, four or five N-glycans, wherein 40% or more by number of said N-glycans, e.g., 50% or more, 60% or more, 70% or more, 80% or more, 90% or more, or 95% or more by number of said N-glycans are phosphorylated, uncapped and demannosylated. By means of example, 40% or more, 50% or more, 60% or more, 70% or more, 80% or more, 90% or more, or 95% or more by number of said N-glycans may be selected from the group comprising, consisting essentially of or consisting of PMan$_3$GlcNAc$_2$ and P$_2$Man$_5$GlcNAc$_2$.

Glycoproteins containing a phosphorylated N-glycan can be demannosylated, and glycoproteins containing a phosphorylated N-glycan containing a mannose-1-phospho-6-mannose linkage or moiety can be uncapped and demannosylated by contacting the glycoprotein with a mannosidase capable of (i) hydrolyzing a mannose-1-phospho-6-mannose linkage or moiety to mannose-6-phosphate and (ii) hydrolyzing a terminal alpha-1,2 mannose, alpha-1,3 mannose and/or alpha-1,6 mannose linkage or moiety. Non-limiting examples of such mannosidases include a *Canavalia ensiformis* (Jack bean) mannosidase and a *Yarrowia lipolytica* mannosidase (e.g., AMS1). Both the Jack bean and AMS1 mannosidase are family 38 glycoside hydrolases.

The Jack bean mannosidase is commercially available, for example, from Sigma-Aldrich (St. Louis, Mo.) as an ammonium sulfate suspension (Catalog No. M7257) and a proteomics grade preparation (Catalog No. M5573). Such commercial preparations can be further purified, for example, by gel filtration chromatography to remove contaminants such as phosphatases.

The *Yarrowia lipolytica* AMS1 mannosidase can be recombinantly produced. The amino acid sequence of the AMS1 polypeptide is set forth in WO 2013/136189 as SEQ ID NO: 5.

In some embodiments, the uncapping and demannosylating steps are catalyzed by two different enzymes. For example, uncapping of a mannose-1-phospho-6-mannose linkage or moiety can be performed using a mannosidase from *Cellulosimicrobium cellulans* (e.g., CcMan5). The nucleotide sequence encoding the CcMan5 polypeptide is set forth in WO 2013/136189 as SEQ ID NO: 2. The amino acid sequence of the CcMan5 polypeptide containing a signal sequence is set forth in WO 2013/136189 as SEQ ID NO: 3. The amino acid sequence of the CcMan5 polypeptide without signal sequence is set forth in WO 2013/136189 as SEQ ID NO: 4. In some embodiments, a biologically active fragment of the CcMan5 polypeptide is used. For example, a biologically active fragment can include residues 1-774 of the amino acid sequence set forth in WO 2013/136189 as SEQ ID NO: 4. See also WO 2011/039634. The CcMan5 mannosidase is a family 92 glycoside hydrolase.

Demannosylation of an uncapped glycoprotein or molecular complexes of glycoproteins can be catalyzed using a mannosidase from *Aspergillus satoi* (As) (also known as *Aspergillus phoenicis*) or a mannosidase from *Cellulosimicrobium cellulans* (e.g., CcMan4). The *Aspergillus satoi* mannosidase is a family 47 glycoside hydrolase and the CcMan4 mannosidase is a family 92 glycoside hydrolase. The amino acid sequence of the *Aspergillus satoi* mannosidase is set forth in WO 2013/136189 as SEQ ID NO: 6 and in Genbank Accession No. BAA08634.1. The amino acid sequence of the CcMan4 polypeptide is set forth in FIG. 8 of WO 2013/136189.

Demannosylation of an uncapped glycoprotein or molecular complexes of glycoproteins also can be catalyzed using a mannosidase from the family 38 glycoside hydrolases such as a *Canavalia ensiformis* (Jack bean) mannosidase or a *Yarrowia lipolytica* mannosidase (e.g., AMS1). For example, CcMan5 can be used to uncap a mannose-1-phospho-6 mannose moiety on a glycoprotein (or molecular complex of glycoproteins) and the Jack bean mannosidase can be used to demannosylate the uncapped glycoprotein (or molecular complex of glycoproteins).

To produce demannosylated glycoproteins, or uncapped and demannosylated glycoproteins, a glycoprotein containing a mannose-1-phospho-6-mannose linkage or moiety is contacted under suitable conditions with a suitable mannosidase(s) and/or a cell lysate containing a suitable native or recombinantly produced mannosidase(s). Suitable mannosidases are described above. The cell lysate can be from any genetically engineered cell, including a fungal cell, a plant cell, or animal cell. Non-limiting examples of animal cells include nematode, insect, plant, bird, reptile, and mammals such as a mouse, rat, rabbit, hamster, gerbil, dog, cat, goat, pig, cow, horse, whale, monkey, or human.

Upon contacting the glycoprotein with the purified mannosidases and/or cell lysate, the mannose-1-phospho-6-mannose linkage or moiety can be hydrolyzed to phospho-6-mannose and the terminal alpha-1,2 mannose, alpha-1,3 mannose and/or (preferably "and") alpha-1,6 mannose linkage or moiety of such a phosphate containing glycan can be hydrolyzed to produce an uncapped and demannosylated glycoprotein. In some embodiments, one mannosidase is used that catalyzes both the uncapping and demannosylating steps. In some embodiments, one mannosidase is used to catalyze the uncapping step and a different mannosidase is used to catalyze the demannosylating step. Following processing by the mannosidase, the glycoprotein can be isolated.

Suitable methods for obtaining cell lysates that preserve the activity or integrity of the mannosidase activity in the lysate can include the use of appropriate buffers and/or inhibitors, including nuclease, protease and phosphatase inhibitors that preserve or minimize changes in N-glycosylation activities in the cell lysate. Such inhibitors include, for example, chelators such as ethylenediamine tetraacetic acid (EDTA), ethylene glycol-bis(P-aminoethyl ether) N,N,N', N'-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for obtaining lysates containing enzymatic activities are described in, e.g., Ausubel et al. Current Protocols in Molecular Biology (Supplement 47), John Wiley & Sons, New York (1999); Harlow and Lane, Antibodies: A Laboratory Manual Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999).

A cell lysate can be further processed to eliminate or minimize the presence of interfering substances, as appropriate. If desired, a cell lysate can be fractionated by a variety of methods well known to those skilled in the art, including subcellular fractionation, and chromatographic techniques such as ion exchange, hydrophobic and reverse phase, size exclusion, affinity, hydrophobic charge-induction chromatography, and the like.

In some embodiments, a cell lysate can be prepared in which whole cellular organelles remain intact and/or functional. For example, a lysate can contain one or more of intact rough endoplasmic reticulum, intact smooth endoplasmic reticulum, or intact Golgi apparatus. Suitable methods for preparing lysates containing intact cellular organelles and testing for the functionality of the organelles are described in, e.g., Moreau et al., 1991, J. Biol. Chem., 266(7):4329-4333; Moreau et al., 1991, J. Biol. Chem., 266(7):4322-4328; Rexach et al., 1991, J. Cell Biol., 114 (2):219-229; and Paulik et al., 1999, Arch. Biochem. Biophys. 367(2):265-273.

Upon contact of a mammalian cell with a glycoprotein containing uncapped and demannosylated phosphorylated N-glycans, the glycoprotein can be transported to the interior of the mammalian cell (e.g., a human cell). A glycoprotein having an uncapped, but not demannosylated, phosphorylated N-glycan does not substantially bind mannose-6-phosphate receptors on mammalian cells, and as such, is not efficiently transported to the interior of the cell. However, if such a glycoprotein is contacted with a mannosidase capable of hydrolyzing a terminal alpha-1,2 mannose linkage or moiety when the underlying mannose is phosphorylated, a demannosylated glycoprotein is produced that substantially binds to the mannose-6-phosphate receptor on the mammalian cells and is efficiently transported to the interior of the cell. It is understood that a preparation (e.g., a recombinant host cell or a cell-free preparation) containing an enzyme that uncaps but does not demannosylate phosphorylated N-glycans could be contaminated with an enzyme that demannosylates phosphorylated N-glycans. A glycoprotein sample after contact with such a preparation can contain protein molecules with some phosphorylated N-glycans that are uncapped only and others that are uncapped and demannosylated. Naturally those protein molecules containing uncapped and demannosylated phosphorylated N-glycans can substantially bind to mannose-6-phosphate receptors.

Thus, this document provides methods of converting a glycoprotein, in particular, human NAGAL polypeptide or functionally active variant or fragment thereof, from a first form that does not bind to a mannose-6-phosphate receptor on a mammalian cell to a second form that does bind to a mannose-6-phosphate receptor on a mammalian cell. In the first form, the glycoprotein comprises one or more N-glycans containing one or more mannose residues that are linked at the 1 position to a mannose residue that contains a phosphate residue at the 6 position. In such methods, the first form of the glycoprotein is contacted with a mannosidase that demannosylates the terminal mannose residues to result in the mannose containing the phosphate at the 6 position to become the terminal mannose. In some embodiments, the mannosidase has both uncapping and demannosylating activity (e.g., *Canavalia ensiformis* (Jack bean) or *Yarrowia lipolytica* (AMS1 mannosidase)). In some embodiments, the mannosidase does not have uncapping activity (e.g., a mannosidase from *Aspergillus satoi* or a mannosidase from *Cellulosimicrobium cellulans* (e.g., CcMan4)).

Transport of a glycoprotein to the interior of the cell can be assessed using a cell uptake assay. For example, mammalian cells and a glycoprotein containing uncapped and demannosylated phosphorylated N-glycans can be incubated, then the cells washed and lysed. Cell lysates can be assessed for the presence of the glycoprotein, in particular modified human NAGAL polypeptide or functionally active variant or fragment thereof, e.g., by Western blotting, or by activity of NAGAL or α-Gal A activity in the cell lysate. For example, uptake can be assessed in fibroblasts deficient in NAGAL or α-Gal A activity. Intracellular NAGAL activity can be assayed using MU-α-D-N-acetylgalactosamine as a substrate, as described elsewhere in this specification. Intracellular α-Gal A activity can be assayed using 4MU-α-Gal as a substrate, as described elsewhere in this specification.

The present inventors have realised that the human NAGAL polypeptide or functionally active variant or fragment thereof as taught herein can advantageously be used in therapy such as enzyme replacement therapy, for instance in the treatment of lysosomal storage diseases such as Fabry disease, and Schindler disease or Kanzaki disease, for which no other treatment options are available. The term "enzyme replacement therapy" broadly refers to medical treatment replacing an enzyme in subjects in whom that particular enzyme is deficient or absent.

Accordingly, a further aspect relates to the human NAGAL polypeptide or functionally active variant or fragment thereof as taught herein for use in therapy.

A further aspect relates to the human NAGAL polypeptide or functionally active variant or fragment thereof as taught herein, in particular wherein the human NAGAL polypeptide or functionally active variant or fragment thereof is further modified such as to acquire α-galactosidase activity, for use in a method of treating Fabry disease, or for use in the treatment (including throughout the present specification therapeutic and/or preventative measures) of Fabry disease. Such treatment may typically involve parenteral administration, preferably intravenous administration (e.g., infusion) of the human NAGAL polypeptide or functionally active variant or fragment thereof.

A related aspect thus provides the use of the human NAGAL polypeptide or functionally active variant or fragment thereof as taught herein, in particular wherein the human NAGAL polypeptide or functionally active variant or fragment thereof is further modified such as to acquire α-galactosidase activity, for the manufacture of a medicament for the treatment of Fabry disease. Such treatment may typically involve parenteral administration, preferably intravenous administration (e.g., infusion) of the human NAGAL polypeptide or functionally active variant or fragment thereof.

A related aspect provides a method of treating Fabry disease in a human subject in need of such treatment comprising administering to said subject a therapeutically effective amount of the human NAGAL polypeptide or functionally active variant or fragment thereof as taught herein, in particular wherein the human NAGAL polypeptide or functionally active variant or fragment thereof is further modified such as to acquire α-galactosidase activity. Such method of treatment may typically involve parenteral administration, preferably intravenous administration (e.g., infusion) of the human NAGAL polypeptide or functionally active variant or fragment thereof.

The terms "Fabry disease", "Fabry's disease", "Anderson-Fabry disease", "angiokeratoma corporis diffusum", and "alpha-galactosidase A deficiency" can be used interchangeably and refer to a rare genetic lysosomal storage disease, inherited in an X-linked manner, caused by a deficiency in the lysosomal enzyme α-galactosidase A (α-Gal A). The enzyme α-Gal A cleaves terminal α-D-galactose residues from glycolipids. The α-Gal A deficiency results in a systemic and lifetime lysosomal accumulation of glycosphingolipids, primarily globotriaosylceramide (Gb3), in the vascular endothelium and other tissues. This leads to a multiorgan pathology that mostly affects the kidneys, the heart, and the cerebrovascular system. Patients with Fabry disease suffer from a plethora of symptoms including gastro-intestinal diseases, pain, stroke, and cardiac and renal defects, and often die prematurely of complications from strokes, heart disease, or renal failure. Signs and symptoms that can provide for a presumptive diagnosis of Fabry disease include angiokeratomas and corneal verticillata. Taking a family history, noting other family members with symptoms such as early renal disease, early stroke, and early cardiac problems, may provide further support. Definitive diagnosis can be made in males by testing for deficient α-galactosidase A (α-Gal A) enzyme activity in a biological sample, such as plasma, leukocytes, cultured skin fibroblasts, biopsied tissue, or dried blood. In females, mutation or linkage analysis can identify heterozygous mutation carriers. Many female carriers (with or without symptoms) have below-normal levels of α-Gal A activity and/or characteristic corneal opacities.

Another aspect relates to the human NAGAL polypeptide or functionally active variant or fragment thereof as taught herein, for use in a method of treating Schindler disease or Kanzaki disease, or for use in the treatment (including throughout the present specification therapeutic and/or preventative measures) of Schindler disease or Kanzaki disease. Such treatment may typically involve parenteral administration, preferably intravenous administration (e.g., infusion) of the human NAGAL polypeptide or functionally active variant or fragment thereof.

A related aspect thus provides a use of the human NAGAL polypeptide or functionally active variant or fragment thereof as taught herein for the manufacture of a medicament for the treatment of Schindler disease or Kanzaki disease. Such treatment may typically involve parenteral administration, preferably intravenous administration (e.g., infusion) of the human NAGAL polypeptide or functionally active variant or fragment thereof.

A related aspect provides a method of treating Schindler disease or Kanzaki disease in a human subject in need of such treatment comprising administering to said subject a therapeutically effective amount of the human NAGAL polypeptide or functionally active variant or fragment thereof as taught herein. Such method of treatment may typically involve parenteral administration, preferably intravenous administration (e.g., infusion) of the human NAGAL polypeptide or functionally active variant or fragment thereof.

The terms "Schindler disease", "Kanzaki disease", and "alpha-N-acetylgalactosaminidase deficiency" can be used interchangeably and refer to a rare congenital lysosomal storage disorder caused by a deficiency in the enzyme alpha-N-acetylgalactosaminidase (NAGAL). The deficiency in the enzyme alpha-N-acetylgalactosaminidase is attributable to mutations in the NAGA gene on chromosome 22, which leads to excessive lysosomal accumulation of glycoproteins. A deficiency of the NAGAL enzyme leads to an accumulation of glycosphingolipids throughout the body. There are three main types of the disease (i.e., Type I infantile form, Type II adult form, and Type III) each with its own distinctive symptoms.

Except when noted, "subject" or "patient" are used interchangeably and refer to animals, preferably warm-blooded animals, more preferably vertebrates, even more preferably mammals, still more preferably primates, and specifically includes human patients and non-human mammals and primates. Preferred patients are human subjects.

The term "mammal" includes any animal classified as such, including, but not limited to, humans, domestic and farm animals, zoo animals, sport animals, pet animals, companion animals and experimental animals, such as, for example, mice, rats, hamsters, rabbits, dogs, cats, guinea pigs, gerbils, cattle, cows, sheep, horses, pigs and primates, e.g., monkeys and apes (e.g., chimpanzee, baboon, or monkey). Particularly preferred are human subjects, including both genders and all age categories thereof.

The term "diseased subject" as used herein refers to a subject diagnosed with or having Fabry disease, or to a subject diagnosed with or having Schindler disease or Kanzaki disease. As used herein, a phrase such as "a subject in need of treatment" includes subjects that would benefit from treatment of a given condition, particularly Fabry disease, or Schindler disease or Kanzaki disease. Such subjects may include, without limitation, those that have been diagnosed with said condition, those prone to develop said condition (e.g., due to a mutation in the gene encoding α-Gal A (Fabry disease) or NAGAL (Schindler disease or Kanzaki disease)) and/or those in whom said condition is to be prevented.

The terms "treat" or "treatment" encompass both the therapeutic treatment of an already developed disease or condition, such as the therapy of an already developed Fabry disease, or Schindler disease or Kanzaki disease, as well as prophylactic or preventive measures, wherein the aim is to prevent or lessen the chances of incidence of an undesired affliction, such as to prevent occurrence, development and progression of Fabry disease, or Schindler disease or Kanzaki disease. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The term "prophylactically effective amount" refers to an amount of an active compound or pharmaceutical agent that inhibits or delays in a subject the onset of a disorder as being sought by a researcher, veterinarian, medical doctor or other clinician. The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or condition being treated. Methods are known in the art for determining therapeutically and prophylactically effective doses for the pharmaceutical formulation as taught herein.

The dosage or amount of the human NAGAL polypeptide or functionally active variant or fragment thereof as taught herein, optionally in combination with one or more other active compounds to be administered, depends on the individual case and is, as is customary, to be adapted to the individual circumstances to achieve an optimum effect. Thus, the unit dose and regimen depend on the nature and the severity of the disorder to be treated, and also on factors such as the species of the subject, the sex, age, body weight, general health, diet, mode and time of administration, immune status, and individual responsiveness of the human or animal to be treated, efficacy, metabolic stability and duration of action of the compounds used, on whether the therapy is acute or chronic or prophylactic, or on whether other active compounds are administered in addition to the agent(s) of the invention. In order to optimize therapeutic efficacy, human NAGAL polypeptide or functionally active variant or fragment thereof as described herein can be first administered at different dosing regimens. Typically, levels of the human NAGAL polypeptide or functionally active variant or fragment thereof in a tissue can be monitored using appropriate screening assays as part of a clinical testing procedure, e.g., to determine the efficacy of a given treatment regimen. The frequency of dosing is within the skills and clinical judgement of medical practitioners (e.g., doctors or nurses). Typically, the administration regime is established by clinical trials which may establish optimal administration parameters. However, the practitioner may vary such administration regimes according to the one or more of the aforementioned factors, e.g., subject's age, health, weight, sex and medical status. The frequency of dosing can be varied depending on whether the treatment is prophylactic or therapeutic.

Toxicity and therapeutic efficacy of human NAGAL polypeptide or functionally active variant or fragment thereof, as described herein, or pharmaceutical compositions comprising the same can be determined by known pharmaceutical procedures in, for example, cell cultures or experimental animals. These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Pharmaceutical compositions that exhibit high therapeutic indices are preferred. While pharmaceutical compositions that exhibit toxic side effects can be used, care should be taken to design a delivery system that targets such compounds to the site of affected tissue in order to minimize potential damage to normal cells (e.g., non-target cells) and, thereby, reduce side effects.

The data obtained from the cell culture assays and animal studies can be used in formulating a range of dosage for use in appropriate subjects (e.g., human patients). The dosage of such pharmaceutical compositions lies generally within a range of circulating concentrations that include the $ED_{50}$ with little or no toxicity. The dosage may vary within this range depending upon the dosage form employed and the route of administration utilized. For a pharmaceutical composition used as described herein, the therapeutically effective dose can be estimated initially from cell culture assays. A dose can be formulated in animal models to achieve a circulating plasma concentration range that includes the IC50 (i.e., the concentration of the pharmaceutical composition which achieves a half-maximal inhibition of symptoms) as determined in cell culture. Such information can be used to more accurately determine useful doses in humans. Levels in plasma can be measured, for example, by high performance liquid chromatography.

Without limitation, depending on the type and severity of the disease, a typical dosage (e.g., a typical daily dosage or a typical intermittent dosage, e.g., a typical dosage for every two days, every three days, every four days, every five days, every six days, every week, every 1.5 weeks, every two weeks, every three weeks, every month, or other) of the human NAGAL polypeptide or functionally active variant or fragment thereof as taught herein may range from about 10 µg/kg to about 100 mg/kg body weight of the subject, per dose, depending on the factors mentioned above, e.g., may range from about 100 µg/kg to about 10 mg/kg body weight of the subject, per dose, or from about 200 µg/kg to about 2 mg/kg body weight of the subject, per dose, e.g., may be about 100 µg/kg, about 200 µg/kg, about 300 µg/kg, about 400 µg/kg, about 500 µg/kg, about 600 µg/kg, about 700 µg/kg, about 800 µg/kg, about 900 µg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, or about 2.0 mg/kg body weight of the subject, per dose, daily or intermittently, preferably intermittently, more preferably every week, even more preferably every other week, yet more preferably every month or even less frequently. By means of example and without limitation, the human NAGAL may be administered at about 0.5 mg/kg, or at about 0.6 mg/kg, or at about 0.7 mg/kg, or at about 0.8 mg/kg, or at about 0.9 mg/kg, or at about 1.0 mg/kg, or at about 1.5 mg/kg, or at about 2.0 mg/kg, or at about 2.5 mg/kg, or at about 3.0 mg/kg, or at about 3.5 mg/kg, or at about 4.0 mg/kg, e.g., at about 0.6-0.8 mg/kg or at about 3-4 mg/kg, preferably bi-weekly.

A further aspect relates to a pharmaceutical composition comprising the human NAGAL polypeptide or functionally active variant or fragment thereof as taught herein. A further aspect provides a pharmaceutical composition comprising the nucleic acid molecule as defined herein or the expression cassette or expression vector as defined herein.

The terms "pharmaceutical composition" and "pharmaceutical formulation" may be used interchangeably. The pharmaceutical formulations as taught herein may comprise in addition to the herein particularly specified components one or more pharmaceutically acceptable excipients. Suitable pharmaceutical excipients depend on the dosage form and identities of the active ingredients and can be selected by the skilled person (e.g., by reference to the Handbook of Pharmaceutical Excipients $7^{th}$ Edition 2012, eds. Rowe et al.). As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. Acceptable diluents, carriers and excipients typically do not adversely affect a recipient's homeostasis (e.g., electrolyte balance). The use of such media and agents for pharmaceutical active substances is well known in the art. Such materials should be non-toxic and should not interfere with the activity of the human NAGAL polypeptide or functionally active variant or fragment thereof. Acceptable carriers may include biocompatible, inert or bioabsorbable salts, buffering agents, oligo- or polysaccharides, polymers, viscosity-improving agents, preservatives and the like. One exemplary carrier is physiologic saline (0.15 M NaCl, pH 7.0 to 7.4). Another exemplary carrier is 50 mM sodium phosphate, 100 mM sodium chloride.

The precise nature of the carrier or other material will depend on the route of administration. For example, the pharmaceutical composition may be in the form of a parenterally acceptable aqueous solution, which is pyrogen-free and has suitable pH, isotonicity and stability.

The pharmaceutical formulations may comprise pharmaceutically acceptable auxiliary substances as required to approximate physiological conditions, such as pH adjusting and buffering agents, preservatives, complexing agents, tonicity adjusting agents, wetting agents and the like, for example, sodium acetate, sodium lactate, sodium phosphate, sodium hydroxide, hydrogen chloride, benzyl alcohol, parabens, EDTA, sodium oleate, sodium chloride, potassium chloride, calcium chloride, sorbitan monolaurate, triethanolamine oleate, etc. Preferably, the pH value of the pharmaceutical formulation is in the physiological pH range, such as particularly the pH of the formulation is between about 5 and about 9.5, more preferably between about 6 and about 8.5, even more preferably between about 7 and about 7.5. The preparation of such pharmaceutical formulations is within the ordinary skill of a person skilled in the art.

Administration of the pharmaceutical composition can be systemic or local. Pharmaceutical compositions can be formulated such that they are suitable for parenteral and/or non-parenteral administration. Specific administration modalities include subcutaneous, intravenous, intramuscular, intraperitoneal, transdermal, intrathecal, oral, rectal, buccal, topical, nasal, ophthalmic, intra-articular, intra-arterial, sub-arachnoid, bronchial, lymphatic, vaginal, and intra-uterine administration.

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted host cells). Administration of a pharmaceutical composition can be achieved using suitable delivery means such as: a pump, microencapsulation, continuous release polymer implants, macroencapsulation, injection, either subcutaneously, intravenously, intra-arterially, intramuscularly, or to other suitable site, or oral administration, in capsule, liquid, tablet, pill, or prolonged release formulation.

Examples of parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch.

Formulations suitable for parenteral administration conveniently contain a sterile aqueous preparation of the human NAGAL polypeptide or functionally active variant or fragment thereof, which preferably is isotonic with the blood of the recipient (e.g., physiological saline solution). Formulations can be presented in unit-dose or multi-dose form.

Formulations suitable for oral administration can be presented as discrete units such as capsules, cachets, tablets, or lozenges, each containing a predetermined amount of the human NAGAL polypeptide or functionally active variant or fragment thereof, or a suspension in an aqueous liquor or a non-aqueous liquid, such as a syrup, an elixir, an emulsion, or a draught.

Formulations suitable for topical administration can be presented as, e.g., a cream, a spray, a foam, a gel, an ointment, a salve, or a dry rub. A dry rub can be rehydrated at the site of administration. Such formulations can also be infused directly into (e.g., soaked into and dried) a bandage, gauze, or patch, which can then be applied topically. Such formulations can also be maintained in a semi-liquid, gelled, or fully-liquid state in a bandage, gauze, or patch for topical administration.

Typically, ERT may be performed by giving the patient an intravenous (IV) injection or infusion containing the enzyme. In certain embodiments, the pharmaceutical composition as taught herein may thus be configured for parenteral administration, such as parenteral infusion or injection. Preferably, the pharmaceutical composition as taught herein may be configured for intravenous administration, such as intravenous infusion.

In certain embodiments, the human NAGAL polypeptide or functionally active variant or fragment thereof may be lyophilised. Any of the pharmaceutical compositions described herein can be included in a container, pack, or dispenser together with instructions for administration. In some embodiments, the composition is packaged as a single use vial.

Further, there are several well-known methods of introducing nucleic acids into animal cells, any of which may be used herein. At the simplest, the nucleic acid can be directly injected into the target cell/target tissue. Other methods include fusion of the recipient cell with bacterial protoplasts containing the nucleic acid, the use of compositions like calcium chloride, rubidium chloride, lithium chloride, calcium phosphate, DEAE dextran, cationic lipids or liposomes or methods like receptor-mediated endocytosis, biolistic particle bombardment ("gene gun" method), infection with viral vectors, for example such as taught herein, electroporation, and the like. Other techniques or methods which are suitable for delivering nucleic acid molecules to target cells include the continuous delivery of an NA molecule from poly (lactic-Co-Glycolic Acid) polymeric microspheres or the direct injection of protected (stabilized) NA molecule(s) into micropumps delivering the product. Another possibility is the use of implantable drug-releasing biodegradable microspheres. Also envisaged is encapsulation of NA in various types of liposomes (immunoliposomes, PEGylated (immuno) liposomes), cationic lipids and polymers, nanoparticles or dendrimers, poly (lactic-Co-Glycolic Acid) polymeric microspheres, implantable drug-releasing biodegradable microspheres, etc; and co-injection of NA with protective agent like the nuclease inhibitor aurintricarboxylic acid. It shall be clear that also a combination of different above-mentioned delivery modes or methods may be used.

A preferred method of intracellular delivery of nucleic acids may include infection with viral vectors as taught herein. In such method, a recombinant viral vector as taught herein, is brought in contact with a host cell, such as introduced (e.g., locally or systemically) to a host organism, and incubated at conditions favourable to viral infection and hence, makes use of the natural ability of a virus to infect a cell. For example, a retrovirus obtains entry to a host cell via the interaction of a retroviral protein with a transmembrane protein acting as a receptor on the surface of the host cell. Another approach of viral vector-mediated delivery of nucleic acids may encompass a physical cell entry-based technique, such as for example the use of ultrasound and microbubbles, in combination with viral vector-mediated delivery as described in WO 2006/129080.

Further ways of delivery of nucleic acids may employ previously published methods. For example, intracellular delivery of the nucleic acids may be via a composition comprising an admixture of the nucleic acid molecule and an effective amount of a block copolymer. An example of this method is described in US 2004/0248833.

Other methods of delivery of nucleic acids to the nucleus are described in Mann et al. 2001 (Proc Natl Acad Science 98(1): 42-47) and in Gebski et al. 2003 (Human Molecular Genetics 12(15): 1801-1811).

A method for introducing a nucleic acid molecule into a cell by way of an expression vector either as naked DNA or complexed to lipid carriers, is described in U.S. Pat. No. 6,806,084.

It may be desirable to deliver a nucleic acid molecule in a colloidal dispersion system. Colloidal dispersion systems include macromolecule complexes, nanocapsules, microspheres, beads, and lipid-based systems including oil-in-water emulsions, micelles, mixed micelles, and liposomes or liposome formulations. Liposomes are artificial membrane vesicles which are useful as delivery vehicles in vitro and in vivo. These formulations may have net cationic, anionic or neutral charge characteristics and are useful characteristics with in vitro, in vivo and ex vivo delivery methods. It has been shown that large unilamellar vesicles (LUV), which range in size from 0.2-4.0 PHI.m can encapsulate a substantial percentage of an aqueous buffer containing large macromolecules. RNA, and DNA can be encapsulated within the aqueous interior and be delivered to cells in a biologically active form (Fraley et al. 1981 (Trends Biochem ScL 6: 77).

In order for a liposome to be an efficient gene transfer vehicle, the following characteristics should be present: (1) encapsulation of the nucleic acid molecule of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al. 1988 (Biotechniques 6: 682).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Alternatively, the nucleic acid molecule may be combined with other pharmaceutically acceptable carriers or diluents to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration.

The routes of administration described are intended only as a guide since a skilled practitioner will be able to determine readily the optimum route of administration and any dosage for any particular animal and condition. Multiple approaches for introducing functional new genetic material into cells, both in vitro and in vivo have been attempted (Friedmann 1989 (Science 244: 1275-1280)). These approaches include integration of the gene to be expressed into modified retroviruses (Friedmann 1989, supra; Rosenberg 1991(Cancer Research 51(18), suppl.: 5074S-5079S)); integration into non-retrovirus vectors (Rosenfeld et al. 1992 (Cell 68: 143-155); Rosenfeld et al. 1991 (Science 252: 431-434)); or delivery of a transgene linked to a heterologous promoter-enhancer element via liposomes (Friedmann 1989, supra; Brigham et al. 1989 (Am J Med Sci 298: 278-281); Nabel et al. 1990 (Science 249: 1285-1288); Hazinski et al. 1991 (Am J Resp Cell Molec Biol 4: 206-209); and Wang and Huang 1987 (Proc Natl Acad Sci USA, 84: 7851-7855); coupled to ligand-specific, citation-based transport systems (Wu and Wu 1988 (J Biol Chem 263: 14621-14624)) or the use of naked DNA, expression vectors (Nabel et al. 1990, supra); Wolff et al. 1990 (Science 247: 1465-1468)). Direct injection of transgenes into tissue produces only localized expression (Rosenfeld 1992, supra; Rosenfeld et al. 1991, supra; Brigham et al. 1989, supra; Nabel et al. 1990, supra; and Hazinski et al. 1991, supra). The Brigham et al. group (Am J Med Sci 298: 278-281 (1989) and Clinical Research 39 (abstract) (1991)) have reported in vivo transfection only of lungs of mice following either intravenous or intratracheal administration of a DNA liposome complex. An example of a review article of human gene therapy procedures is: Anderson 1992 (Science 256: 808-813).

In certain embodiments, the human NAGAL polypeptide or functionally active variant or fragment thereof as taught herein may be used alone or in combination with (i.e., combination therapy) one or more active compounds that are suitable in the treatment of a Fabry disease, or in the treatment of Schindler disease or Kanzaki disease. The one or more active compounds can be administered before, after, or simultaneously with the administration of the human NAGAL polypeptide or functionally active variant or fragment thereof as taught herein.

The recitations "active compound" or "active pharmaceutical ingredient" refer in this context to a substance or composition other than the human NAGAL polypeptide or functionally active variant or fragment thereof as taught herein. The term "active" in the recitations "active compound" or "active pharmaceutical ingredient" refers to "pharmacologically active".

By means of example, such other therapy may be another enzyme replacement therapy, such as in case of Fabry disease, a recombinant α-Gal A protein, e.g., agalsidase alpha (Replagal®: Shire Human Genetic Therapies, Dublin, Ireland) or agalsidase beta (Fabrazyme®: Genzyme Corporation—a Sanofi company, Cambridge, USA). By means of another example, such other therapy may be symptomatic therapy, e.g., anticonvulsants such as phenytoin and carbamazepine for treating pain, metoclopramide for treating gastrointestinal hyperactivity, and/or dialysis or kidney transplantation.

A further aspect relates to a nucleic acid molecule comprising a nucleic acid sequence encoding the human NAGAL polypeptide or functionally active variant or fragment thereof as taught herein.

By "encoding" is particularly meant that a nucleic acid sequence or part(s) thereof corresponds to another nucleic acid sequence in a template—transcription product (e.g., RNA or RNA analogue) relationship, or corresponds, by virtue of the genetic code of an organism in question, to a particular amino acid sequence, e.g., the amino acid sequence of one or more desired proteins or polypeptides.

In certain embodiments, the nucleic acid molecule may be codon optimized for expression of the human NAGAL polypeptide or functionally active variant or fragment thereof in a host cell. For example in a bacterial cell, a fungal cell, including yeast cells, an animal cell, or a mammalian cell, including human cells and non-human mammalian cells. Preferably, the nucleic acid molecule is codon optimized for expression of the human NAGAL polypeptide or functionally active variant or fragment thereof in a fungal cell, more preferably in *Yarrowia lipolytica* or *Arxula adeninivorans*.

In certain embodiments, the nucleic acid molecule may further comprise a CACA nucleotide sequence before the start codon of the human NAGAL nucleotide sequence.

A further aspect relates to an expression cassette or an expression vector comprising the nucleic acid molecule as defined herein and a promoter operably linked to the nucleic acid molecule.

Preferably, the expression cassette or expression vector may be configured to effect expression of the human NAGAL polypeptide or functionally active variant or fragment thereof in a host cell. For example, in a bacterial cell, a fungal cell, including yeast cells, an animal cell, or a mammalian cell, including human cells and non-human mammalian cells. Preferably, the expression cassette or expression vector is configured to effect expression of the human NAGAL polypeptide or functionally active variant or fragment thereof in a fungal cell, more preferably in *Yarrowia lipolytica* or *Arxula adeninivorans*.

The terms "expression vector" or "vector" as used herein refers to nucleic acid molecules, typically DNA, to which nucleic acid fragments, preferably the recombinant nucleic acid molecule as defined herein, may be inserted and cloned, i.e., propagated. Hence, a vector will typically contain one or more unique restriction sites, and may be capable of autonomous replication in a defined host cell or vehicle organism such that the cloned sequence is reproducible. A vector may also preferably contain a selection marker, such as, e.g., an antibiotic resistance gene, to allow selection of recipient cells that contain the vector. Vectors may include, without limitation, plasmids, phagemids, bacteriophages, bacteriophage-derived vectors, PAC, BAC, linear nucleic acids, e.g., linear DNA, viral vectors, etc., as appropriate (see, e.g., Sambrook et al., 1989; Ausubel 1992). Expression vectors are generally configured to allow for and/or effect the expression of nucleic acids or ORFs introduced thereto in a desired expression system, e.g., in vitro, in a host cell, host organ and/or host organism. For example, expression vectors may advantageously comprise suitable regulatory sequences.

Factors of importance in selecting a particular vector include inter alia: choice of recipient host cell, ease with which recipient cells that contain the vector may be recognised and selected from those recipient cells which do not contain the vector; the number of copies of the vector which are desired in particular recipient cells; whether it is desired for the vector to integrate into the chromosome or to remain extra-chromosomal in the recipient cells; and whether it is desirable to be able to "shuttle" the vector between recipient cells of different species.

Expression vectors can be autonomous or integrative. A recombinant nucleic acid can be in introduced into the host cell in the form of an expression vector such as a plasmid, phage, transposon, cosmid or virus particle. The recombinant nucleic acid can be maintained extrachromosomally or it can be integrated into the cell chromosomal DNA. Expression vectors can contain selection marker genes encoding proteins required for cell viability under selected conditions (e.g., URA3, which encodes an enzyme necessary for uracil biosynthesis or TRP1, which encodes an enzyme required for tryptophan biosynthesis) to permit detection and/or selection of those cells transformed with the desired nucleic acids. Expression vectors can also include an autonomous replication sequence (ARS).

Integrative vectors generally include a serially arranged sequence of at least a first insertable DNA fragment, a selectable marker gene, and a second insertable DNA fragment. The first and second insertable DNA fragments are each about 200 (e.g., about 250, about 300, about 350, about 400, about 450, about 500, or about 1000 or more) nucleotides in length and have nucleotide sequences which are homologous to portions of the genomic DNA of the host cell species to be transformed. A nucleotide sequence containing a gene of interest for expression is inserted in this vector between the first and second insertable DNA fragments, whether before or after the marker gene. Integrative vectors can be linearized prior to transformation to facilitate the integration of the nucleotide sequence of interest into the host cell genome.

As used herein, the term "promoter" refers to a DNA sequence that enables a gene to be transcribed. A promoter is recognized by RNA polymerase, which then initiates transcription. Thus, a promoter contains a DNA sequence that is either bound directly by, or is involved in the recruitment, of RNA polymerase. A promoter sequence can also include "enhancer regions", which are one or more regions of DNA that can be bound with proteins (namely the trans-acting factors) to enhance transcription levels of genes in a gene-cluster. The enhancer, while typically at the 5' end of a coding region, can also be separate from a promoter sequence, e.g., can be within an intronic region of a gene or 3' to the coding region of the gene.

An "operable linkage" is a linkage in which regulatory sequences and sequences sought to be expressed are connected in such a way as to permit said expression. For example, sequences, such as, e.g., a promoter and an ORF, may be said to be operably linked if the nature of the linkage between said sequences does not: (1) result in the introduction of a frame-shift mutation, (2) interfere with the ability of the promoter to direct the transcription of the ORF, (3) interfere with the ability of the ORF to be transcribed from the promoter sequence. Hence, "operably linked" may mean incorporated into a genetic construct so that expression control sequences, such as a promoter, effectively control expression of a coding sequence of interest, such as the nucleic acid molecule as defined herein.

The promotor may be a constitutive or inducible (conditional) promoter. A constitutive promoter is understood to be a promoter whose expression is constant under the standard culturing conditions. Inducible promoters are promoters that are responsive to one or more induction cues. For example, an inducible promoter can be chemically regulated (e.g., a promoter whose transcriptional activity is regulated by the presence or absence of a chemical inducing agent such as an alcohol, tetracycline, a steroid, a metal, or other small molecule) or physically regulated (e.g., a promoter whose transcriptional activity is regulated by the presence or absence of a physical inducer such as light or high or low temperatures). An inducible promoter can also be indirectly regulated by one or more transcription factors that are themselves directly regulated by chemical or physical cues.

For example, the promoter may be a promoter for expression in a fungal cell, such as a *Yarrowia lipolytica* cell, e.g., a promoter from a suitable fungal species, such as *Yarrowia lipolytica, Arxula adeninivorans, P. pastoris*, or other suitable fungal species. Suitable fungal or yeast promoters include, e.g., ADC1, TPI1, ADH2, hp4d, TEF1, POX2, or Gal10 promoter. Preferably, the promoter is hp4d or POX2. More preferably, the promoter is hp4d. See, e.g., Guarente et al., 1982, Proc. Natl. Acad. Sci. USA 79(23):7410; Zhu and Zhang, 1999, Bioinformatics 15(7-8):608-611; or U.S. Pat. No. 6,265,185.

A recombinant nucleic acid can be introduced into a host cell using a variety of methods such as the spheroplast technique or the whole-cell lithium chloride yeast transformation method. Other methods useful for transformation of plasmids or linear nucleic acid vectors into cells are described in, for example, U.S. Pat. No. 4,929,555; Hinnen et al., 1978, Proc. Nat. Acad. Sci. USA, 75:1929; Ito et al., 1983, J. Bacteriol., 153:163; U.S. Pat. No. 4,879,231; and Sreekrishna et al., 1987, Gene, 59:115. Electroporation and PEG1000 whole cell transformation procedures may also be used, as described by Cregg and Russel, Methods in Molecular Biology: Pichia Protocols, Chapter 3, Humana Press, Totowa, N.J., pp. 27-39 (1998).

Transformed fungal cells can be selected for by using appropriate techniques including, but not limited to, culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by, e.g., Southern blot or PCR analysis.

Prior to introducing the vectors into a target cell of interest, the vectors can be grown (e.g., amplified) in bacterial cells such as *Escherichia coli* (*E. coli*). The vector DNA can be isolated from bacterial cells by any of the methods known in the art which result in the purification of vector DNA from the bacterial milieu. The purified vector DNA can be extracted extensively with phenol, chloroform, and ether, to ensure that no *E. coli* proteins are present in the plasmid DNA preparation, since these proteins can be toxic to mammalian cells.

It is understood that any genetically engineered modification as intended herein can also be conditional. For example, a gene can be conditionally deleted using, e.g., a site-specific DNA recombinase such as the Cre-loxP system (see, e.g., Gossen et al., 2002, Aim. Rev. Genetics, 36:153-173 and U.S. 20060014264).

The expression vector or cassette may further comprise one or more selection markers, including any one or more genes needed for the production of leucine (e.g. LEU2), uracil (e.g. URA3), adenine (e.g. ADE2), Lysine (e.g. LYS5), Arginine, Tryptophan, or for glycerol utilization (Gut), and the hygromycin B phosphotransferase (hph) markers.

The expression vector or expression cassette may be integrated into the genome of the host cell. For example, the expression vector or expression cassette may comprise a zeta element such as a long terminal repeat of a retrotransposon, such as without limitation, a Ylt1 or Tyl6 retrotransposon or others known to those skilled in the art. In one embodiment of the invention, the integration is targeted integration.

Alternatively, the expression vector or expression cassette may be replicative rather than integrated. For example, the replicative expression vector or expression cassette may comprise one or more autosomal replication sequences (ARS). The ARS may comprise a centromere (CEN) and an origin of replication (ORI). For example, the ARS may be ARS18 or ARS68.

A further aspect provides the nucleic acid molecule as defined above or the expression cassette or expression vector as defined above, for use in therapy.

Preferably, the therapy may be gene therapy or mRNA therapy.

The general principles of gene therapy and mRNA therapy, more particularly as applied to Enzyme Replacement Treatment (ERT) of inter alia Lysosomal Storage Diseases (LSDs), are well developed in the art.

In general, the term "gene therapy" refers to the treatment or prevention of a condition, such as LSD, by means of ex vivo or in vivo delivery, through viral or non-viral vectors, of a composition containing genetic material, such as a nucleic acid molecule or an expression cassette or expression vector encoding a therapeutic product of interest, e.g., the nucleic acid molecule or the expression cassette or expression vector encoding the human NAGAL polypeptide or functionally active variant or fragment thereof as taught herein.

In certain embodiments, the delivered recombinant genetic material may comprise, consist essentially of or consist of DNA encoding the therapeutic product of interest, whereby the cellular transcription and translation machineries are employed to produce the therapeutic product of interest in the target cells.

In certain other embodiments, the delivered genetic material may comprise, consist essentially of or consist of RNA, more particularly messenger RNA (mRNA) encoding the therapeutic product of interest, whereby the mRNA can be directly translated by the target cell's translation machinery to produce the therapeutic product of interest ("mRNA therapy").

The term "ex vivo" delivery in this context denotes the introduction, outside of the body of a subject such as human, of a composition containing the genetic material into a cell, tissue, organoid, organ, or the like, followed by the administration of the cell, tissue, organoid, organ, or the like which contains such introduced composition into the body of the same (autologous) or a different (allogeneic) subject, without limitation as to the formulation, site or route of administration.

Advantageously, for the treatment of LSD by ERT as envisaged herein, the nucleic acid molecule (e.g., DNA or mRNA) or the expression cassette or expression vector as taught herein may be delivered to the liver of a subject, more particularly to parenchymal liver cells of the subject, even more particularly to hepatocytes of the subject. Preferably, when so delivered, the therapeutic product of interest, e.g., the human NAGAL polypeptide or functionally active variant or fragment thereof as taught herein, may be targeted for secretion by the liver cells, e.g., by inclusion of a suitable secretion signal in the sequence of the polypeptide. Hereby, the liver cells containing the nucleic acid molecule or the expression cassette or expression vector as taught herein produce and secrete the therapeutic product of interest, which is released into the blood stream of the subject and thus delivered to and taken up by cells, tissues and organs other than the liver, where it can exert a prophylactic or therapeutic effect.

The administration of the nucleic acid molecule (e.g., DNA or mRNA) or the expression cassette or expression vector as taught herein may be repeated as necessary, e.g., based on the level of the therapeutic product of interest detected in the bloodstream of the subject. By means of an example, for mRNA therapy, the administration may be repeated about every 2 weeks, or about every 3 weeks, or about every 4, 5, 6, 7 or 8 weeks.

Without limitation, suitable vectors for use in gene therapy may include viral vectors, which are well known and include vectors derived from for example, but without limitation, retroviruses, vaccinia viruses, poxviruses, adenoviruses, and adeno-associated viruses (AAV). Such viral vectors may be engineered by recombinant techniques as known per se to introduce thereto nucleic acid sequence(s) disclosed herein.

For example, a retroviral vector may be used herein. Generally, retroviral vectors may comprise the retroviral genomic sequences encoding components necessary for the integration of the recombinant viral genome (randomly) into the host cell genome and the nucleic acid sequence(s) of interest. Such retroviral vectors may be readily constructed using standard recombinant techniques (e.g., Sambrook et al., Molecular Cloning: A Laboratory Manual, 2d ed., Cold Spring Harbor Laboratory Press, 1989) from a wide variety of retroviruses, including for example, B, C, and D type retroviruses as well as spumaviruses and lentiviruses (see RNA Tumor Viruses, Second Edition, Cold Spring Harbor Laboratory, 1985).

Recombinant adenoviral vectors may also be contemplated for delivery and expression of nucleic acid sequence(s) of interest in a host cell. Adenovirus-based viral vectors have the advantage of being capable of infecting non-dividing host cells, but the recombinant viral genome is not integrated into the host cell genome. For example, a suitable adenoviral vector, a method for constructing a recombinant adenoviral vector thereof, and a method for delivering the recombinant vector into host cells, are described in Xia H et al. (2002) (Nat. Biotech. 20: 1006-1010). Use of recombinant AAV (rAAV) vectors is also contemplated herein. rAAV vectors can infect both dividing and non-dividing cells and may incorporate its recombinant viral genome into that of the host cell. rAAV vectors may be generated from a variety of adeno-associated viruses, including for example, serotypes 1 through 6. Generally, rAAV vectors may comprise, in order, a 5' adeno-associated virus inverted terminal repeat (ITR), a nucleic acid of interest, operatively linked to a sequence which regulates its expression in a host cell or host organism, and a 3' adeno-associated virus ITR. In addition, the rAAV vector may preferably have a polyadenylation signal. Suitable rAAV vectors are described inter alia in WO 1994/13788, WO 1993/24641, and in Goyenvalle et al. 2004 (Science 306: 1796-1799).

Other preferred viral vectors for use herein are vectors derived from a pox virus such as a vaccinia virus, for example an attenuated vaccinia virus such as Modified Virus Ankara (MVA) or NYVAC, an avipox virus such as fowl pox virus or canary pox virus.

Hence, also provided is the nucleic acid molecule as defined herein or the expression cassette or expression vector as defined herein encoding the human NAGAL polypeptide or functionally active variant or fragment thereof as taught herein, for use in a method of treating Fabry disease. Preferably, the therapy may be gene therapy or mRNA therapy.

Further provided is the nucleic acid molecule as defined herein or the expression cassette or expression vector as defined herein encoding the human NAGAL polypeptide or functionally active variant or fragment thereof as taught herein for use in a method of treating Schindler disease or Kanzaki disease. Preferably, the therapy may be gene therapy method or mRNA therapy.

Further provided is a method of treating Fabry disease in a human subject in need of such treatment comprising administering to said subject a therapeutically effective amount of the nucleic acid molecule as defined herein or the expression cassette or expression vector as defined herein encoding the human NAGAL polypeptide or functionally active variant or fragment thereof as taught herein. Preferably, the therapy may be gene therapy method or mRNA therapy.

Also provided is a method of treating Schindler disease or Kanzaki disease in a human subject in need of such treatment comprising administering to said subject a therapeutically effective amount of the nucleic acid molecule as defined herein or the expression cassette or expression vector as defined herein encoding the human NAGAL polypeptide or functionally active variant or fragment thereof as taught herein. Preferably, the therapy may be gene therapy method or mRNA therapy.

A further aspect relates to a host cell comprising the nucleic acid molecule as defined herein or the expression cassette or expression vector as defined herein.

By means of an example, the host cell may be a bacterial cell, a fungal cell, including yeast cells, an animal cell, or a mammalian cell, including human cells and non-human mammalian cells.

Expression systems (host cells) that can be used for small or large scale production of polypeptides include, without limitation, microorganisms such as bacteria (e.g., *Escherichia coli, Yersinia enterocolitica, Brucella* sp., *Salmonella tymphimurium, Serratia marcescens,* or *Bacillus subtilis*), for example transformed with recombinant bacteriophage DNA, plasmid DNA, or cosmid DNA expression vectors; or fungal cells (e.g., *Yarrowia lipolytica, Arxula adeninivorans,* methylotrophic yeast (e.g., methylotrophic yeast of the genus *Candida, Hansenula, Oogataea, Pichia* or *Torulopsis,* e.g., *Pichia pastoris, Hansenula polymorpha, Oogataea minuta,* or *Pichia methanolica*), or filamentous fungi of the genus *Aspergillus, Trichoderma, Neurospora, Fusarium*, or *Chrysosporium*, e.g., *Aspergillus niger, Trichoderma reesei*, or yeast of the genus *Saccharomyces* or *Schizosaccharomyces*, e.g., *Saccharomyces cerevisiae*, or *Schizosaccharomyces pombe*), for example transformed with recombinant fungal expression vectors. Useful expression systems also include insect cell systems (e.g., cells derived from *Drosophila melanogaster*, such as Schneider 2 cells, cell lines derived from the army worm *Spodoptera frugiperda*, such as Sf9 and Sf21 cells, or cells derived from the cabbage looper *Trichoplusia ni*, such as High Five cells) infected with recombinant virus expression vectors (e.g., baculovirus) containing the nucleic acid molecules, and plant cell systems infected with recombinant virus expression vectors (e.g., tobacco mosaic virus) or transformed with recombinant plasmid expression vectors (e.g., Ti plasmid). Mammalian expression systems include human and non-human mammalian cells, such as rodent cells, primate cells, or human cells. Mammalian cells, such as human or non-human mammalian cells, may include primary cells, secondary, tertiary etc. cells, or may include immortalised cell lines, including clonal cell lines. Preferred animal cells can be readily maintained and transformed in tissue culture. Non-limiting example of human cells include the human HeLa (cervical cancer) cell line. Other human cell lines common in tissue culture practice include inter alia human embryonic kidney 293 cells (HEK cells), DU145 (prostate cancer), Lncap (prostate cancer), MCF-7 (breast cancer), MDA-MB-438 (breast cancer), PC3 (prostate cancer), T47D (breast cancer), THP-1 (acute myeloid leukemia), U87 (glioblastoma), SHSYSY (neuroblastoma), or Saos-2 cells (bone cancer). A non-limiting example of primate cells are Vero (African green monkey Chlorocebus kidney epithelial cell line) cells, and COS cells. Non-limiting examples of rodent cells are rat GH3 (pituitary tumor), CHO (Chinese hamster ovary), PC12 (pheochromocytoma) cell lines, or mouse MC3T3 (embryonic calvarium) cell line. Such cells, prior to the genetic engineering as specified herein, can be obtained from a variety of commercial sources and research resource facilities, such as, for example, the American Type Culture Collection (Rockville, Md.). Various promoters may be suitable for expression in mammalian cells, e.g., the metallothionein promoter, the adenovirus late promoter, or the cytomegalovirus promoter.

In preferred embodiments, the host cell may be a fungal cell. The fungal cell may be a yeast cell, e.g., a *Yarrowia lipolytica* cell, a *Arxula adeninivorans* cell, a *Saccharomyces cerevisiae* cell, or a cell of a methylotrophic yeast (e.g., *Pichia pastoris, Pichia methanolica, Ogataea minuta, Kluyveromyces lactis, Schizosaccharomyces pombe* or *Hansenula polymorpha*). Alternatively, the fungal cell may be a cell of a filamentous fungus (e.g., *Aspergillus caesiellus, Aspergillus candidus, Aspergillus carneus, Aspergillus clavatus, Aspergillus deflectus, Aspergillus flavus, Aspergillus fumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowi, Aspergillus tamari, Aspergillus terreus, Aspergillus ustus, Aspergillus versicolor, Trichoderma*, or *Neurospora*).

In certain embodiments, the host cell may be *Yarrowia lipolytica* or *Arxula adeninivorans*. Preferably, the host cell is *Yarrowia lipolytica*. Advantageously, as illustrated in the examples, production of the human NAGAL polypeptide or functionally active variant or fragment thereof in a fungal cell, in particular in *Yarrowia lipolytica*, results in satisfactory expression levels of the human NAGAL polypeptide or functionally active variant or fragment thereof.

In certain embodiments, the host cell may be genetically engineered to:

comprise a deficiency in outer chain elongation of N-glycans activity, such as a deficiency in OCH1 activity; and/or comprise expression of a polypeptide capable of effecting mannosyl phosphorylation of N-glycans, such as MNN4, PNO1, MNN6 or a biologically active variant or fragment of any one thereof.

In certain embodiments, the host cell may be genetically engineered to express a mannosidase, or a functional fragment of a mannosidase, capable of hydrolyzing a terminal mannose-1-phospho-6-mannose moiety to a terminal phospho-6-mannose. For example, the mannosidase may be a family 92 glycoside hydrolase, including CcMan5 from *Cellulosimicrobium cellulans*.

The mannosidase, or the functional fragment of the mannosidase, may also be capable of removing a mannose residue bound by an alpha 1,2 linkage to the underlying mannose within a mannose-1-phospho-6-mannose or phospho-6-mannose moiety. In addition, the mannosidase, or the functional fragment of the mannosidase, may be capable of hydrolyzing a mannose residue bound by a terminal alpha-1,3 mannose and/or alpha-1,6 mannose and/or alpha-1,2 mannose linkage to the underlying mannose of the glycan that contains a mannose-1-phospho-6-mannose or phospho-6-mannose moiety. For example, the mannosidase may be a family 38 glycoside hydrolase selected from the group consisting of a *Canavalia ensiformis* (Jack Bean) mannosidase and a *Yarrowia lipolytica* AMS1 mannosidase.

In certain embodiments, the host cell may be genetically engineered to express a mannosidase or functional fragment or variant thereof that is capable of removing a mannose residue bound by an alpha 1,2 linkage to the underlying mannose within mannose-1-phospho-6-mannose or phospho-6-mannose moiety. For example, the mannosidase may be a family 38 glycoside hydrolase including a *Canavalia ensiformis* (Jack Bean) mannosidase and a *Yarrowia lipolytica* AMS1 mannosidase; a family 47 glycoside hydrolase, including an *Aspergillus satoi* (AS) mannosidase; or a family 92 glycoside hydrolase, including a *Cellulosimicrobium cellulans* CcMan4 mannosidase.

The mannosidase, or the functional fragment of the mannosidase, may also be capable of hydrolyzing a mannose residue bound by a terminal alpha-1,3 mannose and/or alpha-1,6 mannose and/or alpha-1,2 mannose linkage to the underlying mannose in the glycan containing the mannose-1-phospho-6-mannose or phospho-6-mannose moiety. For example, the mannosidase may be a family 38 glycoside hydrolase selected from but not limited to the group consisting of a *Canavalia ensiformis* (Jack Bean) mannosidase and a *Yarrowia lipolytica* AMS1 mannosidase.

A further aspect relates to a substantially pure culture of host cells as defined herein.

As used herein, a "substantially pure culture" of a host cell is a culture of that cell in which less than about 40% (i.e., less than about 35%, 30%, 25%, 20%, 15%, 10%, 5%, 2%, 1%, 0.50%, 0.25%; 0.10%; 0.01%, 0.001%, 0.0001%, or even less) of the total number of viable cells in the culture are viable cells other than the host cell.

Such a culture of host cells includes the cells and a growth, storage, or transport medium. Media can be liquid, semi-solid (e.g., gelatinous media), solid, or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube). The host cells described herein can be stored, for example, as frozen cell suspensions, e.g., in buffer containing a cryoprotectant such as glycerol or sucrose, as lyophilized cells. Alternatively, they can be stored, for example, as dried cell preparations obtained, e.g., by fluidized bed drying or spray drying, or any other suitable drying method.

A further aspect of the invention provides the use of the nucleic acid molecule as defined herein or the expression cassette or expression vector as defined herein for achieving expression of the human NAGAL polypeptide or functionally active variant or fragment thereof as taught herein in a host cell. Preferably, the host cell is a fungal cell, more preferably *Yarrowia lipolytica*.

A further aspect provides a method for producing the human NAGAL polypeptide or functionally active variant or fragment thereof as taught herein, comprising:

a) culturing the host cell as defined herein, such that the host cell expresses the human NAGAL polypeptide or functionally active variant or fragment thereof, b) collecting, and optionally isolating, the human NAGAL polypeptide or functionally active variant or fragment thereof from the host cell, or from the host cell cultivation medium. In certain embodiments, the host cell is a fungal cell. Preferably, the host cell is a *Yarrowia lipolytica* cell.

In certain embodiments, the method may further comprise uncapping and/or (preferably "and") demannosylation of at least a fraction of phosphorylated N-glycans comprised by the human NAGAL polypeptide or functionally active variant or fragment thereof, for example wherein the uncapping and demannosylation take place in vitro, or in the host cell, or in a lysate of the host cell.

Genetically engineered host cells as described herein can thus be used to produce the human NAGAL polypeptide or functionally active variant or fragment thereof as taught herein. Genetically engineered host cells as described herein also can be used to produce uncapped and demannosylated human NAGAL polypeptide or functionally active variant or fragment thereof as taught herein.

A cell-based method of producing an uncapped and demannosylated glycoprotein can include introducing into a fungal host cell genetically engineered to include a nucleic acid encoding a mannosidase that is capable of hydrolyzing a mannose-1-phospho-6-mannose linkage or moiety to phospho-6-mannose, a nucleic acid encoding the glycoprotein, in particular human NAGAL polypeptide or functionally active variant or fragment thereof as taught herein, whereby the host cell produces the glycoprotein containing uncapped phosphorylated N-glycans. Such phosphorylated N-glycans can be demannosylated as described elsewhere in this specification. In some embodiments, the nucleic acids encoding the mannosidase and the glycoprotein contain a secretion sequence such that the mannosidase and the glycoprotein are co-secreted.

Another cell-based method can include the steps of introducing into a fungal host cell genetically engineered to include a nucleic acid encoding a mannosidase that is capable of (i) hydrolyzing a mannose-1-phospho-6-mannose linkage or moiety to phospho-6-mannose and (ii) hydrolyzing a terminal alpha-1,2 mannose, alpha-1,3 mannose and/or alpha-1,6 mannose linkage or moiety of a phosphate containing glycan, a nucleic acid encoding the glycoprotein, in particular human NAGAL polypeptide or functionally active variant or fragment thereof as taught herein, whereby the host cell produces the uncapped and demannosylated glycoprotein. In some embodiments, the nucleic acids encoding the mannosidase and the glycoprotein contain a secretion sequence such that the mannosidase and the glycoprotein are co-secreted.

Host cells suitable for in vivo production of glycoproteins can be of fungal origin as taught elsewhere in this specification, e.g., *Yarrowia lipolytica* or *Arxula adeninivorans*, preferably *Yarrowia lipolytica*.

Genetic engineering of a host cell intended to or configured to recombinantly express the glycoprotein, in particular the human NAGAL polypeptide or functionally active variant or fragment thereof as taught herein, can further include, one or more genetic modifications such as: (i) deletion of an endogenous gene encoding an Outer CHain elongation (OCH1) protein; (ii) introduction of a recombinant nucleic acid encoding a polypeptide capable of promoting mannosyl phosphorylation (e.g, a MNN4 polypeptide from *Yarrowia lipolytica, S. cerevisiae, Ogataea minuta, Pichia pastoris*, or *C. albicans*, or PNO1 polypeptide from *P. pastoris*) to increasing phosphorylation of mannose residues; (iii) introduction or expression of an RNA molecule that interferes with the functional expression of an OCH1 protein; (iv) introduction of a recombinant nucleic acid encoding a wild-type (e.g., endogenous or exogenous) protein having a N-glycosylation activity (i.e., expressing a protein having an N-glycosylation activity); or (v) altering the promoter or enhancer elements of one or more endogenous genes encoding proteins having N-glycosylation activity to thus alter the expression of their encoded proteins. RNA molecules include, e.g., small-interfering RNA (siRNA), short hairpin RNA (shRNA), anti-sense RNA, or micro RNA (miRNA). Genetic engineering also includes altering an endogenous gene encoding a protein having an N-glycosylation activity to produce a protein having additions (e.g., a heterologous sequence), deletions, or substitutions (e.g., mutations such as point mutations; conservative or non-conservative mutations). Mutations can be introduced specifically (e.g., by site-directed mutagenesis or homologous recombination) or can be introduced randomly (for example, cells can be chemically mutagenized as described in, e.g., £Newman and Ferro-Novick, 1987, J. Cell Biol., 105(4):1587.

Genetic modifications described herein can result in one or more of (i) an increase in one or more activities in the genetically modified cell, (ii) a decrease in one or more activities in the genetically modified cell, or (iii) a change in the localization or intracellular distribution of one or more activities in the genetically modified cell. It is understood that an increase in the amount of a particular activity (e.g., promoting mannosyl phosphorylation) can be due to over-expressing one or more proteins capable of promoting mannosyl phosphorylation, an increase in copy number of an endogenous gene (e.g., gene duplication), or an alteration in the promoter or enhancer of an endogenous gene that stimulates an increase in expression of the protein encoded by the gene. A decrease in one or more particular activities can be due to overexpression of a mutant form (e.g., a dominant negative form), introduction or expression of one or more interfering RNA molecules that reduce the expression of one or more proteins having a particular activity, or deletion of one or more endogenous genes that encode a protein having the particular activity.

To disrupt a gene by homologous recombination, a "gene replacement" vector can be constructed in such a way to include a selectable marker gene. The selectable marker gene can be operably linked, at both 5' and 3' end, to portions of the gene of sufficient length to mediate homologous recombination. The selectable marker can be one of any number of genes which either complement host cell auxotrophy or provide antibiotic resistance, including URA3, LEU2 and HIS3 genes. Other suitable selectable markers include the CAT gene, which confers chloramphenicol resistance to yeast cells, or the lacZ gene, which results in blue colonies due to the expression of β-galactosidase. Linearized DNA fragments of the gene replacement vector are then introduced into the cells using methods well known in the art. Integration of the linear fragments into the genome and the disruption of the gene can be determined based on the selection marker and can be verified by, for example, Southern blot analysis. A selectable marker can be removed from the genome of the host cell by, e.g., Cre-loxP systems.

Alternatively, a gene replacement vector can be constructed in such a way as to include a portion of the gene to be disrupted, which portion is devoid of any endogenous gene promoter sequence and encodes none or an inactive fragment of the coding sequence of the gene. An "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of the gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene.

Hence, in some embodiments, the host cell, particularly fungal host cell, lacks the OCH1 gene or gene products (e.g., mRNA or protein) thereof, and is deficient in OCH1 activity. As elucidated in inter alia WO 2008/120107, OCH1 deficiency, e.g., in *Yarrowia lipolytica* cells, can result in substantially homogeneous production of glycosylated proteins having alpha-1,2-linked mannose residues on the Man₅GlcNAc₂ N-glycan structure, for example, in the predominant production of Man₈GlcNAc₂ N-glycans.

In certain embodiments, the method may further comprise a step of introducing into the host cell a nucleic acid encoding a polypeptide capable of effecting mannosyl phosphorylation, including MNN4 (e.g., a MNN4 polypeptide from *Yarrowia lipolytica, S. cerevisiae, Ogataea minuta, Pichia pastoris,* or *C. albicans*), PNO1 (e.g., PNO1 from *P. pastoris*), or MNN6, or a functional fragment of such a polypeptide. For example, the fungal cell can express a MNN4 polypeptide from *Y. lipolytica* (Genbank acccession no: XM_503217.1).

In some embodiments, the genetically engineered cell is deficient in OCH1 activity and expresses a polypeptide capable of promoting mannosyl phosphorylation.

In certain embodiments, the method may further comprise a step of introducing into the host cell a RNA molecule or a nucleic acid for transcription of a RNA molecule that interferes with the functional expression of a protein having an N-glycosylation activity. Preferably, the protein having N-glycosylation activity is OCH1. For example, the RNA molecule may include small-interfering RNA (siRNA), short hairpin RNA (shRNA), anti-sense RNA, or micro RNA (miRNA).

In certain embodiments, the method may further comprise a step of introducing into the host cell a nucleic acid encoding a mannosidase, or a functional fragment or variant of a mannosidase, capable of hydrolyzing a terminal mannose-1-phospho-6-mannose moiety to a terminal phospho-6-mannose. For example, the mannosidase may be a family 92 glycoside hydrolase, such as but not limited to CcMan5 from *Cellulosimicrobium cellulans*, or a family 38 glycoside hydrolase such as *Canavalia ensiformis* (Jack bean) mannosidase and a *Yarrowia lipolytica* AMS1 mannosidase.

The mannosidase, or the functional fragment or variant of the mannosidase, may also be capable of removing a mannose residue bound by an alpha 1,2 linkage to the underlying mannose that within the mannose-1-phospho-6-mannose or phospho-6-mannose moiety. For example, the mannosidase may be a family 38 glycoside hydrolase selected from the group consisting of a *Canavalia ensiformis* (Jack Bean) mannosidase and a *Yarrowia lipolytica* AMS1 mannosidase.

The mannosidase or functional fragment or variant thereof may further be capable of hydrolyzing a terminal alpha-1,3 mannose and/or alpha-1,6 mannose and/or alpha-1,2 mannose linkage or moiety of the glycan moiety that contains the mannose-1-phospho-6-mannose or phospho-6-mannose moiety. For example, such a mannosidase may be a family 38 glycoside hydrolase selected from the group consisting of a *Canavalia ensiformis* (Jack Bean) mannosidase and a *Yarrowia lipolytica* AMS1 mannosidase.

In certain embodiments, the method may further comprise a step of introducing into the host cell a nucleic acid encoding a mannosidase or functional fragment or variant thereof that is capable of removing a mannose residue bound by an alpha-1,2 linkage to the underlying mannose within mannose-1-phospho-6-mannose or phospho-6-mannose moiety. For example, the mannosidase may be a family 38 glycoside hydrolase selected from but not limited to the group consisting of a *Canavalia ensiformis* (Jack Bean) mannosidase and a *Yarrowia lipolytica* AMS1 mannosidase, or a family 47 glycoside hydrolase including but not limited to an *Aspergillus satoi* (AS) mannosidase, or a family 92 glycoside hydrolase, including a *Cellulosimicrobium cellulans* CcMan4 mannosidase.

Alternatively, in certain embodiments, the method may comprise a step of incubating the human NAGAL polypeptide or functionally active variant or fragment thereof collected in step (b), with a mannosidase, or a functional fragment of a mannosidase, capable of hydrolyzing a terminal mannose-1-phospho-6-mannose moiety to a terminal phospho-6-mannose. For example, the mannosidase may be a family 92 glycoside hydrolase, such as but not limited to CcMan5 from *Cellulosimicrobium cellulans*, or a family 38 glycoside hydrolase such as *Canavalia ensiformis* (Jack bean) mannosidase and a *Yarrowia lipolytica* AMS1 mannosidase.

The mannosidase, or the functional fragment of the mannosidase, may also be capable of removing a mannose residue bound by an alpha 1,2 linkage to the underlying mannose within the mannose-1-phospho-6-mannose or phospho-6-mannose moiety. For example, the mannosidase may be a family 38 glycoside hydrolase selected from the group consisting of a *Canavalia ensiformis* (Jack Bean) mannosidase and a *Yarrowia lipolytica* AMS1 mannosidase.

The mannosidase may further be capable of hydrolyzing a terminal alpha-1,3 mannose and/or alpha-1,6 mannose and/or alpha-1,2 mannose linkage or moiety of the glycan moiety that contains the mannose-1-phospho-6-mannose or phospho-6-mannose moiety. For example, such a mannosidase may be be a family 38 glycoside hydrolase selected from the group consisting of a *Canavalia ensiformis* (Jack Bean) mannosidase and a *Yarrowia lipolytica* AMS1 mannosidase.

In certain embodiments, the method may further comprise a step of incubating the human NAGAL polypeptide or functionally active variant or fragment thereof collected in step (b), with a mannosidase that is capable of removing a mannose residue bound by an alpha 1,2 linkage to the underlying mannose within mannose-1-phospho-6-mannose or phospho-6-mannose moiety. For example, the mannosidase may be a family 38 glycoside hydrolase selected from but not limited to the group consisting of a *Canavalia ensiformis* (Jack Bean) mannosidase and a *Yarrowia lipolytica* AMS1 mannosidase, or a family 47 glycoside hydrolase including but not limited to an *Aspergillus satoi* (AS) mannosidase, or a family 92 glycoside hydrolase, including a *Cellulosimicrobium cellulans* CcMan4 mannosidase. The mannosidase may further be capable of hydrolyzing a terminal alpha-1,3 mannose and/or alpha-1,6 mannose and/or alpha-1,2 mannose linkage or moiety of the glycan moiety that contains the mannose-1-phospho-6-mannose or phospho-6-mannose moiety. For example, the mannosidase may be a family 38 glycoside hydrolase selected from but not limited to the group consisting of a *Canavalia ensiformis* (Jack Bean) mannosidase and a *Yarrowia lipolytica* AMS1 mannosidase.

Methods for detecting glycosylation of molecules include DNA sequencer-assisted (DSA), fluorophore-assisted carbohydrate electrophoresis (FACE) or surface-enhanced laser desorption/ionization time-of-flight mass spectrometry (SELDI-TOF MS). For example, an analysis can utilize DSA-FACE in which, for example, glycoproteins are denatured followed by immobilization on, e.g., a membrane. The glycoproteins can then be reduced with a suitable reducing agent such as dithiothreitol (DTT) or beta-mercaptoethanol. The sulfhydryl groups of the proteins can be carboxylated using an acid such as iodoacetic acid. Next, the N-glycans can be released from the protein using an enzyme such as N-glycosidase F. N-glycans, optionally, can be reconstituted and derivatized by reductive amination. For example, the released N-glycans can be labeled with a fluorophore such as APTS (8-aminopyrene-1,3,6-trisulfonic acid), at the reducing terminus by reductive amination. The stoichiometry of labeling is such that only one APTS molecule is attached to each molecule of oligosaccharide. The derivatized N-glycans can then be concentrated. Instrumentation suitable for N-glycan analysis includes, e.g., the ABI PRISM® 377 DNA sequencer (Applied Biosystems). Data analysis can be performed using, e.g., GENESCAN® 3.1 software (Applied Biosystems). Isolated N-glycans can be further treated with one or more enzymes such mannosidases and/or calf intestine phosphatase to confirm their N-glycan status. Additional methods of N-glycan analysis include, e.g., mass spectrometry (e.g., MALDI-TOF-MS), high-pressure liquid chromatography (HPLC) on normal phase, reversed phase and ion exchange chromatography (e.g., with pulsed amperometric detection when glycans are not labeled and with UV absorbance or fluorescence if glycans are appropriately labeled). See also Callewaert et al., 2001, Glycobiology, 11(4):275-281 and Freire et al., 2006, Bioconjug. Chem., 17(2):559-564.

In some embodiments, the glycoprotein, in particular the human NAGAL polypeptide or functionally active variant or fragment thereof, which may be uncapped and demannosylated, may be maintained within the host cell, such as a fungal host cell, and released upon cell lysis. In some embodiments, the glycoprotein may be secreted into the culture medium via a mechanism provided by a coding sequence (either native to the exogenous nucleic acid or engineered into the expression vector), which directs secretion of the glycoprotein from the cell. The presence of the glycoprotein in the cell lysate or culture medium can be verified by a variety of standard detection protocols, e g., immunoblotting or radioimmunoprecipitation with an antibody specific for the glycoprotein, or testing for a specific enzyme activity.

In certain embodiments, the step of isolation or purification may comprise any one or more steps known to those skilled in the art, including but not limited to, centrifugation, medium clarification by filtration, desalting, concentration, ammonium precipitation, chromatography (e.g., ion exchange chromatography, hydrophobic interaction chromatography, reverse phase chromatography, size exclusion chromatography, affinity chromatography, and/or hydrophobic charge-induction chromatography), selective purification via a polypeptide tag (e.g., a FLAG tag, polyhistidine (e.g., hexahistidine) tag, hemagluttanin (HA) tag, glutathione-S-transferase (GST) tag, or maltose-binding protein (MBP) tag), or any combination thereof. See, e.g., Scopes, Protein Purification: Principles and Practice, third edition, Springer-Verlag, New York (1993); Burton and Harding, J. Chromatogr. A 814:71-81 (1998).

In some embodiments, following isolation, the glycoprotein, in particular the human NAGAL polypeptide or functionally active variant or fragment thereof, which may be uncapped and demannosylated, can be attached to a heterologous moiety, e.g., using enzymatic or chemical means. A "heterologous moiety" refers to any constituent that is joined (e.g., covalently or non-covalently) to the glycoprotein, which constituent is different from a constituent originally present on the glycoprotein. Heterologous moieties include, e.g., polymers, carriers, adjuvants, immunotoxins, or detectable (e.g., fluorescent, luminescent, or radioactive) moieties. In some embodiments, an additional N-glycan can be added to the altered target molecule.

Amino acids with their three letter code and one letter code are listed in Table 2.

TABLE 2

Amino acids with their three letter code and one letter code

| Amino acid | Three letter code | One letter code |
| --- | --- | --- |
| glycine | Gly | G |
| alanine | Ala | A |
| valine | Val | V |
| leucine | Leu | L |
| isoleucine | Ile | I |
| proline | Pro | P |
| tyrosine | Tyr | Y |
| tryptophan | Trp | W |
| phenylalanine | Phe | F |
| cysteine | Cys | C |
| methionine | Met | M |
| serine | Ser | S |
| threonine | Thr | T |
| lysine | Lys | K |
| arginine | Arg | R |
| histidine | His | H |
| aspartic acid | Asp | D |
| glutamic acid | Glu | E |
| asparagine | Asn | N |
| glutamine | Gln | Q |

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The herein disclosed aspects and embodiments of the invention are further supported by the following non-limiting examples.

EXAMPLES

Example 1

Generation of *Yarrowia lipolytica* Strains Expressing Human NAGAL with Increased α-Galactosidase Activity (NAGAL1)

The aim of the experiment was to develop a *Yarrowia lipolytica* strain for the secreted expression of a human lysosomal α-N-Acetylgalactosaminidase (NAGAL) enzyme modified by the amino acid substitutions Ser188Glu and Ala191Leu (amino acid numbering starting from the starting methionine and including a 17-amino acid signal peptide of human NAGAL; in human NAGAL polypeptide as set forth in SEQ ID NO: 1, this corresponds to substitutions Ser171Glu and Ala174Leu) to have increased α-galactosidase activity. For this purpose, a *Yarrowia* codon-optimized synthetic gene was ordered with GenScript encoding the fusion between the signal peptide of the *Yarrowia* Lip2p (Lip2pre sequence) and the mature form of NAGAL (omitting the mammalian secretion signal peptide and starting from amino acid 18 of human NAGAL). The synthetic gene also encoded for two X-Ala repeats between the Lip2pre sequence and the first NAGAL-specific amino acid, to ensure efficient processing of the signal peptide within the yeast endoplasmatic reticulum (ER) (Gasmi et al., 2012, Appl. Microbiol. Biotechnol., 96(1):89-101). A CACA nucleotide sequence was introduced before the ATG start codon, as it was found to be beneficial for translation initiation in *Yarrowia* (Gasmi et al., 2011, Appl. Microbiol. Biotechnol., 89(1):109-19). Henceforth, the human NAGAL containing the amino acid substitutions Ser188Glu and Ala191Leu (amino acid numbering starting from the starting methionine) is conveniently referred to as "NAGAL1" or "NAGAL1(Mut)". The nucleotide sequence of the synthetic NAGAL1 gene for expression in *Yarrowia lipolytica* is given as SEQ ID NO: 10 (bold underlined: start ATG; italics underlined: stop codons):

```
                                           (SEQ ID NO: 10)
CACAATGAAGCTCTCTACTATTCTCTTTACCGCCTGCGCCACCCTCGCCG

CTGCTCTCGACAACGGACTCCTCCAGACTCCTCCTATGGGCTGGCTGGCT

TGGGAGCGATTCCGATGCAACATCAACTGTGACGAGGACCCCAAGAACTG

CATTTCTGAGCAGCTCTTTATGGAGATGGCTGACCGAATGGCCCAGGACG

GATGGCGAGATATGGGCTACACCTACCTGAACATCGACGATTGTTGGATT

GGCGGTCGAGACGCCTCTGGTCGACTCATGCCCGATCCTAAGCGATTCCC

CCACGGAATCCCTTTTCTGGCTGACTACGTCCATTCCCTGGGCCTCAAGC

TGGGTATTTACGCCGACATGGGCAACTTCACCTGCATGGGCTACCCCGGT

ACCACTCTCGACAAGGTCGTGCAGGATGCTCAGACCTTCGCCGAGTGGAA

GGTGGACATGCTCAAGCTGGATGGATGTTTTTCCACTCCTGAGGAGCGAG

CTCAGGGATACCCTAAGATGGCCGCTGCCCTGAACGCTACCGGTCGACCC

ATCGCCTTCTCCTGCGAGTGGCCTCTCTACGAGGGAGGACTGCCTCCTCG

AGTCAACTACTCTCTGCTCGCTGACATCTGTAACCTCTGGCGAAACTACG

ACGATATTCAGGATTCGTGGTGGTCCGTCCTCTCTATCCTGAACTGGTTC

GTGGAGCACCAGGACATTCTGCAGCCCGTGGCCGGTCCTGGACATTGGAA

CGACCCCGATATGCTGCTCATCGGAAACTTTGGCCTCTCGCTGGAGCAGT

CCCGAGCTCAGATGGCTCTCTGGACCGTTCTGGCTGCTCCTCTGCTCATG

TCGACCGACCTGCGAACTATCTCCGCTCAGAACATGGATATTCTCCAGAA

CCCCCTGATGATCAAGATTAACCAGGACCCTCTCGGTATCCAGGGACGAC

GAATCCACAAGGAGAAGTCGCTGATTGAGGTTTACATGCGACCCCTCTCT

AACAAGGCTTCGGCCCTGGTCTTCTTTTCCTGCCGAACCGACATGCCTTA

CCGATACCATTCCTCTCTCGGCCAGCTGAACTTCACTGGTTCTGTGATCT

ACGAGGCCCAGGACGTTTACTCCGGTGATATCATTTCTGGACTGCGAGAC

GAGACCAACTTTACTGTGATCATTAACCCCTCTGGAGTTGTCATGTGGTA

CCTCTACCCTATTAAGAACCTGGAGATGTCGCAGCAGTAATAG
```

The amino acid sequence of the recombinant NAGAL1 (including the *Yarrowia* Lip2pre signal peptide and two X-Ala repeats) is given as SEQ ID NO: 11 (bold underlined: *Yarrowia* Lip2pre signal peptide and two X-Ala repeats):

```
                                           (SEQ ID NO: 11)
MKLSTILFTACATLAAALDNGLLQTPPMGWLAWERFRCNINCDEDPKNCI

SEQLFMEMADRMAQDGWRDMGYTYLNIDDCWIGGRDASGRLMPDPKRFPH

GIPFLADYVHSLGLKLGIYADMGNFTCMGYPGTTLDKVVQDAQTFAEWKV

DMLKLDGCFSTPEERAQGYPKMAAALNATGRPIAFSCEWPLYEGGLPPRV

NYSLLADICNLWRNYDDIQDSWWSVLSILNWFVEHQDILQPVAGPGHWND

PDMLLIGNFGLSLEQSRAQMALWTVLAAPLLMSTDLRTISAQNMDILQNP

LMIKINQDPLGIQGRRIHKEKSLIEVYMRPLSNKASALVFFSCRTDMPYR

YHSSLGQLNFTGSVIYEAQDVYSGDIISGLRDETNFTVIINPSGVVMWYL

YPIKNLEMSQQ
```

For comparison, a synthetic gene encoding human α-galactosidase A (α-Gal A) and codon-optimized for expression in *Yarrowia lipolityca* was ordered as well with GeneArt. Secretion of this protein was also driven by fusing the first amino acid of mature human α-galactosidase A to the *Yarrowia* Lip2p pre-sequence. In this case, the *Yarrowia* Lip2p pre-sequence was followed by 1 X-Ala to ensure better processing at the signal peptidase cleavage site (Pignéde et al., 2000, J. Bacteriol., 182(10):2802-10). The nucleotide sequence of the synthetic α-GalA gene for expression in *Yarrowia lipolytica* is given as SEQ ID NO: 12 (bold underlined: start ATG; italics underlined: stop codons):

```
                                           (SEQ ID NO: 12)
ATGAAGCTTTCCACCATCCTCTTCACAGCCTGCGCTACCCTGGCCCTGGA

CAACGCCTGGCCCGAACCCCCACCATGGGCTGGCTGCACTGGGAGCGAT

TCATGTGTAACCTGGACTGTCAGGAAGAGCCCGACTCTTGTATCTCTGAG
```

```
-continued
AAGCTGTTCATGGAAATGGCCGAGCTGATGGTGTCTGAGGGCTGGAAGGA

CGCCGGCTACGAGTACCTGTGTATCGACGACTGTTGGATGGCCCCCCAGC

GAGACTCTGAGGGCCGACTCCAGGCCGACCCCCAGCGATTCCCCCACGGC

ATCCGACAGCTCGCCAACTACGTGCACTCTAAGGGCCTGAAGCTGGGCAT

CTACGCCGACGTGGGCAACAAGACCTGTGCCGGCTTCCCCGGCTCTTTCG

GCTACTACGACATCGACGCCCAGACCTTCGCCGACTGGGGCGTGGACCTG

CTGAAGTTCGACGGCTGTTACTGTGACTCTCTCGAGAACCTGGCCGACGG

CTACAAGCACATGTCTCTGGCCCTGAACCGAACCGGCCGATCTATCGTGT

ACTCTTGTGAGTGGCCCCTGTACATGTGGCCCTTCCAGAAGCCCAACTAC

ACCGAGATCCGACAGTACTGTAACCACTGGCGAAACTTCGCCGACATCGA

CGACTCGTGGAAGTCTATCAAGTCTATTCTGGACTGGACCTCTTTCAACC

AGGAGCGAATCGTCGACGTCGCCGGACCCGGCGGATGGAACGACCCCGAC

ATGCTGGTGATCGGCAACTTCGGCCTGTCTTGGAACCAGCAGGTGACCCA

GATGGCCCTGTGGGCTATCATGGCTGCCCCCCTGTTCATGTCTAACGACC

TGCGACACATCTCTCCCCAGGCCAAGGCCCTGCTCCAGGACAAGGACGTG

ATCGCCATCAACCAGGACCCCCTGGGCAAGCAGGGCTACCAGCTCCGACA

GGGCGACAACTTCGAGGTGTGGGAGCGACCCCTGTCTGGCCTGGCCTGGG

CCGTGGCCATGATCAACCGACAGGAGATCGGCGGACCCCGATCTTACACC

ATCGCCGTGGCCTCCCTGGGAAAGGGCGTGGCCTGTAACCCCGCCTGTTT

CATCACCCAGCTCCTGCCCGTGAAGCGAAAGCTGGGATTCTACGAGTGGA

CCTCTCGACTGCGATCTCACATCAACCCCACCGGCACCGTGCTGCTCCAG

CTCGAGAACACCATGCAGATGTCTCTGAAGGACCTGCTGTAATAA
```

The amino acid sequence of the recombinant α-GalA (including the *Yarrowia* Lip2pre signal peptide and one X-Ala) is given as SEQ ID NO: 13 (bold underlined: *Yarrowia* Lip2pre signal peptide and one X-Ala repeat):

```
                                        (SEQ ID NO: 13)
MKLSTILFTACATLALDNGLARTPTMGWLHWERFMCNLDCQEEPDSCISE

KLFMEMAELMVSEGWKDAGYEYLCIDDCWMAPQRDSEGRLQADPQRFPHG

IRQLANYVHSKGLKLGIYADVGNKTCAGFPGSFGYYDIDAQTFADWGVDL

LKFDGCYCDSLENLADGYKHMSLALNRTGRSIVYSCEWPLYMWPFQKPNY

TEIRQYCNHWRNFADIDDSWKSIKSILDWTSFNQERIVDVAGPGGWNDPD

MLVIGNFGLSWNQQVTQMALWAIMAAPLFMSNDLRHISPQAKALLQDKDV

IAINQDPLGKQGYQLRQGDNFEVWERPLSGLAWAVAMINRQEIGGPRSYT

IAVASLGKGVACNPACFITQLLPVKRKLGFYEWTSRLRSHINPTGTVLLQ

LENTMQMSLKDLL
```

The synthetic sequences encoding for NAGAL1 and α-Gal A were cloned behind the semi-constitutive growth phase-dependent Hp4d promoter. Plasmid variants carrying the URA3, the LEU2, or the ADE2 selection marker were generated to allow selection of *Yarrowia* transformants on minimal medium lacking uracil, leucine, or adenine, respectively. The expression plasmids were transformed into the *Yarrowia lipolytica* strain OXYY2163 via random integration. The parental strain OXYY2163 has a high capacity to synthesize high levels of phosphorylated N-glycans and comprises the following genotype features: MatA, leu2-958, ura3-302, xpr2-322, ade2-844, ΔScsuc2, Δoch1, URA3::PDX2-MNN4, OCH1::Hp4d-MNN4. Hence, OXYY2163 is deleted for the URA3 gene, for the extracellular protease gene XPR2, for the initiating α-1,6-mannosyltransferase gene OCH1 to reduce N-glycan hyperglycosylation. Overexpression of the Y1MNN4 gene ensures increased N-glycan phosphorylation, and the ade-, leu- and ura- auxotrophies allow for multiple transformation events.

A single copy NAGAL1 or α-Gal A strain was generated via integration of the expression plasmid containing the ADE2 selection marker into the OXYY2163 genome. A 3-copy expression strain was generated from this background via co-transformation of the LEU2 and URA3 containing expression constructs. To allow controlled bioreactor cultivations of a single copy strain in defined mineral medium, it was transformed with the URA3 and LEU2 selection markers only to regain prototrophy. Alternatively, strain OXYY1315, which is a URA3 and LEU2 complemented variant of OXYY2163, was transformed with a single ADE2 containing expression plasmid. The presence of the expression constructs into the genome of the selected transformants was checked via PCR. Here and below, PCR screenings of *Yarrowia* transformants were performed using either SapphireAmp Fast PCR Master Mix (Takara, RR350A) or EmeraldAmpMaxHS PCR Master Mix (Takara, RR330A). The PCR reactions were performed on either cell suspensions or on prepared genomic DNA, according to the recommendations of the manufacturer.

The expression levels of the NAGAL1 and α-Gal A were evaluated for PCR-positive *Yarrowia* transformants via 24-well cultivation in 2 ml rich medium. In brief, several transformants were inoculated in wells containing 2 ml YPD (YPD: 1% w/v yeast extract; 2% w/v pepton; 2% w/v glucose/dextrose), and cultivated overnight at 28° C. and 180 rpm. The next day (+/−24 hours later), 1 to 2 µl of this culture was transferred to a new well with fresh YPD and recultivated overnight at 28° C. and 180 rpm. The following day, the 24-well plate was centrifuged and the medium was removed from the cell pellets. The cells were resuspended in 2 ml SuperT/glycerol rich medium (0.5% w/v yeast extract; 2% w/v malt extract; 1% w/v trypton; 1.5% v/v glycerol; 200 mM phosphate buffer pH 6.8) and grown at 28° C. for 3 days. At the end of the cultivation, the medium was harvested and analysed for the expression of NAGAL1 or α-Gal A.

The secretion of the recombinant proteins in the culture medium was first analyzed via standard SDS-PAGE and Western blot detection. Fabrazyme® (agalsidase beta, recombinant human α-galactosidase A) (Genzyme Corporation, a Sanofi company, Cambridge, USA) or commercially available CHO-produced human NAGAL (catalogue #6717-GH-020, R&D Systems, Inc., Minneapolis, USA) were loaded to serve as positive control (FIG. 10). Analysis was done using reducing and non-reducing SDS-PAGE conditions. Based on the amino acid composition and taking into consideration the size of potentially added N-glycans (3 N-sites for α-Gal A and 5 N-sites for NAGAL1), the monomeric form of the recombinant proteins was expected to run at about 50 kDa.

The analysis showed that NAGAL1 was expressed less well by *Yarrowia* when compared with the expression levels obtained for α-galactosidase. Moreover, a significant amount of NAGAL1-specific proteolytic products was observed. In the non-reducing Western blot analysis, the full-size monomeric NAGAL1 product was even less visible (also the control recombinant NAGAL). In addition, for the yeast-derived NAGAL1, a significant smearing of NAGAL-related material was observed in the higher molecular weight (MW) range, while the low MW degradation bands were hardly present. This was indicative of aggregation between full-size monomeric NAGAL1 and its degradation products, e.g., potentially via the formation of unwanted disulfide bridges.

Figure 11:
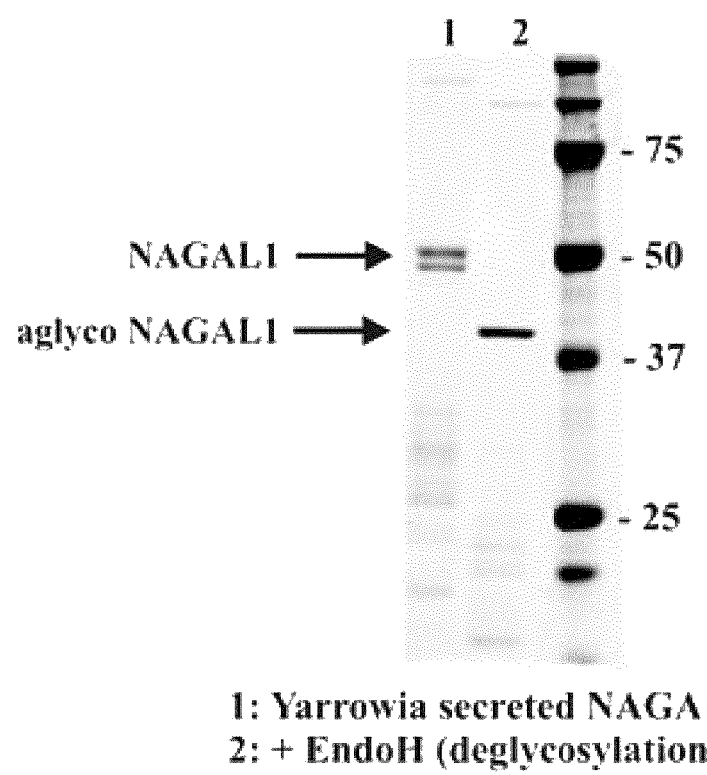
FIG. 11 represents a Western blot analysis on medium samples of a NAGAL1 *Yarrowia lipolytica* expression strain before (lane 1) and after (lane 2) deglycosylation using EndoH (Bioke; P0702L).

The reducing Western blot analysis showed that the full-size monomeric α-Gal A was running somewhat faster than the monomeric NAGAL1 and that the latter was actually running as a double band. This was due to differences in N-glycosylation site occupancy as shown for the NAGAL1 doublet after deglycosylating the sample with Endoglycosidase H (EndoH) (Bioke; P0702L) (FIG. 11). Removal of the N-glycans resulted in a single band (FIG. 11, lane 2), indicating that the double NAGAL1 band observed before EndoH treatment (FIG. 11, lane 1) was indeed glycosylation related.

Example 2

Controlled Bioreactor Cultivation of Yarrowia lipolytica Strains Expressing Human NAGAL with Increased α-Galactosidase Activity (NAGAL1)

For initial controlled bioreactor cultivations of the NAGAL1 expression strains, an eight-parallel 1L fermentation system developed by DASGIP was used. The system is equipped for online monitoring of pH, temperature, dissolved oxygen, as well as off-gas analysis to assess oxygen uptake rate (OUR) and carbon dioxide evolution rate (CER) during the cultivation.

A seed culture of the selected strains was grown at 28° C. in a shake flask containing rich medium. The seed culture was then inoculated into the fermenter, containing defined mineral medium with glycerol as only carbon source, to start the batch phase at 28° C. with unrestricted growth. This phase was used to rapidly reach a high biomass concentration. After glycerol depletion the process was run in carbon limitation by applying two successive exponential glycerol feeds. The first feed phase was a relative fast exponential glycerol feed for 44 hours to reach the beginning of the stationary phase. The following feed phase was a relative slower exponential glycerol feed for approximately another 130 hours. Throughout the fermentation process, dissolved oxygen, pH, temperature, foam levels, and feed rates were actively controlled. Dissolved oxygen levels were maintained by stirring and spiking with pure oxygen. The pH was adjusted by adding 14% v/v ammonium hydroxide. Foam was counteracted by adding antifoam agent upon activation of the antifoam probe. During the process, samples were taken regularly to assess the following parameters: 1) recombinant protein expression, 2) expression of functional enzyme via an activity assay, 3) evolution of the N-glycosylation profile of the secretome, 4) biomass concentration, 5) pH, 6) cell morphology, and 7) total protein concentration.

Figure 12:
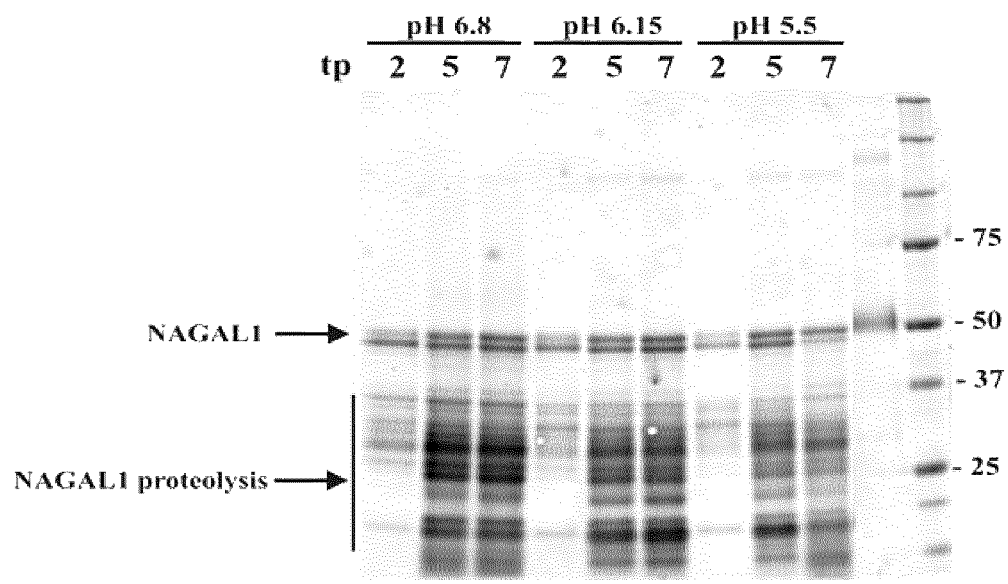
FIG. 12 represents a Western blot analysis on different time-point (tp) samples of the bioreactor cultivation of a 3-copy NAGAL1 expression strain, run at 3 different medium pH's. Tp's 2, 5 and 7 represent 35 hours, 106 hours, and 178 hours after the start of the carbon limitation. Last lane before marker is 20 ng recombinant human NAGAL (catalogue #6717-GH-020, R&D Systems, Inc., Minneapolis, USA).

Western blot analysis was performed to evaluate the NAGAL1 expression levels at different time-points during the bioreactor cultivation of a 3-copy strain (FIG. 12). This analysis illustrated that significant NAGAL1 degradation was still observed even after controlled cultivation. It has been described that a reduced degradation is observed of yeast expressed chicken NAGAL when the pH of the cultivation medium was maintained at 5.0 to 5.5 (Zhu et al., 1996, Protein Expr Purif., 8(4):456-62). However, in our case, a reduction of the pH from 6.8 towards 5.5 did not reduce NAGAL1 proteolysis (FIG. 12).

Comparison of the Western blot signals from the fermentation samples with that of 20 ng of co-loaded recombinant human NAGAL (HuNAGAL) clearly showed the low levels of secreted NAGAL1, even after controlled bioreactor cultivation of the expression strain (FIG. 12).

In a second analysis method, the presence of extracellular α-galactosidase activity (derived from either the NAGAL1 or α-Gal A Yarrowia expression) was monitored via an enzymatic assay at pH 4.5 and a temperature of 37° C., using 4-methylumberriferyl-α-D-galactopyranoside (4MU-α-Gal) as a substrate. This fluorometric assay was basically performed as described by Tajima et al. 2009 (Am. J. Hum. Genet., 85(5): 569-80) and Tomasic et al., 2010 (J. Biol. Chem., 285(28):21560-6). In brief, when active α-galactosidase is present in the cultivation medium, the 4MU-α-Gal is hydrolysed, thereby releasing 4-methylumbelliferyl. The latter can be measured at 450 nm after excitation at 365 nm.

Evaluation via the 4MU-α-Gal assay of an equal volume of fermentation medium (taken at harvest time) from a single copy α-GalA expression strain versus a 3-copy NAGAL1 strain, showed a more than 100-fold difference in the total μM amount of released 4-methylumbelliferyl (not shown). In other words, the extracellular α-galactosidase activity levels were more than 100 times higher for the single copy α-GalA strain than for the 3-copy NAGAL1 strain. This again indicated the low levels of Yarrowia-produced NAGAL1.

Attempts have been made to increase the expression level of the recombinant NAGAL1 via co-expression of chaperones such as Yarrowia calnexin, Yarrowia protein disulphide isomerase (PDI), Yarrowia binding protein (BiP), human calnexin, human PDI or human BiP, without any success. Co-expression of the spliced variant of the unfolded protein response (UPR) sensitive transcription factor HAC1 proved to be unsuccessful as well. Exchanging the Lip2pre leader sequence for the Lip2prepro sequence also did not result in increased secretion of NAGAL1. We also tried to restrict the level of NAGAL1 degradation by performing expression studies in multi-protease knock-out strains. A knock-out of ProT01 seemed to result in an increase of secreted full-size NAGAL1 (as indicated via western blot). Contrary to these results however, no increase in total secreted α-galactosidase activity could be observed in the medium of these NAGAL1-producing ProT01 knock-out strains.

Example 3

Generation of Yarrowia lipolytica Strains Expressing Variants of Human NAGAL with Increased α-Galactosidase Activity (NAGAL1)

Based on the high sequence similarity (46% overall) and the very similar protein fold between α-GalA and NAGAL, the significantly lower expression levels for the Yarrowia-produced NAGAL1 were unexpected.

In order to try to increase the expression of NAGAL1 in Yarrowia lipolytica, different strategies were tested:
(i) In a first strategy, a full domain II swapping was performed in which the domain II of NAGAL1 was replaced by the domain II of human α-GalA;
(ii) In a second strategy, based on a hypothesis that the possibility of forming an (additional) ion pair between domain I and domain II of NAGAL1 could be introduced, a NAGAL1 variant was expressed where asparagine 213 of domain I of NAGAL1 was replaced by an aspartic acid and where cysteine 326 of domain II of NAGAL1 was replaced by an arginine (numbering of the amino acids starting from first amino acid in mature NAGAL1, i.e., omitting the mammalian secretion signal); and (iii) In a third strategy, based on a hypothesis that the unpaired cysteine 326 of domain II of NAGAL1 (numbering of the amino acids starting from first amino acid in mature NAGAL1, i.e., omitting the mammalian secretion signal) could be an instigator of unwanted disulphide bridge scrambling, cysteine 326 was replaced by the amino acid serine (which is similar in size and hydrophobicity).

Accordingly, three new variants of NAGAL1 were generated: #1: resulting from the domain II swap; #2: resulting from a double amino acid change: Asn213Asp and Cys326Arg; and #3: resulting from a single amino acid change: Cys326Ser. Synthetic nucleotide sequences, codon optimized for *Yarrowia lipolytica*, were designed to allow the domain II swap on the one hand or the introduction of the single or double amino acid substitution on the other hand in the NAGAL1 sequence. Subcloning of these sequences resulted into plasmids encoding each of the new NAGAL1 variants with an N-terminal Lip2pre secretion signal, followed by two X-Ala repeats, namely NAGAL1 #1 (SEQ ID NO: 14), NAGAL1 #2 (SEQ ID NO: 15), and NAGAL1 #3 (SEQ ID NO: 16):

SEQ ID NO: 14 (bold underlined: *Yarrowia* Lip2pre signal peptide and two X-Ala repeats, underlined: sequence divergence from NAGAL1)

MKLSTILFTACATLAAALDNGLLQTPPMGWLAWERFRCNINCDEDPKNCI

SEQLFMEMADRMAQDGWRDMGYTYLNIDDCWIGGRDASGRLMPDPKRFPH

GIPFLADYVHSLGLKLGIYADMGNFTCMGYPGTTLDKVVQDAQTFAEWKV

DMLKLDGCFSTPEERAQGYPKMAAALNATGRPIAFSCEWPLYEGGLPPRV

NYSLLADICNLWRNYDDIQDSWWSVLSILNWFVEHQDILQPVAGPGHWND

PDMLLIGNFGLSLEQSRAQMALWTVLAAPLLMSTDLRTISAQNMDILQNP

LMIKINQDPLGKQGYQLRQGDNFEVWERPLSGLAWAVAMINRQEIGGPRS

YTIAVASLGKGVACNPACFITQLLPVKRKLGFYEWTSRLRSHINPTGTVL

LQLENTMQMSLKDLL

SEQ ID NO: 15 (bold underlined: *Yarrowia* Lip2pre signal peptide and two X-Ala repeats, underlined: sequence divergence from NAGAL1)

MKLSTILFTACATLAAALDNGLLQTPPMGWLAWERFRCNINCDEDPKNCI

SEQLFMEMADRMAQDGWRDMGYTYLNIDDCWIGGRDASGRLMPDPKRFPH

GIPFLADYVHSLGLKLGIYADMGNFTCMGYPGTTLDKVVQDAQTFAEWKV

DMLKLDGCFSTPEERAQGYPKMAAALNATGRPIAFSCEWPLYEGGLPPRV

NYSLLADICNLWRNYDDIQDSWWSVLSIL<u>D</u>WFVEHQDILQPVAGPGHWND

PDMLLIGNFGLSLEQSRAQMALWTVLAAPLLMSTDLRTISAQNMDILQNP

LMIKINQDPLGIQGRRIHKEKSLIEVYMRPLSNKASALVFFS<u>R</u>RTDMPYR

YHSSLGQLNFTGSVIYEAQDVYSGDIISGLRDETNFTVIINPSGVVMWYL

YPIKNLEMSQQ

SEQ ID NO: 16 (bold underlined: *Yarrowia* Lip2pre signal peptide and two X-Ala repeats, underlined: sequence divergence from NAGAL1)

MKLSTILFTACATLAAALDNGLLQTPPMGWLAWERFRCNINCDEDPKNCI

SEQLFMEMADRMAQDGWRDMGYTYLNIDDCWIGGRDASGRLMPDPKRFPH

GIPFLADYVHSLGLKLGIYADMGNFTCMGYPGTTLDKVVQDAQTFAEWKV

DMLKLDGCFSTPEERAQGYPKMAAALNATGRPIAFSCEWPLYEGGLPPRV

NYSLLADICNLWRNYDDIQDSWWSVLSILNWFVEHQDILQPVAGPGHWND

PDMLLIGNFGLSLEQSRAQMALWTVLAAPLLMSTDLRTISAQNMDILQNP

LMIKINQDPLGIQGRRIHKEKSLIEVYMRPLSNKASALVFFS<u>S</u>RTDMPYR

YHSSLGQLNFTGSVIYEAQDVYSGDIISGLRDETNFTVIINPSGVVMWYL

YPIKNLEMSQQ

Expression of the NAGAL1 variants was driven by the semi-constitutive growth-phase related Hp4d promotor.

Single copy expression strains of the variants NAGAL1 #1, NAGAL 1 #2 and NAGAL1 #3 were generated via transformation of the corresponding ADE2 containing expression plasmids into *Yarrowia* strain OXYY1315. Transformants were selected based on their capacity to grow on minimal medium plates without any added adenine. For comparison, the ADE2 expression plasmid for NAGAL1 was also transformed to the same strain background. The presence of the expression constructs into the genome of the selected transformants was checked via PCR. The expression level of the different NAGAL variants by the *Yarrowia* transformants that scored positive on PCR analysis was evaluated after 24-well cultivation in 2 ml rich medium. In brief, several transformants were inoculated in wells containing 2 ml yeast extract-peptone-dextrose (YPD), and cultivated overnight at 28° C. and 180 rpm. The next day, 1 to 2 µl of this culture was transferred to a new well with fresh YPD and recultivated overnight at 28° C. and 180 rpm. The following day, the 24-well plate was centrifuged and the medium was removed from the cell pellets. The cells were resuspended in 2 ml SuperT/glycerol rich medium (0.5% w/v yeast extract; 2% w/v malt extract; 1% w/v trypton; 1.5% v/v glycerol; 200 mM phosphate buffer pH 6.8) and grown at 28° C. for 3 days. At the end of the cultivation, the medium was harvested and analysed for the expression of the different modified NAGAL1 polypeptides.

Figure 13:
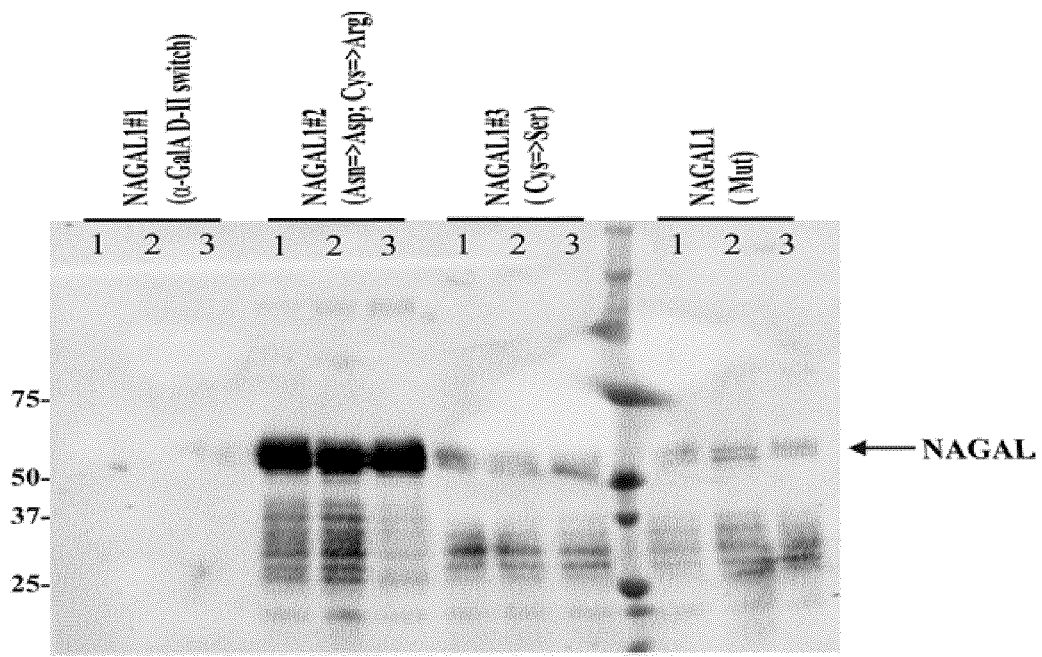
FIG. 13 represents a Western blot analysis on 24-well cultivation samples of different single-copy expression strains for NAGAL1(Mut), NAGAL1 #1, NAGAL1 #2 and NAGAL1 #3.

The secretion of the recombinant proteins in the culture medium was first analysed via reducing SDS-PAGE electrophoresis, followed by Western blot analysis (FIG. 13; 3 clones per variant). Based on the amino acid composition and taking into consideration the size of potentially added N-glycans, the monomeric form of the four NAGAL variants was expected to run at about 50 kDa. Expression was observed for the original NAGAL 1 (Mut) and for NAGAL1 #3 in which the Cys326Ser amino acid conversion had taken place. No expression was observed for clones transformed with the NAGAL1 #1, whereas a substantial increase in NAGAL1 expression was obtained for transformants of the NAGAL1 #2 expression construct, containing the two amino acid changes Asn213Asp and Cys326Arg. These results indicated that replacing the NAGAL1 domain II with that of human α-GalA resulted in the inability to stably produce the corresponding hybrid protein. Exchange of Cys326 by serine, as an attempt to reduce potential aberrant disulfide bridge formation, had some effect on the NAGAL1 expression levels. The double amino acid substitution that is contemplated to introduce a stabilizing ion pair between the NAGAL1 domains I and II, resulted in considerably better expression of secreted NAGAL1 (FIG. 13, NAGAL1 #2).

The modified NAGAL1 #2 polypeptide represents an embodiment illustrating the principles of the present invention.

Figure 14:
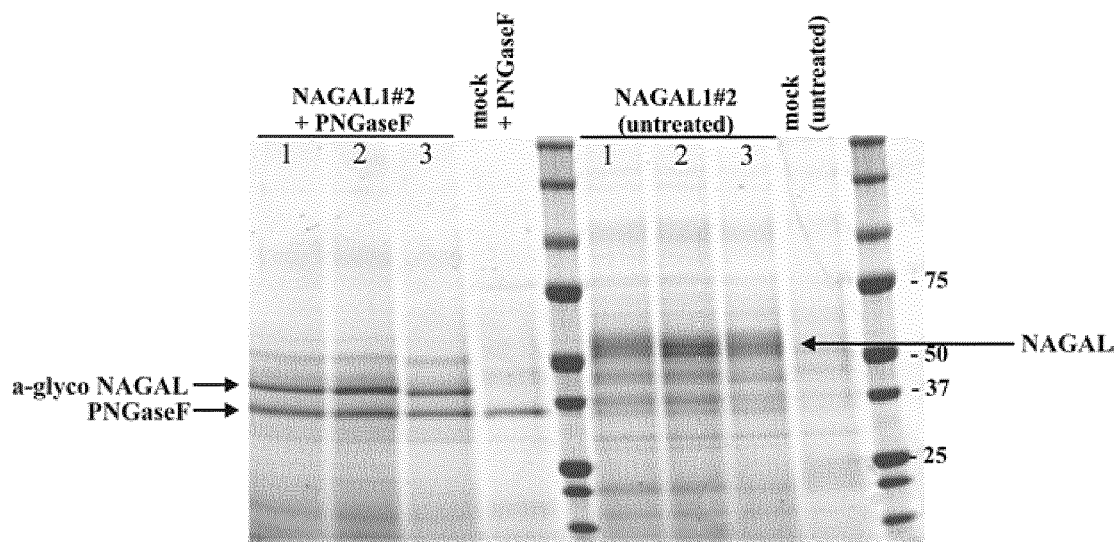
FIG. 14 represents a reducing SDS-PAGE analysis on 24-well medium samples of different single-copy expression strains for NAGAL1 #2, before (right) or after (left) Peptide-N-Glycosidase F (PNGaseF; Bioke; P0704L) treatment.

The modified NAGAL1 #2 polypeptide was very well detectable after Coomassie staining of a reducing SDS-PAGE gel (FIG. 14). Peptide-N-Glycosidase F (PNGaseF) (Bioke; P0704L) treatment to deglycosylate the samples resulted in a single lower MW NAGAL1 band indicating that the modified NAGAL1 #2 polypeptide was produced as two forms, only differing from each other in their degree of N-glycosylation (FIG. 14).

Figure 15:
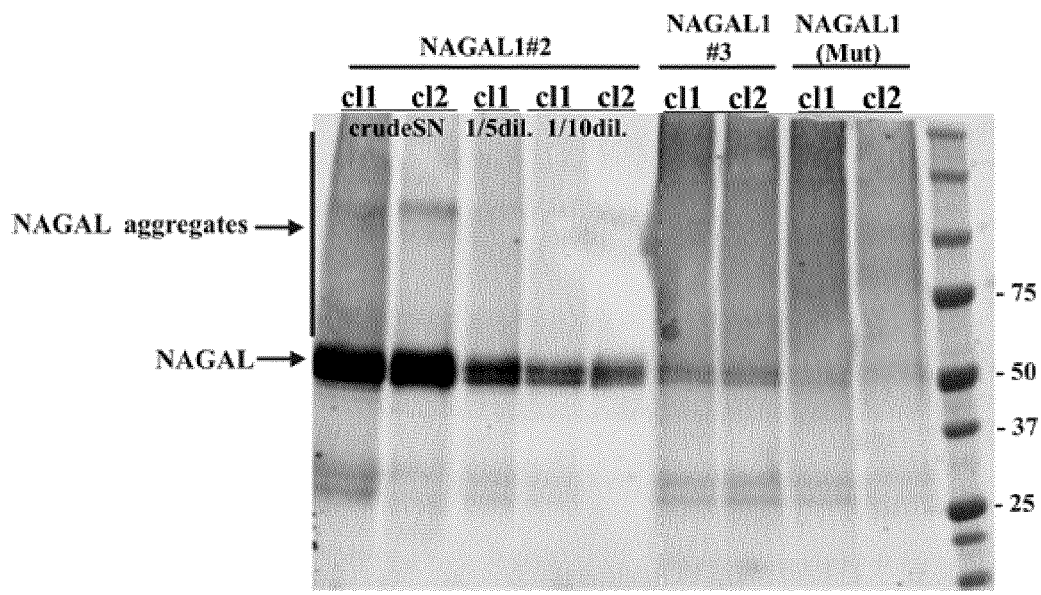
FIG. 15 represents a non-reducing SDS-PAGE, followed by Western blot analysis using an anti-NAGAL antibody (Abcam; Ab139526), on 24-well medium samples of different single-copy expression strains of NAGAL1(Mut), NAGAL1 #2 and NAGAL1 #3.

Next, it was investigated how the Yarrowia-produced modified NAGAL1 #2 polypeptide behaved after non-reducing SDS-PAGE electrophoresis and Western blot analysis. Crude medium for two NAGAL1 #2 expression clones was loaded on gel, as well as a ⅕ dilution (for one clone) and a 1/10 dilution (for both clones) (FIG. 15). These samples were compared with crude (undiluted) medium of two NAGAL1 (Mut) and two NAGAL1 #3 (Cys326Ser) expression clones. In the undiluted samples for NAGAL1 #2, there was still a fraction that seemed to form aggregates. However, based on the dilutions series, it can be concluded that the ratio of aggregates versus non-aggregated product (i.e., the monomeric NAGAL1 bands running at approximately 50 kDa) was much more favourable for expression of the modified NAGAL1 #2 polypeptide versus expression of NAGAL1(Mut) or NAGAL1 #3. Compared to the undiluted samples of the latter two variants, the 1/10 dilution of the NAGAL1 #2 samples showed significantly more 50 kDa monomeric product, whereas the aggregated material became hardly detectable (FIG. 15). Comparison between NAGAL1(Mut) and NAGAL1 #3 showed a slight improvement for the latter in the ratio between non-aggregated versus aggregated material.

Figure 16:
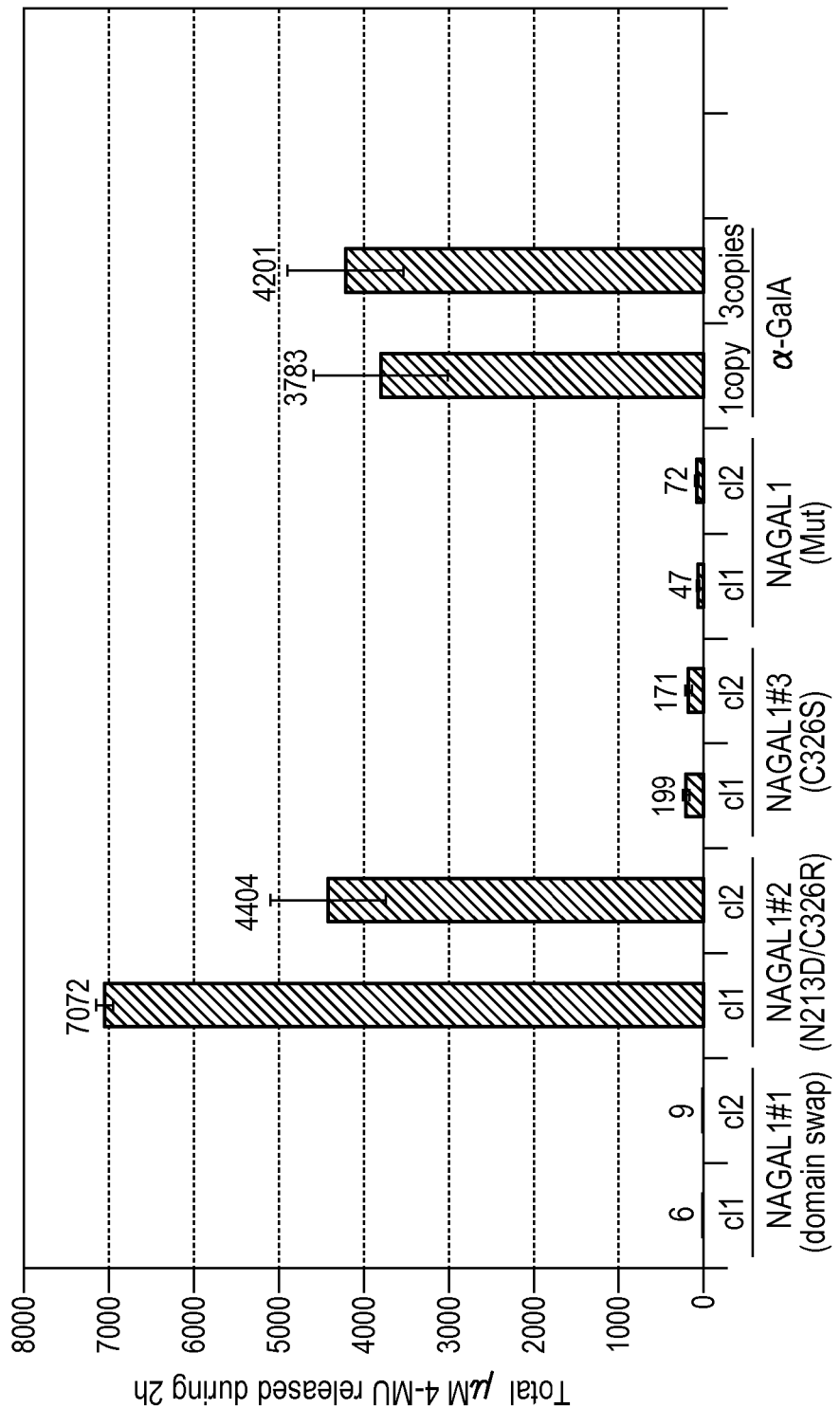
FIG. 16 represents the released 4-methylumberriferyl (μM) after a 2 hour incubation of 24-well cultivation medium with the fluorometric substrate 4MU-α-Gal (Carbosynth Limited; EM05182). The numbers represent the average of measured values.

As another analysis on the 24-well cultivations of the different NAGAL1 variants, the release of active α-galactosidase enzyme activity into the medium was tested. A standard fluorometric assay was performed at pH 4.5 on a dilution series of the medium, using 4-methylumberriferyl-α-D-galactopyranoside (4MU-α-Gal) as a substrate as described before. The extracellular presence of α-galactosidase was measured as the amount of released 4-methyl-umbelliferyl during a two hour incubation at 37° C. (FIG. 16) and compared with 24-well cultivations of a single copy and 3-copy Yarrowia expression strain for human α-GalA. The variation observed between clones expressing the same variant can be due to the cultivation condition (e.g., the growth conditions during deep-well cultivation in rich medium cannot be controlled) or to clonal differences (e.g., the Yarrowia transformants are generated by random integration of the expression cassettes resulting into genomic difference between clones).

The analysis showed an up to 100-fold increase of α-galactosidase activity for the Yarrowia strains expressing modified NAGAL1 #2 polypeptide illustrating the principles of present invention compared with the NAGAL1(Mut) clones. The obtained activity levels for the Yarrowia strains expressing modified NAGAL1 #2 polypeptide were in the range of those produced by the human α-GalA expression strains. The analysis also showed a measurable increase of α-galactosidase activity for the Yarrowia strains expressing modified NAGAL1 #3 polypeptide.

Example 4

Controlled Bioreactor Cultivation of Yarrowia lipolytica Strains Expressing the Different Human NAGAL1 Variants Controlled bio-reactor cultivations were performed in a 1L fermentation system (DASGIP). In short, a seed culture of the selected strains was grown overnight at 28° C. in a shake flask containing rich medium. The seed was then inoculated into a fermenter vessel containing defined mineral medium with glycerol as only carbon source to start the batch phase at 28° C. with unrestricted growth. After glycerol depletion the process was run in carbon limitation by applying two successive exponential glycerol feeds: a first phase with a relative fast exponential glycerol feed for 40 hours and a second phase with a slower exponential feed for approximately another 115 hours. Throughout the fermentation process, dissolved oxygen (around 20%), pH (6.8), temperature (28° C.), foam levels, and feed rates were actively controlled. Dissolved oxygen levels were maintained by stirring and spiking with pure oxygen, pH was adjusted by adding 14% ammonium hydroxide, and foam was counteracted by adding antifoam agent upon activation of the antifoam probe. During the process, samples were taken regularly to assess the following parameters: 1) recombinant protein expression, 2) expression of functional enzyme via an activity assay, 3) evolution of the N-glycosylation profile of the secretome, 4) biomass concentration, 5) external pH, 6) cell morphology, and 7) total protein concentration.

Figure 17:
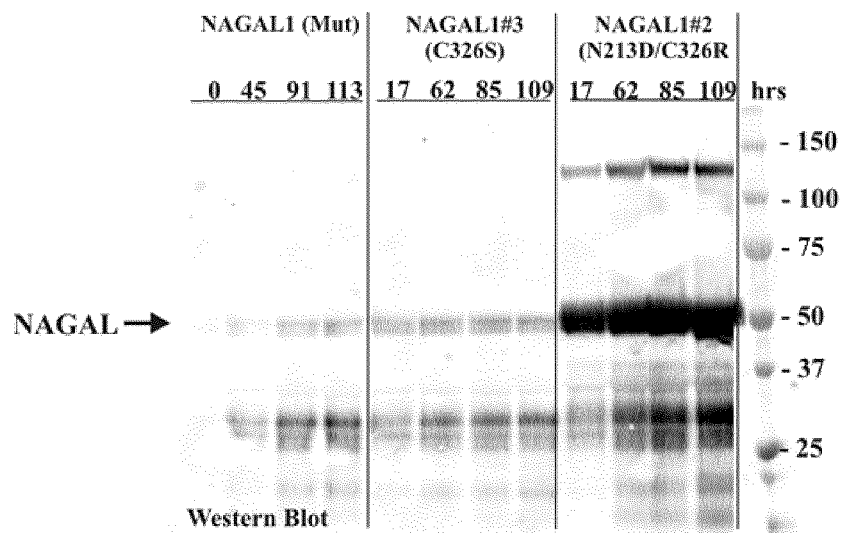
FIG. 17 represents Western blot analysis of different time-points during the bioreactor cultivation of *Yarrowia lipolytica* strains expressing the different NAGAL1 variants. The numbers on top of the blot represent the number of cultivation hours in feed phase II.
Figure 18:
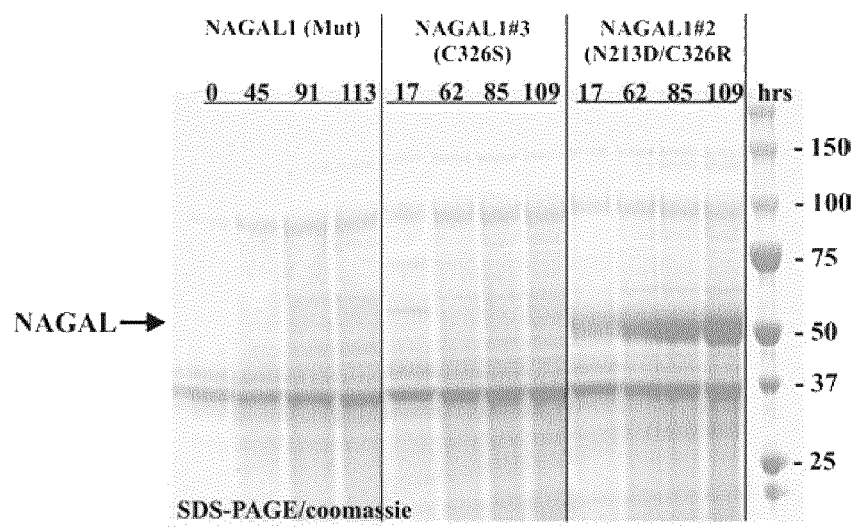
FIG. 18 represents a Coomassie staining of an SDS-PAGE gel of different time-points during the bioreactor cultivation of *Yarrowia lipolytica* strains expressing the different NAGAL1 variants. The numbers on top of the gel represent the number of cultivation hours in feed phase II.

Expression over time of the different NAGAL1 variants during the 1L bioreactor cultivations was analysed via reducing SDS-PAGE/Coomassie staining and via Western blot detection (FIGS. 17 and 18). Similar to the 24-well cultivations, no expression of NAGAL1 #1 (domain II swap) could be observed (not shown). NAGAL1 #3 (Cys326Ser) was produced slightly better compared to the original NAGAL1 (Mut) variants, however neither of both variant could be detected upon Coomassie staining of an SDS-PAGE gel (FIG. 18). In contrast, the expression of NAGAL1 #2 (Asn213Asp/Cys326Arg) was clearly visible upon Coomassie staining and already well detected early during the fermentation (FIG. 18). Western blot analysis showed clearly superior expression levels of NAGAL1 #2 compared to NAGAL1(Mut) or NAGAL1 #3 (FIG. 17).

Figure 19:
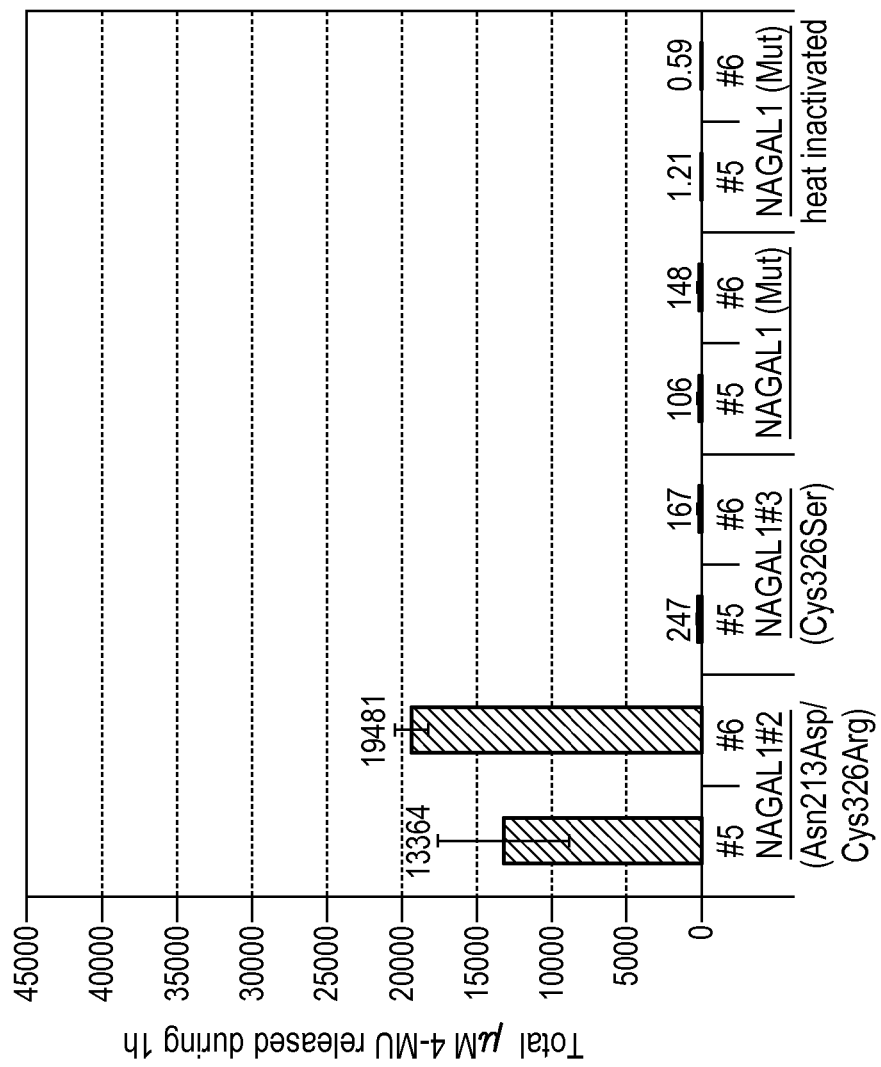
FIG. 19 represents the released 4-methylumberriferyl (μM) after a 1 hour incubation of the fluorometric substrate 4MU-α-Gal with fermentation samples of a single copy NAGAL1 (Mut), NAGAL1 #2, and NAGAL1 #3 expression strains: per strain the activity levels were assessed on the penultimate and final time-point of the fermentation run. The numbers represent the average of measured values. Heat inactivation (20 minutes at 99° C.) of α-galactosidase activity in the NAGAL(Mut) medium samples prior to the activity test indicates that the low levels of released 4MU in case of untreated NAGAL1 #3 and NAGAL(Mut) samples are clearly above the background measurements and thus representing actual enzyme activities.

Next, the levels of secreted α-galactosidase activity were measured as described before using 4-MU-α-Gal as substrate (FIG. 19). Some increase in secreted enzyme was observed in the penultimate time-point of the NAGAL1 #3 fermentation broth versus that of the NAGAL 1(Mut) broth, although the final levels seemed to equalize at the end of the fermentation. Repetitive bioreactor cultivations may determine a statistical difference in secreted α-galactosidase activity at the end of fermentation between NAGAL1 #3 and NAGAL1(Mut) expression clones. Over 100-fold increase in secreted α-galactosidase activity was observed in the bioreactor cultivation broth of a NAGAL1 #2 expression strain compared to the activity in a similar fermentation on a NAGAL1(Mut) strain.

Example 5

Multi-Copy Yarrowia lipolytica Strain for the Expression of NAGAL1 #2

Figure 20:
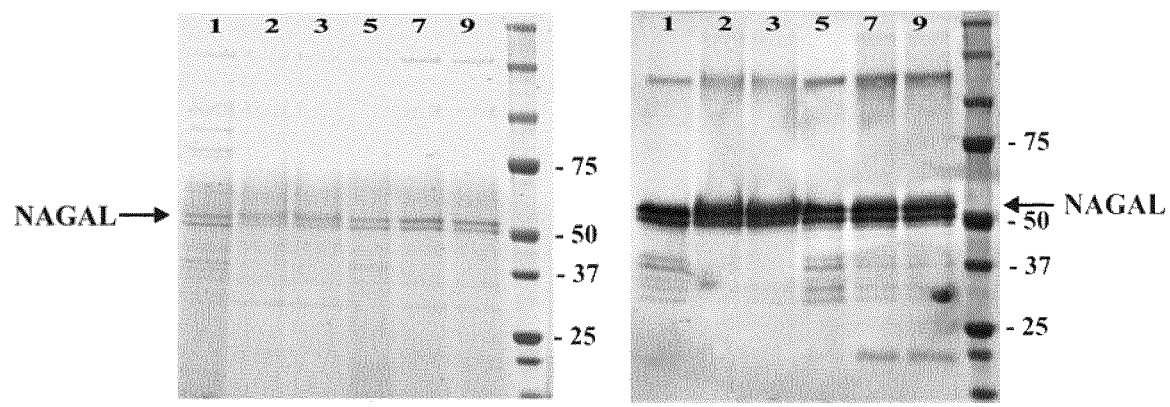
FIG. 20 represents SDS-PAGE/Coomassie staining (left) and western blot analysis (right) of interim single copy transformants in OXYY2163 expressing NAGAL1 #2.

First, the ADE2 variant of the NAGAL1 #2 expression construct, encoding a modified NAGAL polypeptide illustrating the principles of the present invention, was transformed into OXYY2163 to generate a single copy expression strain with leu2- and ura3-auxotrophy. Genomic integration of the plasmid was checked by PCR screening on the transformants. Several PCR-positive clones were tested for production of the recombinant NAGAL1 #2 after cultivation in 24 deep-well plates. In brief, several transformants were inoculated in wells containing 2 ml YPD, and cultivated overnight at 28° C. and 180 rpm. The next day 1 to 2 µl of this culture was transferred to a new well with fresh YPD and recultivated overnight at 28° C. and 180 rpm. The following day, the 24-well plate was centrifuged and the medium was removed from the cell pellets. The cells were resuspended in 2 ml SuperT/glycerol rich medium and grown at 28° C. for 3 to 4 days. At the end of the cultivation, the medium was harvested and the NAGAL1 #2 expression was evaluated via SDS-PAGE/Coomassie staining and Western blot analysis (FIG. 20).

Based hereon, two single copy transformants were selected for co-transformation with the LEU2 and URA3 containing NAGAL1 #2 expression constructs and clones were selected based on the ability to grow on minimal medium without added adenine, uracil, and leucine. Integration of the two extra expression cassettes was confirmed via PCR analysis and several PCR-positive clones were tested for the production of the recombinant NAGAL1 #2 after 24-well cultivation (as described above).

Figure 21:
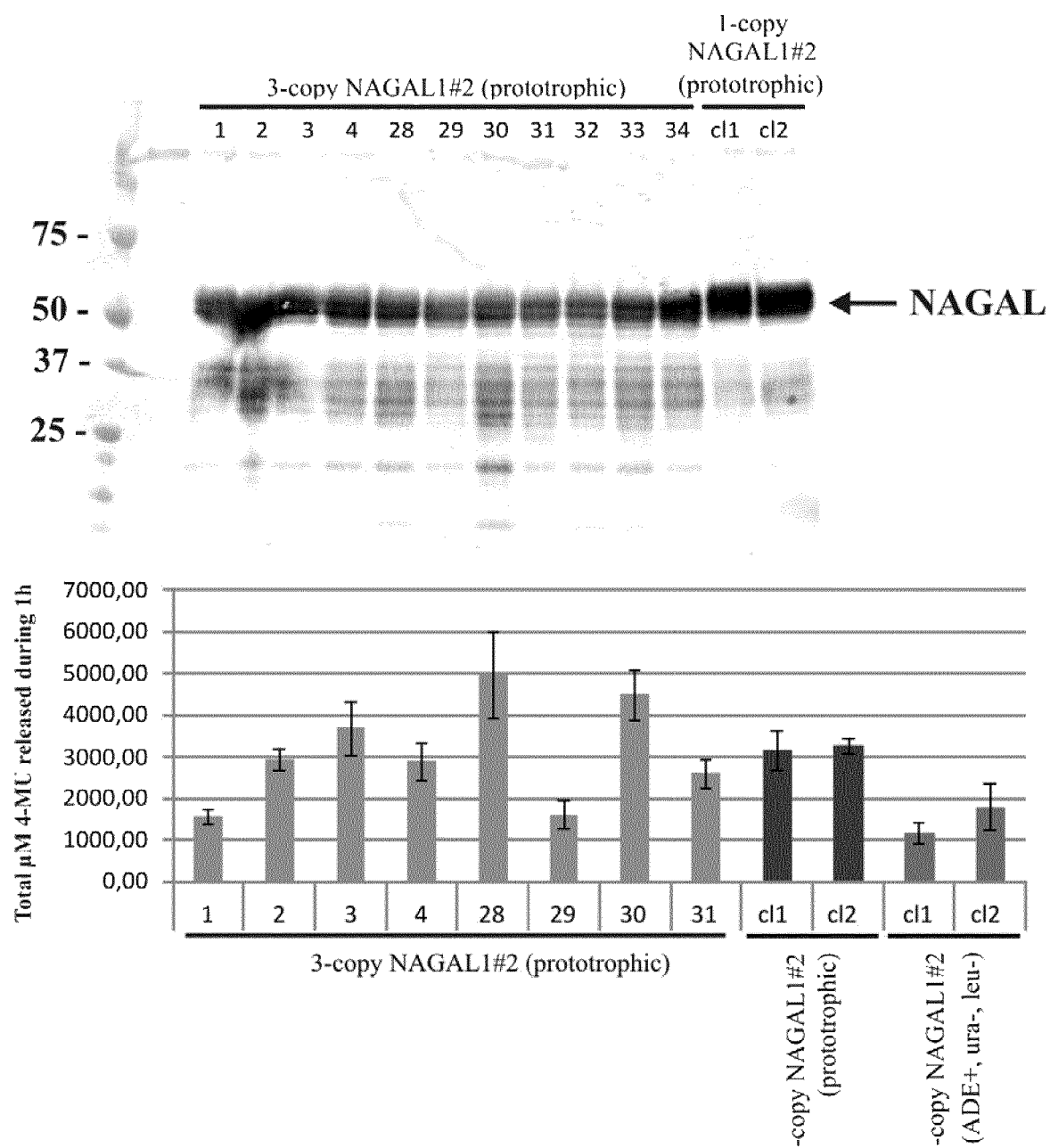
FIG. 21 represents Western blot analysis (top panel) and α-galactosidase activity assay (bottom panel) on 24-well medium samples of 3-copy NAGAL1 #2 expression strains versus a few reference single copy strains.

Crude medium was analyzed for the expression of the recombinant protein via Western blot analysis and the α-galactosidase enzyme activity was measured as described before using 4-MU-α-Gal as substrate (FIG. 21). Based on the Western blot analysis, it appeared that overall, the prototrophic 3-copy strains were producing less recombinant NAGAL1 #2 compared to the prototrophic single copy strains. As mentioned before, some clonal variation could be observed due to either the uncontrolled nature of the cultivation conditions or due to the differences in genotype as a result of the random integration of the expression plasmids. Clonal variation was more pronounced upon assessment of the levels of secreted α-galactosidase activity: on average the activity levels observed for the 3-copy strains are in the same range as those of the prototrophic single copy strains. This observation could indicate that the translation and/or folding machinery of *Yarrowia* may become saturated or limiting for the expression of the NAGAL1 #2 variant in the multi-copy strains under the cultivation conditions applied in this example.

Controlled bio-reactor cultivations of two selected multi-copy NAGAL1 #2 strains were performed in a 1L fermentation system. In short, a seed culture of the selected strains was grown overnight at 28° C. in a shake flask containing rich medium. The seed was then inoculated into a fermenter vessel containing defined mineral medium with glycerol as only carbon source to start the batch phase at 28° C. with unrestricted growth. After glycerol depletion the process was run in carbon limitation by applying two successive exponential glycerol feeds: a first phase with a relative fast exponential glycerol feed for 44 hours and a second phase with a slower exponential feed for approximately another 110 hours. Throughout the fermentation process, dissolved oxygen (around 20%), pH (6.8), temperature (28° C.), foam levels, and feed rates were actively controlled and where needed adjusted. During the process, samples were taken regularly to assess the different fermentation parameters, as described herein.

Figure 22:
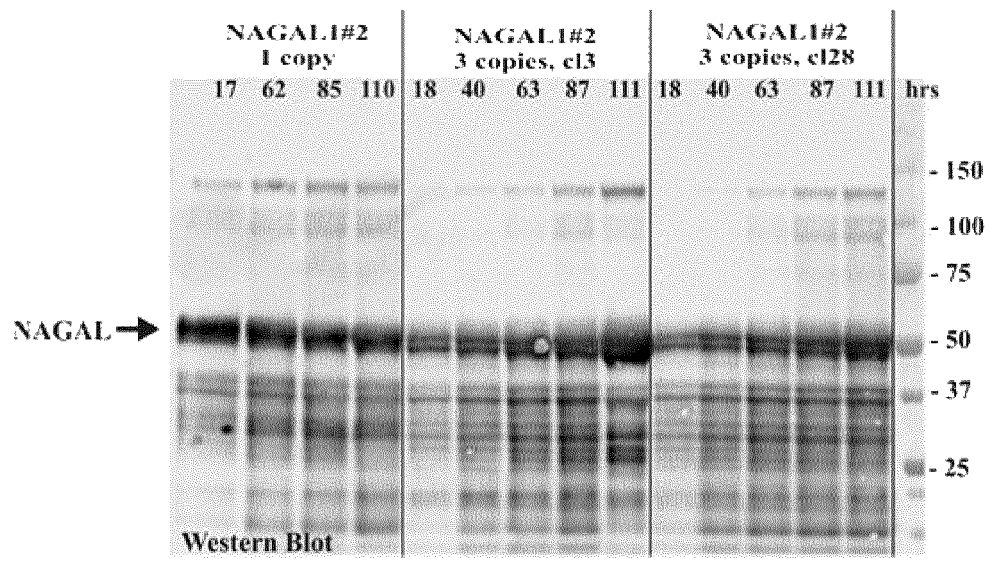
FIG. 22 represents a Western blot analysis of different time-points during the bioreactor cultivation of a single copy and two 3-copy NAGAL1 #2 expression strains. The numbers on top of the blot represent the number of cultivation hours in feed phase II.
Figure 23:
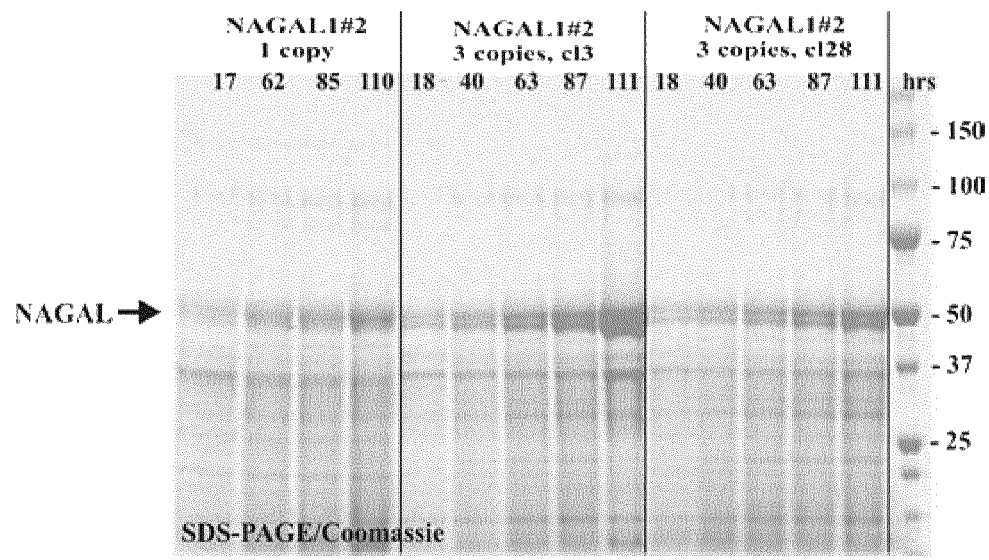
FIG. 23 represents a Coomassie staining of an SDS-PAGE gel of different time-points during the bioreactor cultivation of a single copy and two 3-copy NAGAL1 #2 expression strains. The numbers on top of the gel represent the number of cultivation hours in feed phase II.

The production of the modified NAGAL1 #2 polypeptide after bioreactor cultivation of two multi-copy expression strains was compared with that of a single copy clone. Production over time during the 1L fermentations was analysed via reducing SDS-PAGE/Coomassie staining and via Western blot detection (FIGS. 22 and 23). A clear increase in protein expression was observed for the multi-copy strain clone 3 when compared to the NAGAL1 expression levels of the single copy variant. This indicated that during the controlled bioreactor cultivation in minimal medium the strain's capacity to produce even higher levels of the modified NAGAL1 #2 polypeptide illustrating the present invention was not yet saturated.

Figure 24:
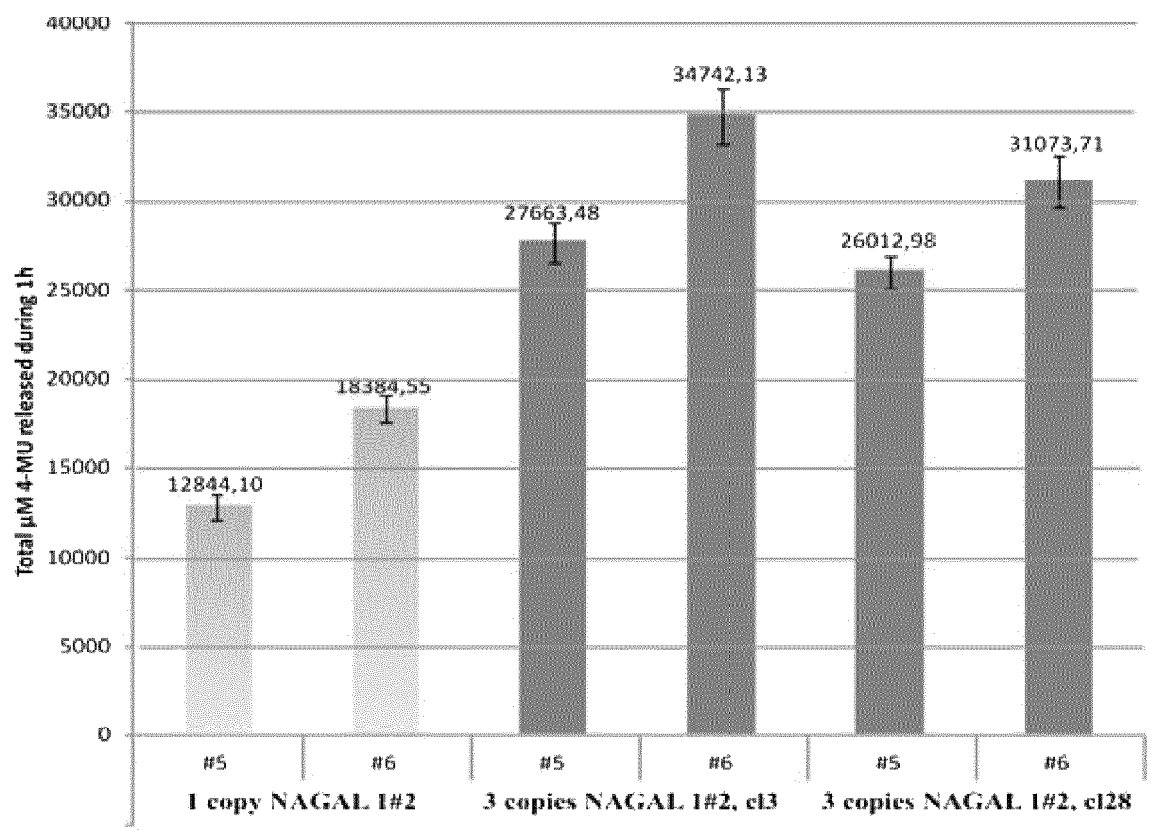
FIG. 24 represents the released 4-methylumberriferyl (μM) after a 1 hour incubation of the fluorometric substrate 4MU-α-Gal with fermentation samples of single- and multi-copy NAGAL1 #2 expression strains: per strain the activity levels were assessed on the penultimate and final time-point of the fermentation run. The numbers represent the average of measured values.

Increased expression of functional NAGAL1 #2 was also observed when performing the α-galactosidase enzyme activity assay on crude fermentation samples using 4-MU-α-Gal as substrate (FIG. 24). The level of functional enzyme was expressed as the µM amount of hydrolyzed 4-methylumberriferyl after a 1 hour incubation at 37° C. When comparing the same time-points with each other, the α-galactosidase levels in the multi-copy strains were approximately 1.7 to 2.15 fold higher than in the single-copy strain (FIG. 24).

Figure 25:
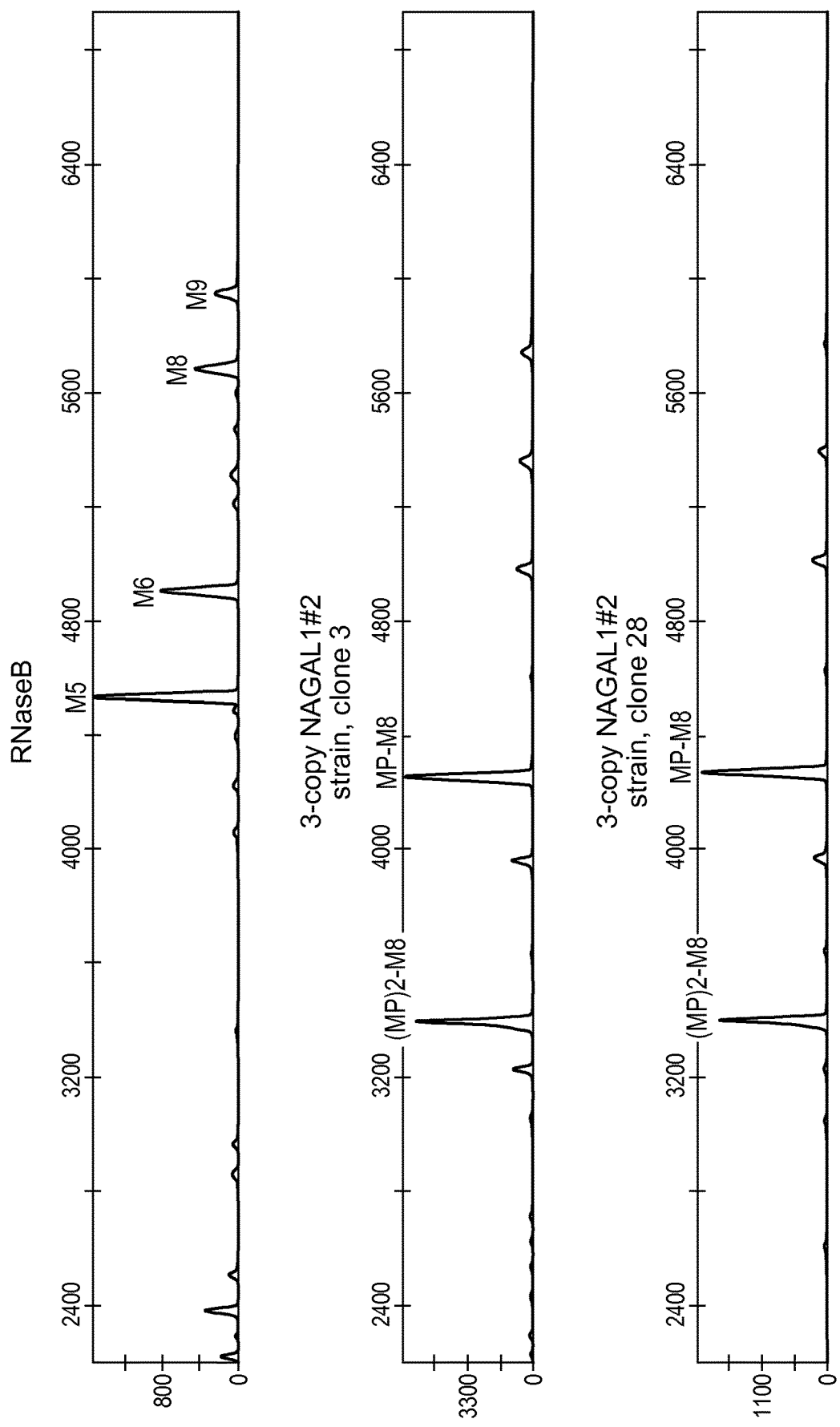
FIG. 25 represents N-glycan profiling via capillary electrophoresis on APTS-labelled N-glycans derived from the total protein content in the 1L fermentation broth of multi-copy NAGAL1 #2 expression clones. M5, M6, M8, M9: $Man_{5-6-8-9}GlcNAc_2$; MP-M8, (MP)2-M8: $Man_8GlcNAc_2$ carrying one or two mannosephosphate moieties, respectively.

The SDS-PAGE/Coomassie staining showed that a large fraction of the total protein in the fermentation broth consisted of NAGAL-related product. An N-glycan profiling was performed as described (Laroy et al., 2006, Nat Protoc., 1(1):397-405) on a crude harvest medium sample to get a first indication on the main N-glycans that are present on the recombinant protein. In short, medium proteins were captured and denatured on a membrane, followed by PNGaseF treatment to trim off the N-linked oligosaccharides. After labelling with the fluorophore APTS (8-aminopyrene-1,3,6-trisulfonic acid), the N-glycans were analysed via capillary electrophoresis, and their running behaviour was compared with that of known standard oligosaccharides. The results are shown in FIG. 25 for the total protein in the fermentation broth of the multi-copy strains expressing the modified NAGAL1 #2 polypeptide. Two main peaks were identified in the N-glycan profile, corresponding to monophosphorylated (MP-M8) and biphosphorylated ((MP)2-M8) Man8GlcNAc2 (FIG. 25, clone 3 and clone 8).

Example 6

3D-Modelling of NAGAL Polypeptides

The PyMOL software (DeLano, 2002, The PyMOL Molecular Graphics System, www.pymol.org) was used for structural alignment and superposition of human NAGAL (PDB 3H54, dark grey) and chicken NAGAL (PDB 1KTB, light grey). This shows that both enzymes have a very similar tertiary fold (see FIG. 26). The interface between domains I and II in chicken NAGAL reveals two stabilizing ion pairs Asp214-Arg327 and Asp221-Arg299 (as described in Garman et al., 2002, Structure, 10(3):425-34). The latter one (see box, FIG. 26) seems to be strictly conserved in position in the human NAGAL, whereas the first one seems to be absent in the human orthologue. A 3D variant of human NAGAL in which Asn213 has been converted into Asp213 and in which simultaneously Cys326 has been converted into Arg326 was modelled in silico using the PyMOL mutagenesis tool, and specific rotamers were selected to avoid steric clashes with neighbouring residues. The inventors assessed the distances between the introduced Asp213 and Arg326 side chains using the PyMOL measurement tool and found these to be equal to or lower than 4 Å. Without limitation, the inventors postulate that this finding confirms the possibility to form a second Asp-Arg ion pair in the mutated human NAGAL, that may stabilize the interaction between domains I and II of the NAGAL polypeptide.

Figure 26:
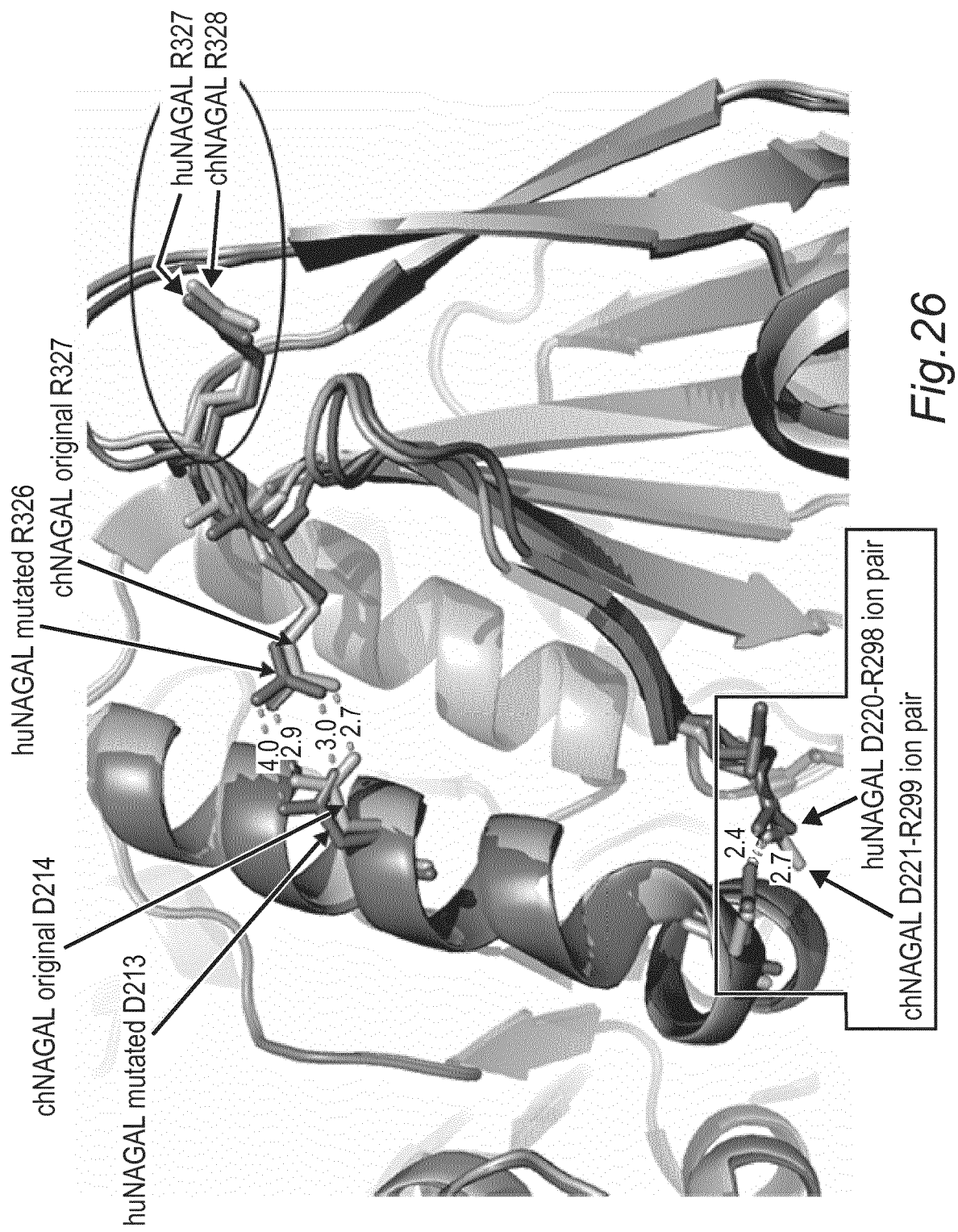
FIG. 26 illustrates superposition of chicken (ch; light grey) and human (hu; dark grey) NAGAL, the latter after conversion of Asn213 (N213) into Asp (D213) and of Cys326 (C326) into Arg (R326). In the box: conserved ion pair between chicken and human NAGAL. In the ellipse: conserved Arg between chicken (R328) and human NAGAL (R327). The distances of 4 and 3 Å between the amino acid site chains of the mutated human NAGAL are within the range to allow ion pairing.

In wild-type human NAGAL, Cys326 is followed by an Arg at position 327 (see ellipse, FIG. 26). However, based on the 3D structure the inventors postulate that the amino acid side chain of Arg327 is positioned in such a way that it would be impossible to form an ion pair with the introduced Asp213 in the mutant NAGAL. Hence, the inventors predicted that conversion of only Asn213 into Asp would not result into ion pairing with the already existing Arg327.

Figure 27:
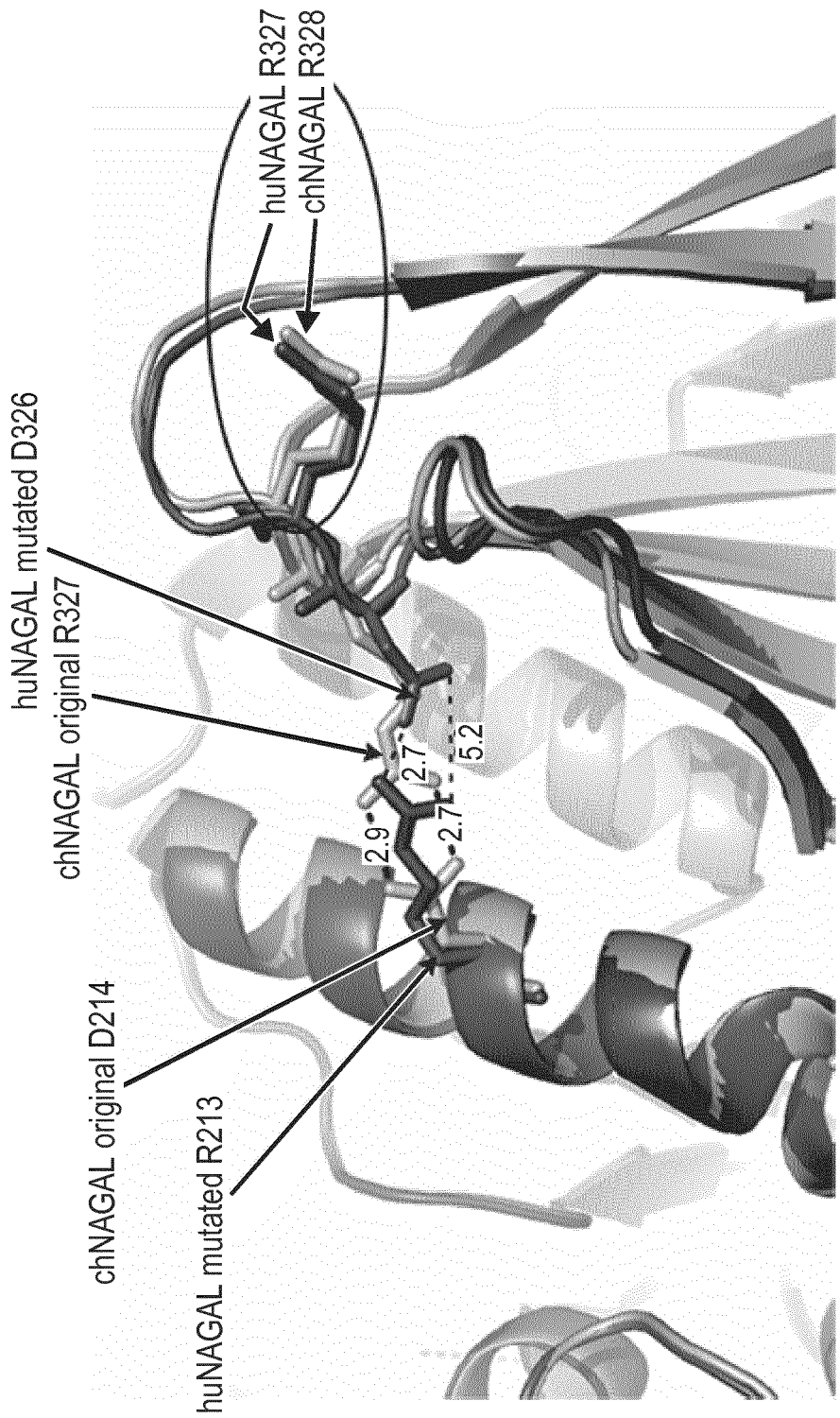
FIG. 27 illustrates superposition of chicken (ch; light grey) and human (hu; dark grey) NAGAL, the latter after conversion of Asn213 (N213) into Arg (R213) and of Cys326 (C326) into Asp (D326). In the ellipse: conserved Arg between chicken (R328) and human NAGAL (R327). The distance of 5.2 Å between the amino acid site chains of the mutated human NAGAL are not within the optimal range to allow ion pairing.

In a second in silico exercise, the inventors assessed whether inversion of charges as introduced in NAGAL1 #2 could result into a second ion pairing between domains I and II of human NAGAL. For this, a variant of human NAGAL in which Asn213 has been converted into Arg213 and in which simultaneously Cys326 has been converted into Asp326 was 3D modelled in silico using the PyMOL mutagenesis tool, and rotamers were selected to avoid steric clashes with neighbouring residues (FIG. 27).

The distances between the introduced Arg213 and Asp326 site chains were assessed using the PyMOL measurement tool, with one of them (5.2 Å) being significantly higher than 4 Å. On the basis of this model it could therefore be predicted that the geometry of the mutated amino acids within such human NAGAL was not optimal for the formation of a second Asp-Arg ion pair in this alternative variant of the enzyme.

A synthetic nucleotide sequence, codon optimized for *Yarrowia lipolytica*, was designed to introduce the above double amino acid substitution in the NAGAL1 sequence. The resulting new variant is designated as NAGAL1 #7 (SEQ ID NO: 17). Subcloning of the synthetic fragment into the original NAGAL1 expression vector resulted in a *Yarrowia* expression plasmid encoding the NAGAL1 #7 variant with an N-terminal Lip2pre secretion signal, followed by two X-Ala repeats. Similarly to the previously expressed NAGAL1 variants, the expression of NAGAL1 #7 is driven by the semi-constitutive growth-phase related Hp4d promotor.

SEQ ID NO: 17 (bold underlined: *Yarrowia* Lip2pre signal peptide and two X-Ala repeats, underlined: sequence divergence from NAGAL1)

MKLSTILFTACATLAAALDNGLLQTPPMGWLAWERFRCNINCDEDPKNCI

SEQLFMEMADRMAQDGWRDMGYTYLNIDDCWIGGRDASGRLMPDPKRFPH

GIPFLADYVHSLGLKLGIYADMGNFTCMGYPGTTLDKVVQDAQTFAEWKV

DMLKLDGCFSTPEERAQGYPKMAAALNATGRPIAFSCEWPLYEGGLPPRV

NYSLLADICNLWRNYDDIQDSWWSVLSIL<u>R</u>WFVEHQDILQPVAGPGHWND

PDMLLIGNFGLSLEQSRAQMALWTVLAAPLLMSTDLRTISAQNMDILQNP

LMIKINQDPLGIQGRRIHKEKSLIEVYMRPLSNKASALVFFS<u>D</u>RTDMPYR

YHSSLGQLNFTGSVIYEAQDVYSGDIISGLRDETNFTVIINPSGVVMWYL

YPIKNLEMSQQ

A single copy expression strain of NAGAL1 #7 was generated via transformation of the corresponding ADE2 containing expression plasmids into strain OXYY1315. Transformants were selected based on their capacity to grow on minimal medium plates without any added adenine. The presence of the expression construct in the genome of the selected transformants was checked via PCR and the expression level of the NAGAL1 #7 variant was evaluated after 24-well cultivation in 2 ml rich medium. Cultivation was done as above. In brief, several transformants were inoculated in wells containing 2 ml YPD, and cultivated overnight at 28° C. and 180 rpm. The next day 1 to 2 µl of this culture was transferred to a new well with fresh YPD and recultivated overnight at 28° C. and 180 rpm. The following day, the 24-well plate was centrifuged and the medium was removed from the cell pellets. The cells were resuspended in 2 ml SuperT/glycerol rich medium and grown at 28° C. for 3 to 4 days. At the end of the cultivation, the medium was harvested and analysed for the expression of the different NAGAL variants.

Figure 28:
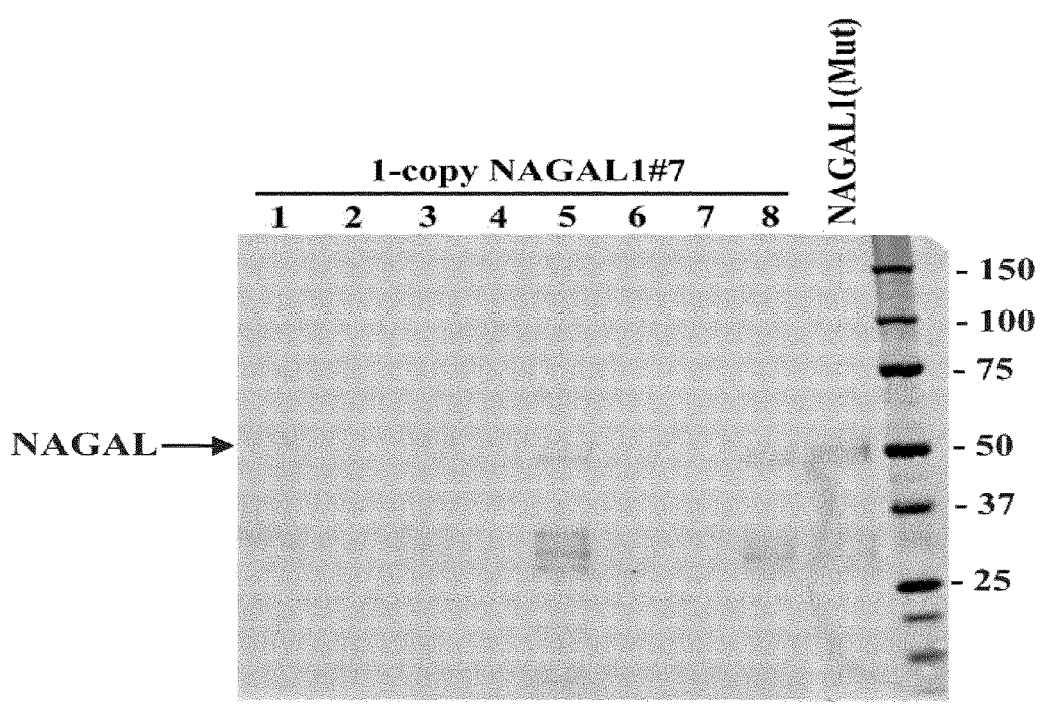
FIG. 28 represents Western blot analysis on 24-well cultivation samples of 8 different single-copy expression strains for NAGAL1 #7; comparison with a single copy NAGAL1(Mut) expression clone.

The secretion of the recombinant NAGAL1 #7 in the culture medium was analysed via reducing SDS-PAGE electrophoresis, followed by western blot analysis, and compared to that of the original NAGAL1(Mut) variant (FIG. 28). The expression levels of the NAGAL1 #7 from single copy *Yarrowia* transformants were similar or even lower compared to the expression levels obtained for a single copy NAGAL1 (Mut) production clone. Hence, the inversion of the introduced charges compared to NAGAL1 #2 (i.e., Arg213 instead of Asp213 in domain I and Asp326 instead of Arg326 in domain II) does not have the same effect as the introduced Asn213Asp and Cys326Arg modifications for variant NAGAL1 #2. This was consistent with the inventors' prediction based on in silico modelling that the geometry of the mutated amino acids in NAGAL1 #7 was not optimal for the formation of a second Asp-Arg ion pair between the domains I and II of the NAGAL polypeptide.

Example 7

Further Human NAGAL Polypeptides Demonstrating Improved Interaction Between Residues at Positions 213 and 326

The inventors further prepared the following further variants of NAGAL1: #4: resulting from a single amino acid change: Cys326Arg (SEQ ID NO: 18); #5: resulting from a single amino acid change Asn213Asp (SEQ ID NO: 19); and #6: resulting from a double amino acid change Cys326Ser and Asn213Asp (SEQ ID NO: 20).

SEQ ID NO: 18 (bold underlined: *Yarrowia* Lip2pre signal peptide and two X-Ala repeats, underlined: sequence divergence from NAGAL1)

MKLSTILFTACATLAAALDNGLLQTPPMGWLAWERFRCNINCDEDPKNCI

SEQLFMEMADRMAQDGWRDMGYTYLNIDDCWIGGRDASGRLMPDPKRFPH

GIPFLADYVHSLGLKLGIYADMGNFTCMGYPGTTLDKVVQDAQTFAEWKV

DMLKLDGCFSTPEERAQGYPKMAAALNATGRPIAFSCEWPLYEGGLPPRV

NYSLLADICNLWRNYDDIQDSWWSVLSILNWFVEHQDILQPVAGPGHWND

PDMLLIGNFGLSLEQSRAQMALWTVLAAPLLMSTDLRTISAQNMDILQNP

LMIKINQDPLGIQGRRIHKEKSLIEVYMRPLSNKASALVFFS<u>RR</u>TDMPYR

YHSSLGQLNFTGSVIYEAQDVYSGDIISGLRDETNFTVIINPSGVVMWYL

YPIKNLEMSQQ

SEQ ID NO: 19 (bold underlined: *Yarrowia* Lip2pre signal peptide and two X-Ala repeats, underlined: sequence divergence from NAGAL1)

MKLSTILFTACATLAAALDNGLLQTPPMGWLAWERFRCNINCDEDPKNCI

SEQLFMEMADRMAQDGWRDMGYTYLNIDDCWIGGRDASGRLMPDPKRFPH

GIPFLADYVHSLGLKLGIYADMGNFTCMGYPGTTLDKVVQDAQTFAEWKV

DMLKLDGCFSTPEERAQGYPKMAAALNATGRPIAFSCEWPLYEGGLPPRV

-continued

```
NYSLLADICNLWRNYDDIQDSWWSVLSILDWFVEHQDILQPVAGPGHWND

PDMLLIGNFGLSLEQSRAQMALWTVLAAPLLMSTDLRTISAQNMDILQNP

LMIKINQDPLGIQGRRIHKEKSLIEVYMRPLSNKASALVFFSCRTDMPYR

YHSSLGQLNFTGSVIYEAQDVYSGDIISGLRDETNFTVIINPSGVVMWYL

YPIKNLEMSQQ
```

SEQ ID NO: 20 (bold underlined: *Yarrowia* Lip2pre signal peptide and two X-Ala repeats, underlined: sequence divergence from NAGAL1)

```
MKLSTILFTACATLAAALDNGLLQTPPMGWLAWERFRCNINCDEDPKNCI

SEQLFMEMADRMAQDGWRDMGYTYLNIDDCWIGGRDASGRLMPDPKRFPH

GIPFLADYVHSLGLKLGIYADMGNFTCMGYPGTTLDKVVQDAQTFAEWKV

DMLKLDGCFSTPEERAQGYPKMAAALNATGRPIAFSCEWPLYEGGLPPRV

NYSLLADICNLWRNYDDIQDSWWSVLSILDWFVEHQDILQPVAGPGHWND

PDMLLIGNFGLSLEQSRAQMALWTVLAAPLLMSTDLRTISAQNMDILQNP

LMIKINQDPLGIQGRRIHKEKSLIEVYMRPLSNKASALVFFSSRTDMPYR

YHSSLGQLNFTGSVIYEAQDVYSGDIISGLRDETNFTVIINPSGVVMWYL

YPIKNLEMSQQ
```

All three variants NAGAL #4, #5 and #6 would be predicted to lack the ability to form the extra stabilizing ion pairing between the amino acid positions 213 (mutated to Asp in the high expression variant NAGAL1 #2) and 326 (mutated to Arg in the high expression variant NAGAL1 #2): variant NAGAL1 #4 only contains the positively charged amino acid at position 326, while variants NAGAL1 #5 and NAGAL1 #6 only contain the negatively charged amino acid at position 213. In the case of NAGAL1 #6, and similar to variant NAGAL1 #3, the free Cys326 was also mutated into Ser to prevent potential aberrant disulphide bridge formation.

Expression plasmids encoding each of the above NAGAL1 variants (with an N-terminal Lip2pre secretion signal, followed by two X-Ala repeats) were generated via standard DNA cloning techniques using the expression constructs for NAGAL 1(Mut), NAGAL1 #2 and NAGAL1 #3. Expression of these NAGAL1 variants was also driven by the semi-constitutive growth-phase dependent Hp4d promotor. Single copy expression strains of the NAGAL1 #4, NAGAL1 #5 and NAGAL1 #6 variants were generated via transformation of the corresponding ADE2 containing expression plasmids into strain OXYY1315. Transformants were selected based on their capacity to grow on minimal medium plates without any added adenine. The integration of the expression constructs into the genome of the selected transformants was checked via PCR. The capacity of the *Yarrowia* transformants to express the different NAGAL variants was evaluated after 24-well cultivation in 2 ml rich medium as above. In brief, several transformants were inoculated in wells containing 2 ml YPD, and cultivated overnight at 28° C. and 180 rpm. The next day 1 to 2 µl of this culture was transferred to a new well with fresh YPD and recultivated overnight at 28° C. and 180 rpm. The following day, the 24-well plate was centrifuged and the medium was removed from the cell pellets. The cells were resuspended in 2 ml SuperT/glycerol rich medium and grown at 28° C. for 3 to 4 days. At the end of the cultivation, the medium was harvested and analysed for the expression of the different NAGAL variants.

Figure 29:
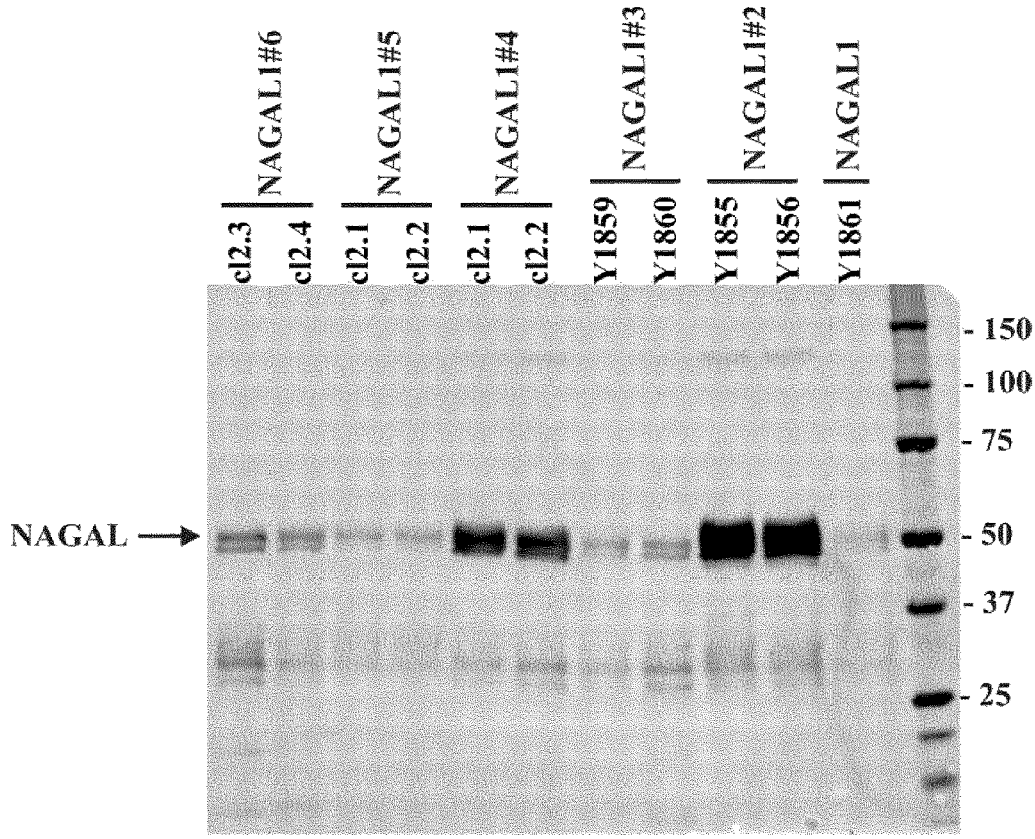
FIG. 29 represents Western blot analysis on 24-well cultivation samples of different single-copy expression strains for NAGAL1(Mut), NAGAL1 #2, NAGAL1 #3, NAGAL1 #4, NAGAL1 #5 and NAGAL1 #6.

The secretion of the recombinant proteins in the culture medium was first analysed via reducing SDS-PAGE electrophoresis, followed by western blot analysis (FIG. 29).

As shown previously, low expression levels were observed for the original NAGAL1 (Mut) and high levels for NAGAL1 #2 (Asn213Asp and Cys326Arg). Variant NAGAL1 #5, where only Asn213 was converted to Asp, showed similar low expression levels as NAGAL 1 (Mut). Variant NAGAL1 #6 showed a slightly higher expression level compared to NAGAL1 #5, potentially due to the extra amino acid modification within domain II (Cys326Ser). This agreed with the previous observation that NAGAL1 #3 (only Cys326Ser modification) also had a slightly higher expression level compared to NAGAL1(Mut) (containing free Cys326).

The significantly higher expression level observed for NAGAL1 #4 suggests that the single amino acid modification Cys326Arg in domain II does, on its own, already represent an important factor in the very high increase in expression level that was observed for the NAGAL1 #2 variant. The secreted levels of NAGAL1 #4 were about 2.5- to 3-fold lower (quantified via the Odyssey software) than those observed for NAGAL1 #2, which seems to support the inventors' hypothesis that the possibility of Arg326 to form an ion pair with Asp213 further increases the expression potential of NAGAL1 #2.

Figure 30:
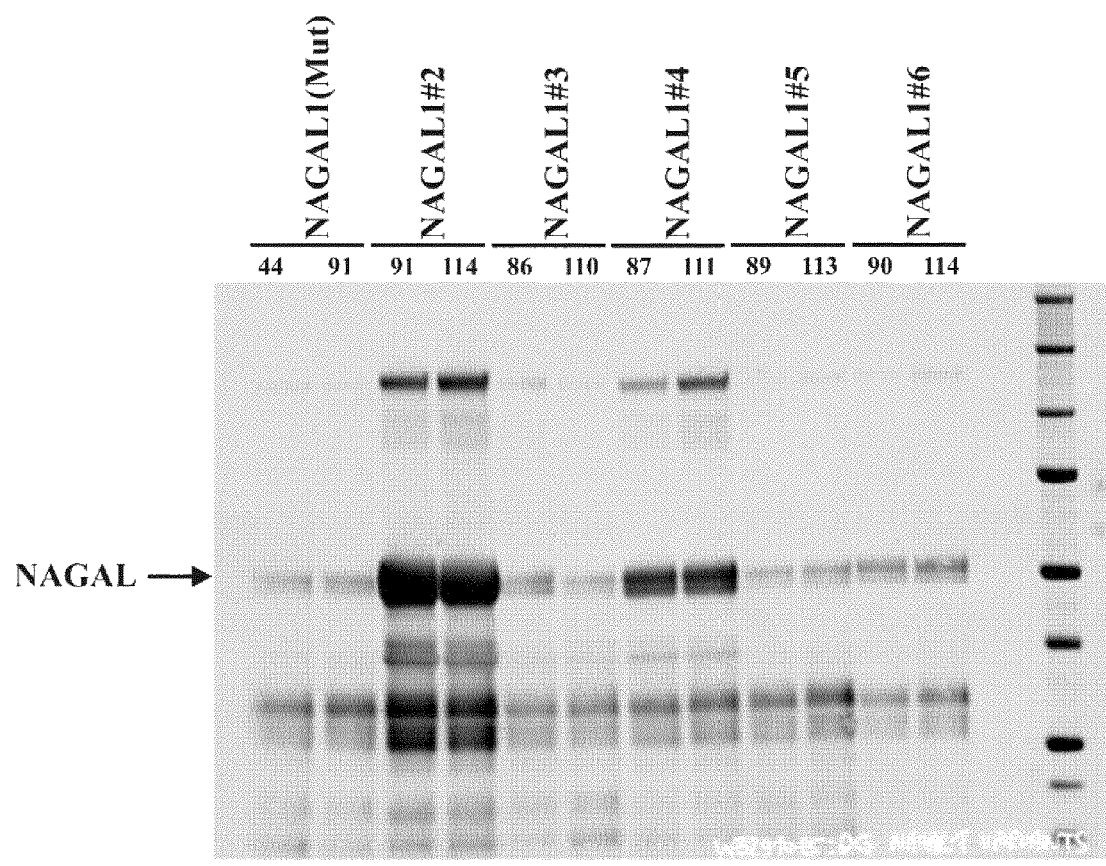
FIG. 30 represents Western blot analysis of different time-points during the bioreactor cultivation of strains expressing the different NAGAL1 variants. The numbers on top of the blot represent the number of cultivation hours in feed phase II. DG072, unit 3: NAGAL1(Mut); DG100, unit 8: NAGAL1 #2; DG069, unit 6: NAGAL1 #3; DG098, units 6 to 8: NAGAL1 #4 resp. #5, resp. #6.

Small-scale bioreactor cultivations were performed as described above on *Yarrowia* expression strains for variants NAGAL1 #4, NAGAL1 #5 and NAGAL1 #6 and a comparison was made with fermentations of NAGAL1(Mut), NAGAL1 #2 and NAGAL1 #3 expression strains. Analysis of the cultivation broth at different time-points of the fermentation via reducing SDS-PAGE/western blot analysis further confirmed the expression behavior of the different variants compared to each other: NAGAL1 #2>NAGAL1 #4>>all other NAGAL1 variants (FIG. 30). After controlled bioreactor cultivation, the NAGAL1 #4 expression levels were approximately 5-fold lower than those of NAGAL1 #2.

The secretion of active NAGAL1 protein was checked by analysing the α-galactosidase activity in the cultivation broth of the *Yarrowia* strains expressing the different NAGAL1 variants. An activity assay was performed at pH 4.5 on a dilution series of either 24-well cultivation or small-scale fermentation medium, using 4-methylumberrif-eryl-α-D-galactopyranoside (4MU-α-Gal) as a substrate (Tajima et al. 2009; Tomasic et al., 2010). The extracellular presence of α-galactosidase was measured as the amount of released 4-methylumbelliferyl during a one hour incubation at 37° C. and compared between the different samples (FIG. 31).

Figure 31:
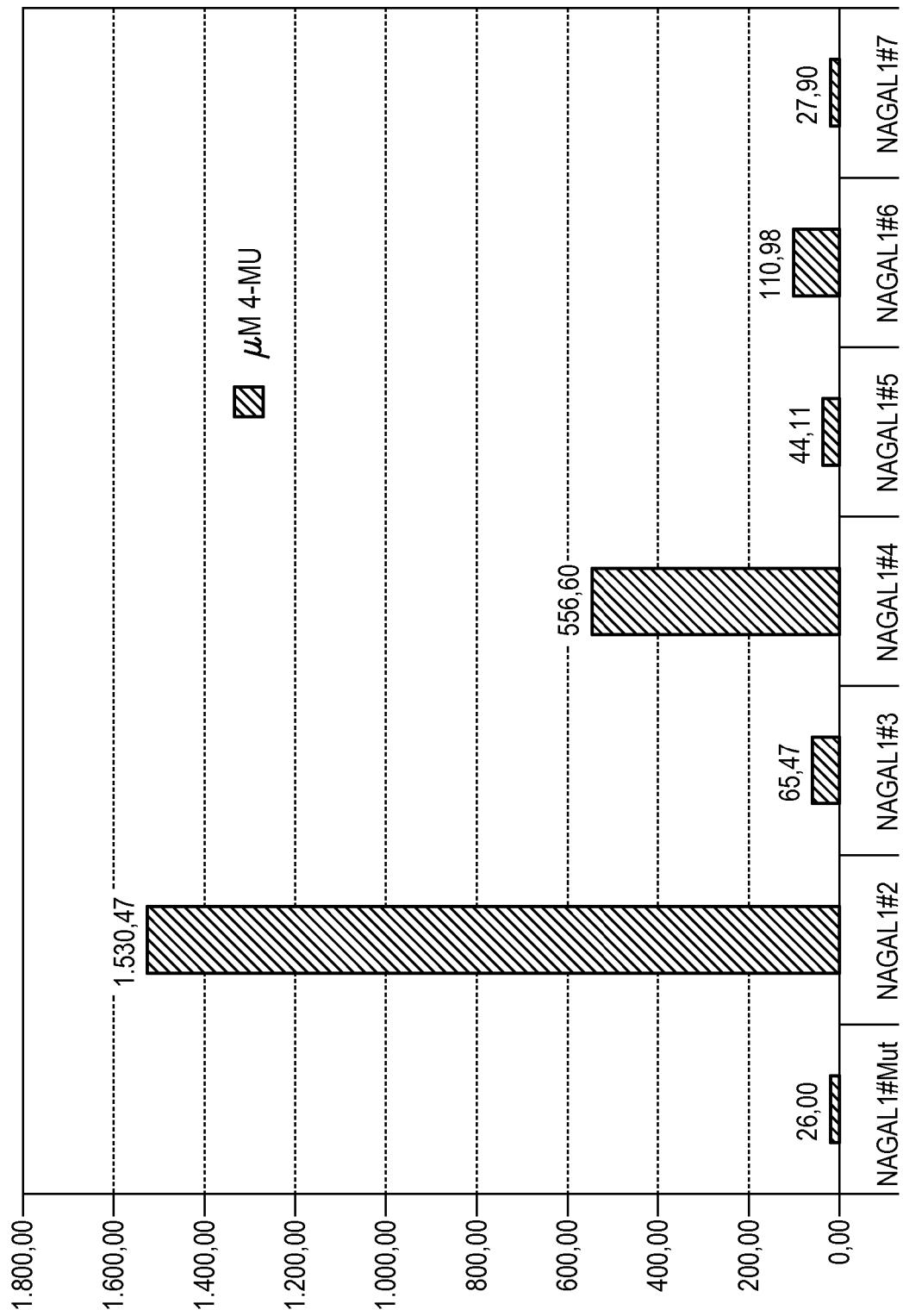
FIG. 31 represents overview of the μM amount of released 4-methylumberriferyl after a 1 hr incubation of the fluorometric substrate 4MU-α-Gal with 24-well cultivation (Left) or small-scale fermentation (Right) samples of single-copy expression strains of the different NAGAL1 variants. The numbers on top of each bar represent the average of measured values. DG072, unit 3: NAGAL1(Mut); DG100, unit 8: NAGAL1 #2; DG098, unit 6: NAGAL1 #4.

The above results showed that the selected NAGAL1 #2 strain is secreting 2.5- to 3-fold more α-galactosidase activity than the NAGAL1 #4 expression clone during 24-well cultivations (FIG. 31, left). This is similar to the quantification of secreted NAGAL, made after the western blot analysis on extracellular protein and indicates that the increase in NAGAL1 expression, as observed via Western blot, upon introduction of the extra Asn213Asp mutation is mainly representing the extra production of active protein. Activity measurements on the fermentation cultivation broth show an approximate 6-fold increase in secreted α-galactosidase activity for the NAGAL1 #2 versus the NAGAL1 #4 expression strain, and only very low amounts of active product for the NAGAL1(Mut) strain.

Example 8

Overview of Generated Plasmids and Strains

Figure 32:
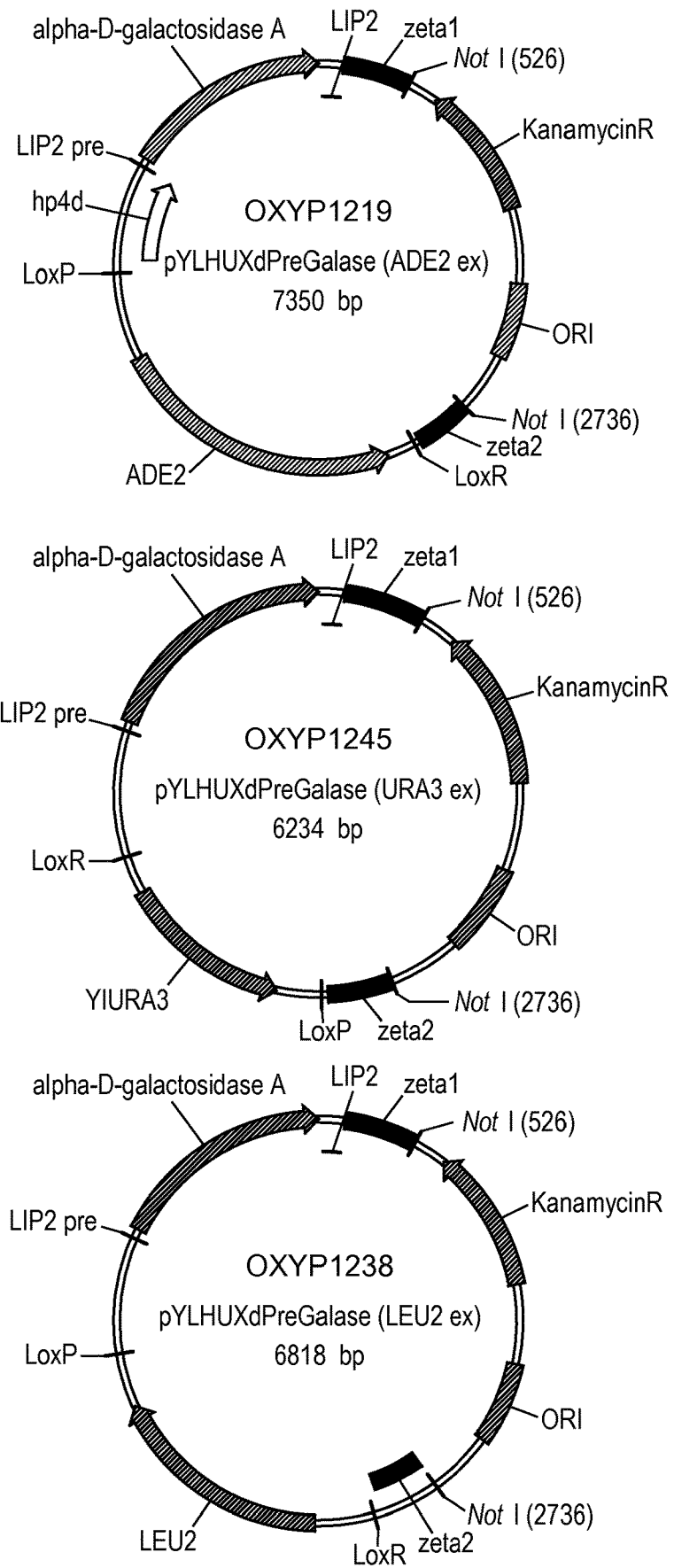

The plasmids used in the foregoing experiments are further described in FIGS. 32 and 33.

The strains used in the foregoing experiments are further described in FIG. 34A-C.

The invention claimed is:

1. A human α-N-acetylgalactosaminidase (NAGAL) polypeptide comprising the amino acid sequence as set forth in SEQ ID NO: 1 or having at least 95% sequence identity to SEQ ID NO: 1, and further comprising S to E substitution at an amino acid position corresponding to the position of amino acid 171 of human NAGAL polypeptide as set forth in SEQ ID NO: 1, and A to L substitution at an amino acid position corresponding to the position of amino acid 174 of human NAGAL polypeptide as set forth in SEQ ID NO: 1, whereby the human NAGAL polypeptide exhibits α-galactosidase activity, wherein the human NAGAL polypeptide is modified such that:

a first amino acid, corresponding to asparagine 213 of human NAGAL polypeptide as set forth in SEQ ID NO: 1, is substituted with one or more amino acids; or a second amino acid, corresponding to cysteine 326 of human NAGAL polypeptide as set forth in SEQ ID NO: 1, is substituted with one or more amino acids; or a first amino acid, corresponding to asparagine 213 of human NAGAL polypeptide as set forth in SEQ ID NO: 1, is substituted with one or more amino acids, and a second amino acid, corresponding to cysteine 326 of human NAGAL polypeptide as set forth in SEQ ID NO: 1, is substituted with one or more amino acids.

2. The modified human NAGAL polypeptide exhibiting α-galactosidase activity, according to claim 1, wherein:
the first amino acid is substituted with one, two or three amino acids; or
the second amino acid is substituted with one, two or three amino acids; or
the first amino acid is substituted with one, two or three amino acids and the second amino acid is substituted with one, two or three amino acids.

3. The modified human NAGAL polypeptide exhibiting α-galactosidase activity, according to claim 1, wherein:
the first amino acid is substituted with one amino acid; or
the second amino acid is substituted with one amino acid; or
the first amino acid is substituted with one amino acid and the second amino acid is substituted with one amino acid.

4. The modified human NAGAL polypeptide exhibiting α-galactosidase activity, according to claim 1, wherein the first amino acid is an asparagine and wherein:
the asparagine is substituted with one or more amino acids other than asparagine; or
the asparagine is substituted with one, two or three amino acids other than asparagine; or
the asparagine is substituted with one amino acid other than asparagine.

5. The modified human NAGAL polypeptide exhibiting α-galactosidase activity, according to claim 1, wherein the second amino acid is a cysteine and wherein:
the cysteine is substituted with one or more amino acids other than cysteine; or
the cysteine is substituted with one, two or three amino acids other than cysteine; or
the cysteine is substituted with one amino acid other than cysteine.

6. The modified human NAGAL polypeptide exhibiting α-galactosidase activity, according to claim 1, wherein the amino acid or amino acids substituting the first amino acid is or are each independently selected from the group consisting of alanine, arginine, aspartic acid, cysteine, glutamic acid, glutamine, glycine, histidine, isoleucine, leucine, lysine, methionine, phenylalanine, proline, serine, threonine, tryptophan, tyrosine, and valine.

7. The modified human NAGAL polypeptide exhibiting α-galactosidase activity, according to claim 1, wherein the amino acid or amino acids substituting the second amino acid is or are each independently selected from the group consisting of alanine, arginine, asparagine, aspartic acid, glutamic acid, glutamine, glycine, histidine, isoleucine, leucine, lysine, methionine, phenylalanine, proline, serine, threonine, tryptophan, tyrosine, and valine.

8. The modified human NAGAL polypeptide exhibiting α-galactosidase activity, according to claim 1, wherein:
the first amino acid is substituted with one or more amino acids at least one of which contains a negatively charged side-chain group; or
the first amino acid is substituted with one, two or three amino acids at least one of which contains a negatively charged side-chain group; or
the first amino acid is substituted with one amino acid which contains a negatively charged side-chain group.

9. The modified human NAGAL polypeptide exhibiting α-galactosidase activity, according to claim 8, wherein the at least one amino acid which contains a negatively charged side-chain group is aspartic acid or glutamic acid, preferably aspartic acid.

10. The modified human NAGAL polypeptide exhibiting α-galactosidase activity, according to claim 1, wherein:
the second amino acid is substituted with one or more amino acids at least one of which contains a positively charged side-chain group or a polar uncharged side-chain group; or
the second amino acid is substituted with one, two or three amino acids at least one of which contains a positively charged side-chain group or a polar uncharged side-chain group; or
the second amino acid is substituted with one amino acid which contains a positively charged side-chain group or a polar uncharged side-chain group.

11. The modified human NAGAL polypeptide exhibiting α-galactosidase activity, according to claim 10, wherein the at least one amino acid which contains a positively charged side-chain group is arginine, histidine or lysine, preferably arginine, or the at least one amino acid which contains a polar uncharged side-chain group is serine, threonine, asparagine or glutamine, preferably serine.

12. The modified human NAGAL polypeptide exhibiting α-galactosidase activity, according to claim 1, wherein:
the first amino acid is substituted with aspartic acid and the second amino acid is substituted with arginine; or
the second amino acid is substituted with arginine; or
the first amino acid is substituted with aspartic acid and the second amino acid is substituted with serine; or
the second amino acid is substituted with serine.

13. A human NAGAL polypeptide comprising the amino acid sequence as set forth in SEQ ID NO: 1 or having at least 95% sequence identity to SEQ ID NO: 1,
and further comprising S to E substitution at an amino acid position corresponding to the position of amino acid 171 of human NAGAL polypeptide as set forth in SEQ ID NO: 1, and A to L substitution at an amino acid position corresponding to the position of amino acid 174 of human NAGAL polypeptide as set forth in SEQ ID NO: 1, whereby the human NAGAL polypeptide exhibits α-galactosidase activity,
wherein the human NAGAL polypeptide exhibiting α-galactosidase activity, is modified such that:
a first amino acid, corresponding to asparagine 213 of human NAGAL polypeptide as set forth in SEQ ID NO: 1, is substituted with one or more amino acids, such that at least one of said one or more amino acids is capable of directly or indirectly interacting with a second amino acid corresponding to cysteine 326 of human NAGAL polypeptide as set forth in SEQ ID NO: 1; or
a second amino acid, corresponding to cysteine 326 of human NAGAL polypeptide as set forth in SEQ ID NO: 1, is substituted with one or more amino acids, such that at least one of said one or more amino acids is capable of directly or indirectly interacting with a first amino acid corresponding to asparagine 213 of human NAGAL polypeptide as set forth in SEQ ID NO: 1; or a first amino acid, corresponding to asparagine 213 of human NAGAL polypeptide as set forth in SEQ ID NO: 1, is substituted with one or more amino acids, and a second amino acid, corresponding to cysteine 326 of human NAGAL polypeptide as set forth in SEQ ID NO: 1, is substituted with one or more amino acids, such that at least one of said one or more amino acids substituting the first amino acid is capable of directly or indirectly interacting with at least one of said one or more amino acids substituting the second amino acid.

14. The modified human NAGAL polypeptide exhibiting α-galactosidase activity according to claim 13, wherein:
the first amino acid is substituted with one, two or three amino acids; or
the second amino acid is substituted with one, two or three amino acids; or
the first amino acid is substituted with one, two or three amino acids and the second amino acid is substituted with one, two or three amino acids.

15. The modified human NAGAL polypeptide exhibiting α-galactosidase activity, according to claim 13, wherein:
the first amino acid is substituted with one amino acid; or
the second amino acid is substituted with one amino acid; or
the first amino acid is substituted with one amino acid and the second amino acid is substituted with one amino acid.

16. The modified human NAGAL polypeptide exhibiting α-galactosidase activity, according to claim 13, wherein the first amino acid is an asparagine and wherein:
the asparagine is substituted with one or more amino acids other than asparagine; or
the asparagine is substituted with one, two or three amino acids other than asparagine; or
the asparagine is substituted with one amino acid other than asparagine.

17. The modified human NAGAL polypeptide exhibiting α-galactosidase activity, according to claim 13, wherein the second amino acid is a cysteine and wherein:
the cysteine is substituted with one or more amino acids other than cysteine; or
the cysteine is substituted with one, two or three amino acids other than cysteine; or
the cysteine is substituted with one amino acid other than cysteine.

18. The modified human NAGAL polypeptide exhibiting α-galactosidase activity according to claim 13, wherein the interaction is an ionic interaction or a hydrogen bonding interaction or a Van der Waals interaction.

19. The modified human NAGAL polypeptide exhibiting α-galactosidase activity, according to claim 18, wherein the ionic interaction comprises the formation of at least one ion pair.

20. The modified human NAGAL polypeptide exhibiting α-galactosidase activity, according to claim 19, wherein the at least one ion pair is formed between a negatively charged side-chain group of an amino acid comprised by said one or more amino acids substituting the first amino acid and a positively charged side-chain group of an amino acid comprised by said one or more amino acids substituting the second amino acid.

21. The modified human NAGAL polypeptide exhibiting α-galactosidase activity, according to claim 18, wherein the hydrogen bonding interaction is a direct interaction, or wherein the hydrogen bonding interaction comprises one or more solvent molecules, preferably one or more water molecules.

22. The modified human NAGAL polypeptide exhibiting α-galactosidase activity according to claim 1, wherein:
the amino acid sequence of the human NAGAL polypeptide is as set forth in SEQ ID NO: 6, or displays at least 95% sequence identity to SEQ ID NO: 6; or
the amino acid sequence of the human NAGAL polypeptide is as set forth in SEQ ID NO: 7, or displays at least 95% sequence identity to SEQ ID NO: 7; or
the amino acid sequence of the human NAGAL polypeptide is as set forth in SEQ ID NO: 8, or displays at least 95% sequence identity to SEQ ID NO: 8; or
the amino acid sequence of the human NAGAL polypeptide is as set forth in SEQ ID NO: 9, or displays at least 95% sequence identity to SEQ ID NO: 9.

23. The modified human NAGAL polypeptide exhibiting α-galactosidase activity, according to claim 1, further comprising one or more heterologous amino acid sequences, such as one or more heterologous amino acid sequences connected, optionally by means of one or more linker peptides, to either the C- or N- terminus or to both termini of the human NAGAL polypeptide.

24. The modified human NAGAL polypeptide exhibiting α-galactosidase activity, according to claim 1, comprising one or more N-glycans, preferably wherein one or more of said N-glycans are phosphorylated, more preferably wherein 40% or more by number of said N-glycans are phosphorylated.

25. The human NAGAL polypeptide exhibiting α-galactosidase activity, according to claim 24, wherein one or more of said phosphorylated N-glycans are uncapped and demannosylated, preferably wherein 40% or more by number of said phosphorylated N-glycans are uncapped and demannosylated.

26. A method of treating Fabry disease in a human subject in need of such treatment comprising administering to said subject effective amount of the modified human NAGAL polypeptide exhibiting α-galactosidase activity as defined in claim 1.

27. A composition comprising the human NAGAL polypeptide exhibiting α-galactosidase activity as defined in claim 1.

28. A nucleic acid molecule comprising a nucleic acid sequence encoding the human NAGAL polypeptide exhibiting α-galactosidase activity as defined in claim 1 or an expression cassette or an expression vector comprising said nucleic acid molecule and a promoter operably linked to the nucleic acid molecule, preferably wherein the expression cassette or expression vector is configured to effect expression of the human NAGAL polypeptide exhibiting α-galactosidase activity in a host cell, preferably in a fungal cell, more preferably in *Yarrowia lipolytica* or *Arxula adeninivorans*.

29. A method of treating Fabry disease in a human subject in need of such treatment comprising administering to said subject an effective amount of the nucleic acid molecule or the expression cassette or expression vector as defined in claim 28, preferably wherein the method is a gene therapy method or an mRNA therapy method.

30. A pharmaceutical composition comprising the nucleic acid molecule or the expression cassette or expression vector as defined in claim 28.

31. A host cell comprising the nucleic acid molecule or the expression cassette or expression vector as defined in claim 28.

32. The host cell according to claim 31, wherein the host cell is a fungal cell, preferably *Yarrowia lipolytica* or *Arxula adeninivorans*.

33. The host cell according to claim 31, wherein the host cell is genetically engineered to:
- comprise a deficiency in outer chain elongation of N-glycans activity, such as a deficiency in OCH1 activity; and/or
- comprise expression of a polypeptide capable of effecting mannosyl phosphorylation of N-glycans, such as MNN4, PNO1, MNN6 or a biologically active variant or fragment of any one thereof.

34. A substantially pure culture of host cells as defined in claim 31.

35. A method for producing a human NAGAL polypeptide exhibiting α-galactosidase activity, comprising:
- a) culturing the host cell as defined in claim 31, such that the host cell expresses the human NAGAL polypeptide fragment thereof,
- b) collecting, and optionally isolating, the human NAGAL polypeptide exhibiting α-galactosidase activity from the host cell, or from the host cell cultivation medium.

36. The method according to claim 35, further comprising uncapping and demannosylation of at least a fraction of phosphorylated N-glycans comprised by the human NAGAL polypeptide exhibiting α-galactosidase activity, for example wherein the uncapping and demannosylation take place in vitro, or in the host cell, or in a lysate of the host cell.

37. The pharmaceutical composition of claim 30, wherein the composition is configured for gene therapy or mRNA therapy.

* * * * *

SEQUENCE LISTING

```
<160> NUMBER OF SEQ ID NOS: 23

<210> SEQ ID NO 1
<211> LENGTH: 394
<212> TYPE: PRT
<213> ORGANISM: Homo sapiens

<400> SEQUENCE: 1

Leu Asp Asn Gly Leu Leu Gln Thr Pro Pro Met Gly Trp Leu Ala Trp
1               5                  10                  15

Glu Arg Phe Arg Cys Asn Ile Asn Cys Asp Glu Asp Pro Lys Asn Cys
            20                  25                  30

Ile Ser Glu Gln Leu Phe Met Glu Met Ala Asp Arg Met Ala Gln Asp
        35                  40                  45

Gly Trp Arg Asp Met Gly Tyr Thr Tyr Leu Asn Ile Asp Asp Cys Trp
    50                  55                  60

Ile Gly Gly Arg Asp Ala Ser Gly Arg Leu Met Pro Asp Pro Lys Arg
65                  70                  75                  80

Phe Pro His Gly Ile Pro Phe Leu Ala Asp Tyr Val His Ser Leu Gly
                85                  90                  95

Leu Lys Leu Gly Ile Tyr Ala Asp Met Gly Asn Phe Thr Cys Met Gly
            100                 105                 110

Tyr Pro Gly Thr Thr Leu Asp Lys Val Val Gln Asp Ala Gln Thr Phe
        115                 120                 125

Ala Glu Trp Lys Val Asp Met Leu Lys Leu Asp Gly Cys Phe Ser Thr
    130                 135                 140

Pro Glu Glu Arg Ala Gln Gly Tyr Pro Lys Met Ala Ala Ala Leu Asn
145                 150                 155                 160

Ala Thr Gly Arg Pro Ile Ala Phe Ser Cys Ser Trp Pro Ala Tyr Glu
                165                 170                 175

Gly Gly Leu Pro Pro Arg Val Asn Tyr Ser Leu Leu Ala Asp Ile Cys
            180                 185                 190

Asn Leu Trp Arg Asn Tyr Asp Asp Ile Gln Asp Ser Trp Trp Ser Val
        195                 200                 205

Leu Ser Ile Leu Asn Trp Phe Val Glu His Gln Asp Ile Leu Gln Pro
    210                 215                 220

Val Ala Gly Pro Gly His Trp Asn Asp Pro Asp Met Leu Leu Ile Gly
225                 230                 235                 240

Asn Phe Gly Leu Ser Leu Glu Gln Ser Arg Ala Gln Met Ala Leu Trp
                245                 250                 255

Thr Val Leu Ala Ala Pro Leu Leu Met Ser Thr Asp Leu Arg Thr Ile
            260                 265                 270

Ser Ala Gln Asn Met Asp Ile Leu Gln Asn Pro Leu Met Ile Lys Ile
        275                 280                 285

Asn Gln Asp Pro Leu Gly Ile Gln Gly Arg Arg Ile His Lys Glu Lys
    290                 295                 300
```

```
Ser Leu Ile Glu Val Tyr Met Arg Pro Leu Ser Asn Lys Ala Ser Ala
305                 310                 315                 320

Leu Val Phe Phe Ser Cys Arg Thr Asp Met Pro Tyr Arg Tyr His Ser
                325                 330                 335

Ser Leu Gly Gln Leu Asn Phe Thr Gly Ser Val Ile Tyr Glu Ala Gln
            340                 345                 350

Asp Val Tyr Ser Gly Asp Ile Ile Ser Gly Leu Arg Asp Glu Thr Asn
        355                 360                 365

Phe Thr Val Ile Ile Asn Pro Ser Gly Val Val Met Trp Tyr Leu Tyr
370                 375                 380

Pro Ile Lys Asn Leu Glu Met Ser Gln Gln
385                 390

<210> SEQ ID NO 2
<211> LENGTH: 394
<212> TYPE: PRT
<213> ORGANISM: Artificial sequence
<220> FEATURE:
<223> OTHER INFORMATION: modified human NAGAL polypeptide N213D C326R
      (amino acid numbering as in mature human NAGAL)

<400> SEQUENCE: 2

Leu Asp Asn Gly Leu Leu Gln Thr Pro Pro Met Gly Trp Leu Ala Trp
1               5                   10                  15

Glu Arg Phe Arg Cys Asn Ile Asn Cys Asp Glu Asp Pro Lys Asn Cys
            20                  25                  30

Ile Ser Glu Gln Leu Phe Met Glu Met Ala Asp Arg Met Ala Gln Asp
        35                  40                  45

Gly Trp Arg Asp Met Gly Tyr Thr Tyr Leu Asn Ile Asp Asp Cys Trp
    50                  55                  60

Ile Gly Gly Arg Asp Ala Ser Gly Arg Leu Met Pro Asp Pro Lys Arg
65                  70                  75                  80

Phe Pro His Gly Ile Pro Phe Leu Ala Asp Tyr Val His Ser Leu Gly
                85                  90                  95

Leu Lys Leu Gly Ile Tyr Ala Asp Met Gly Asn Phe Thr Cys Met Gly
            100                 105                 110

Tyr Pro Gly Thr Thr Leu Asp Lys Val Val Gln Asp Ala Gln Thr Phe
        115                 120                 125

Ala Glu Trp Lys Val Asp Met Leu Lys Leu Asp Gly Cys Phe Ser Thr
    130                 135                 140

Pro Glu Glu Arg Ala Gln Gly Tyr Pro Lys Met Ala Ala Ala Leu Asn
145                 150                 155                 160

Ala Thr Gly Arg Pro Ile Ala Phe Ser Cys Ser Trp Pro Ala Tyr Glu
                165                 170                 175

Gly Gly Leu Pro Pro Arg Val Asn Tyr Ser Leu Leu Ala Asp Ile Cys
            180                 185                 190

Asn Leu Trp Arg Asn Tyr Asp Asp Ile Gln Asp Ser Trp Trp Ser Val
        195                 200                 205

Leu Ser Ile Leu Asp Trp Phe Val Glu His Gln Asp Ile Leu Gln Pro
    210                 215                 220

Val Ala Gly Pro Gly His Trp Asn Asp Pro Asp Met Leu Leu Ile Gly
225                 230                 235                 240

Asn Phe Gly Leu Ser Leu Glu Gln Ser Arg Ala Gln Met Ala Leu Trp
                245                 250                 255

Thr Val Leu Ala Ala Pro Leu Leu Met Ser Thr Asp Leu Arg Thr Ile
```

```
                  260                 265                 270
Ser Ala Gln Asn Met Asp Ile Leu Gln Asn Pro Leu Met Ile Lys Ile
            275                 280                 285

Asn Gln Asp Pro Leu Gly Ile Gln Gly Arg Arg Ile His Lys Glu Lys
        290                 295                 300

Ser Leu Ile Glu Val Tyr Met Arg Pro Leu Ser Asn Lys Ala Ser Ala
305                 310                 315                 320

Leu Val Phe Phe Ser Arg Arg Thr Asp Met Pro Tyr Arg Tyr His Ser
                325                 330                 335

Ser Leu Gly Gln Leu Asn Phe Thr Gly Ser Val Ile Tyr Glu Ala Gln
            340                 345                 350

Asp Val Tyr Ser Gly Asp Ile Ile Ser Gly Leu Arg Asp Glu Thr Asn
        355                 360                 365

Phe Thr Val Ile Ile Asn Pro Ser Gly Val Val Met Trp Tyr Leu Tyr
    370                 375                 380

Pro Ile Lys Asn Leu Glu Met Ser Gln Gln
385                 390

<210> SEQ ID NO 3
<211> LENGTH: 394
<212> TYPE: PRT
<213> ORGANISM: Artificial sequence
<220> FEATURE:
<223> OTHER INFORMATION: modified human NAGAL polypeptide C326R (amino
      acid numbering as in mature human NAGAL)

<400> SEQUENCE: 3

Leu Asp Asn Gly Leu Leu Gln Thr Pro Pro Met Gly Trp Leu Ala Trp
1               5                   10                  15

Glu Arg Phe Arg Cys Asn Ile Asn Cys Asp Glu Asp Pro Lys Asn Cys
            20                  25                  30

Ile Ser Glu Gln Leu Phe Met Glu Met Ala Asp Arg Met Ala Gln Asp
        35                  40                  45

Gly Trp Arg Asp Met Gly Tyr Thr Tyr Leu Asn Ile Asp Asp Cys Trp
50                  55                  60

Ile Gly Gly Arg Asp Ala Ser Gly Arg Leu Met Pro Asp Pro Lys Arg
65                  70                  75                  80

Phe Pro His Gly Ile Pro Phe Leu Ala Asp Tyr Val His Ser Leu Gly
                85                  90                  95

Leu Lys Leu Gly Ile Tyr Ala Asp Met Gly Asn Phe Thr Cys Met Gly
            100                 105                 110

Tyr Pro Gly Thr Thr Leu Asp Lys Val Val Gln Asp Ala Gln Thr Phe
        115                 120                 125

Ala Glu Trp Lys Val Asp Met Leu Lys Leu Asp Gly Cys Phe Ser Thr
130                 135                 140

Pro Glu Glu Arg Ala Gln Gly Tyr Pro Lys Met Ala Ala Ala Leu Asn
145                 150                 155                 160

Ala Thr Gly Arg Pro Ile Ala Phe Ser Cys Ser Trp Pro Ala Tyr Glu
                165                 170                 175

Gly Gly Leu Pro Pro Arg Val Asn Tyr Ser Leu Leu Ala Asp Ile Cys
            180                 185                 190

Asn Leu Trp Arg Asn Tyr Asp Asp Ile Gln Asp Ser Trp Trp Ser Val
        195                 200                 205

Leu Ser Ile Leu Asn Trp Phe Val Glu His Gln Asp Ile Leu Gln Pro
    210                 215                 220
```

```
Val Ala Gly Pro Gly His Trp Asn Asp Pro Asp Met Leu Leu Ile Gly
225                 230                 235                 240

Asn Phe Gly Leu Ser Leu Glu Gln Ser Arg Ala Gln Met Ala Leu Trp
            245                 250                 255

Thr Val Leu Ala Ala Pro Leu Leu Met Ser Thr Asp Leu Arg Thr Ile
            260                 265                 270

Ser Ala Gln Asn Met Asp Ile Leu Gln Asn Pro Leu Met Ile Lys Ile
            275                 280                 285

Asn Gln Asp Pro Leu Gly Ile Gln Gly Arg Arg Ile His Lys Glu Lys
            290                 295                 300

Ser Leu Ile Glu Val Tyr Met Arg Pro Leu Ser Asn Lys Ala Ser Ala
305                 310                 315                 320

Leu Val Phe Phe Ser Arg Arg Thr Asp Met Pro Tyr Arg Tyr His Ser
                325                 330                 335

Ser Leu Gly Gln Leu Asn Phe Thr Gly Ser Val Ile Tyr Glu Ala Gln
                340                 345                 350

Asp Val Tyr Ser Gly Asp Ile Ile Ser Gly Leu Arg Asp Glu Thr Asn
            355                 360                 365

Phe Thr Val Ile Ile Asn Pro Ser Gly Val Val Met Trp Tyr Leu Tyr
370                 375                 380

Pro Ile Lys Asn Leu Glu Met Ser Gln Gln
385                 390

<210> SEQ ID NO 4
<211> LENGTH: 394
<212> TYPE: PRT
<213> ORGANISM: Artificial sequence
<220> FEATURE:
<223> OTHER INFORMATION: modified human NAGAL polypeptide N213D C326S
      (amino acid numbering as in mature human NAGAL)

<400> SEQUENCE: 4

Leu Asp Asn Gly Leu Leu Gln Thr Pro Pro Met Gly Trp Leu Ala Trp
1               5                   10                  15

Glu Arg Phe Arg Cys Asn Ile Asn Cys Asp Glu Asp Pro Lys Asn Cys
                20                  25                  30

Ile Ser Glu Gln Leu Phe Met Glu Met Ala Asp Arg Met Ala Gln Asp
            35                  40                  45

Gly Trp Arg Asp Met Gly Tyr Thr Tyr Leu Asn Ile Asp Asp Cys Trp
50                  55                  60

Ile Gly Gly Arg Asp Ala Ser Gly Arg Leu Met Pro Asp Pro Lys Arg
65                  70                  75                  80

Phe Pro His Gly Ile Pro Phe Leu Ala Asp Tyr Val His Ser Leu Gly
                85                  90                  95

Leu Lys Leu Gly Ile Tyr Ala Asp Met Gly Asn Phe Thr Cys Met Gly
            100                 105                 110

Tyr Pro Gly Thr Thr Leu Asp Lys Val Val Gln Asp Ala Gln Thr Phe
            115                 120                 125

Ala Glu Trp Lys Val Asp Met Leu Lys Leu Asp Gly Cys Phe Ser Thr
130                 135                 140

Pro Glu Glu Arg Ala Gln Gly Tyr Pro Lys Met Ala Ala Ala Leu Asn
145                 150                 155                 160

Ala Thr Gly Arg Pro Ile Ala Phe Ser Cys Ser Trp Pro Ala Tyr Glu
                165                 170                 175

Gly Gly Leu Pro Pro Arg Val Asn Tyr Ser Leu Leu Ala Asp Ile Cys
            180                 185                 190
```

```
Asn Leu Trp Arg Asn Tyr Asp Asp Ile Gln Asp Ser Trp Trp Ser Val
            195                 200                 205

Leu Ser Ile Leu Asp Trp Phe Val Glu His Gln Asp Ile Leu Gln Pro
            210                 215                 220

Val Ala Gly Pro Gly His Trp Asn Asp Pro Asp Met Leu Leu Ile Gly
225                 230                 235                 240

Asn Phe Gly Leu Ser Leu Glu Gln Ser Arg Ala Gln Met Ala Leu Trp
            245                 250                 255

Thr Val Leu Ala Ala Pro Leu Leu Met Ser Thr Asp Leu Arg Thr Ile
            260                 265                 270

Ser Ala Gln Asn Met Asp Ile Leu Gln Asn Pro Leu Met Ile Lys Ile
            275                 280                 285

Asn Gln Asp Pro Leu Gly Ile Gln Gly Arg Arg Ile His Lys Glu Lys
            290                 295                 300

Ser Leu Ile Glu Val Tyr Met Arg Pro Leu Ser Asn Lys Ala Ser Ala
305                 310                 315                 320

Leu Val Phe Phe Ser Ser Arg Thr Asp Met Pro Tyr Arg Tyr His Ser
            325                 330                 335

Ser Leu Gly Gln Leu Asn Phe Thr Gly Ser Val Ile Tyr Glu Ala Gln
            340                 345                 350

Asp Val Tyr Ser Gly Asp Ile Ile Ser Gly Leu Arg Asp Glu Thr Asn
            355                 360                 365

Phe Thr Val Ile Ile Asn Pro Ser Gly Val Val Met Trp Tyr Leu Tyr
            370                 375                 380

Pro Ile Lys Asn Leu Glu Met Ser Gln Gln
385                 390

<210> SEQ ID NO 5
<211> LENGTH: 394
<212> TYPE: PRT
<213> ORGANISM: Artificial sequence
<220> FEATURE:
<223> OTHER INFORMATION: modified human NAGAL polypeptide C326S (amino
      acid numbering as in mature human NAGAL)

<400> SEQUENCE: 5

Leu Asp Asn Gly Leu Leu Gln Thr Pro Pro Met Gly Trp Leu Ala Trp
1               5                   10                  15

Glu Arg Phe Arg Cys Asn Ile Asn Cys Asp Glu Asp Pro Lys Asn Cys
            20                  25                  30

Ile Ser Glu Gln Leu Phe Met Glu Met Ala Asp Arg Met Ala Gln Asp
            35                  40                  45

Gly Trp Arg Asp Met Gly Tyr Thr Tyr Leu Asn Ile Asp Asp Cys Trp
        50                  55                  60

Ile Gly Gly Arg Asp Ala Ser Gly Arg Leu Met Pro Asp Pro Lys Arg
65                  70                  75                  80

Phe Pro His Gly Ile Pro Phe Leu Ala Asp Tyr Val His Ser Leu Gly
            85                  90                  95

Leu Lys Leu Gly Ile Tyr Ala Asp Met Gly Asn Phe Thr Cys Met Gly
            100                 105                 110

Tyr Pro Gly Thr Thr Leu Asp Lys Val Val Gln Asp Ala Gln Thr Phe
            115                 120                 125

Ala Glu Trp Lys Val Asp Met Leu Lys Leu Asp Gly Cys Phe Ser Thr
            130                 135                 140

Pro Glu Glu Arg Ala Gln Gly Tyr Pro Lys Met Ala Ala Ala Leu Asn
```

```
            145                 150                 155                 160
    Ala Thr Gly Arg Pro Ile Ala Phe Ser Cys Ser Trp Pro Ala Tyr Glu
                    165                 170                 175

Gly Gly Leu Pro Pro Arg Val Asn Tyr Ser Leu Leu Ala Asp Ile Cys
                    180                 185                 190

Asn Leu Trp Arg Asn Tyr Asp Asp Ile Gln Asp Ser Trp Ser Val
                195                 200                 205

Leu Ser Ile Leu Asn Trp Phe Val Glu His Gln Asp Ile Leu Gln Pro
        210                 215                 220

Val Ala Gly Pro Gly His Trp Asn Asp Pro Asp Met Leu Leu Ile Gly
    225                 230                 235                 240

Asn Phe Gly Leu Ser Leu Glu Gln Ser Arg Ala Gln Met Ala Leu Trp
                    245                 250                 255

Thr Val Leu Ala Ala Pro Leu Leu Met Ser Thr Asp Leu Arg Thr Ile
                    260                 265                 270

Ser Ala Gln Asn Met Asp Ile Leu Gln Asn Pro Leu Met Ile Lys Ile
                275                 280                 285

Asn Gln Asp Pro Leu Gly Ile Gln Gly Arg Arg Ile His Lys Glu Lys
                290                 295                 300

Ser Leu Ile Glu Val Tyr Met Arg Pro Leu Ser Asn Lys Ala Ser Ala
    305                 310                 315                 320

Leu Val Phe Phe Ser Ser Arg Thr Asp Met Pro Tyr Arg Tyr His Ser
                    325                 330                 335

Ser Leu Gly Gln Leu Asn Phe Thr Gly Ser Val Ile Tyr Glu Ala Gln
                    340                 345                 350

Asp Val Tyr Ser Gly Asp Ile Ile Ser Gly Leu Arg Asp Glu Thr Asn
                355                 360                 365

Phe Thr Val Ile Ile Asn Pro Ser Gly Val Val Met Trp Tyr Leu Tyr
                370                 375                 380

Pro Ile Lys Asn Leu Glu Met Ser Gln Gln
    385                 390

<210> SEQ ID NO 6
<211> LENGTH: 394
<212> TYPE: PRT
<213> ORGANISM: Artificial sequence
<220> FEATURE:
<223> OTHER INFORMATION: modified human NAGAL polypeptide N213D C326R
      S171E A174L (amino acid numbering as in mature human NAGAL)

<400> SEQUENCE: 6

Leu Asp Asn Gly Leu Leu Gln Thr Pro Pro Met Gly Trp Leu Ala Trp
    1               5                   10                  15

Glu Arg Phe Arg Cys Asn Ile Asn Cys Asp Glu Asp Pro Lys Asn Cys
                    20                  25                  30

Ile Ser Glu Gln Leu Phe Met Glu Met Ala Asp Arg Met Ala Gln Asp
                35                  40                  45

Gly Trp Arg Asp Met Gly Tyr Thr Tyr Leu Asn Ile Asp Asp Cys Trp
        50                  55                  60

Ile Gly Gly Arg Asp Ala Ser Gly Arg Leu Met Pro Asp Pro Lys Arg
    65                  70                  75                  80

Phe Pro His Gly Ile Pro Phe Leu Ala Asp Tyr Val His Ser Leu Gly
                    85                  90                  95

Leu Lys Leu Gly Ile Tyr Ala Asp Met Gly Asn Phe Thr Cys Met Gly
                    100                 105                 110
```

Tyr Pro Gly Thr Thr Leu Asp Lys Val Val Gln Asp Ala Gln Thr Phe
            115                 120                 125

Ala Glu Trp Lys Val Asp Met Leu Lys Leu Asp Gly Cys Phe Ser Thr
130                 135                 140

Pro Glu Glu Arg Ala Gln Gly Tyr Pro Lys Met Ala Ala Leu Asn
145                 150                 155                 160

Ala Thr Gly Arg Pro Ile Ala Phe Ser Cys Glu Trp Pro Leu Tyr Glu
            165                 170                 175

Gly Gly Leu Pro Pro Arg Val Asn Tyr Ser Leu Leu Ala Asp Ile Cys
            180                 185                 190

Asn Leu Trp Arg Asn Tyr Asp Asp Ile Gln Asp Ser Trp Trp Ser Val
            195                 200                 205

Leu Ser Ile Leu Asp Trp Phe Val Glu His Gln Asp Ile Leu Gln Pro
            210                 215                 220

Val Ala Gly Pro Gly His Trp Asn Asp Pro Asp Met Leu Leu Ile Gly
225                 230                 235                 240

Asn Phe Gly Leu Ser Leu Glu Gln Ser Arg Ala Gln Met Ala Leu Trp
            245                 250                 255

Thr Val Leu Ala Ala Pro Leu Leu Met Ser Thr Asp Leu Arg Thr Ile
            260                 265                 270

Ser Ala Gln Asn Met Asp Ile Leu Gln Asn Pro Leu Met Ile Lys Ile
            275                 280                 285

Asn Gln Asp Pro Leu Gly Ile Gln Gly Arg Arg Ile His Lys Glu Lys
            290                 295                 300

Ser Leu Ile Glu Val Tyr Met Arg Pro Leu Ser Asn Lys Ala Ser Ala
305                 310                 315                 320

Leu Val Phe Phe Ser Arg Arg Thr Asp Met Pro Tyr Arg Tyr His Ser
            325                 330                 335

Ser Leu Gly Gln Leu Asn Phe Thr Gly Ser Val Ile Tyr Glu Ala Gln
            340                 345                 350

Asp Val Tyr Ser Gly Asp Ile Ile Ser Gly Leu Arg Asp Glu Thr Asn
            355                 360                 365

Phe Thr Val Ile Ile Asn Pro Ser Gly Val Val Met Trp Tyr Leu Tyr
            370                 375                 380

Pro Ile Lys Asn Leu Glu Met Ser Gln Gln
385                 390

<210> SEQ ID NO 7
<211> LENGTH: 394
<212> TYPE: PRT
<213> ORGANISM: Artificial sequence
<220> FEATURE:
<223> OTHER INFORMATION: modified human NAGAL polypeptide C326R S171E
      A174L (amino acid numbering as in mature human NAGAL)

<400> SEQUENCE: 7

Leu Asp Asn Gly Leu Leu Gln Thr Pro Met Gly Trp Leu Ala Trp
1               5                   10                  15

Glu Arg Phe Arg Cys Asn Ile Asn Cys Asp Glu Asp Pro Lys Asn Cys
                20                  25                  30

Ile Ser Glu Gln Leu Phe Met Glu Met Ala Asp Arg Met Ala Gln Asp
            35                  40                  45

Gly Trp Arg Asp Met Gly Tyr Thr Tyr Leu Asn Ile Asp Asp Cys Trp
    50                  55                  60

Ile Gly Gly Arg Asp Ala Ser Gly Arg Leu Met Pro Asp Pro Lys Arg
65                  70                  75                  80

-continued

```
Phe Pro His Gly Ile Pro Phe Leu Ala Asp Tyr Val His Ser Leu Gly
                85                  90                  95

Leu Lys Leu Gly Ile Tyr Ala Asp Met Gly Asn Phe Thr Cys Met Gly
            100                 105                 110

Tyr Pro Gly Thr Thr Leu Asp Lys Val Val Gln Asp Ala Gln Thr Phe
        115                 120                 125

Ala Glu Trp Lys Val Asp Met Leu Lys Leu Asp Gly Cys Phe Ser Thr
130                 135                 140

Pro Glu Glu Arg Ala Gln Gly Tyr Pro Lys Met Ala Ala Ala Leu Asn
145                 150                 155                 160

Ala Thr Gly Arg Pro Ile Ala Phe Ser Cys Glu Trp Pro Leu Tyr Glu
                165                 170                 175

Gly Gly Leu Pro Pro Arg Val Asn Tyr Ser Leu Leu Ala Asp Ile Cys
            180                 185                 190

Asn Leu Trp Arg Asn Tyr Asp Asp Ile Gln Asp Ser Trp Trp Ser Val
        195                 200                 205

Leu Ser Ile Leu Asn Trp Phe Val Glu His Gln Asp Ile Leu Gln Pro
210                 215                 220

Val Ala Gly Pro Gly His Trp Asn Asp Pro Asp Met Leu Leu Ile Gly
225                 230                 235                 240

Asn Phe Gly Leu Ser Leu Glu Gln Ser Arg Ala Gln Met Ala Leu Trp
                245                 250                 255

Thr Val Leu Ala Ala Pro Leu Leu Met Ser Thr Asp Leu Arg Thr Ile
            260                 265                 270

Ser Ala Gln Asn Met Asp Ile Leu Gln Asn Pro Leu Met Ile Lys Ile
        275                 280                 285

Asn Gln Asp Pro Leu Gly Ile Gln Gly Arg Arg Ile His Lys Glu Lys
290                 295                 300

Ser Leu Ile Glu Val Tyr Met Arg Pro Leu Ser Asn Lys Ala Ser Ala
305                 310                 315                 320

Leu Val Phe Phe Ser Arg Arg Thr Asp Met Pro Tyr Arg Tyr His Ser
                325                 330                 335

Ser Leu Gly Gln Leu Asn Phe Thr Gly Ser Val Ile Tyr Glu Ala Gln
            340                 345                 350

Asp Val Tyr Ser Gly Asp Ile Ile Ser Gly Leu Arg Asp Glu Thr Asn
        355                 360                 365

Phe Thr Val Ile Ile Asn Pro Ser Gly Val Val Met Trp Tyr Leu Tyr
370                 375                 380

Pro Ile Lys Asn Leu Glu Met Ser Gln Gln
385                 390
```

<210> SEQ ID NO 8
<211> LENGTH: 394
<212> TYPE: PRT
<213> ORGANISM: Artificial sequence
<220> FEATURE:
<223> OTHER INFORMATION: modified human NAGAL polypeptide N213D C326S
    S171E A174L (amino acid numbering as in mature human NAGAL)

<400> SEQUENCE: 8

```
Leu Asp Asn Gly Leu Leu Gln Thr Pro Pro Met Gly Trp Leu Ala Trp
1               5                   10                  15

Glu Arg Phe Arg Cys Asn Ile Asn Cys Asp Glu Asp Pro Lys Asn Cys
                20                  25                  30

Ile Ser Glu Gln Leu Phe Met Glu Met Ala Asp Arg Met Ala Gln Asp
```

```
                35                  40                  45
Gly Trp Arg Asp Met Gly Tyr Thr Tyr Leu Asn Ile Asp Asp Cys Trp
 50                  55                  60
Ile Gly Gly Arg Asp Ala Ser Gly Arg Leu Met Pro Asp Pro Lys Arg
 65                  70                  75                  80
Phe Pro His Gly Ile Pro Phe Leu Ala Asp Tyr Val His Ser Leu Gly
                 85                  90                  95
Leu Lys Leu Gly Ile Tyr Ala Asp Met Gly Asn Phe Thr Cys Met Gly
                100                 105                 110
Tyr Pro Gly Thr Thr Leu Asp Lys Val Val Gln Asp Ala Gln Thr Phe
            115                 120                 125
Ala Glu Trp Lys Val Asp Met Leu Lys Leu Asp Gly Cys Phe Ser Thr
130                 135                 140
Pro Glu Glu Arg Ala Gln Gly Tyr Pro Lys Met Ala Ala Ala Leu Asn
145                 150                 155                 160
Ala Thr Gly Arg Pro Ile Ala Phe Ser Cys Glu Trp Pro Leu Tyr Glu
                165                 170                 175
Gly Gly Leu Pro Pro Arg Val Asn Tyr Ser Leu Leu Ala Asp Ile Cys
            180                 185                 190
Asn Leu Trp Arg Asn Tyr Asp Asp Ile Gln Asp Ser Trp Trp Ser Val
            195                 200                 205
Leu Ser Ile Leu Asp Trp Phe Val Glu His Gln Asp Ile Leu Gln Pro
210                 215                 220
Val Ala Gly Pro Gly His Trp Asn Asp Pro Asp Met Leu Leu Ile Gly
225                 230                 235                 240
Asn Phe Gly Leu Ser Leu Glu Gln Ser Arg Ala Gln Met Ala Leu Trp
                245                 250                 255
Thr Val Leu Ala Ala Pro Leu Leu Met Ser Thr Asp Leu Arg Thr Ile
            260                 265                 270
Ser Ala Gln Asn Met Asp Ile Leu Gln Asn Pro Leu Met Ile Lys Ile
            275                 280                 285
Asn Gln Asp Pro Leu Gly Ile Gln Gly Arg Arg Ile His Lys Glu Lys
290                 295                 300
Ser Leu Ile Glu Val Tyr Met Arg Pro Leu Ser Asn Lys Ala Ser Ala
305                 310                 315                 320
Leu Val Phe Phe Ser Ser Arg Thr Asp Met Pro Tyr Arg Tyr His Ser
                325                 330                 335
Ser Leu Gly Gln Leu Asn Phe Thr Gly Ser Val Ile Tyr Glu Ala Gln
            340                 345                 350
Asp Val Tyr Ser Gly Asp Ile Ile Ser Gly Leu Arg Asp Glu Thr Asn
            355                 360                 365
Phe Thr Val Ile Ile Asn Pro Ser Gly Val Val Met Trp Tyr Leu Tyr
            370                 375                 380
Pro Ile Lys Asn Leu Glu Met Ser Gln Gln
385                 390
```

<210> SEQ ID NO 9
<211> LENGTH: 394
<212> TYPE: PRT
<213> ORGANISM: Artificial sequence
<220> FEATURE:
<223> OTHER INFORMATION: modified human NAGAL polypeptide C326S S171E
    A174L (amino acid numbering as in mature human NAGAL)

<400> SEQUENCE: 9

Leu Asp Asn Gly Leu Gln Thr Pro Pro Met Gly Trp Leu Ala Trp
1               5                   10                  15

Glu Arg Phe Arg Cys Asn Ile Asn Cys Asp Glu Asp Pro Lys Asn Cys
            20                  25                  30

Ile Ser Glu Gln Leu Phe Met Glu Met Ala Asp Arg Met Ala Gln Asp
            35                  40                  45

Gly Trp Arg Asp Met Gly Tyr Thr Tyr Leu Asn Ile Asp Asp Cys Trp
50                  55                  60

Ile Gly Gly Arg Asp Ala Ser Gly Arg Leu Met Pro Asp Pro Lys Arg
65              70                  75                  80

Phe Pro His Gly Ile Pro Phe Leu Ala Asp Tyr Val His Ser Leu Gly
                85                  90                  95

Leu Lys Leu Gly Ile Tyr Ala Asp Met Gly Asn Phe Thr Cys Met Gly
            100                 105                 110

Tyr Pro Gly Thr Thr Leu Asp Lys Val Val Gln Asp Ala Gln Thr Phe
            115                 120                 125

Ala Glu Trp Lys Val Asp Met Leu Lys Leu Asp Gly Cys Phe Ser Thr
            130                 135                 140

Pro Glu Glu Arg Ala Gln Gly Tyr Pro Lys Met Ala Ala Ala Leu Asn
145                 150                 155                 160

Ala Thr Gly Arg Pro Ile Ala Phe Ser Cys Glu Trp Pro Leu Tyr Glu
            165                 170                 175

Gly Gly Leu Pro Pro Arg Val Asn Tyr Ser Leu Leu Ala Asp Ile Cys
            180                 185                 190

Asn Leu Trp Arg Asn Tyr Asp Asp Ile Gln Asp Ser Trp Trp Ser Val
            195                 200                 205

Leu Ser Ile Leu Asn Trp Phe Val Glu His Gln Asp Ile Leu Gln Pro
210                 215                 220

Val Ala Gly Pro Gly His Trp Asn Asp Pro Asp Met Leu Leu Ile Gly
225                 230                 235                 240

Asn Phe Gly Leu Ser Leu Glu Gln Ser Arg Ala Gln Met Ala Leu Trp
            245                 250                 255

Thr Val Leu Ala Ala Pro Leu Leu Met Ser Thr Asp Leu Arg Thr Ile
            260                 265                 270

Ser Ala Gln Asn Met Asp Ile Leu Gln Asn Pro Leu Met Ile Lys Ile
            275                 280                 285

Asn Gln Asp Pro Leu Gly Ile Gln Gly Arg Arg Ile His Lys Glu Lys
            290                 295                 300

Ser Leu Ile Glu Val Tyr Met Arg Pro Leu Ser Asn Lys Ala Ser Ala
305                 310                 315                 320

Leu Val Phe Phe Ser Ser Arg Thr Asp Met Pro Tyr Arg Tyr His Ser
            325                 330                 335

Ser Leu Gly Gln Leu Asn Phe Thr Gly Ser Val Ile Tyr Glu Ala Gln
            340                 345                 350

Asp Val Tyr Ser Gly Asp Ile Ile Ser Gly Leu Arg Asp Glu Thr Asn
            355                 360                 365

Phe Thr Val Ile Ile Asn Pro Ser Gly Val Val Met Trp Tyr Leu Tyr
            370                 375                 380

Pro Ile Lys Asn Leu Glu Met Ser Gln Gln
385                 390

<210> SEQ ID NO 10
<211> LENGTH: 1243
<212> TYPE: DNA

<213> ORGANISM: Artificial sequence
<220> FEATURE:
<223> OTHER INFORMATION: nucleotide sequence encoding modified human
      NAGAL polypeptide S188E A191L (amino acid numbering starting from
      the starting methionine) for expression in Yarrowia lipolytica

<400> SEQUENCE: 10

```
cacaatgaag ctctctacta ttctctttac cgcctgcgcc accctcgccg ctgctctcga      60
caacggactc ctccagactc ctcctatggg ctggctggct tgggagcgat tccgatgcaa     120
catcaactgt gacgaggacc ccaagaactg catttctgag cagctcttta tggagatggc     180
tgaccgaatg gcccaggacg gatggcgaga tatgggctac acctacctga acatcgacga     240
ttgttggatt ggcggtcgag acgcctctgg tcgactcatg cccgatccta agcgattccc     300
ccacggaatc cctttctgg ctgactacgt ccattccctg gcctcaagc tgggtattta      360
cgccgacatg ggcaacttca cctgcatggg ctaccccggt accactctcg acaaggtcgt     420
gcaggatgct cagaccttcg ccgagtggaa ggtggacatg ctcaagctgg atggatgttt     480
ttccactcct gaggagcgag ctcagggata ccctaagatg gccgctgccc tgaacgctac     540
cggtcgaccc atcgccttct cctgcgagtg gcctctctac gagggaggac tgcctcctcg     600
agtcaactac tctctgctcg ctgacatctg taacctctgg cgaaactacg acgatattca     660
ggattcgtgg tggtccgtcc tctctatcct gaactggttc gtggagcacc aggacattct     720
gcagcccgtg gccggtcctg acattggaa cgaccccgat atgctgctca tcggaaactt     780
tggcctctcg ctggagcagt cccgagctca gatggctctc tggaccgttc tggctgctcc     840
tctgctcatg tcgaccgacc tgcgaactat ctccgctcag aacatggata ttctccagaa     900
cccccctgatg atcaagatta accaggaccc tctcggtatc cagggacgac gaatccacaa     960
ggagaagtcg ctgattgagg tttacatgcg acccctctct aacaaggctt cggccctggt    1020
cttctttcc tgccgaaccg acatgcctta ccgataccat tcctctctcg gccagctgaa    1080
cttcactggt tctgtgatct acgaggccca ggacgtttac tccggtgata tcatttctgg    1140
actgcgagac gagaccaact ttactgtgat cattaacccc tctggagttg tcatgtggta    1200
cctctaccct attaagaacc tggagatgtc gcagcagtaa tag                      1243
```

<210> SEQ ID NO 11
<211> LENGTH: 411
<212> TYPE: PRT
<213> ORGANISM: Artificial sequence
<220> FEATURE:
<223> OTHER INFORMATION: modified human NAGAL polypeptide S188E A191L
      (amino acid numbering starting from the starting methionine)

<400> SEQUENCE: 11

```
Met Lys Leu Ser Thr Ile Leu Phe Thr Ala Cys Ala Thr Leu Ala Ala
1               5                   10                  15

Ala Leu Asp Asn Gly Leu Leu Gln Thr Pro Pro Met Gly Trp Leu Ala
            20                  25                  30

Trp Glu Arg Phe Arg Cys Asn Ile Asn Cys Asp Glu Asp Pro Lys Asn
        35                  40                  45

Cys Ile Ser Glu Gln Leu Phe Met Glu Met Ala Asp Arg Met Ala Gln
    50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95
```

```
Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
        115                 120                 125

Gly Tyr Pro Gly Thr Thr Leu Asp Lys Val Val Gln Asp Ala Gln Thr
    130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Glu Trp Pro Leu Tyr
            180                 185                 190

Glu Gly Gly Leu Pro Pro Arg Val Asn Tyr Ser Leu Leu Ala Asp Ile
        195                 200                 205

Cys Asn Leu Trp Arg Asn Tyr Asp Asp Ile Gln Asp Ser Trp Trp Ser
    210                 215                 220

Val Leu Ser Ile Leu Asn Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
        275                 280                 285

Ile Ser Ala Gln Asn Met Asp Ile Leu Gln Asn Pro Leu Met Ile Lys
    290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Cys Arg Thr Asp Met Pro Tyr Arg Tyr His
            340                 345                 350

Ser Ser Leu Gly Gln Leu Asn Phe Thr Gly Ser Val Ile Tyr Glu Ala
        355                 360                 365

Gln Asp Val Tyr Ser Gly Asp Ile Ile Ser Gly Leu Arg Asp Glu Thr
    370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
                405                 410

<210> SEQ ID NO 12
<211> LENGTH: 1245
<212> TYPE: DNA
<213> ORGANISM: Artificial sequence
<220> FEATURE:
<223> OTHER INFORMATION: nucleotide sequence encoding human
      alpha-galactosidase for expression in Yarrowia lipolytica

<400> SEQUENCE: 12
atgaagcttt ccaccatcct cttcacagcc tgcgctaccc tggccctgga caacggcctg      60
gcccgaaccc ccaccatggg ctggctgcac tgggagcgat tcatgtgtaa cctggactgt     120
caggaagagc ccgactcttg tatctctgag aagctgttca tggaaatggc cgagctgatg     180
gtgtctgagg gctggaagga cgccggctac gagtacctgt gtatcgacga ctgttggatg     240
```

-continued

```
gccccccagc gagactctga gggccgactc caggccgacc cccagcgatt ccccacggc    300 atccgacagc tcgccaacta cgtgcactct aagggcctga agctgggcat ctacgccgac    360
gtgggcaaca agacctgtgc cggcttcccc ggctctttcg gctactacga catcgacgcc    420
cagaccttcg ccgactgggg cgtggacctg ctgaagttcg acggctgtta ctgtgactct    480
ctcgagaacc tggccgacgg ctacaagcac atgtctctgg ccctgaaccg aaccggccga    540
tctatcgtgt actcttgtga gtggcccctg tacatgtggc ccttccagaa gcccaactac    600
accgagatcc gacagtactg taaccactgg cgaaacttcg ccgacatcga cgactcgtgg    660
aagtctatca gtctattct ggactggacc tctttcaacc aggagcgaat cgtcgacgtc    720
gccggacccg gcggatggaa cgaccccgac atgctggtga cggcaacttt cggcctgtct    780
tggaaccagc aggtgaccca gatggccctg tgggctatca tggctgcccc cctgttcatg    840
tctaacgacc tgcgacacat ctctccccag gccaaggccc tgctccagga caaggacgtg    900
atcgccatca accaggaccc cctgggcaag cagggctacc agctccgaca gggcgacaac    960
ttcgaggtgt gggagcgacc cctgtctggc ctggcctggg ccgtggccat gatcaaccga   1020
caggagatcg gcggaccccg atcttacacc atcgccgtgg cctccctggg aaagggcgtg   1080
gcctgtaacc ccgcctgttt catcacccag ctcctgcccg tgaagcgaaa gctgggattc   1140
tacgagtgga cctctcgact gcgatctcac atcaacccca ccggcaccgt gctgctccag   1200
ctcgagaaca ccatgcagat gtctctgaag gacctgctgt aataa                    1245
```

<210> SEQ ID NO 13
<211> LENGTH: 413
<212> TYPE: PRT
<213> ORGANISM: Artificial sequence
<220> FEATURE:
<223> OTHER INFORMATION: human alpha-galactosidase containing Yarrowia Lip2pre signal peptide and one X-Ala repeat

<400> SEQUENCE: 13

Met Lys Leu Ser Thr Ile Leu Phe Thr Ala Cys Ala Thr Leu Ala Leu
1               5                   10                  15

Asp Asn Gly Leu Ala Arg Thr Pro Thr Met Gly Trp Leu His Trp Glu
            20                  25                  30

Arg Phe Met Cys Asn Leu Asp Cys Gln Glu Glu Pro Asp Ser Cys Ile
        35                  40                  45

Ser Glu Lys Leu Phe Met Glu Met Ala Glu Leu Met Val Ser Glu Gly
    50                  55                  60

Trp Lys Asp Ala Gly Tyr Glu Tyr Leu Cys Ile Asp Asp Cys Trp Met
65                  70                  75                  80

Ala Pro Gln Arg Asp Ser Glu Gly Arg Leu Gln Ala Asp Pro Gln Arg
                85                  90                  95

Phe Pro His Gly Ile Arg Gln Leu Ala Asn Tyr Val His Ser Lys Gly
            100                 105                 110

Leu Lys Leu Gly Ile Tyr Ala Asp Val Gly Asn Lys Thr Cys Ala Gly
        115                 120                 125

Phe Pro Gly Ser Phe Gly Tyr Tyr Asp Ile Asp Ala Gln Thr Phe Ala
    130                 135                 140

Asp Trp Gly Val Asp Leu Leu Lys Phe Asp Gly Cys Tyr Cys Asp Ser
145                 150                 155                 160

Leu Glu Asn Leu Ala Asp Gly Tyr Lys His Met Ser Leu Ala Leu Asn
                165                 170                 175

Arg Thr Gly Arg Ser Ile Val Tyr Ser Cys Glu Trp Pro Leu Tyr Met

```
            180                 185                 190
Trp Pro Phe Gln Lys Pro Asn Tyr Thr Glu Ile Arg Gln Tyr Cys Asn
                195                 200                 205

His Trp Arg Asn Phe Ala Asp Ile Asp Asp Ser Trp Lys Ser Ile Lys
    210                 215                 220

Ser Ile Leu Asp Trp Thr Ser Phe Asn Gln Glu Arg Ile Val Asp Val
225                 230                 235                 240

Ala Gly Pro Gly Gly Trp Asn Asp Pro Asp Met Leu Val Ile Gly Asn
                245                 250                 255

Phe Gly Leu Ser Trp Asn Gln Gln Val Thr Gln Met Ala Leu Trp Ala
            260                 265                 270

Ile Met Ala Ala Pro Leu Phe Met Ser Asn Asp Leu Arg His Ile Ser
        275                 280                 285

Pro Gln Ala Lys Ala Leu Leu Gln Asp Lys Asp Val Ile Ala Ile Asn
            290                 295                 300

Gln Asp Pro Leu Gly Lys Gln Gly Tyr Gln Leu Arg Gln Gly Asp Asn
305                 310                 315                 320

Phe Glu Val Trp Glu Arg Pro Leu Ser Gly Leu Ala Trp Ala Val Ala
                325                 330                 335

Met Ile Asn Arg Gln Glu Ile Gly Gly Pro Arg Ser Tyr Thr Ile Ala
            340                 345                 350

Val Ala Ser Leu Gly Lys Gly Val Ala Cys Asn Pro Ala Cys Phe Ile
        355                 360                 365

Thr Gln Leu Leu Pro Val Lys Arg Lys Leu Gly Phe Tyr Glu Trp Thr
    370                 375                 380

Ser Arg Leu Arg Ser His Ile Asn Pro Thr Gly Thr Val Leu Leu Gln
385                 390                 395                 400

Leu Glu Asn Thr Met Gln Met Ser Leu Lys Asp Leu Leu
                405                 410

<210> SEQ ID NO 14
<211> LENGTH: 415
<212> TYPE: PRT
<213> ORGANISM: Artificial sequence
<220> FEATURE:
<223> OTHER INFORMATION: modified human NAGAL polypeptide S171E A174L
      (amino acid numbering as in mature human NAGAL), domain II swapped
      with human alpha-galactosidase, and containing Yarrowia Lip2pre
      signal peptide and two X-Ala repeats

<400> SEQUENCE: 14

Met Lys Leu Ser Thr Ile Leu Phe Thr Ala Cys Ala Thr Leu Ala Ala
1               5                   10                  15

Ala Leu Asp Asn Gly Leu Leu Gln Thr Pro Pro Met Gly Trp Leu Ala
            20                  25                  30

Trp Glu Arg Phe Arg Cys Asn Ile Asn Cys Asp Glu Asp Pro Lys Asn
        35                  40                  45

Cys Ile Ser Glu Gln Leu Phe Met Glu Met Ala Asp Arg Met Ala Gln
    50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
```

```
                    115                 120                 125
Gly Tyr Pro Gly Thr Thr Leu Asp Lys Val Val Gln Asp Ala Gln Thr
            130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Glu Trp Pro Leu Tyr
            180                 185                 190

Glu Gly Gly Leu Pro Pro Arg Val Asn Tyr Ser Leu Leu Ala Asp Ile
                195                 200                 205

Cys Asn Leu Trp Arg Asn Tyr Asp Asp Ile Gln Asp Ser Trp Trp Ser
            210                 215                 220

Val Leu Ser Ile Leu Asn Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
            275                 280                 285

Ile Ser Ala Gln Asn Met Asp Ile Leu Gln Asn Pro Leu Met Ile Lys
            290                 295                 300

Ile Asn Gln Asp Pro Leu Gly Lys Gln Gly Tyr Gln Leu Arg Gln Gly
305                 310                 315                 320

Asp Asn Phe Glu Val Trp Glu Arg Pro Leu Ser Gly Leu Ala Trp Ala
                325                 330                 335

Val Ala Met Ile Asn Arg Gln Glu Ile Gly Gly Pro Arg Ser Tyr Thr
            340                 345                 350

Ile Ala Val Ala Ser Leu Gly Lys Gly Val Ala Cys Asn Pro Ala Cys
            355                 360                 365

Phe Ile Thr Gln Leu Leu Pro Val Lys Arg Lys Leu Gly Phe Tyr Glu
            370                 375                 380

Trp Thr Ser Arg Leu Arg Ser His Ile Asn Pro Thr Gly Thr Val Leu
385                 390                 395                 400

Leu Gln Leu Glu Asn Thr Met Gln Met Ser Leu Lys Asp Leu Leu
                405                 410                 415

<210> SEQ ID NO 15
<211> LENGTH: 411
<212> TYPE: PRT
<213> ORGANISM: Artificial sequence
<220> FEATURE:
<223> OTHER INFORMATION: modified human NAGAL polypeptide N213D C326R
      S171E A174L (amino acid numbering as in mature human NAGAL), and
      containing Yarrowia Lip2pre signal peptide and two X-Ala repeats

<400> SEQUENCE: 15

Met Lys Leu Ser Thr Ile Leu Phe Thr Ala Cys Ala Thr Leu Ala Ala
1               5                   10                  15

Ala Leu Asp Asn Gly Leu Leu Gln Thr Pro Pro Met Gly Trp Leu Ala
            20                  25                  30

Trp Glu Arg Phe Arg Cys Asn Ile Asn Cys Asp Glu Asp Pro Lys Asn
            35                  40                  45

Cys Ile Ser Glu Gln Leu Phe Met Glu Met Ala Asp Arg Met Ala Gln
50                  55                  60
```

```
Asp Gly Trp Arg Asp Met Gly Tyr Thr Tyr Leu Asn Ile Asp Asp Cys
 65                  70                  75                  80

Trp Ile Gly Gly Arg Asp Ala Ser Gly Arg Leu Met Pro Asp Pro Lys
                 85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
            115                 120                 125

Gly Tyr Pro Gly Thr Thr Leu Asp Lys Val Val Gln Asp Ala Gln Thr
            130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Glu Trp Pro Leu Tyr
            180                 185                 190

Glu Gly Gly Leu Pro Pro Arg Val Asn Tyr Ser Leu Leu Ala Asp Ile
            195                 200                 205

Cys Asn Leu Trp Arg Asn Tyr Asp Asp Ile Gln Asp Ser Trp Trp Ser
210                 215                 220

Val Leu Ser Ile Leu Asp Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
            275                 280                 285

Ile Ser Ala Gln Asn Met Asp Ile Leu Gln Asn Pro Leu Met Ile Lys
            290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Arg Arg Thr Asp Met Pro Tyr Arg Tyr His
            340                 345                 350

Ser Ser Leu Gly Gln Leu Asn Phe Thr Gly Ser Val Ile Tyr Glu Ala
            355                 360                 365

Gln Asp Val Tyr Ser Gly Asp Ile Ile Ser Gly Leu Arg Asp Glu Thr
            370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
                405                 410

<210> SEQ ID NO 16
<211> LENGTH: 411
<212> TYPE: PRT
<213> ORGANISM: Artificial sequence
<220> FEATURE:
<223> OTHER INFORMATION: modified human NAGAL polypeptide C326S S171E
      A174L (amino acid numbering as in mature human NAGAL), and
      containing Yarrowia Lip2pre signal peptide and two X-Ala repeats

<400> SEQUENCE: 16
```

```
Met Lys Leu Ser Thr Ile Leu Phe Thr Ala Cys Ala Thr Leu Ala Ala
1               5                   10                  15
Ala Leu Asp Asn Gly Leu Leu Gln Thr Pro Pro Met Gly Trp Leu Ala
            20                  25                  30
Trp Glu Arg Phe Arg Cys Asn Ile Asn Cys Asp Glu Asp Pro Lys Asn
            35                  40                  45
Cys Ile Ser Glu Gln Leu Phe Met Glu Met Ala Asp Arg Met Ala Gln
50                  55                  60
Asp Gly Trp Arg Asp Met Gly Tyr Thr Tyr Leu Asn Ile Asp Asp Cys
65                  70                  75                  80
Trp Ile Gly Gly Arg Asp Ala Ser Gly Arg Leu Met Pro Asp Pro Lys
                85                  90                  95
Arg Phe Pro His Gly Ile Pro Phe Leu Ala Asp Tyr Val His Ser Leu
            100                 105                 110
Gly Leu Lys Leu Gly Ile Tyr Ala Asp Met Gly Asn Phe Thr Cys Met
            115                 120                 125
Gly Tyr Pro Gly Thr Thr Leu Asp Lys Val Val Gln Asp Ala Gln Thr
            130                 135                 140
Phe Ala Glu Trp Lys Val Asp Met Leu Lys Leu Asp Gly Cys Phe Ser
145                 150                 155                 160
Thr Pro Glu Glu Arg Ala Gln Gly Tyr Pro Lys Met Ala Ala Ala Leu
            165                 170                 175
Asn Ala Thr Gly Arg Pro Ile Ala Phe Ser Cys Glu Trp Pro Leu Tyr
            180                 185                 190
Glu Gly Gly Leu Pro Pro Arg Val Asn Tyr Ser Leu Leu Ala Asp Ile
            195                 200                 205
Cys Asn Leu Trp Arg Asn Tyr Asp Asp Ile Gln Asp Ser Trp Trp Ser
210                 215                 220
Val Leu Ser Ile Leu Asn Trp Phe Val Glu His Gln Asp Ile Leu Gln
225                 230                 235                 240
Pro Val Ala Gly Pro Gly His Trp Asn Asp Pro Asp Met Leu Leu Ile
            245                 250                 255
Gly Asn Phe Gly Leu Ser Leu Glu Gln Ser Arg Ala Gln Met Ala Leu
            260                 265                 270
Trp Thr Val Leu Ala Ala Pro Leu Leu Met Ser Thr Asp Leu Arg Thr
            275                 280                 285
Ile Ser Ala Gln Asn Met Asp Ile Leu Gln Asn Pro Leu Met Ile Lys
            290                 295                 300
Ile Asn Gln Asp Pro Leu Gly Ile Gln Gly Arg Arg Ile His Lys Glu
305                 310                 315                 320
Lys Ser Leu Ile Glu Val Tyr Met Arg Pro Leu Ser Asn Lys Ala Ser
            325                 330                 335
Ala Leu Val Phe Phe Ser Ser Arg Thr Asp Met Pro Tyr Arg Tyr His
            340                 345                 350
Ser Ser Leu Gly Gln Leu Asn Phe Thr Gly Ser Val Ile Tyr Glu Ala
            355                 360                 365
Gln Asp Val Tyr Ser Gly Asp Ile Ile Ser Gly Leu Arg Asp Glu Thr
            370                 375                 380
Asn Phe Thr Val Ile Ile Asn Pro Ser Gly Val Val Met Trp Tyr Leu
385                 390                 395                 400
Tyr Pro Ile Lys Asn Leu Glu Met Ser Gln Gln
            405                 410
```

<210> SEQ ID NO 17
<211> LENGTH: 411
<212> TYPE: PRT
<213> ORGANISM: Artificial sequence
<220> FEATURE:
<223> OTHER INFORMATION: modified human NAGAL polypeptide N213R C326D
S171E A174L (amino acid numbering as in mature human NAGAL), and
containing Yarrowia Lip2pre signal peptide and two X-Ala repeats

<400> SEQUENCE: 17

```
Met Lys Leu Ser Thr Ile Leu Phe Thr Ala Cys Ala Thr Leu Ala Ala
1               5                   10                  15

Ala Leu Asp Asn Gly Leu Leu Gln Thr Pro Pro Met Gly Trp Leu Ala
            20                  25                  30

Trp Glu Arg Phe Arg Cys Asn Ile Asn Cys Asp Glu Asp Pro Lys Asn
        35                  40                  45

Cys Ile Ser Glu Gln Leu Phe Met Glu Met Ala Asp Arg Met Ala Gln
    50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
        115                 120                 125

Gly Tyr Pro Gly Thr Thr Leu Asp Lys Val Val Gln Asp Ala Gln Thr
    130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Glu Trp Pro Leu Tyr
            180                 185                 190

Glu Gly Gly Leu Pro Pro Arg Val Asn Tyr Ser Leu Leu Ala Asp Ile
        195                 200                 205

Cys Asn Leu Trp Arg Asn Tyr Asp Asp Ile Gln Asp Ser Trp Trp Ser
    210                 215                 220

Val Leu Ser Ile Leu Arg Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
        275                 280                 285

Ile Ser Ala Gln Asn Met Asp Ile Leu Gln Asn Pro Leu Met Ile Lys
    290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Asp Arg Thr Asp Met Pro Tyr Arg Tyr His
            340                 345                 350

Ser Ser Leu Gly Gln Leu Asn Phe Thr Gly Ser Val Ile Tyr Glu Ala
        355                 360                 365
```

```
Gln Asp Val Tyr Ser Gly Asp Ile Ile Ser Gly Leu Arg Asp Glu Thr
        370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
            405                 410

<210> SEQ ID NO 18
<211> LENGTH: 411
<212> TYPE: PRT
<213> ORGANISM: Artificial sequence
<220> FEATURE:
<223> OTHER INFORMATION: modified human NAGAL polypeptide C326R S171E
      A174L (amino acid numbering as in mature human NAGAL), and
      containing Yarrowia Lip2pre signal peptide and two X-Ala repeats

<400> SEQUENCE: 18

Met Lys Leu Ser Thr Ile Leu Phe Thr Ala Cys Ala Thr Leu Ala Ala
1               5                   10                  15

Ala Leu Asp Asn Gly Leu Leu Gln Thr Pro Pro Met Gly Trp Leu Ala
                20                  25                  30

Trp Glu Arg Phe Arg Cys Asn Ile Asn Cys Asp Glu Asp Pro Lys Asn
            35                  40                  45

Cys Ile Ser Glu Gln Leu Phe Met Glu Met Ala Asp Arg Met Ala Gln
50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
        115                 120                 125

Gly Tyr Pro Gly Thr Thr Leu Asp Lys Val Val Gln Asp Ala Gln Thr
130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Glu Trp Pro Leu Tyr
            180                 185                 190

Glu Gly Gly Leu Pro Pro Arg Val Asn Tyr Ser Leu Leu Ala Asp Ile
        195                 200                 205

Cys Asn Leu Trp Arg Asn Tyr Asp Asp Ile Gln Asp Ser Trp Trp Ser
210                 215                 220

Val Leu Ser Ile Leu Asn Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
        275                 280                 285

Ile Ser Ala Gln Asn Met Asp Ile Leu Gln Asn Pro Leu Met Ile Lys
290                 295                 300
```

```
Ile Asn Gln Asp Pro Leu Gly Ile Gln Gly Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Arg Arg Thr Asp Met Pro Tyr Arg Tyr His
            340                 345                 350

Ser Ser Leu Gly Gln Leu Asn Phe Thr Gly Ser Val Ile Tyr Glu Ala
        355                 360                 365

Gln Asp Val Tyr Ser Gly Asp Ile Ile Ser Gly Leu Arg Asp Glu Thr
    370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
                405                 410

<210> SEQ ID NO 19
<211> LENGTH: 411
<212> TYPE: PRT
<213> ORGANISM: Artificial sequence
<220> FEATURE:
<223> OTHER INFORMATION: modified human NAGAL polypeptide N213D S171E
      A174L (amino acid numbering as in mature human NAGAL), and
      containing Yarrowia Lip2pre signal peptide and two X-Ala repeats

<400> SEQUENCE: 19

Met Lys Leu Ser Thr Ile Leu Phe Thr Ala Cys Ala Thr Leu Ala Ala
1               5                   10                  15

Ala Leu Asp Asn Gly Leu Leu Gln Thr Pro Pro Met Gly Trp Leu Ala
            20                  25                  30

Trp Glu Arg Phe Arg Cys Asn Ile Asn Cys Asp Glu Asp Pro Lys Asn
        35                  40                  45

Cys Ile Ser Glu Gln Leu Phe Met Glu Met Ala Asp Arg Met Ala Gln
50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
        115                 120                 125

Gly Tyr Pro Gly Thr Thr Leu Asp Lys Val Val Gln Asp Ala Gln Thr
    130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Glu Trp Pro Leu Tyr
            180                 185                 190

Glu Gly Gly Leu Pro Pro Arg Val Asn Tyr Ser Leu Leu Ala Asp Ile
        195                 200                 205

Cys Asn Leu Trp Arg Asn Tyr Asp Asp Ile Gln Asp Ser Trp Trp Ser
    210                 215                 220

Val Leu Ser Ile Leu Asp Trp Phe Val Glu His Gln Asp Ile Leu Gln
225                 230                 235                 240

Pro Val Ala Gly Pro Gly His Trp Asn Asp Pro Asp Met Leu Leu Ile
```

```
                   245                 250                 255
Gly Asn Phe Gly Leu Ser Leu Glu Gln Ser Arg Ala Gln Met Ala Leu
                260                 265                 270

Trp Thr Val Leu Ala Ala Pro Leu Leu Met Ser Thr Asp Leu Arg Thr
            275                 280                 285

Ile Ser Ala Gln Asn Met Asp Ile Leu Gln Asn Pro Leu Met Ile Lys
        290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Cys Arg Thr Asp Met Pro Tyr Arg Tyr His
            340                 345                 350

Ser Ser Leu Gly Gln Leu Asn Phe Thr Gly Ser Val Ile Tyr Glu Ala
        355                 360                 365

Gln Asp Val Tyr Ser Gly Asp Ile Ile Ser Gly Leu Arg Asp Glu Thr
    370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
                405                 410
```

<210> SEQ ID NO 20
<211> LENGTH: 411
<212> TYPE: PRT
<213> ORGANISM: Artificial sequence
<220> FEATURE:
<223> OTHER INFORMATION: modified human NAGAL polypeptide N213D C326S
      S171E A174L (amino acid numbering as in mature human NAGAL), and
      containing Yarrowia Lip2pre signal peptide and two X-Ala repeats

<400> SEQUENCE: 20

```
Met Lys Leu Ser Thr Ile Leu Phe Thr Ala Cys Ala Thr Leu Ala Ala
1               5                   10                  15

Ala Leu Asp Asn Gly Leu Leu Gln Thr Pro Pro Met Gly Trp Leu Ala
                20                  25                  30

Trp Glu Arg Phe Arg Cys Asn Ile Asn Cys Asp Glu Asp Pro Lys Asn
            35                  40                  45

Cys Ile Ser Glu Gln Leu Phe Met Glu Met Ala Asp Arg Met Ala Gln
        50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
        115                 120                 125

Gly Tyr Pro Gly Thr Thr Leu Asp Lys Val Val Gln Asp Ala Gln Thr
    130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Glu Trp Pro Leu Tyr
            180                 185                 190
```

```
Glu Gly Gly Leu Pro Pro Arg Val Asn Tyr Ser Leu Leu Ala Asp Ile
            195                 200                 205

Cys Asn Leu Trp Arg Asn Tyr Asp Asp Ile Gln Asp Ser Trp Trp Ser
    210                 215                 220

Val Leu Ser Ile Leu Asp Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
                260                 265                 270

Trp Thr Val Leu Ala Ala Pro Leu Leu Met Ser Thr Asp Leu Arg Thr
            275                 280                 285

Ile Ser Ala Gln Asn Met Asp Ile Leu Gln Asn Pro Leu Met Ile Lys
            290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Ser Arg Thr Asp Met Pro Tyr Arg Tyr His
                340                 345                 350

Ser Ser Leu Gly Gln Leu Asn Phe Thr Gly Ser Val Ile Tyr Glu Ala
            355                 360                 365

Gln Asp Val Tyr Ser Gly Asp Ile Ile Ser Gly Leu Arg Asp Glu Thr
            370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
                405                 410

<210> SEQ ID NO 21
<211> LENGTH: 411
<212> TYPE: PRT
<213> ORGANISM: Homo sapiens

<400> SEQUENCE: 21

Met Leu Leu Lys Thr Val Leu Leu Gly His Val Ala Gln Val Leu
1               5                   10                  15

Met Leu Asp Asn Gly Leu Leu Gln Thr Pro Pro Met Gly Trp Leu Ala
                20                  25                  30

Trp Glu Arg Phe Arg Cys Asn Ile Asn Cys Asp Glu Asp Pro Lys Asn
            35                  40                  45

Cys Ile Ser Glu Gln Leu Phe Met Glu Met Ala Asp Arg Met Ala Gln
    50                  55                  60

Asp Gly Trp Arg Asp Met Gly Tyr Thr Tyr Leu Asn Ile Asp Asp Cys
65              70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
            115                 120                 125

Gly Tyr Pro Gly Thr Thr Leu Asp Lys Val Val Gln Asp Ala Gln Thr
        130                 135                 140

Phe Ala Glu Trp Lys Val Asp Met Leu Lys Leu Asp Gly Cys Phe Ser
```

```
                145                 150                 155                 160
        Thr Pro Glu Glu Arg Ala Gln Gly Tyr Pro Lys Met Ala Ala Leu
                        165                 170                 175

Asn Ala Thr Gly Arg Pro Ile Ala Phe Ser Cys Ser Trp Pro Ala Tyr
                        180                 185                 190

Glu Gly Gly Leu Pro Pro Arg Val Asn Tyr Ser Leu Leu Ala Asp Ile
                        195                 200                 205

Cys Asn Leu Trp Arg Asn Tyr Asp Asp Ile Gln Asp Ser Trp Trp Ser
                210                 215                 220

Val Leu Ser Ile Leu Asn Trp Phe Val Glu His Gln Asp Ile Leu Gln
        225                 230                 235                 240

Pro Val Ala Gly Pro Gly His Trp Asn Asp Pro Asp Met Leu Leu Ile
                        245                 250                 255

Gly Asn Phe Gly Leu Ser Leu Glu Gln Ser Arg Ala Gln Met Ala Leu
                        260                 265                 270

Trp Thr Val Leu Ala Ala Pro Leu Leu Met Ser Thr Asp Leu Arg Thr
                275                 280                 285

Ile Ser Ala Gln Asn Met Asp Ile Leu Gln Asn Pro Leu Met Ile Lys
                290                 295                 300

Ile Asn Gln Asp Pro Leu Gly Ile Gln Gly Arg Arg Ile His Lys Glu
        305                 310                 315                 320

Lys Ser Leu Ile Glu Val Tyr Met Arg Pro Leu Ser Asn Lys Ala Ser
                        325                 330                 335

Ala Leu Val Phe Phe Ser Cys Arg Thr Asp Met Pro Tyr Arg Tyr His
                        340                 345                 350

Ser Ser Leu Gly Gln Leu Asn Phe Thr Gly Ser Val Ile Tyr Glu Ala
                355                 360                 365

Gln Asp Val Tyr Ser Gly Asp Ile Ile Ser Gly Leu Arg Asp Glu Thr
                370                 375                 380

Asn Phe Thr Val Ile Ile Asn Pro Ser Gly Val Val Met Trp Tyr Leu
        385                 390                 395                 400

Tyr Pro Ile Lys Asn Leu Glu Met Ser Gln Gln
                        405                 410

<210> SEQ ID NO 22
<211> LENGTH: 291
<212> TYPE: PRT
<213> ORGANISM: Artificial sequence
<220> FEATURE:
<223> OTHER INFORMATION: domain I of human NAGAL polypeptide

<400> SEQUENCE: 22

Leu Asp Asn Gly Leu Leu Gln Thr Pro Pro Met Gly Trp Leu Ala Trp
        1               5                   10                  15

Glu Arg Phe Arg Cys Asn Ile Asn Cys Asp Glu Asp Pro Lys Asn Cys
                        20                  25                  30

Ile Ser Glu Gln Leu Phe Met Glu Met Ala Asp Arg Met Ala Gln Asp
                        35                  40                  45

Gly Trp Arg Asp Met Gly Tyr Thr Tyr Leu Asn Ile Asp Asp Cys Trp
                50                  55                  60

Ile Gly Gly Arg Asp Ala Ser Gly Arg Leu Met Pro Asp Pro Lys Arg
        65                  70                  75                  80

Phe Pro His Gly Ile Pro Phe Leu Ala Asp Tyr Val His Ser Leu Gly
                        85                  90                  95

Leu Lys Leu Gly Ile Tyr Ala Asp Met Gly Asn Phe Thr Cys Met Gly
```

```
                100             105             110
Tyr Pro Gly Thr Thr Leu Asp Lys Val Val Gln Asp Ala Gln Thr Phe
            115             120             125

Ala Glu Trp Lys Val Asp Met Leu Lys Leu Asp Gly Cys Phe Ser Thr
130             135             140

Pro Glu Glu Arg Ala Gln Gly Tyr Pro Lys Met Ala Ala Ala Leu Asn
145             150             155             160

Ala Thr Gly Arg Pro Ile Ala Phe Ser Cys Ser Trp Pro Ala Tyr Glu
            165             170             175

Gly Gly Leu Pro Pro Arg Val Asn Tyr Ser Leu Leu Ala Asp Ile Cys
            180             185             190

Asn Leu Trp Arg Asn Tyr Asp Asp Ile Gln Asp Ser Trp Trp Ser Val
            195             200             205

Leu Ser Ile Leu Asn Trp Phe Val Glu His Gln Asp Ile Leu Gln Pro
            210             215             220

Val Ala Gly Pro Gly His Trp Asn Asp Pro Asp Met Leu Leu Ile Gly
225             230             235             240

Asn Phe Gly Leu Ser Leu Glu Gln Ser Arg Ala Gln Met Ala Leu Trp
            245             250             255

Thr Val Leu Ala Ala Pro Leu Leu Met Ser Thr Asp Leu Arg Thr Ile
            260             265             270

Ser Ala Gln Asn Met Asp Ile Leu Gln Asn Pro Leu Met Ile Lys Ile
            275             280             285

Asn Gln Asp
    290

<210> SEQ ID NO 23
<211> LENGTH: 98
<212> TYPE: PRT
<213> ORGANISM: Artificial sequence
<220> FEATURE:
<223> OTHER INFORMATION: domain II of human NAGAL polypeptide

<400> SEQUENCE: 23

Gly Arg Arg Ile His Lys Glu Lys Ser Leu Ile Glu Val Tyr Met Arg
1               5               10              15

Pro Leu Ser Asn Lys Ala Ser Ala Leu Val Phe Phe Ser Cys Arg Thr
            20              25              30

Asp Met Pro Tyr Arg Tyr His Ser Ser Leu Gly Gln Leu Asn Phe Thr
            35              40              45

Gly Ser Val Ile Tyr Glu Ala Gln Asp Val Tyr Ser Gly Asp Ile Ile
        50              55              60

Ser Gly Leu Arg Asp Glu Thr Asn Phe Thr Val Ile Ile Asn Pro Ser
65              70              75              80

Gly Val Val Met Trp Tyr Leu Tyr Pro Ile Lys Asn Leu Glu Met Ser
            85              90              95

Gln Gln
```